(12) United States Patent
Ewald et al.

(10) Patent No.: US 12,077,561 B2
(45) Date of Patent: Sep. 3, 2024

(54) CNP COMPOUNDS

(71) Applicant: Novo Nordisk A/S, Bagsvaerd (DK)

(72) Inventors: Jakob Ewald, Koebenhavn N (DK); Anne Louise Bank Kodal, Frederiksberg (DK); Jonas Alfred Karl Wilbs, Ballerup (DK); Christian Poulsen, Ballerup (DK); Peter Madsen, Bagsvaerd (DK); Kilian Waldemar Conde Frieboes, Maaloev (DK); Christian Wenzel Tornoee, Lyngby (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 18/385,946

(22) Filed: Nov. 1, 2023

(65) Prior Publication Data

US 2024/0209028 A1    Jun. 27, 2024

(30) Foreign Application Priority Data

Nov. 2, 2022   (EP) .................................... 22205128

(51) Int. Cl.
   *C07K 14/00*   (2006.01)
(52) U.S. Cl.
   CPC ................................. *C07K 14/001* (2013.01)
(58) Field of Classification Search
   CPC ..................................................... C07K 14/001
   See application file for complete search history.

(56) References Cited

U.S. PATENT DOCUMENTS

| | | | |
|---|---|---|---|
| 5,352,770 A | 10/1994 | Matsuo | |
| 5,434,133 A | 7/1995 | Tanaka et al. | |
| 6,034,231 A | 3/2000 | Tanaka et al. | |
| 8,636,965 B2 | 1/2014 | Lohn | |
| 2005/0059600 A1 | 3/2005 | Burnett et al. | |
| 2009/0170756 A1 | 7/2009 | Burnett, Jr. et al. | |
| 2010/0331256 A1 | 12/2010 | Wendt et al. | |
| 2012/0164142 A1 | 6/2012 | Crine et al. | |
| 2014/0179605 A1 | 6/2014 | Chen et al. | |
| 2014/0274901 A1 | 9/2014 | Ichiki et al. | |
| 2017/0028023 A1 | 2/2017 | Bullens et al. | |
| 2018/0133289 A1 | 5/2018 | Endo | |
| 2018/0207239 A1 | 7/2018 | Bullens et al. | |
| 2019/0015481 A1 | 1/2019 | Rau et al. | |
| 2020/0017567 A1 | 1/2020 | Castillo et al. | |

FOREIGN PATENT DOCUMENTS

| | | | |
|---|---|---|---|
| CA | 3153730 A1 | 3/2021 | |
| WO | 200071576 A2 | 11/2000 | |
| WO | 200144284 A2 | 6/2001 | |
| WO | 02074234 A2 | 9/2002 | |
| WO | 2005000095 A2 | 1/2005 | |
| WO | 2008031045 A2 | 3/2008 | |
| WO | 2009015011 A1 | 1/2009 | |
| WO | 2009067639 A2 | 5/2009 | |
| WO | 2009086126 A2 | 7/2009 | |
| WO | 2009149161 A2 | 12/2009 | |
| WO | 2010078325 A2 | 7/2010 | |
| WO | 2010/102886 A1 | 9/2010 | |
| WO | 2010129655 A2 | 11/2010 | |
| WO | 2010135541 A2 | 11/2010 | |
| WO | 2013032784 A1 | 3/2013 | |
| WO | 13059491 A1 | 4/2013 | |
| WO | 2013058833 A1 | 4/2013 | |
| WO | 2013095759 A1 | 6/2013 | |
| WO | 2013103896 A1 | 7/2013 | |
| WO | 2014127120 A1 | 8/2014 | |
| WO | 20165081 A1 | 1/2016 | |
| WO | 2016110577 A1 | 7/2016 | |
| WO | 17020034 A1 | 2/2017 | |
| WO | 2017100400 A2 | 6/2017 | |
| WO | 2017118693 A1 | 7/2017 | |
| WO | 2017118698 A1 | 7/2017 | |
| WO | 2017118700 A1 | 7/2017 | |
| WO | 2017118703 A1 | 7/2017 | |
| WO | 2017118704 A1 | 7/2017 | |
| WO | 2017118707 A1 | 7/2017 | |
| WO | 2018175534 A1 | 9/2018 | |
| WO | 2019197477 A1 | 10/2019 | |
| WO | 21055497 A1 | 3/2021 | |
| WO | 21252910 A2 | 12/2021 | |
| WO | 21252931 A2 | 12/2021 | |
| WO | 2021252910 A2 | 12/2021 | |
| WO | 2021252931 A2 | 12/2021 | |

OTHER PUBLICATIONS

Breinholt et al., "TransCon CNP, a Sustained-Release C-Type Natriuretic Peptide Prodrug, a Potentially Safe and Efficacious New Therapeutic Modality for the Treatment of Comorbidities Associated with Fibroblast Growth Factor Receptor 3-Related Skeletal Dysplasias", Drug Discovery and Translational Medicine, Sep. 2019, vol. 370, No. 3, pp. 459-471.
Broadhead et al., "The spray drying of pharmaceuticals", Drug Development and Industrial Pharmacy, 1992, vol. 18, No. 11-12, pp. 1169-1206.
Carpenter et al., "Modes of stabilization of a protein by organic solutes during desiccation", Cryobiology, Oct. 1988, vol. 25, pp. 459-470.
Decker et al. "FGFR3 is a target of the homeobox transcription factor SHOX in limb development". Hum Mol Genet, Apr. 2011, vol. 20, No. 8, pp. 1524-1535.
Hisado-Oliva, "Mutations in C-natriuretic peptide (NPPC): a novel cause of autosomal dominant short stature", Genet Med, Jun. 2017, vol. 20 20, pp. 91-97.
Hopkins et al., Physiology, Acid Base Balance, Sep. 2022, pp. 1-7.
Kozlowski et al., "IPC—Isoelectric Point Calculator", Biology Direct, Oct. 2016, vol. 11, Article No. 55, pp. 1-16.
Krakow et al., "The skeletal dysplasias", Genet Med, Jun. 2010, vol. 12, No. 6, pp. 327-341.
Levine III, "Quantification of Beta-sheet amyloid fibril structures with thioflavin T", Methods in Enzymology, 1999, vol. 309, pp. 274-284.

(Continued)

*Primary Examiner* — Li N Komatsu
(74) *Attorney, Agent, or Firm* — Leon Y. Lum

(57) ABSTRACT

This application relates to new C-type natriuretic peptide (CNP) compounds, pharmaceutical compositions comprising these compounds, and these compounds for use as medicaments.

13 Claims, 48 Drawing Sheets

Specification includes a Sequence Listing.

(56) References Cited

OTHER PUBLICATIONS

Lisy et al., "Design, Synthesis, and Actions of a Novel Chimeric Natriuretic Peptide: CD-NP", J Am Coll Cardiol., Jul. 2008, vol. 52, No. 1, pp. 60-68.

Longo et al., "The RASopathies: Biology, genetics and therapeutic options", Adv. Cancer Res., Aug. 2021, vol. 153, pp. 305-341.

Masters, "Chapter 13-18", Spray-Drying Handbook, 1991, 5th ed, pp. 491-676.

Moyes et al., "C-type Natriuretic Peptide: A Multifaceted Paracrine Regulator in the Heart and Vasculature", Int. J. Mol. Sci., May 2019, vol. 20, No. 9, Article No. 2281, pp. 1-23.

Mumenthaler et al., "Feasibility study on spray-drying protein pharmaceuticals: recombinant human growth hormone and tissue-type plasminogen activator", Pharm. Res., Jan. 1994, vol. 11, pp. 12-20.

Naiki et al., "Fluorometric determination of amyloid fibrils in vitro using the fluorescent dye, thioflavine T", Analytical Biochemistry, Mar. 1989, vol. 177, No., 2, pp. 244-249.

Petraina et al., "Cyclic GMP modulating drugs in cardiovascular diseases: mechanism-based network pharmacology," Cardiovasc,. Res., Jul. 2022, No. 118, No. 9, pp. 2085-2102.

Roser, "Trehalose Drying: A Novel Replacement for Freeze-Drying", BioPharm, Sep. 1991, vol. 4, pp. 47-53.

Sabir et al., "The evolving therapeutic landscape of genetic skeletal disorders", Orphanet J Rare Dis, Dec. 2019, vol. 14, Article No. 300, pp. 1-20.

Sampson et al., "The synthesis of 'difficult' peptides using 2-hydroxy-4-methoxybenzyl or pseudoproline amino acid building blocks: a comparative study" J. Pep. Sci., 1999, vol. 5, p. 403-409.

Sangaralingham et al., "Natriuretic peptide pathways in heart failure: further therapeutic possibilities", Cardiovasc. Res., Feb. 2023, vol. 118, No. 18, cvac125, pp. 3416-3433.

Savarirayan et al., "Once-daily, subcutaneous vosoritide therapy in children with achondroplasia: a randomised, double-blind, phase 3, placebo-controlled, multicentre trial", The Lancet, Sep. 2020, vol. 396, No. 10252, pp. 684-692.

Skoog et al., "Calculation of the isoelectric points of polypeptides from the amino acid composition," Trends in Analytical Chemistry, 1986, vol. 5, pp. 82-83.

Wendt et al., "Neutral Endopeptidase-Resistant C-Type Natriuretic Peptide Variant Represents a New Therapeutic Approach for Treatment of Fibroblast Growth Factor Receptor 3-Related Dwarfism", Apr. 2015, vol. 353, No. 1, pp. 132-149.

Williams, et al., "The lyophilization of pharmaceuticals: a literature review", J. Parenter Sci. Technol., Mar.-Apr. 1984, vol. 38, No. 2, pp. 48-59.

Yu et al., "Pulmonary drug delivery: Physiologic and mechanistic aspects", Crit Rev Ther Drug Carr Sys, 1997, vol. 14, No. 4, pp. 395-453.

1225

1233

1227

1241

1351

1354

1356

1375

1376

1377

1352

1379

1434

9384

9407

1381

1386

1389

1392

1426

9435

9482

9435

9482

9384

CNP COMPOUNDS

TECHNICAL FIELD OF INVENTION

This invention relates to new C-type natriuretic peptide (CNP) compounds, pharmaceutical compositions comprising these compounds, and these compounds for use as medicaments.

CROSS-REFERENCE TO RELATED APPLICATIONS

This application claims priority to European Patent Application 22205128.6, filed Nov. 2, 2022; the contents of which are incorporated herein by reference.

INCORPORATION-BY-REFERENCE OF THE SEQUENCE LISTING

The instant application contains a Sequence Listing which has been submitted in XML format via the USPTO patent electronic filing system and is hereby incorporated by reference in its entirety. Said XML file, created on Oct. 27, 2023, is named 220034US01.xml and is 216 kilobytes in size.

BACKGROUND OF INVENTION

The natriuretic peptides are a family of three structurally related hormones that play distinctive roles within the cardiovascular system. Atrial natriuretic peptide (ANP) and brain natriuretic peptide (BNP) are expressed in the heart and released in response to a volume-induced stretch of the atria and ventricles, respectively. Their physiological effects include regulation of cardiac structure, blood pressure and blood volume.

C-type natriuretic peptide (CNP) is highly expressed in endothelial cells where it is constitutively released. Other cells within the cardiovascular system, including cardiomyocytes and fibroblasts, also produce CNP, albeit to a lesser extent. CNP has direct effects on inflammation, fibrosis, cardiac contractility, endothelial function, angiogenesis and blood pressure.

There are three known receptors for natriuretic peptides. Natriuretic peptide receptor-1 (NPR1) is a particulate guanylyl cyclase that catalyses the synthesis of cGMP upon binding by ANP or BNP. NPR1 is expressed in kidney, lung, adipose, adrenal, brain, heart, testis, and vascular smooth muscle tissue. NPR2, which is expressed in bone, brain, fibroblasts, heart, kidney, liver, lung, uterine, and vascular smooth muscle tissue, is homologous to NPR1 but is selectively activated by CNP. In contrast, NPR3 only contains a 37-residue intracellular domain and lacks guanylyl cyclase activity. It controls local natriuretic peptide concentrations via receptor-mediated internalization and degradation, but there is accumulating evidence for a signalling function of NPR3. All three natriuretic peptides bind to NPR3 with high affinity and this receptor is the most widely and abundantly expressed of the three receptors. There is also a very high degree of conservation of all three receptors and in line with CNP, NPR2 is the most highly conserved.

Clinical and preclinical data have demonstrated an essential role of CNP and its two receptors for cardio-renal-metabolic function, and there is also accumulating data supporting that targeting of this system holds therapeutic potential in a broad range of cardiovascular, renal, and metabolic diseases (Int. J. Mol. Sci. 2019, 20, 2281; Cardiovasc. Res. 2022, 118, 2085-2102; Cardiovasc. Res. 2022 Aug. 25; cvac125)". Similarly, human genetics, as well as preclinical and clinical data, supports NPR2 and CNP as regulators of bone growth, with therapeutic potential in a broad range of short stature indications that relates to NPR2 and CNP (Lancet, 396:684; J Pharmacol Exp Ther, 370:459; Hisado-Oliva (2018) Genet Med, 20:91, as well as to FGFR3-related skeletal dysplasia (Sabir and Cole Orphanet Journal of Rare Diseases (2019) 14:300; Krakow and Rimoin, Genetics in medicine (2010) 12:6, Decker et al. Human Molecular Genetics (2011), 20:8) and RASopathies (Adv Cancer Res. 153:305). Currently, two CNP compounds are in clinical development for achondroplasia which is a type of Dwarfism (BMN111 (Vosoritide) and TransCon CNP). The Mayo clinic has previously explored a CNP compound designed to activate both NPR2 and NPR1 in heart failure (J Am Coll Cardiol. 2008 Jul. 1; 52(1): 60-68).

The clearance of CNP in human plasma is very rapid, with a calculated half-life of minutes. Given this short half-life, it would be beneficial to develop new long acting CNP compounds which can be administered less frequently, while retaining an acceptable clinical profile.

A range of different approaches have been used for modifying the structure of CNP in order to provide a longer acting profile. WO 2013/058833 discloses fusion peptides of CNP and Fc domains. WO 2018/175534 discloses fatty acid modified NPR1 agonists.

SUMMARY OF INVENTION

The invention provides CNP compounds with improved pharmaceutical properties.

In one aspect, the present invention provides a CNP compound comprising a CNP peptide and a modifying group wherein the net charge of the compound at physiological pH is 0 or negative, wherein the CNP peptide comprises an amino acid sequence according to Formula I:

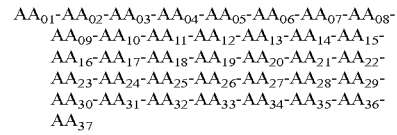

$$AA_{01}\text{-}AA_{02}\text{-}AA_{03}\text{-}AA_{04}\text{-}AA_{05}\text{-}AA_{06}\text{-}AA_{07}\text{-}AA_{08}\text{-}$$
$$AA_{09}\text{-}AA_{10}\text{-}AA_{11}\text{-}AA_{12}\text{-}AA_{13}\text{-}AA_{14}\text{-}AA_{15}\text{-}$$
$$AA_{16}\text{-}AA_{17}\text{-}AA_{18}\text{-}AA_{19}\text{-}AA_{20}\text{-}AA_{21}\text{-}AA_{22}\text{-}$$
$$AA_{23}\text{-}AA_{24}\text{-}AA_{25}\text{-}AA_{26}\text{-}AA_{27}\text{-}AA_{28}\text{-}AA_{29}\text{-}$$
$$AA_{30}\text{-}AA_{31}\text{-}AA_{32}\text{-}AA_{33}\text{-}AA_{34}\text{-}AA_{35}\text{-}AA_{36}\text{-}$$
$$AA_{37}$$

wherein
$AA_{01}$ is Gln or absent,
$AA_{02}$ is Glu or absent,
$AA_{03}$ is His or absent,
$AA_{04}$ is Pro or absent,
$AA_{05}$ is Asn or Gln or Glu or absent,
$AA_{06}$ is Ala or absent,
$AA_{07}$ is Arg or His or Ala or absent,
$AA_{08}$ is Lys or Ser or His or absent,
$AA_{09}$ is Tyr or Glu or absent
$AA_{10}$ is Lys or Glu or Gln or His or absent,
$AA_{11}$ is Gly,
$AA_{12}$ is Ala,
$AA_{13}$ is Gln or Asn or Glu,
$AA_{14}$ is Lys or His or Glu,
$AA_{15}$ is Lys Ser or Glu or Thr or His,
$AA_{16}$ is Gly,
$AA_{17}$ is Leu or Gly or Ser or Val,
$AA_{18}$ is Ser or His
$AA_{19}$ is Gln or Ser or Lys or His,
$AA_{20}$ is Gly,
$AA_{21}$ is Cys,
$AA_{22}$ is Phe,
$AA_{23}$ is Gly, AA$_{24}$ is Leu,
AA$_{25}$ is Pro or Lys,
AA$_{26}$ is Leu,
AA$_{27}$ is Asp or Glu,
AA$_{28}$ is Arg,
AA$_{29}$ is Ile,
AA$_{30}$ is Gly,
AA$_{31}$ is Ser,
AA$_{32}$ is Leu or Nle or Met,
AA$_{33}$ is Ser,
AA$_{34}$ is Gly,
AA$_{35}$ is Leu,
AA$_{36}$ is Gly, and
AA$_{37}$ is Cys;
wherein the modifying group comprises Chem. A, Chem. B and Chem. C; wherein Chem. A is selected from the group consisting of:

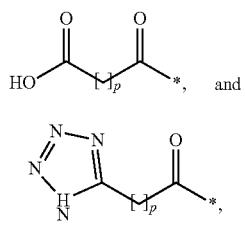
(Chem. A1)

(Chem. A2)

wherein p is an integer in the range of 14-20, and
where * denotes an amide bond connecting Chem. A and Chem. B; and
wherein Chem. B is selected from the group consisting of:

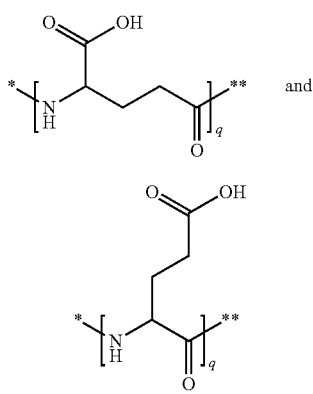
(Chem. B1)

(Chem. B2)

wherein q is an integer in the range of 1-8,
wherein * denotes an amide bond connecting Chem. A- and Chem. B-,
wherein ** denotes an amide bond connecting Chem. B- and Chem. C-; and
wherein Chem. C is selected from the group consisting of:

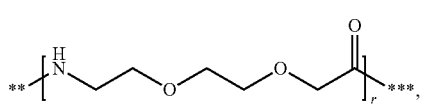
(Chem. C1)

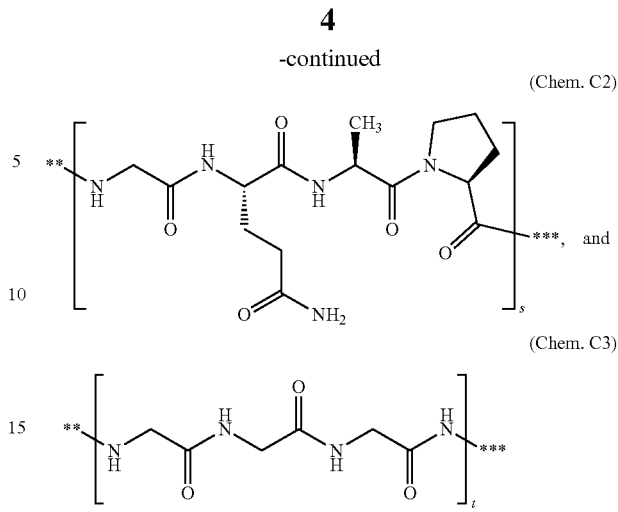
(Chem. C2)

(Chem. C3)

wherein r is an integer in the range of 0-4,
wherein s is an integer in the range of 0-3,
wherein t is an integer in the range of 0-1,
wherein ** denotes an amide bond connecting Chem. B- and Chem. C-,
wherein *** denotes an amide bond connecting Chem. C- and the N-terminal alpha-amine on the CNP peptide.

In one embodiment, the present invention provides a CNP compound, wherein the CNP peptide has any one of the following amino acid sequences:

```
                                      (SEQ ID NO: 136)
GAQKKGSSQGCFGLPLDRIGSLSGLGC, (SEQ ID NO: 77)
ARKYKGAQKKGLSQGCFGLPLDRIGSLSGLGC, (SEQ ID NO: 88)
YKGAQKKGGSQGCFGLPLDRIGSLSGLGC, (SEQ ID NO: 103)
YKGAQKKGLSQGCFGLPLDRIGSLSGLGC, (SEQ ID NO: 67)
QEHPQARKYKGAQKKGLSSGCFGLPLDRIGSLSGLGC,
and (SEQ ID NO: 104)
QEHPQARKYKGAQKKGLSSGCFGLPLERIGSLSGLGC.
```

In another aspect, the present invention provides a pharmaceutical composition comprising a compound according to the invention, and one or more pharmaceutically acceptable excipients.

The present invention also in one aspect provides, the use of the compounds of the invention as medicaments for treating or preventing of cardio-renal-metabolic diseases including heart failure, and achondroplasia.

The short half-life of approximately two minutes of wt CNP makes CNP unsuitable for pharmaceutical use. In the present invention, the half-life of CNP is extended by fatty acid acylation which facilitates albumin binding. However, the combination of the net positively charged CNP peptide (at physiological pH) with a fatty acid albumin binder modification (where the CNP compound is overall positively charged) leads to significant injection site reactions upon subcutaneous injection as well as low bioavailability. This is surprising since a net positively charged CNP peptide without a fatty acid albumin binder attached shows no observable injection site reactions. To solve these problems, amino acid substitutions have been introduced into the CNP peptide and negative charges have been introduced into the modifying group (comprising the fatty acid). The combination of these modifications results in a compound of overall net negative charge at physiological pH which shows good subcutaneous bioavailability and none to mild subcutaneous injection site reactions.

Surprisingly, the addition of negative charges also reduces the in vitro and in vivo potency of the CNP compounds, in a manner such that higher net negative charge generally correlates with lower in vivo potency. To retain sufficient potency of the CNP compounds, only a low number of net negative charges where introduced. However, a low number of net negative charges reduces solubility and biophysical stability of the CNP compounds when formulated for subcutaneous administration at a physiologically relevant pH. The present disclosure strikes a balance with respect to these parameters and, surprisingly, provides CNP compounds with sufficient potency, and also sufficient solubility and biophysical stability for liquid formulation.

Further, wt CNP does not show desired chemical stability in liquid formulation needed for convenient pharmaceutical administration. In the present invention, selected amino acid substitutions of the wt CNP sequence are introduced to facilitate chemical stability in formulation.

The present disclosure provides CNP compounds with extended half-life and good tolerability for subcutaneous administration while retaining sufficient in vivo potency for therapeutic use and high chemical and biophysical stability in liquid formulation.

The invention may also solve further problems that will be apparent from the disclosure of the exemplary embodiments.

DETAILED DESCRIPTION

Figure 1:
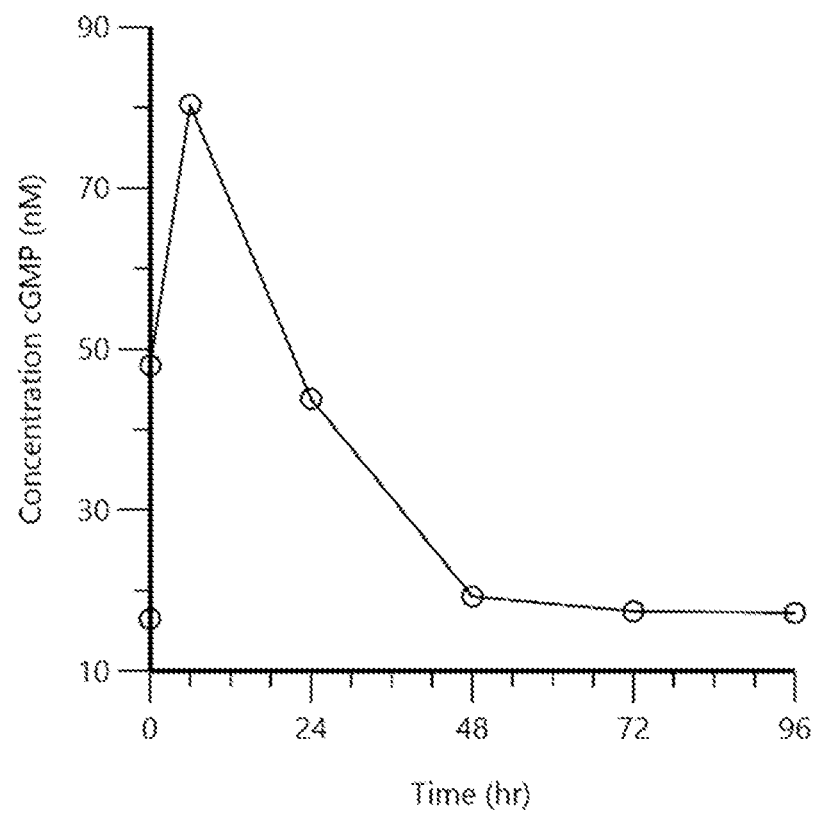
FIG. 1 shows the pharmacodynamic response (cGMP) after i.v. administration of Compound ID 0776 to rats as described in example 11.

The present invention provides CNP compounds with improved pharmaceutical properties. The present invention also provides pharmaceutical compositions and the use of the compounds and compositions of the present invention as medicaments for treating disease.

C-Type Natriuretic Peptide

C-type natriuretic peptide (CNP) (GenBank Accession No. NP 077720) is a small, single chain peptide in a family of peptides (ANP, BNP, CNP) having a 17-amino acid residue disulfide ring structure and have important roles in multiple biological processes. CNP interacts with natriuretic peptide receptor 2 (NPR2, NPR-B, GC-B) to stimulate the generation of cyclic-guanosine monophosphate (cGMP). CNP is expressed more widely, including in the central nervous system, reproductive tract, bone and endothelium of blood vessels. The clearance of CNP in human plasma is rapid, with a half-life of minutes.

Natural CNP gene and polypeptide have been previously described. U.S. Pat. No. 5,352,770 discloses isolated and purified CNP-22 from porcine brain identical in sequence to human CNP (human wild-type CNP-22: GLSKGCFGLKL-DRIGSMSGLGC (SEQ ID NO: 01)). U.S. Pat. No. 6,034,231 discloses the human gene and polypeptide of pre-pro-CNP (126 amino acids) and the human CNP-53 gene and peptide. Human wild-type CNP-37 has the sequence QEHPNARKYKGANKKGLSKGCFGLKLDRI-GSMSGLGC (SEQ ID NO: 02).

CNP Compound

In one aspect, the present invention provides a CNP compound comprising a CNP peptide and a modifying group wherein the net charge of the compound at physiological pH is 0 or negative.

The CNP compounds as described herein, have been engineered to achieve a compound of overall neutral or net negative charge. This was achieved with introduction of amino acid substitutions of the CNP peptide, and with the introduction of negative charges into the modifying group. It is not trivial to reduce the charge of the CNP compound and still retain biological activity of the CNP compound towards the NPR2 receptor.

The term "net charge", as used herein, refers to the sum of all negative and positive charges on the CNP compound at a given pH, where the charges are defined solely by the acid dissociation constant of each ionizable group in the CNP compound.

In one embodiment, the net charge of the CNP compound at physiological pH is negative determined as described in Example 4.

In one embodiment, the net charge of the CNP compound at physiological pH is 0 to −4, determined as described in Example 4.

The term "physiological pH", as used herein, refers to a pH in the range of 7.35 to 7.45 inclusive, more typically averaging 7.4.

In one aspect, the CNP compounds, described herein, have an intramolecular disulfide bridge (disulfide bond between two cysteine residues), resulting in a cyclic structure.

CNP Peptide

The term "CNP peptide" as used herein refers to a peptide being 37 to 22 amino acids long comprising the CNP-22 amino acid sequence (SEQ ID NO: 01), and amino acid sequences thereof including one or more amino acid modifications (e.g. one or more amino acid substitutions, additions, and/or deletions). The term "CNP peptide" as used herein also encompasses CNP variants.

The term "CNP variant", as used herein, refers to a CNP peptide, which is an amino acid variant of the CNP-37 sequence (SEQ ID NO:02). In other words, a CNP variant is a CNP peptide including one or more amino acid modifications, i.e. at least one amino acid has been changed compared to SEQ ID NO: 02. These modifications may represent, independently, one or more amino acid substitutions, additions, and/or deletions.

A CNP variant may be described by reference to the number of the amino acid residue which is changed (i.e. the corresponding position in the CNP-37 sequence (SEQ ID NO:02)), and the change (e.g. the identity of the amino acid residue in variant at the given position.). That is, numerical references to specific amino acid residues of the CNP peptide, if not stated otherwise, refer to the CNP-37 sequence (SEQ ID NO:2) (i.e., residue 1 is Glutamine (Q1), and residue 37 is Cysteine (C37). The following is a non-limiting example of suitable variant nomenclature: the des1-4, 5Q, 13Q, 32Nle CNP variant designates a CNP peptide sequence which, when compared to CNP-37, has the following amino acid changes: deletion of the amino acid residues in positions 1-4, as well as substitutions of asparagine (N) at position 5 with Glutamine (Q), of asparagine (N) at position 13 with Glutamine (Q), of Methionine (M) at position 32 with Norleucine.

The term "amino acid" refers to any amino acid, naturally occurring (including the 20 standard amino acids which are encoded by the standard genetic code in humans) or not naturally occurring. Amino acid residues may be identified by their full name, their one-letter code, and/or their three-letter code as is usual in the art. These three ways are fully equivalent. The term "non-coded amino acids" refers to all amino acids which aren't among the 20 standard amino acids encoded by the standard genetic code in humans. Non-coded amino acids may exist in nature or be purely synthetic. Non-limiting examples of non-coded amino acids are D-isomers of the coded amino acids, and glycine residues with a side chain attached to the nitrogen atom rather than the alpha-carbon atom. D-isomers of coded amino acids may be referred to as (i) "D-" followed by the full name, followed by the one-letter code, or followed by the three-letter code of the amino acid, or as (ii) the lower case one-letter code of the amino acid. Further abbreviations for non-coded amino acids used in this application are presented below.

| Abbreviation | Name of the residue | Chemical structure |
|---|---|---|
| Nle (X) | L-Norleucine | 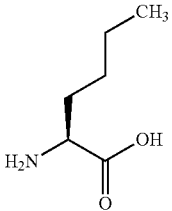 (Chem. D) |

In an aspect of the invention, the CNP peptide, comprises an amino acid sequence according to Formula I:

$AA_{01}$-$AA_{02}$-$AA_{03}$-$AA_{04}$-$AA_{05}$-$AA_{09}$-$AA_{07}$-$AA_{08}$-
$AA_{09}$-$AA_{10}$-$AA_{11}$-$AA_{12}$-$AA_{13}$-$AA_{14}$-$AA_{15}$-
$AA_{16}$-$AA_{17}$-$AA_{18}$-$AA_{19}$-$AA_{20}$-$AA_{21}$-$AA_{22}$-
$AA_{23}$-$AA_{24}$-$AA_{25}$-$AA_{26}$-$AA_{27}$-$AA_{28}$-$AA_{29}$-
$AA_{30}$-$AA_{31}$-$AA_{32}$-$AA_{33}$-$AA_{34}$-$AA_{35}$-$AA_{36}$-
$AA_{37}$ wherein
$AA_{01}$ is Gln or absent,
$AA_{02}$ is Glu or absent,
$AA_{0s}$ is His or absent,
$AA_{04}$ is Pro or absent,
$AA_{05}$ is Asn or Gln or Glu or absent,
$AA_{06}$ is Ala or absent,
$AA_{07}$ is Arg or His or Ala or absent,
$AA_{08}$ is Lys or Ser or His or absent,
$AA_{09}$ is Tyr or Glu or absent
$AA_{10}$ is Lys or Glu or Gln or His or absent,
$AA_{11}$ is Gly,
$AA_{12}$ is Ala,
$AA_{13}$ is Gln or Asn or Glu,
$AA_{14}$ is Lys or His or Glu,
$AA_{15}$ is Lys Ser or Glu or Thr or His,
$AA_{16}$ is Gly,
$AA_{17}$ is Leu or Gly or Ser or Val,
$AA_{18}$ is Ser or His
$AA_{19}$ is Gln or Ser or Lys or His,
$AA_{20}$ is Gly,
$AA_{21}$ is Cys,
$AA_{22}$ is Phe,
$AA_{23}$ is Gly,
$AA_{24}$ is Leu,
$AA_{25}$ is Pro or Lys,
$AA_{26}$ is Leu,
$AA_{27}$ is Asp or Glu,
$AA_{28}$ is Arg,
$AA_{29}$ is Ile,
$AA_{30}$ is Gly,
$AA_{31}$ is Ser,
$AA_{32}$ is Leu or Nle or Met,
$AA_{33}$ is Ser,
$AA_{34}$ is Gly,
$AA_{35}$ is Leu,
$AA_{36}$ is Gly, and
$AA_{37}$ is Cys.

In certain embodiments of the invention, amino acid substitutions of the CNP peptide are introduced in order to reduce the positive charges of the CNP peptide. For example Lys25 ($AA_{25}$) is substituted to Pro and Lys19 ($AA_{19}$) is substituted to Gln or Ser to remove positive charge.

In certain embodiments of the invention, $AA_{13}$ of the CNP peptide is Gln; $AA_{19}$ is Gln or Ser; $AA_{25}$ is Pro; and $AA_{32}$ is Leu.

In certain embodiments of the invention, $AA_5$ of the CNP peptide is Gln; $AA_{13}$ is Gln; $AA_{19}$ is Gln or Ser; $AA_{25}$ is Pro; and $AA_{32}$ is Leu.

In certain embodiments of the invention, the CNP peptide has any one of the following amino acid sequences:

```
                                              (SEQ ID NO: 136)
GAQKKGSSQGCFGLPLDRIGSLSGLGC, (SEQ ID NO: 77)
ARKYKGAQKKGLSQGCFGLPLDRIGSLSGLGC, (SEQ ID NO: 88)
YKGAQKKGGSQGCFGLPLDRIGSLSGLGC, (SEQ ID NO: 103)
YKGAQKKGLSQGCFGLPLDRIGSLSGLGC, (SEQ ID NO: 67)
QEHPQARKYKGAQKKGLSSGCFGLPLDRIGSLSGLGC,
and
                                              (SEQ ID NO: 104)
QEHPQARKYKGAQKKGLSSGCFGLPLERIGSLSGLGC.
```

Modifying Group

In one aspect of the invention, the CNP compound comprises a modifying group covalently attached to an amino acid residue of the CNP peptide.

In one aspect of the invention, the modifying group is capable of forming non-covalent associations with albumin and thereby promoting the circulation of the CNP compound in the blood stream, this having the effect of protracting plasma exposure and extending plasma half-life of the CNP compound compared to plasma half-life of CNP-22 (SEQ ID NO: 01) and CNP-37 (SEQ ID NO: 02). The modifying group having the effect of extending and protracting the time of action of the CNP compound, thus, may also be referred to as a protracting group.

In some embodiments of the invention, the modifying group is covalently attached to the N-terminal amino acid of the CNP peptide.

In some embodiments of the invention, the modifying group is covalently attached to the N-terminal alpha-amine of the CNP peptide.

In an aspect of the invention, the modifying group comprises Chem. A, Chem. B and Chem. C; wherein Chem. A is selected from the group consisting of:

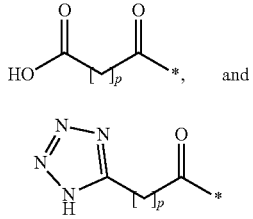
(Chem. A1)

and

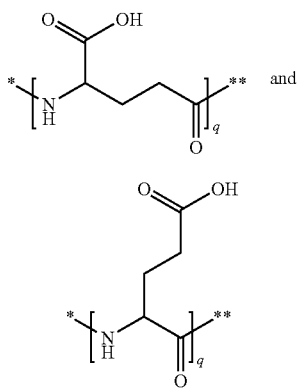
(Chem. A2)

wherein p is an integer in the range of 14-20, and
where * denotes an amide bond connecting Chem. A, and Chem. B; and
wherein Chem. B is selected from the group consisting of:

(Chem. B1)

(Chem. B2)

wherein q is an integer in the range of 1-8,
wherein * denotes an amide bond connecting Chem. A- and Chem. B-,
wherein ** denotes an amide bond connecting Chem. B- and Chem. C-; and Wherein Chem. C is selected from the group consisting of:

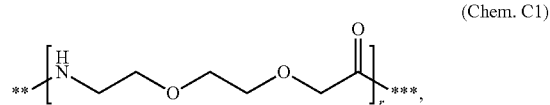
(Chem. C1)

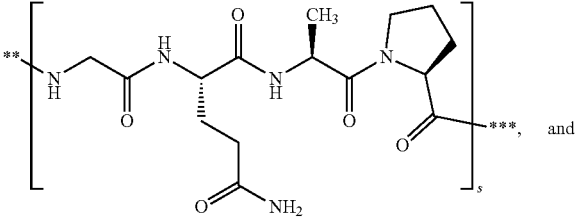
(Chem. C2)

and

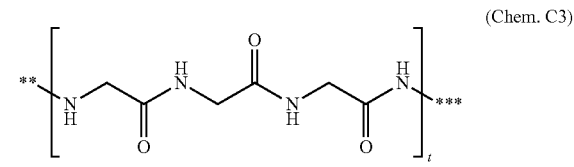
(Chem. C3)

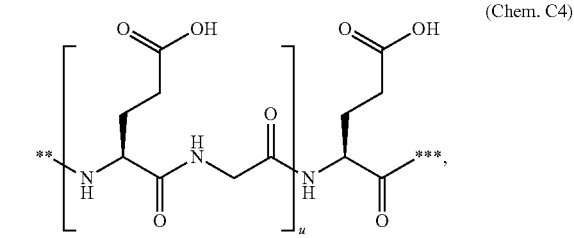
(Chem. C4)

wherein r is an integer in the range of 0-4,
wherein s is an integer in the range of 0-3,
wherein t is an integer in the range of 0-1,
wherein u is an integer in the range of 0-3,
wherein ** denotes an amide bond connecting Chem. B- and Chem. C-,
wherein *** denotes an amide bond connecting Chem. C- and the N-terminal alpha-amine on the CNP peptide.

Abbreviations for modifying group elements used in this application are presented below:

| Abbreviation | Chem. No | Chemical structure |
|---|---|---|
| OEG | Chem. C1 | 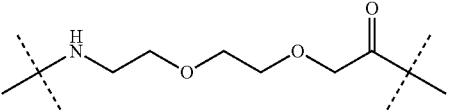 |
| GQAP | Chem. C2 | 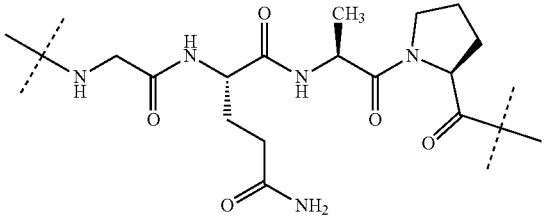 |

| Abbreviation | Chem. No | Chemical structure |
|---|---|---|
| GGG | Chem. C3 | 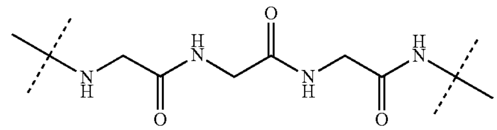 |
| gGlu, | Chem. B1 | 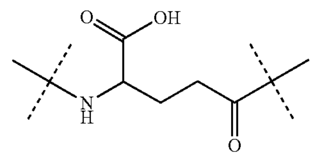 |
| Glu | Chem. B2 | 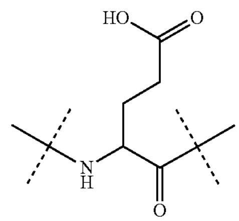 |
| C18d | Chem. A1 where p is equal to 16 | 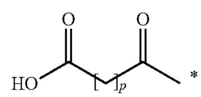 |
| C20d | Chem. A1 where p is equal to 18 | 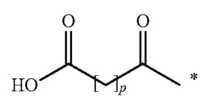 |
| Tetrazole-C18 | Chem. A2 where p is equal to 16 | 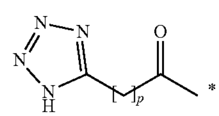 |

In some embodiments of the invention, the modifying group is selected from the following non-limiting examples: Chem. E, Chem. F, Chem. G, Chem. H, Chem. I, and Chem. J (in which the dotted line defines the attachment through an amide bond to the CNP peptide).

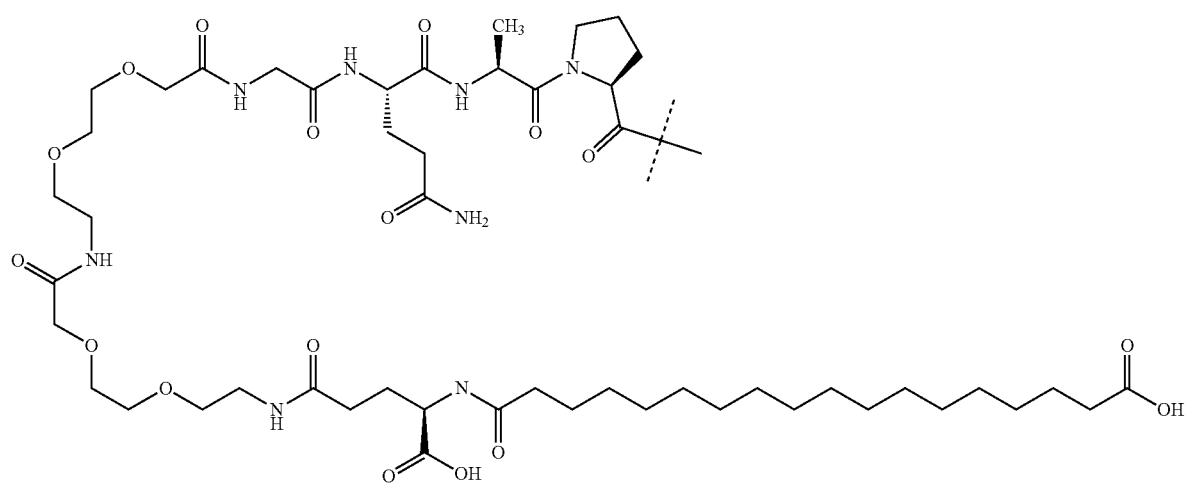

(Chem. E)

(Chem. F)
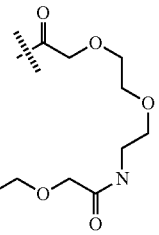
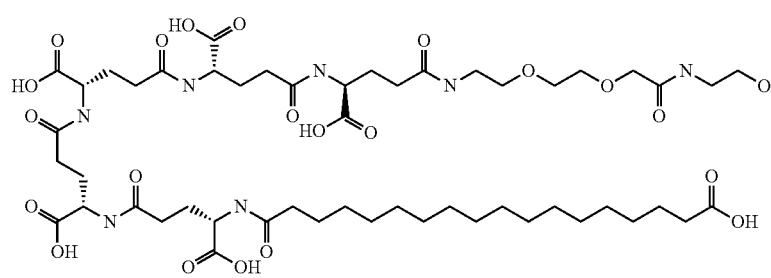
(Chem. G)
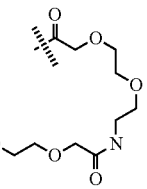
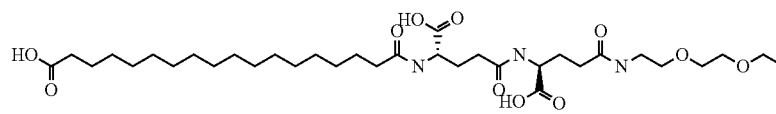
(Chem. H)
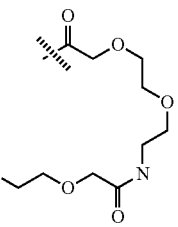
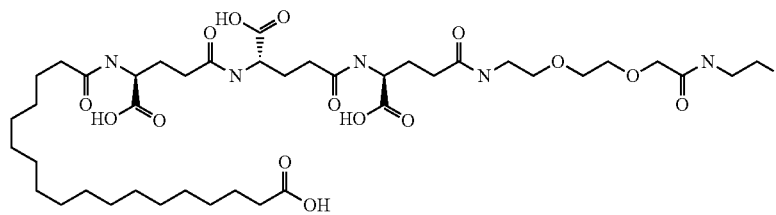
(Chem. I)
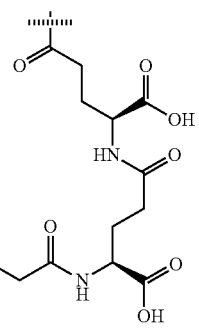
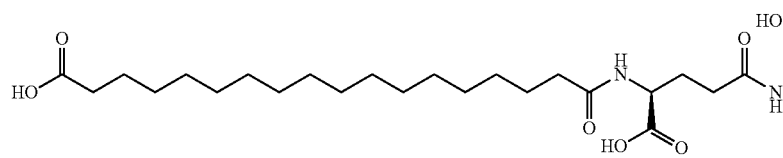

-continued

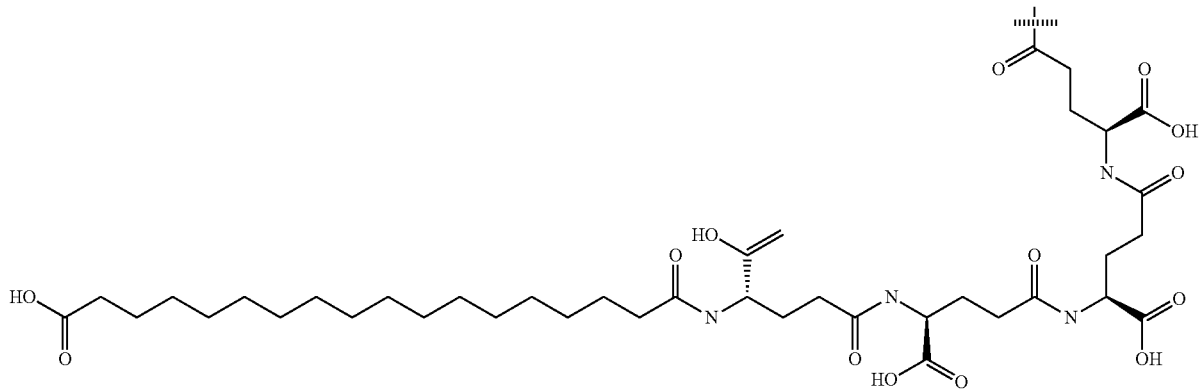
(Chem. J)

The modifying group of the invention may exist in different stereo-isomeric forms having the same molecular formula and sequence of bonded atoms, but differing only in the three-dimensional orientation of their atoms in space. The stereoisomerism of the exemplified modifying groups of the invention is indicated in the experimental section, in the names as well as the structures, using standard nomenclature. Unless otherwise stated the invention relates to all stereoisomeric forms of the claimed modifying groups.

Functional Properties

In some aspects of the invention, the CNP compounds have desirable biophysical properties. The CNP compounds exhibit extended in vivo half-life. Also, the CNP compounds of the invention have biological activity. Further, the compounds of the invention have desirable stability. Furthermore, the compounds of the invention have desirable solubility. Furthermore, the compounds of the invention can be dosed subcutaneously without eliciting an undesirable level of local tissue reaction like necrosis.

Biological Activity

In one aspect of the invention, the compounds have biological activity in vitro, which may be determined as their ability to activate the NPR2 receptor in vitro in a cell line expressing the NPR2 receptor which may be determined as their ability to increase the production and concentration of cGMP, representing receptor activation downstream of NPR2, in the cell. Biological activity in vitro may be determined e.g. as described in Example 2.

In one aspect of the invention, the compounds have biological activity in vivo, which may be determined as their ability to increase the concentration of cGMP in plasma after i.v. or s.c. administration in either rats or Göttingen minipigs or domestic LYD pigs.

The rat is one example of a suitable animal model, and the activity may be determined in such rats in vivo, as described in Example 11.

The Göttingen minipigs or domestic LYD pigs is other examples of a suitable animal models, and the activity may be determined in such pigs in vivo, as described in Example 12.

Plasma Half-Life

In one aspect of the invention, the CNP compounds have a protracted plasma exposure and have an extended in vivo plasma half-life relative to native CNP, which can be determined in a suitable pharmacokinetic in vivo study. Extended plasma exposure may be determined as plasma half-life (T½) after i.v. or s.c. administration to animals such as rats, Göttingen minipigs or domestic LYD pigs.

In some embodiments of the invention, the CNP compounds have a plasma half-life after i.v. administration to rat of at least 4 hours, more preferably at least 8 hours, or most preferably at least 10 hours, determined as described in Example 11.

In some embodiments of the invention, the CNP compounds have an in vivo plasma half-life after i.v. or s.c. administration to Göttingen minipigs of at least 10 hours, more preferably at least 40 hours, or most preferably at least 60 hours, determined as described in Example 12.

Bioavailability

In one aspect of the invention, the compounds have suitable bioavailability after subcutaneous injection. Bioavailability (F %) may be determined as is known in the art in any suitable animal model.

The Göttingen minipigs or domestic LYD pigs are examples of a suitable animal models, and the bioavailability may be determined in such Göttingen minipigs or domestic LYD pigs in vivo, as described in Example 12.

In some embodiments of the invention, the CNP compounds have a bioavailability after s.c. administration to Göttingen minipigs of at least 40%, 50%, 60% or 70%.

Stability

In one aspect of the invention the compounds have suitable physical and chemical stability. Lack of physical or chemical stability could lead to changes in the compound structure leading to formation of chemical degradation products potentially having a reduced biological activity, decreased solubility, and/or increased immunogenic effect as compared to the intact compound.

The physical stability can be evaluated by measuring the propensity for fibril formation, for example using a ThT assay as described in Example 6.

The chemical stability can be evaluated by measuring the amount of chemical degradation products (like isomers, isoAsp and hydrolysis products) at various time-points after exposure to different conditions like elevated temperature, e.g. as described in Example 8.

Stability could also be evaluated by looking into the molecules ability to form covalent dimers and multimers—referred to as HMWP, e.g. as described in Example 7.

Solubility

According to a functional aspect of the invention, the CNP compounds have desirable solubility. Low solubility of CNP may significantly hamper its pharmaceutical formulation properties and therapeutic use, so developing a CNP compound with high solubility in relevant formulations would improve the therapeutic utility.

As described herein, solubility is measured as described in Example 5. In certain embodiments, the CNP compounds of the invention have a solubility of at least at least 2000 µM, 3000 µM, or 4000 µM solubility at either pH 4 or pH 6.5.

Pharmaceutical Compositions

In one aspect the invention concerns a pharmaceutical composition comprising a compound according to the invention, and pharmaceutically acceptable excipients. The compositions are suited for parenteral administration.

In one embodiment the compound is present in the formulation at a concentration of from about 0.1 mg/ml to about 50 mg/ml. In another aspect, the compound is present in the formulation at a concentration of from about 10 mg/ml to about 30 mg/ml. In another embodiment, the formulation has a pH from 3.0 to 8.0. In another embodiment, the formulation has a pH from 3.5 to 5.5. In a further embodiment, the formulation has a pH from 6.0 to 7.0 Pharmaceutical compositions containing a compound according to the present invention may be prepared by conventional techniques, e.g. as described in Remington's *Pharmaceutical Sciences*, 1985 or in Remington: *The Science and Practice of Pharmacy*, 19$^{th}$ edition, 1995.

The formulation may further comprise a buffer system, preservative(s), isotonicity agent(s), chelating agent(s), stabilizers and/or surfactants. The use of such excipients in pharmaceutical compositions is well-known to the skilled person. For convenience reference is made to Remington: *The Science and Practice of Pharmacy*, 19$^{th}$ edition, 1995.

In one embodiment the pharmaceutical formulation is an aqueous formulation, i.e. formulation comprising water. Such formulation is typically a solution or a suspension. In a further embodiment of the invention the pharmaceutical formulation is an aqueous solution. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment the pharmaceutical formulation is a freeze-dried formulation, whereto the physician or the patient adds solvents and/or diluents prior to use. In another embodiment the pharmaceutical formulation is a dried formulation (e.g. freeze-dried or spray-dried) ready for use without any prior dissolution. By "dried form" is intended the liquid pharmaceutical composition or formulation is dried either by freeze drying (i.e., lyophilization; see, for example, Williams and Polli (1984) J. Parenteral Sci. Technol. 38:48-59), spray drying (see Masters (1991) in Spray-Drying Handbook (5$^{th}$ ed; Longman Scientific and Technical, Essez, U.K.), pp. 491-676; Broadhead et al. (1992) Drug Devel. Ind. Pharm. 18:1169-1206; and Mumenthaler et al. (1994) Pharm. Res. 11:12-20), or air drying (Carpenter and Crowe (1988) Cryobiology 25:459-470; and Roser (1991) Biopharm. 4:47-53).

In a further embodiment of the invention the buffer(s) are selected from the group consisting of acetate, carbonate, citrate, glycylglycine, histidine, glycine, lysine, arginine, dihydrogen phosphate, hydrogen phosphate, phosphate, and tris(hydroxymethyl)-aminomethan, bicine, tricine, malic acid, lactic acid, succinate, maleic acid, fumaric acid, tartaric acid, aspartic acid or mixtures thereof. Each one of these specific buffers constitutes an alternative embodiment of the invention.

In another embodiment of the invention the formulation further comprises a pharmaceutically acceptable preservative. In a further embodiment of the invention the formulation further comprises an isotonic agent, e.g. propylene glycol, mannitol or glycerol. In a further embodiment of the invention the formulation further comprises a chelating agent.

In another embodiment of the invention the formulation further comprises a stabilizer. The use of a stabilizer in pharmaceutical compositions is well-known to the skilled person. For convenience reference is made to Remington: *The Science and Practice of Pharmacy*, 19$^{th}$ edition, 1995.

The pharmaceutical compositions of the invention may further comprise an amount of an amino acid base sufficient to decrease aggregate formation by the peptide during storage of the composition.

By "amino acid base" is intended an amino acid or a combination of amino acids, where any given amino acid is present either in its free base form or in its salt form. Where a combination of amino acids is used, all of the amino acids may be present in their free base forms, all may be present in their salt forms, or some may be present in their free base forms while others are present in their salt forms. In one embodiment, amino acids used in preparing the compositions of the invention are those carrying a charged side chain, such as arginine, lysine, aspartic acid, and glutamic acid. Any stereoisomer (i.e., L, D, or a mixture thereof) of a particular amino acid (e.g. methionine, histidine, imidazole, arginine, lysine, isoleucine, aspartic acid, tryptophan, threonine and mixtures thereof) or combinations of these stereoisomers, may be present in the pharmaceutical compositions of the invention so long as the particular amino acid is present either in its free base form or its salt form. In one embodiment the L-stereoisomer is used. Compositions of the invention may also be formulated with derivatives of these amino acids. Suitable arginine derivatives include, for example, aminoguanidine, ornithine and N-monoethyl L-arginine, suitable methionine derivatives include ethionine and buthionine and suitable cysteine derivatives include S-methyl-L cysteine. As with the other amino acids, the amino acid derivatives are incorporated into the compositions in either their free base form or their salt form. In another embodiment of the invention the amino acids or amino acid derivatives thereof are used in a concentration, which is sufficient to prevent or delay aggregation of the protein.

In another embodiment of the invention the formulation further comprises a surfactant. In another embodiment of the invention the formulation further comprises protease inhibitors. The use of a protease inhibitor is particular useful in pharmaceutical compositions comprising zymogens of proteases in order to inhibit autocatalysis.

It is possible that other ingredients may be present in the pharmaceutical formulation of the present invention. Such additional ingredients may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical formulation of the present invention.

Pharmaceutical compositions according to the present invention may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen.

Administration of pharmaceutical compositions according to the invention may be through several routes of administration, for example, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Compositions of the current invention may be administered in several dosage forms, for example, as solutions, suspensions, emulsions, microemulsions, multiple emulsion, foams, salves, pastes, plasters, ointments, tablets, coated tablets, rinses, capsules, for example, hard gelatine capsules and soft gelatine capsules, suppositories, rectal capsules, drops, gels, sprays, powder, aerosols, inhalants, eye drops, ophthalmic ointments, ophthalmic rinses, vaginal pessaries, vaginal rings, vaginal ointments, injection solution, in situ transforming solutions, for example in situ gelling, in situ setting, in situ precipitating, in situ crystallization, infusion solution, and implants.

Compositions of the invention may further be compounded in, or attached to, for example through covalent, hydrophobic and electrostatic interactions, a drug carrier, drug delivery system and advanced drug delivery system in order to further enhance stability of the compound thereof increase bioavailability, increase solubility, decrease adverse effects, achieve chronotherapy well known to those skilled in the art, and increase patient compliance or any combination thereof.

Compositions of the current invention are useful in the formulation of solids, semisolids, powder and solutions for pulmonary administration of the CNP compound of the current invention, using, for example a metered dose inhaler, dry powder inhaler and a nebulizer, all being devices well known to those skilled in the art.

Compositions of the current invention are useful in the formulation of controlled, sustained, protracting, retarded, and slow-release drug delivery systems.

Parenteral administration may be performed by subcutaneous, intramuscular, intraperitoneal or intravenous injection by means of a syringe, optionally a pen-like syringe. Alternatively, parenteral administration can be performed by means of an infusion pump. A further option is a composition which may be a solution or suspension for the administration of the CNP compound of the current invention in the form of a nasal or pulmonal spray. As a still further option, the pharmaceutical compositions containing the peptide of the invention can also be adapted to transdermal administration, e.g. by needle-free injection or from a patch, optionally an iontophoretic patch, or transmucosal, e.g. buccal, administration.

The CNP compound of the current invention can be administered via the pulmonary route in a vehicle, as a solution, suspension or dry powder using any of known types of devices suitable for pulmonary drug delivery. Examples of these comprise of, but are not limited to, the three general types of aerosol-generating for pulmonary drug delivery, and may include jet or ultrasonic nebulizers, metered-dose inhalers, or dry powder inhalers (cf. Yu J, Chien Y W. Pulmonary drug delivery: Physiologic and mechanistic aspects. Crit Rev Ther Drug Carr Sys 14(4) (1997) 395-453).

In one embodiment of the invention the pharmaceutical formulation comprising the compound of the invention is stable for more than 6 weeks of usage and for more than 3 years of storage. In another embodiment of the invention the pharmaceutical formulation comprising the compound of the invention is stable for more than 2 weeks of usage and for more than two years of storage.

In one aspect a process for preparing a pharmaceutical composition comprising the compound according to the invention comprises mixing a compound according to the invention with at least one pharmaceutically acceptable excipient.

Medical Indications

The present invention also relates to a compound for use as a medicament.

The term "treatment", as used herein, refers to the medical treatment of any human subject in need thereof. The timing and purpose of said treatment may vary from one individual to another, according to the status of the subject's health. Said treatment may be prophylactic, palliative, symptomatic and/or curative.

In one aspect, the compound of the invention may be used for treatment of cardio-renal-metabolic diseases. Cardio-renal-metabolic diseases, include, but are not restricted to, the group consisting of hypertension, arteriosclerosis, atherosclerosis, restenosis, acute myocardial infarction, pulmonary hypertension, acute decompensated heart failure, congestive heart failure, cardiac edema, renal edema, hepatic edema*, acute renal insufficiency, chronic renal insufficiency, insulin resistance, and type 2 diabetes.

In one embodiment, the compound of the invention is used for treatment of congestive heart failure.

In one embodiment, the compound of the invention is used for treatment of acute decompensated heart failure.

In one aspect, the compound of the invention may be used for treatment of growth disorders including short stature that may relate to FGFR3-related skeletal dysplasia, and related comorbidities.

In some embodiments, the compound of the invention may be used in the treatment of a disease selected from the group consisting of achondroplasia, hypochondroplasia, thanatophoric dysplasia type 1 and type 2, SHOX deficiency, Noonan syndrome, Costello, LEOPARD syndrome, idiopathic short stature, autosomal dominant short stature, growth hormone deficiency, hypophosphatemic rickets, CNP deficiency, Aggrecan deficiency, Heterozygous NPR2 mutation, osteoarthritis, craniosynostosis, (e.g., Muenke syndrome, Crouzon syndrome, Apert syndrome, Jackson-Weiss syndrome, Pfeiffer syndrome, or Crouzonodermoskeletal syndrome), Lacrimo-Auriculo-Dento-Digital syndrome (LADD), Osteoglophonic dysplasia, and SADDAN (severe achondroplasia developmental delay acanthosis nigricans).

In some embodiments, the compound of the invention may be used in the treatment of a disease selected from the group consisting of osteogenesis imperfecta, achondrogenesis, chondrodysplasia punctata, homozygous achondroplasia, rhizomelic type of chondrodysplasia punctata, spondyloepiphyseal dysplasia congenita, congenital short femur, Langer-type mesomelic dysplasia, Neurofibromatosis, Legius syndrome and neurofibromatosis type 1.

In some embodiments, the compound of the invention may be used in the treatment of phenotypes related to growth disorders including short stature that may relate to FGFR3-related skeletal dysplasia, selected from the group consisting of growth retardation, skull deformities, orthodontic defects, cervical cord compression, spinal stenosis, pain in relation to skeletal dysplasia, hydrocephalus, hearing loss due to chronic otitis, cardiovascular disease, neurological disease, and obesity.

Unless otherwise indicated in the specification, terms presented in singular form also may include the plural situation.

List of Embodiments

The invention is further described by the following non-limiting embodiments:

Embodiment 1: a CNP compound comprising a CNP peptide and a modifying group wherein the net charge of the compound at physiological pH is 0 or negative, wherein the CNP peptide comprises an amino acid sequence according to Formula I:

$AA_{01}$-$AA_{02}$-$AA_{03}$-$AA_{04}$-$AA_{05}$-$AA_{06}$-$AA_{07}$-$AA_{08}$-
$AA_{09}$-$AA_{10}$-$AA_{11}$-$AA_{12}$-$AA_{13}$-$AA_{14}$-$AA_{15}$-
$AA_{16}$-$AA_{17}$-$AA_{18}$-$AA_{19}$-$AA_{20}$-$AA_{21}$-$AA_{22}$-
$AA_{23}$-$AA_{24}$-$AA_{25}$-$AA_{26}$-$AA_{27}$-$AA_{28}$-$AA_{29}$-
$AA_{30}$-$AA_{31}$-$AA_{32}$-$AA_{33}$-$AA_{34}$-$AA_{35}$-$AA_{36}$-
$AA_{37}$ wherein
- $AA_{01}$ is Gln or absent,
- $AA_{02}$ is Glu or absent,
- $AA_{03}$ is His or absent,
- $AA_{04}$ is Pro or absent,
- $AA_{05}$ is Asn or Gln or Glu or absent,
- $AA_{06}$ is Ala or absent,
- $AA_{07}$ is Arg or His or Ala or absent,
- $AA_{08}$ is Lys or Ser or His or absent,
- $AA_{09}$ is Tyr or Glu or absent
- $AA_{10}$ is Lys or Glu or Gln or His or absent,
- $AA_{11}$ is Gly,
- $AA_{12}$ is Ala,
- $AA_{13}$ is Gln or Asn or Glu,
- $AA_{14}$ is Lys or His or Glu,
- $AA_{15}$ is Lys Ser or Glu or Thr or His,
- $AA_{16}$ is Gly,
- $AA_{17}$ is Leu or Gly or Ser or Val,
- $AA_{18}$ is Ser or His
- $AA_{19}$ is Gln or Ser or Lys or His,
- $AA_{20}$ is Gly,
- $AA_{21}$ is Cys,
- $AA_{22}$ is Phe,
- $AA_{23}$ is Gly,
- $AA_{24}$ is Leu,
- $AA_{25}$ is Pro or Lys,
- $AA_{26}$ is Leu,
- $AA_{27}$ is Asp or Glu,
- $AA_{28}$ is Arg,
- $AA_{29}$ is Ile,
- $AA_{30}$ is Gly,
- $AA_{31}$ is Ser,
- $AA_{32}$ is Leu or Nle or Met,
- $AA_{33}$ is Ser,
- $AA_{34}$ is Gly,
- $AA_{35}$ is Leu,
- $AA_{36}$ is Gly, and
- $AA_{37}$ is Cys;

wherein the modifying group comprises Chem. A, Chem. B and Chem. C; wherein Chem. A is selected from the group consisting of:

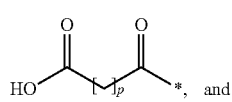

(Chem. A1)

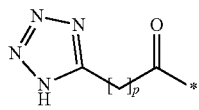

(Chem. A2)

herein p is an integer in the range of 14-20, and
where * denotes an amide bond connecting Chem. A and Chem. B; and wherein Chem. B is selected from the group consisting of: Chem. B1 and Chem. B2

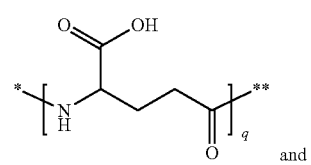

(Chem. B1)

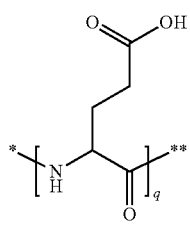

(Chem. B2)

wherein q is an integer in the range of 1-8,
wherein * denotes an amide bond connecting Chem. A- and Chem. B-,
wherein ** denotes an amide bond connecting Chem. B- and Chem. C-; and Wherein Chem. C is selected from the group consisting of:

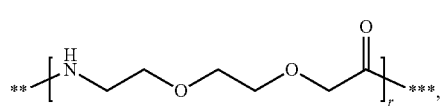

(Chem. C1)

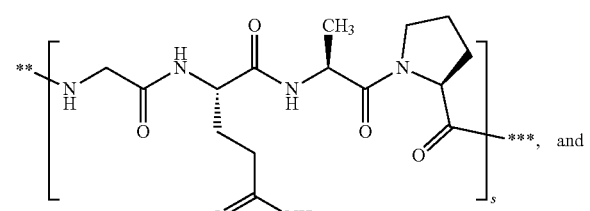

(Chem. C2)

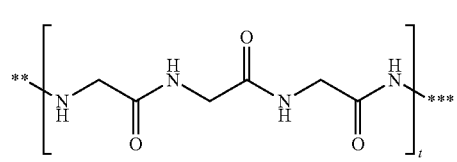

(Chem. C3)

wherein r is an integer in the range of 0-4,
wherein s is an integer in the range of 0-3,
wherein t is an integer in the range of 0-1, wherein
 denotes an amide bond connecting Chem. B- and Chem. C-, wherein * denotes an amide bond connecting Chem. C- and the N-terminal alpha-amine on the CNP peptide.

Embodiment 2: the CNP compound according to embodiment 1, wherein $AA_{13}$ of the CNP peptide is Gln; $AA_{19}$ is Gln or Ser; $AA_{25}$ is Pro; and $AA_{32}$ is Leu.

Embodiment 3: the CNP compound according to embodiment 1, wherein $AA_5$ of the CNP peptide is Gln; $AA_{13}$ is Gln; $AA_{19}$ is Gln or Ser; $AA_{25}$ is Pro; and $AA_{32}$ is Leu.

Embodiment 4: the CNP compound according to embodiment 1, wherein the CNP peptide comprises one of the following amino acid sequences:

```
YKGANKKGLSKGCFGLKLDRIGSXSGLGC              SEQ ID NO: 6

NARKYKGANKSGLSSGCFGLKLDRIGSXSGLGC          SEQ ID NO: 7

GANKKGLSKGCFGLKLDRIGSXSGLGC                SEQ ID NO: 8

GAQKKGLSKGCFGLKLDRIGSXSGLGC                SEQ ID NO: 9

YEGAQKKGLSKGCFGLKLDRIGSLSGLGC              SEQ ID NO: 10

EEGAQKKGLSKGCFGLKLDRIGSLSGLGC              SEQ ID NO: 11

YEGAQEKGLSKGCFGLKLDRIGSLSGLGC              SEQ ID NO: 12

YEGAQKKGLSSGCFGLKLDRIGSLSGLGC              SEQ ID NO: 13

YEGAQKKGLSKGCFGLPLDRIGSLSGLGC              SEQ ID NO: 14

YEGAQEKGLSKGCFGLPLDRIGSLSGLGC              SEQ ID NO: 15

YEGAQKKGLSSGCFGLPLDRIGSLSGLGC              SEQ ID NO: 16

YEGAQEKGLSSGCFGLPLDRIGSLSGLGC              SEQ ID NO: 17

EKGAQEKGLSKGCFGLKLDRIGSLSGLGC              SEQ ID NO: 18

EKGAQEKGLSSGCFGLKLDRIGSLSGLGC              SEQ ID NO: 19

EQGAQEKGLSKGCFGLKLDRIGSLSGLGC              SEQ ID NO: 20

YKGAQEKGLSKGCFGLKLDRIGSLSGLGC              SEQ ID NO: 21

YKGAQKKGLSSGCFGLPLDRIGSLSGLGC              SEQ ID NO: 22

EHGAQEKGLSKGCFGLKLDRIGSLSGLGC              SEQ ID NO: 23

YHGAQEKGLSKGCFGLKLDRIGSLSGLGC              SEQ ID NO: 24

YHGAQEKGLSKGCFGLPLDRIGSLSGLGC              SEQ ID NO: 25

YHGAQKKGLSSGCFGLPLDRIGSLSGLGC              SEQ ID NO: 26

YHGAQEKGLSSGCFGLPLDRIGSLSGLGC              SEQ ID NO: 27

YEGAEKKGLSQGCFGLPLDRIGSLSGLGC              SEQ ID NO: 28

EGAQEKGLSSGCFGLPLDRIGSLSGLGC               SEQ ID NO: 29

EGAQKEGLSSGCFGLPLDRIGSLSGLGC               SEQ ID NO: 30

YEGAQKEGLSSGCFGLPLDRIGSLSGLGC              SEQ ID NO: 31

YHGAQKTGLSSGCFGLPLDRIGSLSGLGC              SEQ ID NO: 32

YHGAQKTGVSSGCFGLPLDRIGSLSGLGC              SEQ ID NO: 33

YHGAQHTGLSSGCFGLPLDRIGSLSGLGC              SEQ ID NO: 34

YKGAQHTGLSSGCFGLPLDRIGSLSGLGC              SEQ ID NO: 35

EHGAQKKGLSKGCFGLPLDRIGSLSGLGC              SEQ ID NO: 36

EHGAQKKGLSSGCFGLPLDRIGSLSGLGC              SEQ ID NO: 37

EHGAQKKGVSSGCFGLPLDRIGSLSGLGC              SEQ ID NO: 38

EHGAQKTGVSSGCFGLPLDRIGSLSGLGC              SEQ ID NO: 39

YHGAQHHGLSKGCFGLKLERIGSLSGLGC              SEQ ID NO: 40

YKGAQHHGLSQGCFGLKLERIGSLSGLGC              SEQ ID NO: 41

YEGAQKKGLSSGCFGLPLERIGSLSGLGC              SEQ ID NO: 42

EGAQKKGLSSGCFGLPLDRIGSLSGLGC               SEQ ID NO: 43

YKGAQHHGLSQGCFGLKLDRIGSLSGLGC              SEQ ID NO: 44

YKGAQHHGLSQGCFGLPLDRIGSLSGLGC              SEQ ID NO: 45

YHGAQHHGLSKGCFGLKLDRIGSLSGLGC              SEQ ID NO: 46

YHGAQHHGLSKGCFGLPLDRIGSLSGLGC              SEQ ID NO: 47

GAQKKGLSHGCFGLPLDRIGSLSGLGC                SEQ ID NO: 48

GAQKKGLHSGCFGLPLDRIGSLSGLGC                SEQ ID NO: 49

ARKYHGAQHTGLSSGCFGLPLDRIGSLSGLGC           SEQ ID NO: 50

ARKYHGAQHTGVSSGCFGLPLDRIGSLSGLGC           SEQ ID NO: 51

ARKYHGAQKTGVSSGCFGLPLDRIGSLSGLGC           SEQ ID NO: 52

ARKEHGAQKTGVSSGCFGLPLDRIGSLSGLGC           SEQ ID NO: 53

ARKEHGAQHTGVSSGCFGLPLDRIGSLSGLGC           SEQ ID NO: 54
```

```
YEGAQKKGGSKGCFGLPLDRIGSLSGLGC                    SEQ ID NO: 55

QEHPQARSYEGAQKKGLSSGCFGLPLDRIGSLSGLGC            SEQ ID NO: 57

QEHPEARSYEGAQKKGLSSGCFGLPLDRIGSLSGLGC            SEQ ID NO: 58

QEHPQAHKYHGAQHHGSSQGCFGLPLDRIGSLSGLGC            SEQ ID NO: 59

QEHPQAHKYKGAQKKGLSQGCFGLPLDRIGSLSGLGC            SEQ ID NO: 60

QEHPQAHKYHGAQKHGSSQGCFGLPLDRIGSLSGLGC            SEQ ID NO: 61

ARKYEGAQKKGLSKGCFGLPLDRIGSLSGLGC                 SEQ ID NO: 63

ARKYKGAQKKGLSSGCFGLPLDRIGSLSGLGC                 SEQ ID NO: 64

QEHPQARKYKGAQKKGLSSGCFGLPLDRIGSLSGLGC            SEQ ID NO: 67

QEHPQARKYEGAQKKGLSSGCFGLPLDRIGSLSGLGC            SEQ ID NO: 68

YEGAQKKGLSQGCFGLPLDRIGSLSGLGC                    SEQ ID NO: 69

QEHPQARKYEGAQKKGLSQGCFGLPLDRIGSLSGLGC            SEQ ID NO: 70

QEHPQAAKYEGAQKKGLSQGCFGLPLDRIGSLSGLGC            SEQ ID NO: 71

QEHPQARHYKGAQKKGSSQGCFGLPLDRIGSLSGLGC            SEQ ID NO: 72

QEHPQAHKYKGAQKKGGSQGCFGLPLDRIGSLSGLGC            SEQ ID NO: 73

QEHPQARKYKGAQKKGLSKGCFGLKLDRIGSLSGLGC            SEQ ID NO: 74

QEHPQARKYKGAQKKGLSQGCFGLPLDRIGSLSGLGC            SEQ ID NO: 75

QEHPQARKYKGAQKKGGSQGCFGLPLDRIGSLSGLGC            SEQ ID NO: 76

ARKYKGAQKKGLSQGCFGLPLDRIGSLSGLGC                 SEQ ID NO: 77

ARKYHGAQHTGVSKGCFGLPLDRIGSLSGLGC                 SEQ ID NO: 78

ARKYKGAQKTGVSSGCFGLPLDRIGSLSGLGC                 SEQ ID NO: 79

ARKYHGAQKKGVSSGCFGLPLDRIGSLSGLGC                 SEQ ID NO: 80

ARKYHGAQKTGVSKGCFGLPLDRIGSLSGLGC                 SEQ ID NO: 81

ARKYKGAQKTGVSKGCFGLPLDRIGSLSGLGC                 SEQ ID NO: 82

YHGAQKTGVSKGCFGLPLDRIGSLSGLGC                    SEQ ID NO: 83

ARKYHGAQKSGLSQGCFGLPLDRIGSLSGLGC                 SEQ ID NO: 84

YEGAQKKGGSHGCFGLPLDRIGSLSGLGC                    SEQ ID NO: 85

ARKYEGAQHKGGSQGCFGLPLDRIGSLSGLGC                 SEQ ID NO: 86

YHGAQKKGGSQGCFGLPLDRIGSLSGLGC                    SEQ ID NO: 87

YKGAQKKGGSQGCFGLPLDRIGSLSGLGC                    SEQ ID NO: 88

YKGAQKKGVSQGCFGLPLDRIGSLSGLGC                    SEQ ID NO: 89

YHGAQKKGVSQGCFGLPLDRIGSLSGLGC                    SEQ ID NO: 90

QEHPQARKYEGAQKKGLSKGCFGLPLDRIGSLSGLGC            SEQ ID NO: 91

ARKYHGAQKKGVSSGCFGLPLERIGSLSGLGC                 SEQ ID NO: 92

ARKYKGAQKKGLSKGCFGLPLDRIGSLSGLGC                 SEQ ID NO: 96

YHGAQKKGLSQGCFGLPLDRIGSLSGLGC                    SEQ ID NO: 97

ARKYKGAQKKGLSQGCFGLKLDRIGSLSGLGC                 SEQ ID NO: 98

ARKYKGANKKGLSQGCFGLPLDRIGSLSGLGC                 SEQ ID NO: 99

ARKYKGAQKKGLSQGCFGLPLDRIGSMSGLGC                 SEQ ID NO: 100

QEHPQARKYKGAQKKGLSKGCFGLPLDRIGSLSGLGC            SEQ ID NO: 101

ARKYKGAQKKGLSQGCFGLPLERIGSLSGLGC                 SEQ ID NO: 102

YKGAQKKGLSQGCFGLPLDRIGSLSGLGC                    SEQ ID NO: 103

QEHPQARKYKGAQKKGLSSGCFGLPLERIGSLSGLGC            SEQ ID NO: 104

YKGAQKKGGSQGCFGLPLERIGSLSGLGC                    SEQ ID NO: 108

YKGAQKKGLSQGCFGLPLERIGSLSGLGC                    SEQ ID NO: 109

GAQKKGLSQGCFGLPLDRIGSLSGLGC                      SEQ ID NO: 112

GAQKKGLSSGCFGLPLDRIGSLSGLGC                      SEQ ID NO: 113

GAQKKGGSQGCFGLPLDRIGSLSGLGC                      SEQ ID NO: 114

GAQKKGGSSGCFGLPLDRIGSLSGLGC                      SEQ ID NO: 115

GAQKKGLSQGCFGLKLDRIGSLSGLGC                      SEQ ID NO: 116

GAQKKGLSSGCFGLKLDRIGSLSGLGC                      SEQ ID NO: 117

GAQKKGGSQGCFGLKLDRIGSLSGLGC                      SEQ ID NO: 118

GAQKKGGSSGCFGLKLDRIGSLSGLGC                      SEQ ID NO: 119

GANKKGLSQGCFGLPLDRIGSLSGLGC                      SEQ ID NO: 120
```

-continued

GANKKGLSSGCFGLPLDRIGSLSGLGC SEQ ID NO: 121

GANKKGGSQGCFGLPLDRIGSLSGLGC SEQ ID NO: 122

GANKKGGSSGCFGLPLDRIGSLSGLGC SEQ ID NO: 123

GAQKKGLSQGCFGLPLDRIGSMSGLGC SEQ ID NO: 124

GAQKKGLSSGCFGLPLDRIGSMSGLGC SEQ ID NO: 125

GAQKKGGSQGCFGLPLDRIGSMSGLGC SEQ ID NO: 126

GAQKKGGSSGCFGLPLDRIGSMSGLGC SEQ ID NO: 127

GAQKKGLSKGCFGLPLDRIGSLSGLGC SEQ ID NO: 128

GAQKKGGSKGCFGLPLDRIGSLSGLGC SEQ ID NO: 129

GAQKKGLSQGCFGLPLERIGSLSGLGC SEQ ID NO: 130

GAQKKGLSSGCFGLPLERIGSLSGLGC SEQ ID NO: 131

GANKKGLSQGCFGLPLDRIGSMSGLGC SEQ ID NO: 132

GANKKGLSSGCFGLPLDRIGSMSGLGC SEQ ID NO: 133

GANKKGLSQGCFGLPLERIGSMSGLGC SEQ ID NO: 134

GANKKGLSSGCFGLPLERIGSMSGLGC SEQ ID NO: 135

GAQKKGSSQGCFGLPLDRIGSLSGLGC SEQ ID NO: 136

GAQKKGSSSGCFGLPLDRIGSLSGLGC SEQ ID NO: 137

GAQKKGSSQGCFGLKLDRIGSLSGLGC SEQ ID NO: 138

GAQKKGSSSGCFGLKLDRIGSLSGLGC SEQ ID NO: 139

GANKKGSSQGCFGLPLDRIGSLSGLGC SEQ ID NO: 140

GANKKGSSSGCFGLPLDRIGSLSGLGC SEQ ID NO: 141

GAQKKGSSQGCFGLPLDRIGSMSGLGC SEQ ID NO: 142

GAQKKGSSSGCFGLPLDRIGSMSGLGC SEQ ID NO: 143

GAQKKGSSKGCFGLPLDRIGSLSGLGC SEQ ID NO: 144

YKGAQKKGGSSGCFGLPLDRIGSLSGLGC SEQ ID NO: 145

YKGAQKKGLSQGCFGLKLDRIGSLSGLGC SEQ ID NO: 146

YKGAQKKGLSSGCFGLKLDRIGSLSGLGC SEQ ID NO: 147

YKGAQKKGGSQGCFGLKLDRIGSLSGLGC SEQ ID NO: 148

YKGAQKKGGSSGCFGLKLDRIGSLSGLGC SEQ ID NO: 149

YKGANKKGLSQGCFGLPLDRIGSLSGLGC SEQ ID NO: 150

YKGANKKGLSSGCFGLPLDRIGSLSGLGC SEQ ID NO: 151

YKGANKKGGSQGCFGLPLDRIGSLSGLGC SEQ ID NO: 152

YKGANKKGGSSGCFGLPLDRIGSLSGLGC SEQ ID NO: 153

YKGAQKKGLSQGCFGLPLDRIGSMSGLGC SEQ ID NO: 154

YKGAQKKGLSSGCFGLPLDRIGSMSGLGC SEQ ID NO: 155

YKGAQKKGGSQGCFGLPLDRIGSMSGLGC SEQ ID NO: 156

YKGAQKKGGSSGCFGLPLDRIGSMSGLGC SEQ ID NO: 157

YKGAQKKGLSKGCFGLPLDRIGSLSGLGC SEQ ID NO: 158

YKGAQKKGGSKGCFGLPLDRIGSLSGLGC SEQ ID NO: 159

YKGAQKKGLSQGCFGLPLERIGSLSGLGC SEQ ID NO: 160

YKGAQKKGLSSGCFGLPLERIGSLSGLGC SEQ ID NO: 161

YKGANKKGLSQGCFGLPLDRIGSMSGLGC SEQ ID NO: 162

YKGANKKGLSSGCFGLPLDRIGSMSGLGC SEQ ID NO: 163

YKGANKKGLSQGCFGLPLERIGSMSGLGC SEQ ID NO: 164

YKGANKKGLSSGCFGLPLERIGSMSGLGC SEQ ID NO: 165

YKGAQKKGSSQGCFGLPLDRIGSLSGLGC SEQ ID NO: 166

YKGAQKKGSSSGCFGLPLDRIGSLSGLGC SEQ ID NO: 167

YKGAQKKGSSQGCFGLKLDRIGSLSGLGC SEQ ID NO: 168

YKGAQKKGSSSGCFGLKLDRIGSLSGLGC SEQ ID NO: 169

YKGANKKGSSQGCFGLPLDRIGSLSGLGC SEQ ID NO: 170

YKGANKKGSSSGCFGLPLDRIGSLSGLGC SEQ ID NO: 171

YKGAQKKGSSQGCFGLPLDRIGSMSGLGC SEQ ID NO: 172

YKGAQKKGSSSGCFGLPLDRIGSMSGLGC SEQ ID NO: 173

YKGAQKKGSSKGCFGLPLDRIGSLSGLGC SEQ ID NO: 174

```
                                        SEQ ID NO: 175
ARKYKGAQKKGGSQGCFGLPLDRIGSLSGLGC

SEQ ID NO: 176
ARKYKGAQKKGGSSGCFGLPLDRIGSLSGLGC

SEQ ID NO: 177
ARKYKGAQKKGLSSGCFGLKLDRIGSLSGLGC

SEQ ID NO: 178
ARKYKGAQKKGGSQGCFGLKLDRIGSLSGLGC

SEQ ID NO: 179
ARKYKGAQKKGGSSGCFGLKLDRIGSLSGLGC

SEQ ID NO: 180
ARKYKGANKKGLSQGCFGLPLDRIGSLSGLGC

SEQ ID NO: 181
ARKYKGANKKGLSSGCFGLPLDRIGSLSGLGC

SEQ ID NO: 182
ARKYKGANKKGGSQGCFGLPLDRIGSLSGLGC

SEQ ID NO: 183
ARKYKGANKKGGSSGCFGLPLDRIGSLSGLGC

SEQ ID NO: 184
ARKYKGAQKKGLSQGCFGLPLDRIGSMSGLGC

SEQ ID NO: 185
ARKYKGAQKKGLSSGCFGLPLDRIGSMSGLGC

SEQ ID NO: 186
ARKYKGAQKKGGSQGCFGLPLDRIGSMSGLGC

SEQ ID NO: 187
ARKYKGAQKKGGSSGCFGLPLDRIGSMSGLGC

SEQ ID NO: 188
ARKYKGAQKKGGSKGCFGLPLDRIGSLSGLGC

SEQ ID NO: 189
ARKYKGAQKKGLSQGCFGLPLERIGSLSGLGC

SEQ ID NO: 190
ARKYKGAQKKGLSSGCFGLPLERIGSLSGLGC

SEQ ID NO: 191
ARKYKGANKKGLSQGCFGLPLDRIGSMSGLGC

SEQ ID NO: 192
ARKYKGANKKGLSSGCFGLPLDRIGSMSGLGC

SEQ ID NO: 193
ARKYKGANKKGLSQGCFGLPLERIGSMSGLGC

SEQ ID NO: 194
ARKYKGANKKGLSSGCFGLPLERIGSMSGLGC

SEQ ID NO: 195
ARKYKGAQKKGSSQGCFGLPLDRIGSLSGLGC

SEQ ID NO: 196
ARKYKGAQKKGSSSGCFGLPLDRIGSLSGLGC

SEQ ID NO: 197
ARKYKGAQKKGSSQGCFGLPLDRIGSLSGLGC

SEQ ID NO: 198
ARKYKGAQKKGSSSGCFGLKLDRIGSLSGLGC

SEQ ID NO: 199
ARKYKGANKKGSSQGCFGLPLDRIGSLSGLGC

SEQ ID NO: 200
ARKYKGANKKGSSSGCFGLPLDRIGSLSGLGC

SEQ ID NO: 201
ARKYKGAQKKGSSQGCFGLPLDRIGSMSGLGC

SEQ ID NO: 202
ARKYKGAQKKGSSSGCFGLPLDRIGSMSGLGC

SEQ ID NO: 203
ARKYKGAQKKGSSKGCFGLPLDRIGSLSGLGC

SEQ ID NO: 232
GAQKKGSSQGCFGLPLERIGSLSGLGC
```

Embodiment 5: the CNP compound according to embodiment 1, wherein the CNP peptide has any one of the following amino acid sequences:

```
                                        SEQ ID NO: 6
YKGANKKGLSKGCFGLKLDRIGSXSGLGC

SEQ ID NO: 7
NARKYKGANKSGLSSGCFGLKLDRIGSXSGLGC

SEQ ID NO: 8
GANKKGLSKGCFGLKLDRIGSXSGLGC

SEQ ID NO: 9
GAQKKGLSKGCFGLKLDRIGSXSGLGC

SEQ ID NO: 10
YEGAQKKGLSKGCFGLKLDRIGSLSGLGC

SEQ ID NO: 11
EEGAQKKGLSKGCFGLKLDRIGSLSGLGC

SEQ ID NO: 12
YEGAQEKGLSKGCFGLKLDRIGSLSGLGC

SEQ ID NO: 13
YEGAQKKGLSSGCFGLKLDRIGSLSGLGC

SEQ ID NO: 14
YEGAQKKGLSKGCFGLPLDRIGSLSGLGC

SEQ ID NO: 15
YEGAQEKGLSKGCFGLPLDRIGSLSGLGC

SEQ ID NO: 16
YEGAQKKGLSSGCFGLPLDRIGSLSGLGC

SEQ ID NO: 17
YEGAQEKGLSSGCFGLPLDRIGSLSGLGC

SEQ ID NO: 18
EKGAQEKGLSKGCFGLKLDRIGSLSGLGC

SEQ ID NO: 19
EKGAQEKGLSSGCFGLKLDRIGSLSGLGC

SEQ ID NO: 20
EQGAQEKGLSKGCFGLKLDRIGSLSGLGC

SEQ ID NO: 21
YKGAQEKGLSKGCFGLKLDRIGSLSGLGC

SEQ ID NO: 22
YKGAQKKGLSSGCFGLPLDRIGSLSGLGC

SEQ ID NO: 23
EHGAQEKGLSKGCFGLKLDRIGSLSGLGC

SEQ ID NO: 24
YHGAQEKGLSKGCFGLKLDRIGSLSGLGC

SEQ ID NO: 25
YHGAQEKGLSKGCFGLPLDRIGSLSGLGC

SEQ ID NO: 26
YHGAQKKGLSSGCFGLPLDRIGSLSGLGC

SEQ ID NO: 27
YHGAQEKGLSSGCFGLPLDRIGSLSGLGC
```

```
                                                        SEQ ID NO: 28
YEGAEKKGLSQGCFGLPLDRIGSLSGLGC

SEQ ID NO: 29
EGAQEKGLSSGCFGLPLDRIGSLSGLGC

SEQ ID NO: 30
EGAQKEGLSSGCFGLPLDRIGSLSGLGC

SEQ ID NO: 31
YEGAQKEGLSSGCFGLPLDRIGSLSGLGC

SEQ ID NO: 32
YHGAQKTGLSSGCFGLPLDRIGSLSGLGC

SEQ ID NO: 33
YHGAQKTGVSSGCFGLPLDRIGSLSGLGC

SEQ ID NO: 34
YHGAQHTGLSSGCFGLPLDRIGSLSGLGC

SEQ ID NO: 35
YKGAQHTGLSSGCFGLPLDRIGSLSGLGC

SEQ ID NO: 36
EHGAQKKGLSKGCFGLPLDRIGSLSGLGC

SEQ ID NO: 37
EHGAQKKGLSSGCFGLPLDRIGSLSGLGC

SEQ ID NO: 38
EHGAQKKGVSSGCFGLPLDRIGSLSGLGC

SEQ ID NO: 39
EHGAQKTGVSSGCFGLPLDRIGSLSGLGC

SEQ ID NO: 40
YHGAQHHGLSKGCFGLKLERIGSLSGLGC

SEQ ID NO: 41
YKGAQHHGLSQGCFGLKLERIGSLSGLGC

SEQ ID NO: 42
YEGAQKKGLSSGCFGLPLERIGSLSGLGC

SEQ ID NO: 43
EGAQKKGLSSGCFGLPLDRIGSLSGLGC

SEQ ID NO: 44
YKGAQHHGLSQGCFGLKLDRIGSLSGLGC

SEQ ID NO: 45
YKGAQHHGLSQGCFGLPLDRIGSLSGLGC

SEQ ID NO: 46
YHGAQHHGLSKGCFGLKLDRIGSLSGLGC

SEQ ID NO: 47
YHGAQHHGLSKGCFGLPLDRIGSLSGLGC

SEQ ID NO: 48
GAQKKGLSHGCFGLPLDRIGSLSGLGC

SEQ ID NO: 49
GAQKKGLHSGCFGLPLDRIGSLSGLGC

SEQ ID NO: 50
ARKYHGAQHTGLSSGCFGLPLDRIGSLSGLGC

SEQ ID NO: 51
ARKYHGAQHTGVSSGCFGLPLDRIGSLSGLGC

SEQ ID NO: 52
ARKYHGAQKTGVSSGCFGLPLDRIGSLSGLGC

SEQ ID NO: 53
ARKEHGAQKTGVSSGCFGLPLDRIGSLSGLGC

SEQ ID NO: 54
ARKEHGAQHTGVSSGCFGLPLDRIGSLSGLGC

SEQ ID NO: 55
YEGAQKKGGSKGCFGLPLDRIGSLSGLGC

SEQ ID NO: 57
QEHPQARSYEGAQKKGLSSGCFGLPLDRIGSLSGLGC

SEQ ID NO: 58
QEHPEARSYEGAQKKGLSSGCFGLPLDRIGSLSGLGC

SEQ ID NO: 59
QEHPQAHKYHGAQHHGSSQGCFGLPLDRIGSLSGLGC

SEQ ID NO: 60
QEHPQAHKYKGAQKKGLSQGCFGLPLDRIGSLSGLGC

SEQ ID NO: 61
QEHPQAHKYHGAQKHGSSQGCFGLPLDRIGSLSGLGC

SEQ ID NO: 63
ARKYEGAQKKGLSKGCFGLPLDRIGSLSGLGC

SEQ ID NO: 64
ARKYKGAQKKGLSSGCFGLPLDRIGSLSGLGC

SEQ ID NO: 67
QEHPQARKYKGAQKKGLSSGCFGLPLDRIGSLSGLGC

SEQ ID NO: 68
QEHPQARKYEGAQKKGLSSGCFGLPLDRIGSLSGLGC

SEQ ID NO: 69
YEGAQKKGLSQGCFGLPLDRIGSLSGLGC

SEQ ID NO: 70
QEHPQARKYEGAQKKGLSQGCFGLPLDRIGSLSGLGC

SEQ ID NO: 71
QEHPQAAKYEGAQKKGLSQGCFGLPLDRIGSLSGLGC

SEQ ID NO: 72
QEHPQARHYKGAQKKGSSQGCFGLPLDRIGSLSGLGC

SEQ ID NO: 73
QEHPQAHKYKGAQKKGGSQGCFGLPLDRIGSLSGLGC

SEQ ID NO: 74
QEHPQARKYKGAQKKGLSKGCFGLKLDRIGSLSGLGC

SEQ ID NO: 75
QEHPQARKYKGAQKKGLSQGCFGLPLDRIGSLSGLGC

SEQ ID NO: 76
QEHPQARKYKGAQKKGGSQGCFGLPLDRIGSLSGLGC

SEQ ID NO: 77
ARKYKGAQKKGLSQGCFGLPLDRIGSLSGLGC

SEQ ID NO: 78
ARKYHGAQHTGVSKGCFGLPLDRIGSLSGLGC

SEQ ID NO: 79
ARKYKGAQKTGVSSGCFGLPLDRIGSLSGLGC

SEQ ID NO: 80
ARKYHGAQKKGVSSGCFGLPLDRIGSLSGLGC

SEQ ID NO: 81
ARKYHGAQKTGVSKGCFGLPLDRIGSLSGLGC

SEQ ID NO: 82
ARKYKGAQKTGVSKGCFGLPLDRIGSLSGLGC

SEQ ID NO: 83
YHGAQKTGVSKGCFGLPLDRIGSLSGLGC

SEQ ID NO: 84
ARKYHGAQKSGLSQGCFGLPLDRIGSLSGLGC

SEQ ID NO: 85
YEGAQKKGGSHGCFGLPLDRIGSLSGLGC
```

-continued

ARKYEGAQHKGGSQGCFGLPLDRIGSLSGLGC SEQ ID NO: 86

YHGAQKKGGSQGCFGLPLDRIGSLSGLGC SEQ ID NO: 87

YKGAQKKGGSQGCFGLPLDRIGSLSGLGC SEQ ID NO: 88

YKGAQKKGVSQGCFGLPLDRIGSLSGLGC SEQ ID NO: 89

YHGAQKKGVSQGCFGLPLDRIGSLSGLGC SEQ ID NO: 90

QEHPQARKYEGAQKKGLSKGCFGLPLDRIGSLSGLGC SEQ ID NO: 91

ARKYHGAQKKGVSSGCFGLPLERIGSLSGLGC SEQ ID NO: 92

YHGAQKKGLSQGCFGLPLDRIGSLSGLGC SEQ ID NO: 97

ARKYKGAQKKGLSKGCFGLPLDRIGSLSGLGC SEQ ID NO: 96

ARKYKGAQKKGLSQGCFGLKLDRIGSLSGLGC SEQ ID NO: 98

ARKYKGANKKGLSQGCFGLPLDRIGSLSGLGC SEQ ID NO: 99

ARKYKGAQKKGLSQGCFGLPLDRIGSMSGLGC SEQ ID NO: 100

QEHPQARKYKGAQKKGLSKGCFGLPLDRIGSLSGLGC SEQ ID NO: 101

ARKYKGAQKKGLSQGCFGLPLERIGSLSGLGC SEQ ID NO: 102

YKGAQKKGLSQGCFGLPLDRIGSLSGLGC SEQ ID NO: 103

QEHPQARKYKGAQKKGLSSGCFGLPLERIGSLSGLGC SEQ ID NO: 104

YKGAQKKGGSQGCFGLPLERIGSLSGLGC SEQ ID NO: 108

YKGAQKKGLSQGCFGLPLERIGSLSGLGC SEQ ID NO: 109

GAQKKGLSQGCFGLPLDRIGSLSGLGC SEQ ID NO: 112

GAQKKGLSSGCFGLPLDRIGSLSGLGC SEQ ID NO: 113

GAQKKGGSQGCFGLPLDRIGSLSGLGC SEQ ID NO: 114

GAQKKGGSSGCFGLPLDRIGSLSGLGC SEQ ID NO: 115

GAQKKGLSQGCFGLKLDRIGSLSGLGC SEQ ID NO: 116

GAQKKGLSSGCFGLKLDRIGSLSGLGC SEQ ID NO: 117

GAQKKGGSQGCFGLKLDRIGSLSGLGC SEQ ID NO: 118

GAQKKGGSSGCFGLKLDRIGSLSGLGC SEQ ID NO: 119

GANKKGLSQGCFGLPLDRIGSLSGLGC SEQ ID NO: 120

GANKKGLSSGCFGLPLDRIGSLSGLGC SEQ ID NO: 121

GANKKGGSQGCFGLPLDRIGSLSGLGC SEQ ID NO: 122

GANKKGGSSGCFGLPLDRIGSLSGLGC SEQ ID NO: 123

GAQKKGLSQGCFGLPLDRIGSMSGLGC SEQ ID NO: 124

GAQKKGLSSGCFGLPLDRIGSMSGLGC SEQ ID NO: 125

GAQKKGGSQGCFGLPLDRIGSMSGLGC SEQ ID NO: 126

GAQKKGGSSGCFGLPLDRIGSMSGLGC SEQ ID NO: 127

GAQKKGLSKGCFGLPLDRIGSLSGLGC SEQ ID NO: 128

GAQKKGGSKGCFGLPLDRIGSLSGLGC SEQ ID NO: 129

GAQKKGLSQGCFGLPLERIGSLSGLGC SEQ ID NO: 130

GAQKKGLSSGCFGLPLERIGSLSGLGC SEQ ID NO: 131

GANKKGLSQGCFGLPLDRIGSMSGLGC SEQ ID NO: 132

GANKKGLSSGCFGLPLDRIGSMSGLGC SEQ ID NO: 133

GANKKGLSQGCFGLPLERIGSMSGLGC SEQ ID NO: 134

GANKKGLSSGCFGLPLERIGSMSGLGC SEQ ID NO: 135

GAQKKGSSQGCFGLPLDRIGSLSGLGC SEQ ID NO: 136

GAQKKGSSSGCFGLPLDRIGSLSGLGC SEQ ID NO: 137

GAQKKGSSQGCFGLKLDRIGSLSGLGC SEQ ID NO: 138

GAQKKGSSSGCFGLKLDRIGSLSGLGC SEQ ID NO: 139

GANKKGSSQGCFGLPLDRIGSLSGLGC SEQ ID NO: 140

GANKKGSSSGCFGLPLDRIGSLSGLGC SEQ ID NO: 141

GAQKKGSSQGCFGLPLDRIGSMSGLGC SEQ ID NO: 142

GAQKKGSSSGCFGLPLDRIGSMSGLGC SEQ ID NO: 143

GAQKKGSSKGCFGLPLDRIGSLSGLGC SEQ ID NO: 144

YKGAQKKGGSSGCFGLPLDRIGSLSGLGC SEQ ID NO: 145

YKGAQKKGLSQGCFGLKLDRIGSLSGLGC SEQ ID NO: 146

YKGAQKKGLSSGCFGLKLDRIGSLSGLGC SEQ ID NO: 147

YKGAQKKGGSQGCFGLKLDRIGSLSGLGC  SEQ ID NO: 148

YKGAQKKGGSSGCFGLKLDRIGSLSGLGC  SEQ ID NO: 149

YKGANKKGLSQGCFGLPLDRIGSLSGLGC  SEQ ID NO: 150

YKGANKKGLSSGCFGLPLDRIGSLSGLGC  SEQ ID NO: 151

YKGANKKGGSQGCFGLPLDRIGSLSGLGC  SEQ ID NO: 152

YKGANKKGGSSGCFGLPLDRIGSLSGLGC  SEQ ID NO: 153

YKGAQKKGLSQGCFGLPLDRIGSMSGLGC  SEQ ID NO: 154

YKGAQKKGLSSGCFGLPLDRIGSMSGLGC  SEQ ID NO: 155

YKGAQKKGGSQGCFGLPLDRIGSMSGLGC  SEQ ID NO: 156

YKGAQKKGGSSGCFGLPLDRIGSMSGLGC  SEQ ID NO: 157

YKGAQKKGLSKGCFGLPLDRIGSLSGLGC  SEQ ID NO: 158

YKGAQKKGGSKGCFGLPLDRIGSLSGLGC  SEQ ID NO: 159

YKGAQKKGLSQGCFGLPLERIGSLSGLGC  SEQ ID NO: 160

YKGAQKKGLSSGCFGLPLERIGSLSGLGC  SEQ ID NO: 161

YKGANKKGLSQGCFGLPLDRIGSMSGLGC  SEQ ID NO: 162

YKGANKKGLSSGCFGLPLDRIGSMSGLGC  SEQ ID NO: 163

YKGANKKGLSQGCFGLPLERIGSMSGLGC  SEQ ID NO: 164

YKGANKKGLSSGCFGLPLERIGSMSGLGC  SEQ ID NO: 165

YKGAQKKGGSQGCFGLPLDRIGSLSGLGC  SEQ ID NO: 166

YKGAQKKGGSSSGCFGLPLDRIGSLSGLGC  SEQ ID NO: 167

YKGAQKKGSSQGCFGLKLDRIGSLSGLGC  SEQ ID NO: 168

YKGAQKKGSSSGCFGLKLDRIGSLSGLGC  SEQ ID NO: 169

YKGANKKGSSQGCFGLPLDRIGSLSGLGC  SEQ ID NO: 170

YKGANKKGSSSGCFGLPLDRIGSLSGLGC  SEQ ID NO: 171

YKGAQKKGSSQGCFGLPLDRIGSMSGLGC  SEQ ID NO: 172

YKGAQKKGSSSGCFGLPLDRIGSMSGLGC  SEQ ID NO: 173

YKGAQKKGSSKGCFGLPLDRIGSLSGLGC  SEQ ID NO: 174

ARKYKGAQKKGGSQGCFGLPLDRIGSLSGLGC  SEQ ID NO: 175

ARKYKGAQKKGGSSGCFGLPLDRIGSLSGLGC  SEQ ID NO: 176

ARKYKGAQKKGLSSGCFGLKLDRIGSLSGLGC  SEQ ID NO: 177

ARKYKGAQKKGGSQGCFGLKLDRIGSLSGLGC  SEQ ID NO: 178

ARKYKGAQKKGGSSGCFGLKLDRIGSLSGLGC  SEQ ID NO: 179

ARKYKGANKKGLSQGCFGLPLDRIGSLSGLGC  SEQ ID NO: 180

ARKYKGANKKGLSSGCFGLPLDRIGSLSGLGC  SEQ ID NO: 181

ARKYKGANKKGGSQGCFGLPLDRIGSLSGLGC  SEQ ID NO: 182

ARKYKGANKKGGSSGCFGLPLDRIGSLSGLGC  SEQ ID NO: 183

ARKYKGAQKKGLSQGCFGLPLDRIGSMSGLGC  SEQ ID NO: 184

ARKYKGAQKKGLSSGCFGLPLDRIGSMSGLGC  SEQ ID NO: 185

ARKYKGAQKKGGSQGCFGLPLDRIGSMSGLGC  SEQ ID NO: 186

ARKYKGAQKKGGSSGCFGLPLDRIGSMSGLGC  SEQ ID NO: 187

ARKYKGAQKKGGSKGCFGLPLDRIGSLSGLGC  SEQ ID NO: 188

ARKYKGAQKKGLSQGCFGLPLERIGSLSGLGC  SEQ ID NO: 189

ARKYKGAQKKGLSSGCFGLPLERIGSLSGLGC  SEQ ID NO: 190

ARKYKGANKKGLSQGCFGLPLDRIGSMSGLGC  SEQ ID NO: 191

ARKYKGANKKGLSSGCFGLPLDRIGSMSGLGC  SEQ ID NO: 192

ARKYKGANKKGLSQGCFGLPLERIGSMSGLGC  SEQ ID NO: 193

ARKYKGANKKGLSSGCFGLPLERIGSMSGLGC  SEQ ID NO: 194

ARKYKGAQKKGSSQGCFGLPLDRIGSLSGLGC  SEQ ID NO: 195

ARKYKGAQKKGSSSGCFGLPLDRIGSLSGLGC  SEQ ID NO: 196

ARKYKGAQKKGSSQGCFGLKLDRIGSLSGLGC  SEQ ID NO: 197

ARKYKGAQKKGSSSGCFGLKLDRIGSLSGLGC  SEQ ID NO: 198

ARKYKGANKKGSSQGCFGLPLDRIGSLSGLGC  SEQ ID NO: 199

ARKYKGANKKGSSSGCFGLPLDRIGSLSGLGC  SEQ ID NO: 200

ARKYKGAQKKGSSQGCFGLPLDRIGSMSGLGC  SEQ ID NO: 201

```
                                 SEQ ID NO: 202
ARKYKGAQKKGSSSGCFGLPLDRIGSMSGLGC

SEQ ID NO: 203
ARKYKGAQKKGSSKGCFGLPLDRIGSLSGLGC

SEQ ID NO: 204
QEHPQARKYKGAQKKGGSSGCFGLPLDRIGSLSGLGC

SEQ ID NO: 205
QEHPQARKYKGAQKKGLSQGCFGLKLDRIGSLSGLGC

SEQ ID NO: 206
QEHPQARKYKGAQKKGLSSGCFGLKLDRIGSLSGLGC

SEQ ID NO: 207
QEHPQARKYKGAQKKGGSQGCFGLKLDRIGSLSGLGC

SEQ ID NO: 208
QEHPQARKYKGAQKKGGSSGCFGLKLDRIGSLSGLGC

SEQ ID NO: 209
QEHPNARKYKGANKKGLSQGCFGLPLDRIGSLSGLGC

SEQ ID NO: 210
QEHPNARKYKGANKKGLSSGCFGLPLDRIGSLSGLGC

SEQ ID NO: 211
QEHPNARKYKGANKKGGSQGCFGLPLDRIGSLSGLGC

SEQ ID NO: 212
QEHPNARKYKGANKKGGSSGCFGLPLDRIGSLSGLGC

SEQ ID NO: 213
QEHPQARKYKGAQKKGLSQGCFGLPLDRIGSMSGLGC

SEQ ID NO: 214
QEHPQARKYKGAQKKGLSSGCFGLPLDRIGSMSGLGC

SEQ ID NO: 215
QEHPQARKYKGAQKKGGSQGCFGLPLDRIGSMSGLGC

SEQ ID NO: 216
QEHPQARKYKGAQKKGGSSGCFGLPLDRIGSMSGLGC

SEQ ID NO: 217
QEHPQARKYKGAQKKGGSKGCFGLPLDRIGSLSGLGC

SEQ ID NO: 218
QEHPQARKYKGAQKKGLSQGCFGLPLERIGSLSGLGC

SEQ ID NO: 219
QEHPNARKYKGANKKGLSQGCFGLPLDRIGSMSGLGC

SEQ ID NO: 220
QEHPNARKYKGANKKGLSSGCFGLPLDRIGSMSGLGC

SEQ ID NO: 221
QEHPNARKYKGANKKGLSQGCFGLPLERIGSMSGLGC

SEQ ID NO: 222
QEHPNARKYKGANKKGLSSGCFGLPLERIGSMSGLGC

SEQ ID NO: 223
QEHPQARKYKGAQKKGSSQGCFGLPLDRIGSLSGLGC

SEQ ID NO: 224
QEHPQARKYKGAQKKGSSSGCFGLPLDRIGSLSGLGC

SEQ ID NO: 225
QEHPQARKYKGAQKKGSSQGCFGLKLDRIGSLSGLGC

SEQ ID NO: 226
QEHPQARKYKGAQKKGSSSGCFGLKLDRIGSLSGLGC

SEQ ID NO: 227
QEHPNARKYKGANKKGSSQGCFGLPLDRIGSLSGLGC

SEQ ID NO: 228
QEHPNARKYKGANKKGSSSGCFGLPLDRIGSLSGLGC

SEQ ID NO: 229
QEHPQARKYKGAQKKGSSQGCFGLPLDRIGSMSGLGC

SEQ ID NO: 230
QEHPQARKYKGAQKKGSSSGCFGLPLDRIGSMSGLGC

SEQ ID NO: 231
QEHPQARKYKGAQKKGSSKGCFGLPLDRIGSLSGLGC

SEQ ID NO: 232
GAQKKGSSQGCFGLPLERIGSLSGLGC
```

Embodiment 6: the CNP compound according to embodiment 1, wherein the CNP peptide has any one of the following amino acid sequences:

```
                                          (SEQ ID NO: 136)
GAQKKGSSQGCFGLPLDRIGSLSGLGC, (SEQ ID NO: 77)
ARKYKGAQKKGLSQGCFGLPLDRIGSLSGLGC, (SEQ ID NO: 88)
YKGAQKKGGSQGCFGLPLDRIGSLSGLGC, (SEQ ID NO: 103)
YKGAQKKGLSQGCFGLPLDRIGSLSGLGC, (SEQ ID NO: 67)
QEHPQARKYKGAQKKGLSSGCFGLPLDRIGSLSGLGC,
and
                                          (SEQ ID NO: 104)
QEHPQARKYKGAQKKGLSSGCFGLPLERIGSLSGLGC.
```

Embodiment 7: the CNP compound according to embodiment 1, wherein the CNP peptide has the following amino acid sequence:

QEHPQARKYKGAQKKGLSSGCFGLPLDRIGSLSGLGC (SEQ ID NO: 67).

Embodiment 8: the CNP compound according to any one of the preceding embodiments, wherein the modifying group is covalently attached to the N-terminal alpha-amine of the CNP peptide.

Embodiment 9: the CNP compound according to any one of the preceding embodiments, wherein Chem. A of the modifying group has a p of 16.

Embodiment 10: the CNP compound according to embodiments 1-8, wherein Chem. A of the modifying group is Chem. A2

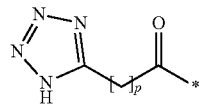

(Chem. A2)

wherein p is 16.

Embodiment 11: the CNP compound according to any one of the preceding embodiments, wherein Chem. B of the modifying group has a q of 1-5.

Embodiment 12: the CNP compound according to any one of the preceding embodiments, wherein the modifying group is selected from the following non-limiting examples Chem. E, Chem. F, Chem. G, Chem. H, Chem. I, and Chem. J (in which the dotted line defines the attachment through an amide bond to the CNP peptide)

(Chem. E)
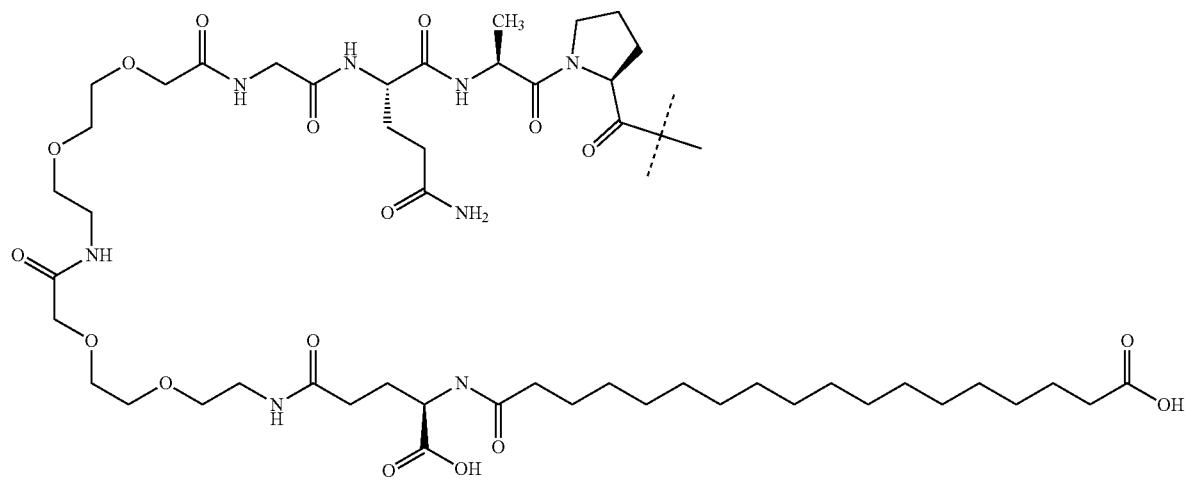
(Chem. F)
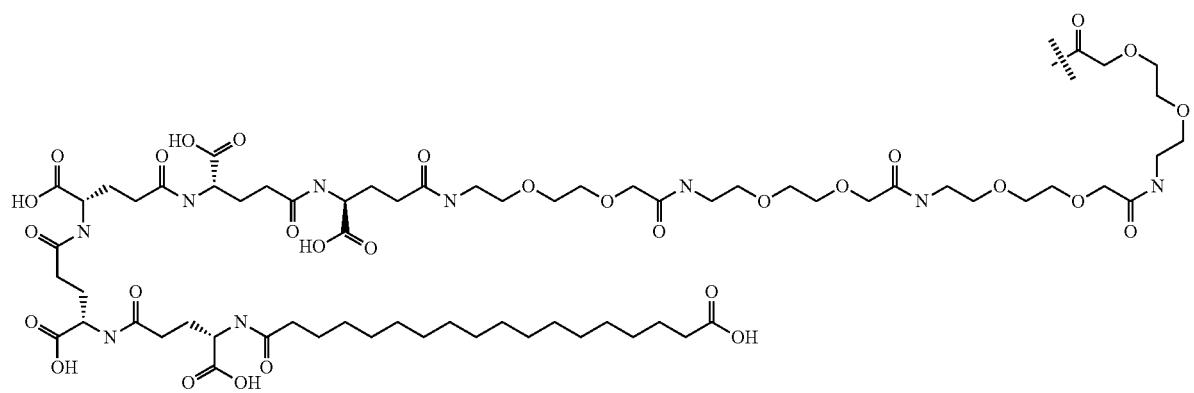
(Chem. G)
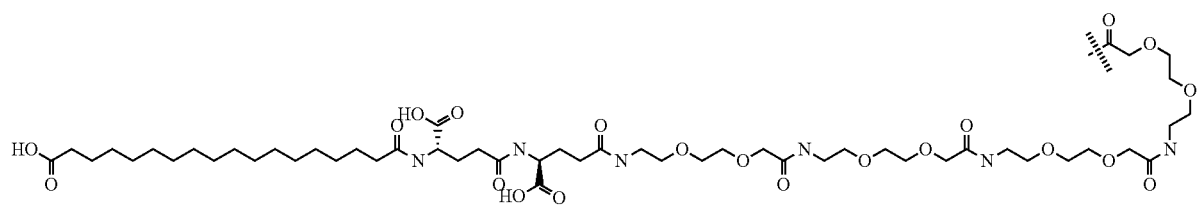
(Chem. H)
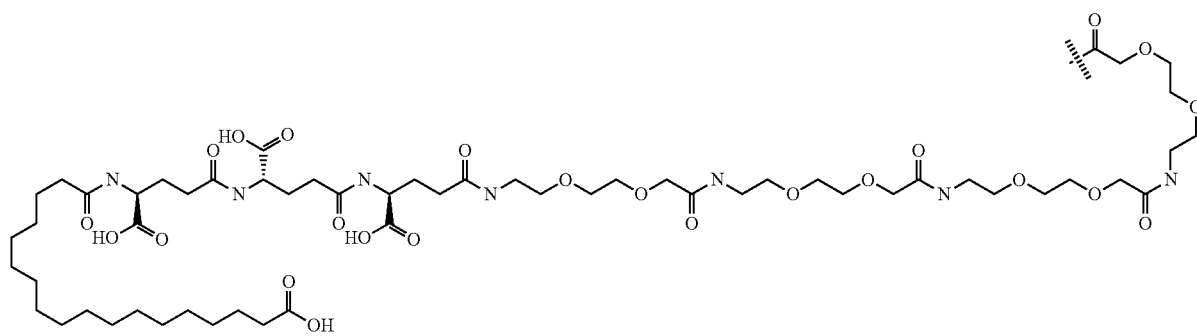

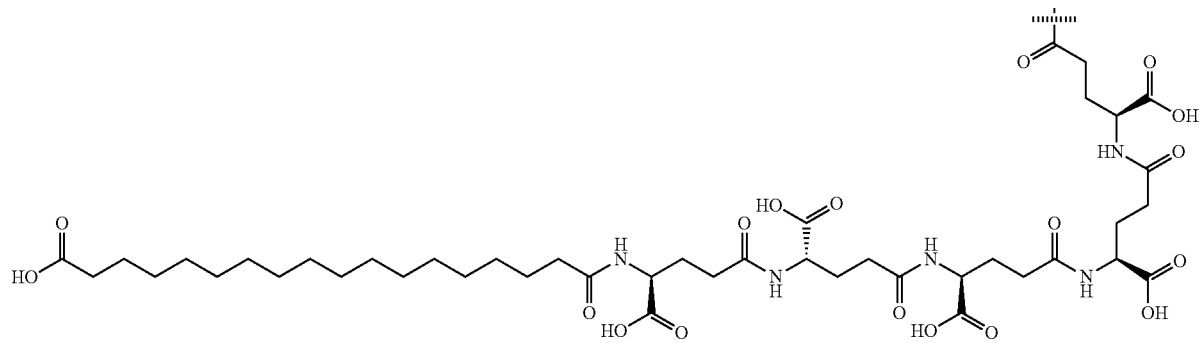
(Chem. I)

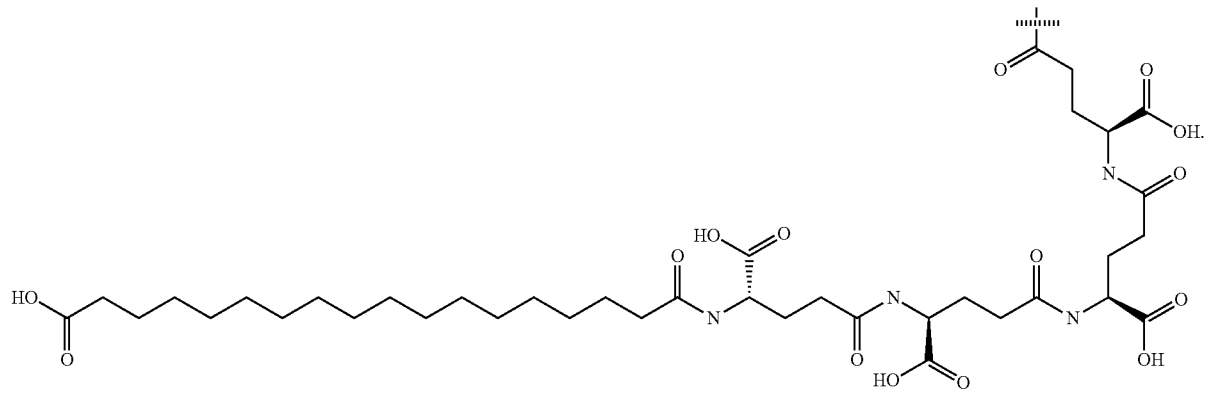
(Chem. J)

Embodiment 13: the CNP compound according to any one of the preceding embodiments, wherein the modifying group is Chem. I.

Embodiment 14: a CNP compound comprising a CNP peptide and a modifying group comprising a Chem. A, a Chem. B and a Chem. C, wherein the compound is according to any one of the compounds disclosed in Table 1 (see below).

Embodiment 15: a CNP compound comprising a CNP peptide and a modifying group wherein the compound is according to any one of the compounds disclosed in Table 1a.

TABLE 1a

| Compound ID | Modifying group | CNP peptide - with sequence modifications vis-a-vis CNP37 | SEQ ID NO |
|---|---|---|---|
| 9384 | C18d gGlu-2xOEG | des1-6, 7G, 8Q, 9A, 10P 13Q, 17S, 19Q, 25P, 32L | 62 |
| 9407 | C18d 5xgGlu-4xOEG | des1-5, 13Q, 19Q, 25P, 32L | 77 |

TABLE 1a-continued

| Compound ID | Modifying group | CNP peptide - with sequence modifications vis-a-vis CNP37 | SEQ ID NO |
|---|---|---|---|
| 9435 | C18d 2xgGlu-4xOEG | des1-8, 13Q, 17G, 19Q, 25P, 32L | 88 |
| 9480 | C18d 3xgGlu-4xOEG | des1-8, 13Q, 19Q, 25P, 32L | 103 |
| 9482 | C18d 5xgGlu | 5Q, 13Q, 19S, 25P, 32L | 67 |
| 9483 | C18d 4xgGlu | 5Q, 13Q, 19S, 25P, 27E, 32L | 104 |

Embodiment 16: a CNP compound comprising a CNP peptide and a modifying group, wherein the CNP peptide has the following amino acid sequence, QEHPQARKYK-GAQKKGLSSGCFGLPLDRIGSLSGLGC (SEQ ID NO: 67), and wherein the modifying group is Chem. I.

Embodiment 17: a CNP compound according to Formula II:
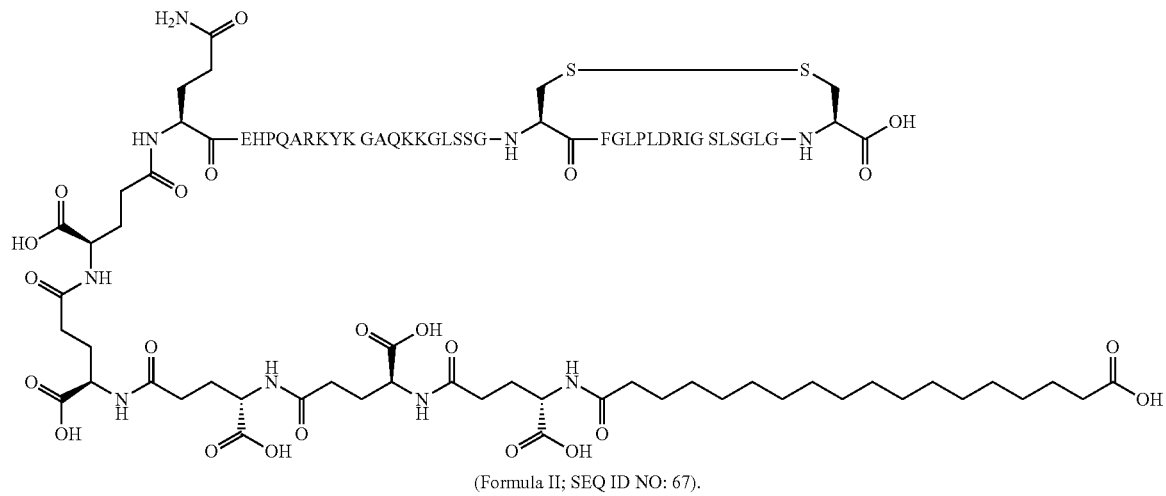
(Formula II; SEQ ID NO: 67).
Embodiment 18: a CNP compound according to any one of Formula II, III, IV, V, VI, and VII:
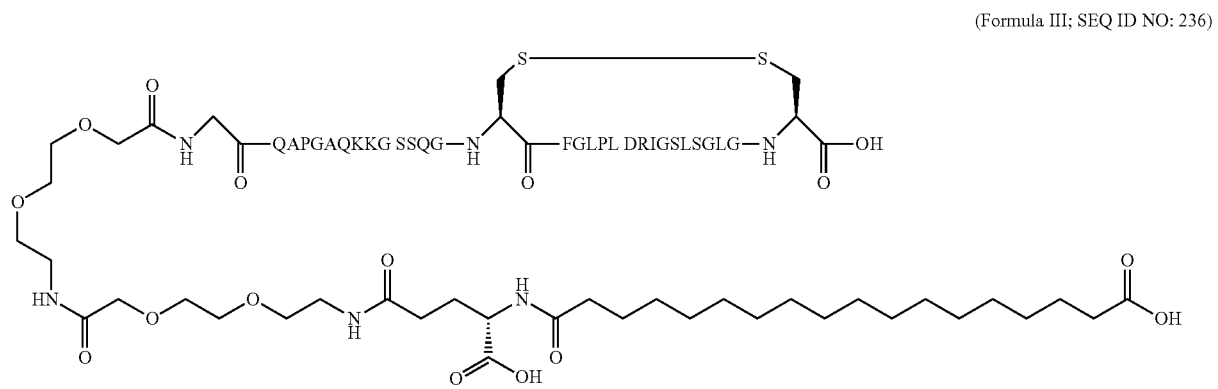
(Formula III; SEQ ID NO: 236)
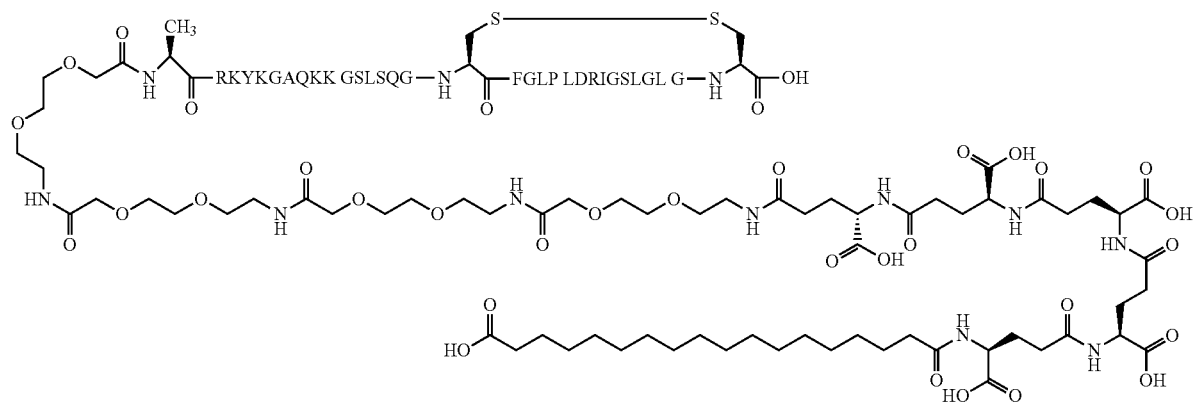
(Formula IV; SEQ ID NO: 77)

(Formula V; SEQ ID NO: 88)
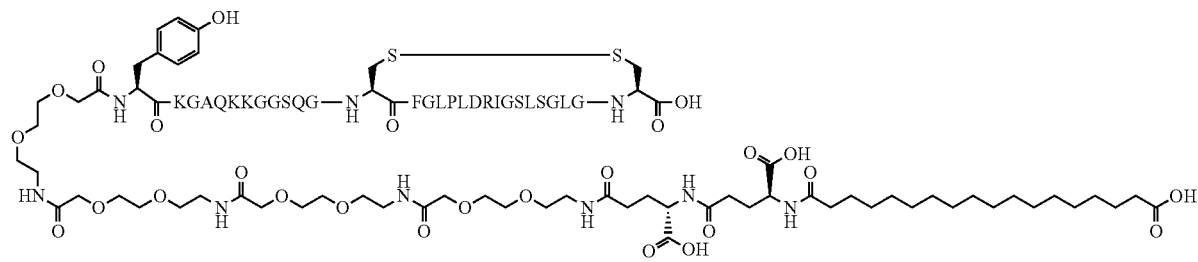
(Formula VI; SEQ ID NO: 103)
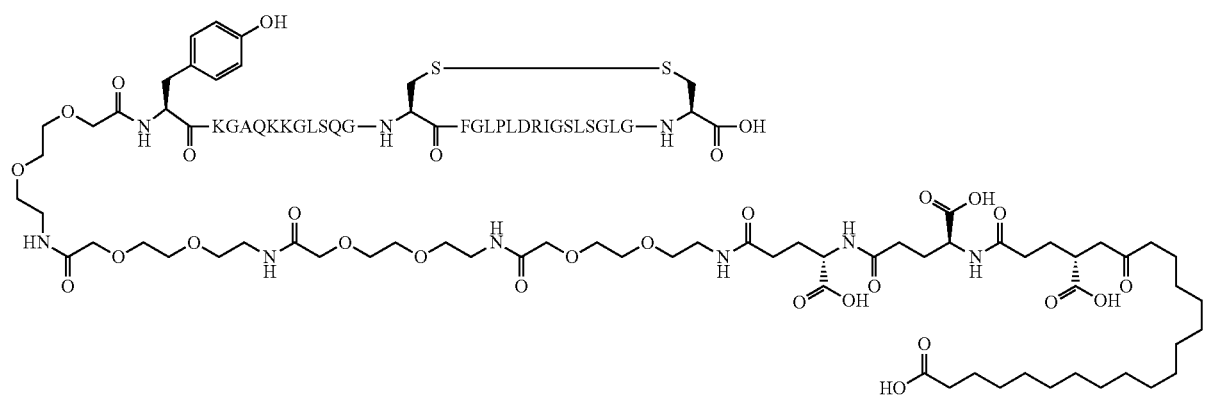
(Formula II; SEQ ID NO: 67)
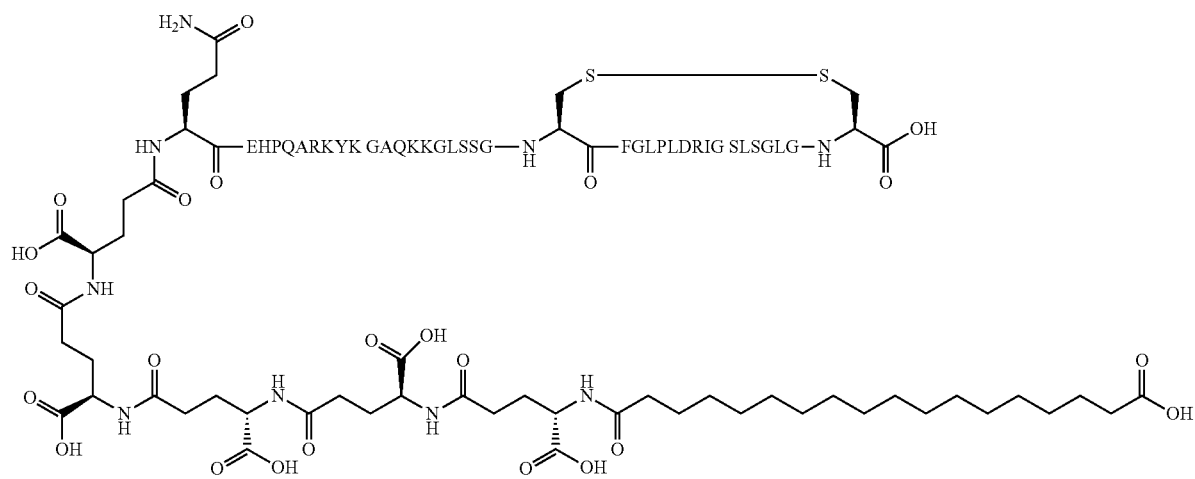

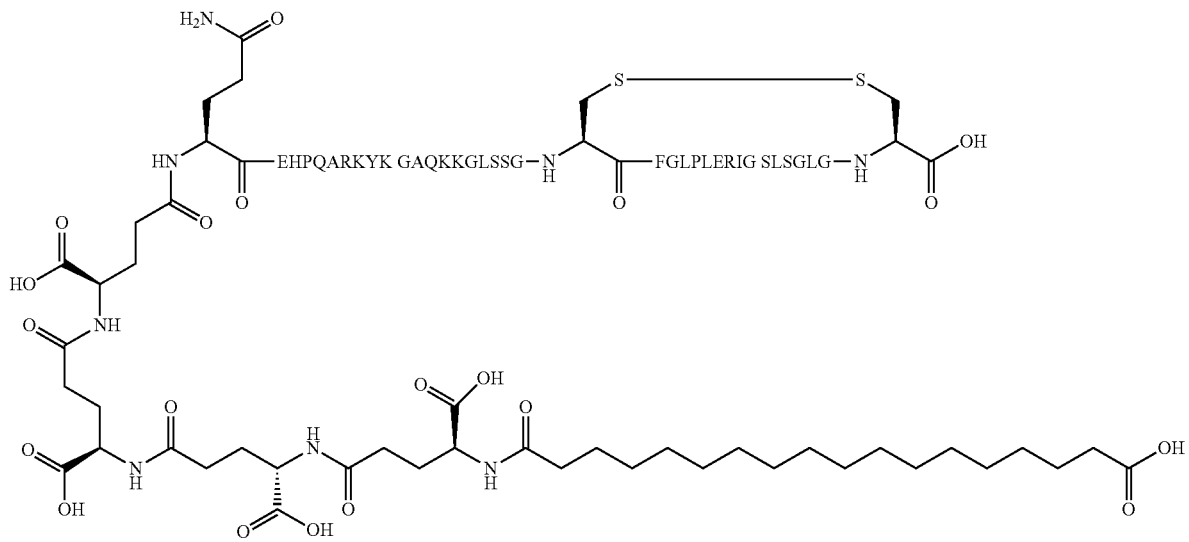

(Formula VII; SEQ ID NO: 104)

Embodiment 19: the compound according to any one of the embodiments 1-18 wherein the net charge of the CNP compound at physiological pH is 0 to −4, determined as described in Example 4.

Embodiment 20: the compound according to any one of the embodiments 1-18 wherein the compound has a in vivo half-life after s.c. administration to Göttingen minipigs of at least 10 hours, determined as described in Example 12.

Embodiment 21: the compound according to any one of the embodiments 1-18 wherein the compound has a in vivo half-life after s.c. administration to Göttingen minipigs of at least 20 hours, determined as described in Example 12.

Embodiment 22: the compound according to any one of the embodiments 1-18 wherein the compound has a in vivo half-life after s.c. administration to Göttingen minipigs of at least 30 hours, determined as described in Example 12.

Embodiment 23: the compound according to any one of the embodiments 1-18 wherein the compound has a in vivo half-life after s.c. administration to Göttingen minipigs of at least 40 hours, determined as described in Example 12.

Embodiment 24: the compound according to any one of the embodiments 1-18 wherein the compound has a in vivo half-life after s.c. administration to Göttingen minipigs of at least 50 hours, determined as described in Example 12.

Embodiment 25: the compound according to any one of the embodiments 1-18 wherein the compound has a bioavailability after s.c. administration to Göttingen minipigs of at least 40%, determined as described in Example 12.

Embodiment 26: the compound according to any one of the embodiments 1-18 wherein the compound has a bioavailability after s.c. administration to Göttingen minipigs of at least 50%, determined as described in Example 12.

Embodiment 27: the compound according to any one of the embodiments 1-18 wherein the compound has a bioavailability after s.c. administration to Göttingen minipigs of at least 60%, determined as described in Example 12.

Embodiment 28: the compound according to any one of the embodiments 1-18 wherein the compound has a bioavailability after s.c. administration to Göttingen minipigs of at least 70%, determined as described in Example 12.

Embodiment 29: the compound according to any one of the embodiments 1-18 wherein the compound has a solubility of at least at least 2000 μM at either pH 4 or pH 6.5 measured as described in Example 5.

Embodiment 30: the compound according to any one of the embodiments 1-18 wherein the compound has a solubility of at least at least 3000 μM at either pH 4 or pH 6.5 measured as described in Example 5.

Embodiment 31: the compound according to any one of the embodiments 1-18 wherein the compound has a solubility of at least at least 4000 μM at either pH 4 or pH 6.5 measured as described in Example 5.

Embodiment 32: the compound according to any one of the embodiments 1-31 wherein the compound comprises an intramolecular disulfide bridge resulting in a cyclic structure.

Embodiment 33: a pharmaceutical composition comprising a compound according to any one of embodiments 1-32, and one or more pharmaceutically acceptable excipients.

Embodiment 34: the compound according to any one of the embodiments 1-32, or a composition according to embodiment 33, for the use in the treatment or prevention of cardio-renal-metabolic diseases.

Embodiment 35: the compound according to any one of the embodiments 1-32, or a composition according to embodiment 33, for the use in the treatment or prevention of cardio-renal-metabolic diseases, including the group consisting of hypertension, arteriosclerosis, atherosclerosis, restenosis, acute myocardial infarction, pulmonary hypertension, acute decompensated heart failure, congestive heart failure, cardiac edema, renal edema, hepatic edema*, acute renal insufficiency, chronic renal insufficiency, insulin resistance, and type 2 diabetes.

Embodiment 36: the compound according to any one of the embodiments 1-32, or a composition according to embodiment 33, for the use in the treatment or prevention of congestive heart failure.

Embodiment 37: the compound according to any one of the embodiments 1-32, or a composition according to embodiment 33, for the use in the treatment or prevention of decompensated heart failure.

Embodiment 38: the compound according to any one of the embodiments 1-32, or a composition according to embodiment 33, for the use in the treatment or prevention of growth disorders including short stature that may relate to FGFR3-related skeletal dysplasia, and related comorbidities.

Embodiment 39: the compound according to any one of the embodiments 1-32, or a composition according to embodiment 33, for the use in the treatment or prevention of achondroplasia, hypochondroplasia, thanatophoric dysplasia type 1 and type 2, SHOX deficiency, Noonan syndrome, Costello, LEOPARD syndrome, idiopathic short stature, autosomal dominant short stature, growth hormone deficiency, hypophosphatemic rickets, CNP deficiency, Aggrecan deficiency, Heterozygous NPR2 mutation, osteoarthritis, craniosynostosis, (e.g., Muenke syndrome, Crouzon syndrome, Apert syndrome, Jackson-Weiss syndrome, Pfeiffer syndrome, or Crouzonodermoskeletal syndrome), Lacrimo-Auriculo-Dento-Digital syndrome (LADD), Osteoglophonic dysplasia, and SADDAN (severe achondroplasia developmental delay acanthosis nigricans).

Embodiment 40: the compound according to any one of the embodiments 1-32, or a composition according to embodiment 33, for the use in the treatment or prevention of osteogenesis imperfecta, achondrogenesis, chondrodysplasia punctata, homozygous achondroplasia, rhizomelic type of chondrodysplasia punctata, spondyloepiphyseal dysplasia congenita, congenital short femur, Langer-type mesomelic dysplasia, Neurofibromatosis, Legius syndrome and neurofibromatosis type 1.

Embodiment 41: the compound according to any one of the embodiments 1-32, or a composition according to embodiment 33, for the use in the treatment or prevention of phenotypes related to growth disorders including short stature that may relate to FGFR3-related skeletal dysplasia, selected from the group consisting of growth retardation, skull deformities, orthodontic defects, cervical cord compression, spinal stenosis, pain in relation to skeletal dysplasia, hydrocephalus, hearing loss due to chronic otitis, cardiovascular disease, neurological disease, and obesity.

Embodiment 42: a method of treating or preventing cardio-renal-metabolic diseases, comprising administering to a patient in need thereof an effective amount of the compound according to any one of the embodiments 1-32, or a composition according to embodiment 33.

Embodiment 43: a method of treating or preventing cardio-renal-metabolic diseases, including the group consisting of hypertension, arteriosclerosis, atherosclerosis, restenosis, acute myocardial infarction, pulmonary hypertension, acute decompensated heart failure, congestive heart failure, cardiac edema, renal edema, hepatic edema*, acute renal insufficiency, chronic renal insufficiency, insulin resistance, and type 2 diabetes, comprising administering to a patient in need thereof an effective amount of the compound according to any one of the embodiments 1-32, or a composition according to embodiment 33.

Embodiment 44: a method of treating or preventing growth disorders including short stature that may relate to FGFR3-related skeletal dysplasia, and related comorbidities, comprising administering to a patient in need thereof an effective amount of the compound according to any one of the embodiments 1-32, or a composition according to embodiment 33.

Embodiment 45: a method of treating or preventing achondroplasia, hypochondroplasia, thanatophoric dysplasia type 1 and type 2, SHOX deficiency, Noonan syndrome, Costello, LEOPARD syndrome, idiopathic short stature, autosomal dominant short stature, growth hormone deficiency, hypophosphatemic rickets, CNP deficiency, Aggrecan deficiency, Heterozygous NPR2 mutation, osteoarthritis, craniosynostosis, (e.g., Muenke syndrome, Crouzon syndrome, Apert syndrome, Jackson-Weiss syndrome, Pfeiffer syndrome, or Crouzonodermoskeletal syndrome), Lacrimo-Auriculo-Dento-Digital syndrome (LADD), Osteoglophonic dysplasia, and SADDAN (severe achondroplasia developmental delay acanthosis nigricans), comprising administering to a patient in need thereof an effective amount of the compound according to any one of the embodiments 1-32, or a composition according to embodiment 33.

Embodiment 46: a method of treating or preventing osteogenesis imperfecta, achondrogenesis, chondrodysplasia punctata, homozygous achondroplasia, rhizomelic type of chondrodysplasia punctata, spondyloepiphyseal dysplasia congenita, congenital short femur, Langer-type mesomelic dysplasia, Neurofibromatosis, Legius syndrome and neurofibromatosis type 1, comprising administering to a patient in need thereof an effective amount of the compound according to any one of the embodiments 1-32, or a composition according to embodiment 33.

Embodiment 47: a method of treating or preventing phenotypes related to growth disorders including short stature that may relate to FGFR3-related skeletal dysplasia, selected from the group consisting of growth retardation, skull deformities, orthodontic defects, cervical cord compression, spinal stenosis, pain in relation to skeletal dysplasia, hydrocephalus, hearing loss due to chronic otitis, cardiovascular disease, neurological disease, and obesity, comprising administering to a patient in need thereof an effective amount of the compound according to any one of the embodiments 1-32, or a composition according to embodiment 33.

EXAMPLES

Materials and Methods

LIST OF ABBREVIATIONS

2-ClTrt 2-Chlorotrityl resin
Aldrithiol-4 4,4'-Dipyridyl disulfide
AUC Area under the curve
BEH Ethylene Bridged Hybrid
Boc tert-Butyloxycarbonyl
C18d Octadecanedioic acid
C20d Eicosanedioic acid
CAD Charged aerosol detector
cGMP Cyclic guanosine monophosphate
CL Clearance
CSH Charged Surface Hybrid
DCM Dichloromethane
DgGlu D-configuration gamma-glutamoyl
DIC N,N'-Diisopropylcarbodiimide
DMEM Dulbecco's Modified Eagle Medium
DMF Dimethylformamide
DMSO Dimethyl sulfoxide
DTT Dithiothreitol
EDTA Ethylenediaminetetraacetic acid
ESI Electrospray ionisation
F % Bioavailability
Fd Faraday
Fmoc Fluorenylmethyloxycarbonyl
FPLC Fast protein liquid chromatography
gGlu Gamma-glutamoyl
HEPES 2-[4-(2-Hydroxyethyl)piperazin-1-yl]ethane-1-sulfonic acid
HFIP Hexafluoro-2-propanol
HMWP High molecular weight protein HSA Human serum albumin
i.v. Intravenous
IPA Isopropanol
LCMS Liquid chromatography-mass spectrometry
LLOQ Lower limit of quantitation
LYD Landrace, Yorkshire & Duroc
MeCN Acetonitrile
MMPX 8-Methoxymethyl-3-isobutyl 1-methylxanthine
MS Mass spectrometry
NAD No abnormalities detected
NCA Non-compartmental analysis
n.d. not detected
Nle (X) Norleucine
NMP N-Methyl-2-pyrrolidone
OEG Oligoethylene glycol
Oxyma Pure Ethyl cyanohydroxyiminoacetate
Pbf 2,2,4,6,7-pentamethyldihydrobenzofuran-5-sulfonyl
PBS Phosphate buffered saline
PD Pharmacodynamics
PDA Photodiode-array detection
PK Pharmacokinetics
QC Quality control
RP Reversed phase
RPM Rounds per minute
s.c. Subcutaneous
SEC Size-exclusion chromatography
SIL Stable isotope labelled
SPPS Solid-phase peptide synthesis
T½ Half-life
tBu tert-Butyl
Tetrazole-C18 17-(2H-Tetrazol-5-yl)heptadecanoic acid
TF Time-of-flight
TFA Trifluoroacetic acid
ThT Thioflavin T
TIPS Triisopropyl silane
Tris 2-Amino-2-(hydroxymethyl)propane-1,3-diol
Trt Trityl
TUV Tunable UV
UPLC Ultra-performance liquid chromatography
UV Ultraviolet General Methods of Preparation Method A—Solid-Phase Peptide Synthesis Peptides can be synthesized by solid-phase peptide synthesis which is well known in the art, below is described methods used to synthesize the exemplified compounds of the present invention.

Synthesis of compounds was performed on a SymphonyX Solid Phase Peptide Synthesizer (GYROS Protein Technologies AB, Tucson, AZ).

Typically synthesis was performed using 450 μmol resin, but syntheses using 150 or 300 μmol resin were also used. In a typical synthesis, the resin was washed in DMF. After washing with DMF, the resin was incubated with Fmoc-protected amino acid (5 eq., 0.3 M in 0.3 M Oxyma Pure in DMF, 7.5 mL), DIC (5 eq., 0.75 M in DMF, 3.0 mL), and collidine (5 eq., 0.75 M in DMF, 3.0 mL) for 30 min. Additional DIC (5 eq., 0.75 M in DMF, 3.0 mL) was then added and the resin incubated for 90 min. After each coupling, the resin was capped by treatment with acetic anhydride (1 M, 7.5 mL) and collidine (0.75 M, 3.0 mL) in DMF for 20 min. Fatty acids were coupled using fatty acid mono-tert-butyl ester (5 eq., 0.3 M in 0.3 M Oxyma Pure, 7.5 mL), DIC (5 eq., 0.75 M in DMF, 3.0 mL), and collidine (5 eq., 0.75 M in DMF, 3.0 mL) for 6 h.

The Fmoc-protected amino acids used were the standard recommended: Fmoc-Ala-OH, Fmoc-Arg(Pbf)-OH, Fmoc-Asn(Trt)-OH, Fmoc-Asp(OtBu)-OH, Fmoc-Cys(Trt)-OH, Fmoc-Gln(Trt)-OH, Fmoc-Glu(OtBu)-OH, Fmoc-Gly-OH, Fmoc-His(Trt)-OH, Fmoc-Ile-OH, Fmoc-Leu-OH, Fmoc-Lys(Boc)-OH, Fmoc-Met-OH, Fmoc-Phe-OH, Fmoc-Pro-OH, Fmoc-Ser(tBu)-OH, Fmoc-Thr(tBu)-OH, Fmoc-Trp(Boc)-OH, Fmoc-Tyr(tBu)-OH, Fmoc-Val-OH and Fmoc-Nle-OH, supplied from e.g. Anaspec, Bachem, Iris Biotech or NovabioChem. Where nothing else is specified the naturally occurring L-form of the amino acids were used. In cases where a serine or a threonine is present in the peptide, pseudoproline di-peptides may be used (see also W. R. Sampson et al., J. Pept. Sci. 1999, 5, 403-409).

For peptides acylated at any position during SPPS the following suitably protected building blocks such as, but not limited to, Fmoc-8-amino-3,6-dioxaoctanoic acid and Boc-Glu(Fmoc)-OH were supplied from e.g. Anaspec, Bachem, Iris Biotech, or Novabiochem.

Octadecanedioic acid mono-tert-butyl-ester and eicosanedioic acid mono-tert-butyl ester was prepared as is known in the art, e.g. as described in WO 2010102886 A1.

17-(2H-tetrazol-5-yl)heptadecanoic acid (Tetrazole-C18) was incorporated by coupling the protected building block (S)-4-(17-(1H-tetrazol-5-yl)heptadecanamido)-5-(tert-butoxy)-5-oxopentanoic acid which was synthesized according to the following procedure: 5-Chloro-1-((dimethylamino)(dimethyliminio)methyl)-1H-benzo[d][1,2,3]triazole 3-oxide tetrafluoroborate (TCTU, 5.87 g, 16.5 mmol) and N-methylmorpholine (NMM, 8.00 mL, 72.8 mmol) were sequentially added to a stirred suspension of 17-(1H-tetrazol-5-yl)heptadecanoic acid (5.10 g, 15.0 mmol) in dry DMF (70 mL). The mixture was stirred at room temperature for 30 minutes. H-L-Glu-OtBu (L-glutamic acid 1-tert-butyl ester, 4.58 g, 22.5 mmol) was added in one portion. The suspension turned into yellow solution in 5 minutes. It was allowed to stand at room temperature for 4 hours and then poured into an ice cooled stirred solution of hydrochloric acid (35%, 20 mL) in water (1 L). The crude product was filtered off and washed with water (3×100 mL) and shortly dried on a glass sintered frit by suction and redissolved in DMF (70 mL). This solution was poured into water (1 L), the resulting suspension stirred for 5 minutes and the solid was filtered off, washed with water (3×100 mL) and dried in vacuo. Crude product was dissolved in ethyl acetate (400 mL) and filtered through a silica gel (Silicagel 60, 0.040-0.063 mm) column (100 g) and the column was washed by ethyl acetate (600 mL). Ethyl acetate was removed in vacuo. Solid residue was boiled in 1,2-dichloroethane (200 mL) with vigorous stirring for 5 minutes, then the emulsion was allowed to cool to room temperature in 5 minutes and allowed to crystallize at the same temperature overnight. The waxy crystals were filtered off and washed by 1,2-dichloromethane (50 mL) and n-heptane (100 mL) and dried on air. This purification step was repeated one more time. Finally the compound was dissolved in 1,4-dioxane (50 mL) and freeze dried to afford (S)-4-(17-(1H-tetrazol-5-yl)heptadecanamido)-5-(tert-butoxy)-5-oxopentanoic acid as off-white powder.

For peptides featuring a C-terminal cysteine the resin was a pre-loaded H-Cys(Trt)-2-ClTrt (e.g. from Bachem or Novabiochem).

Method B—Peptide Cleavage from the Resin.

After synthesis the resin was washed with DCM, and the peptide cleaved from the resin by a 2-3 hours treatment with TFA/TIPS/water/DTT (e.g. in the ratios 90:5:2.5:2.5 or 92.5:2.5:2.5:5) followed by precipitation with diethyl ether. The precipitate was centrifuged and washed several times with diethyl ether.

Method C—Disulfide Bridge Formation

Native CNP contains a disulfide bridge which, if reduced, abolishes binding to the NPR2 receptor. Methods for disulfide bridge formation for synthetic peptides are well known in the art, below is described three methods used to prepare the exemplified compounds of the present invention.

Folding Using Aldrithiol-4

The crude precipitated peptide from a 150 μmol synthesis was dissolved in 10 ml DMSO, followed by addition of water to 700 mL and additional addition of 100 mL MeCN. Finally, 2 mL of 0.5M NaOAc buffer pH 5.0 was added to the peptide solution. The pH was adjusted with 1 M NaOH to pH 5-6.5 until the solution was clear. The amount of peptide in solution was quantified using CAD and a fresh stock solution of Aldrithiol-4 (2 mg/ml in MeOH) was prepared. 1.0 equiv of Aldrithiol-4 in MeOH compared to peptide content was added over 5-10 min. under vigorous stirring. The solution was stirred for 10 min and additional 0.5 or 1.0 equiv of Aldrithiol-4 stock solution added. The reaction was quenched with 2 mL TFA once complete as determined by LCMS. The peptide was purified by RP-HPLC as described below.

Folding Using DMSO

The crude peptide precipitate from a 450 μmol synthesis was dissolved in MeCN/water 1:1 (50 mL), and added to a 500 mM Tris-HCl pH 8.0 buffer (1 L) and diluted with water (1.4 L) and DMSO (600 mL). The solution was left with gentle stirring for 16-24 h at RT. The reaction was quenched by addition of 5.0 equiv. of iodoacetamide (50 mM in water), then acidified after 10 min with TFA to pH 2 and diluted to 5 L with water. The peptide was purified by RP-HPLC as described below.

Folding Using Cysteine/Cystine or Cysteamine/Cystamine Redox Buffer

The crude peptide precipitate from a 150 μmol synthesis was dissolved in DMSO (20 mL) and added to a buffer of 50 mM Tris-HCl, 3 mM cysteine, 0.3 mM cystine pH 8.2 (800 mL) or a buffer of 50 mM Tris-HCl, 3 mM cysteamine, 0.3 mM cystamine pH 8.2. The solution was left with gentle stirring for 16-24 h at RT. The reaction was quenched by addition of 3 mL TFA, diluted with 100 mL MeCN and purified by RP-HPLC as described below.

Method D—Purification

Methods of peptide purification are well known in the art, below is described two methods used to purify the exemplified compounds of the present invention.

Reverse Phase Preparative HPLC Using Acidic Eluents

Crude folded peptides were purified by preparative reverse phase HPLC on a Waters Delta Prep 4000 or a Gilson Model 322 H2 system fitted with a C18 column, e.g. a Waters Xbridge Prep C18 OBD, 5 μm, 250×50 mm or a Phenomenex Gemini Axia NX C18, 5 μm, 250×30 mm. The peptide was eluted from the column using a linear gradient of eluents A (0.1% TFA in water) and B (0.1% TFA in acetonitrile), e.g. from 27-42% eluent B over 30 min at a constant flowrate of 25 mL/min (Ø30 mm column) or from 30-40% eluent B over 10 min at 120 mL/min (Ø50 mm column). The peptide fractions with acceptable purity were collected, pooled and lyophilised to yield the peptide TFA salt as a colourless powder.

Reverse Phase Preparative HPLC Using Near Neutral Eluents

If further purification was required the lyophilised peptide TFA salt was purified on a similar preparative HPLC system in a neutral or near-neutral pH eluent, e.g. eluent A: 100 mM NaOAc pH 6.5, 5% MeCN; eluent B: MeCN. The peptide was eluted from the column using a linear gradient of eluents A and B, e.g. from 25-55% eluent B over 30 min at a constant flowrate of 60 mL/min (Ø50 mm column). The peptide fractions with acceptable purity were collected, pooled and desalted using either of the methods described below.

Method E—Resalting and Desalting

In some instances, it was desirable to change the counter ion to sodium to ease formulation at pH 6.5. Methods for exchanging peptide counter ions are well known in the art, below is described a method used to change counter ion for some of the exemplified compounds of the present invention.

Size Exclusion Desalting

The counter-ion was exchanged by solubilising the peptide TFA salt in 400 mM NaOAc pH 6.5 and 20% MeCN at 2-3 mg/mL. The dissolved peptide was then desalted on an Äkta Purifer FPLC system using a HiPrep 26/10 desalting column. The column was pre-equilibrated with 20% MeCN and the peptide was injected and eluted over 1.5 CV of isocratic 20% MeCN at 6 mL/min. The peptide was collected, quantified by CAD analysis and lyophilised to yield the peptide sodium salt as a colourless powder.

General Methods of Detection and Characterisation:

In order to confirm the identity, to measure the purity and to quantify the amount of a prepared synthetic peptide, the peptide is characterised using methods such as LCMS and reverse-phase UPLC that are well known in the art. Below is described methods used to characterise the exemplified compounds of the present invention.

Method F—Analytical Chromatography Methods

The prepared CNP compounds were characterised by RP-UPLC and LCMS and the amount prepared quantified by RP-UPLC/CAD.

LCMS34

LCMS was performed on a setup consisting of a Waters ACQUITY UPLC system and a Xevo G2-XS QTOF mass spectrometer. The system was fitted with a Waters ACQUITY UPLC BEH C18 Column, 1.7 μm, 2.1 mm×50 mm, column temperature 60° C. UV-detection was at 214 nm. MS ionisation mode was ESI+.

Eluent A: 0.1% formic acid in water; eluent B: 0.1% formic acid in acetonitrile. The analysis was performed by injecting an appropriate volume of the sample (preferably 1-10 μL) onto the column which was eluted with a linear gradient of eluents A and B from 5-95% eluent B over 4.0 min at a constant flowrate of 0.4 mL/min.

RP-UPLC107:

Alternatively, LCMS was performed on a setup consisting of a Waters ACQUITY UPLC system and a Waters QDA mass detector. The system was fitted with a Waters ACQUITY UPLC BEH C18 Column, 1.7 μm, 2.1 mm×50 mm, column temperature 40° C. UV-detection was at 214 nm.

Eluent A: 0.05% TFA in water; eluent B: 0.05% TFA in acetonitrile. The analysis was performed by injecting an appropriate volume of the sample (preferably 1-10 μL) onto the column which was eluted with a linear gradient of eluents A and B from 5-60% eluent B over 1.6 min at a constant flowrate of 0.9 mL/min.

RP-UPLC02:

RP-UPLC02 was performed on a Waters ACQUITY UPLC system with a TUV or PDA detector. The system was fitted with a Waters ACQUITY UPLC BEH C18 column, 1.7 μm, 2.1 mm×150 mm, column temperature 40° C. UV-detection was at 214 nm. Eluent A: 0.05% TFA in water; eluent B: 0.05% TFA in acetonitrile.

The analysis was performed by injecting an appropriate volume of the sample (preferably 1-10 μL) onto the column which was eluted with a linear gradient of eluents A and B from 5-95% eluent B over 16.0 min at a constant flowrate of 0.4 mL/min.

RP-UPLC61:

RP-UPLC61 was performed on a Waters ACQUITY UPLC system with a TUV or PDA detector. The system was fitted with a Waters ACQUITY UPLC BEH Shield C18 column, 1.7 μm, 2.1 mm×150 mm, column temperature 60° C. UV-detection was at 214 nm. Eluent A: 20 mM $Na_2SO_4$, 2 mM $Na_2HPO_4$, 2 mM $NaH_2PO_4$ in water/MeCN 9:1, pH 7.2; eluent B: MeCN/water 7:3. The analysis was performed by injecting an appropriate volume of the sample (preferably 1-10 μL) onto the column which was eluted with a linear gradient of eluents A and B from 5-20% B over 3 min, then 20-80% B over 17 min, then 80-90% B over 1 min at a constant flowrate of 0.4 mL/min.

CAD02 Peptide Quantification:

CAD was performed on a Thermo Scientific Vanquish UPLC system with a UV-DAD and CAD (Charged Aerosol Detector). The system was fitted with a Waters ACQUITY UPLC CSH C18 column, 1.7 μm, 2.1 mm×50 mm, column temperature 40° C. UV-detection was at 214 nm. Eluent A: 0.1% v/v TFA in water; eluent B: 0.1% v/v TFA in MeCN. The analysis was performed by injecting an appropriate volume of the sample onto the column which was eluted with a linear gradient of eluents A and B from 0-95% B over 4 min at a constant flowrate of 0.45 mL/min. Calibration was performed using a standard curve generated by injecting an external standard of Insulin Aspart, 3.55 mg/mL.

Method G—Preparation of CNP Compound Formulations for In Vivo Experiments

Formulations for in vivo studies were prepared according to the principles outlined below.

Procedure: The formulations used for the in-vivo studies were prepared by dissolving the lyophilized peptide in formulation buffers with compositions identical to the final formulations (final formulation composition are specified in Example 9 to Example 15). The following final formulation compositions have been used:

pH 4.0: 5 mM sodium acetate, 250 mM glycerol, pH 4.0 pH 4.0: 5 mM sodium acetate, 240 mM propylene glycol, pH 4.0 pH 4.0: 5 mM sodium acetate, 250 mM glycerol, 0.007% polysorbate 20, pH 4.0 pH 6.0: 20 mM sodium phosphate, 223 mM propylene glycol, pH 6.0 pH 6.5: 8 mM sodium phosphate, 250 mM glycerol, pH 6.5 pH 7.4: 8 mM sodium phosphate, 250 mM glycerol, pH 7.4 pH 7.4: 8 mM sodium phosphate, 250 mM glycerol, 0.007% polysorbate 20, pH 7.4 pH 7.5: 8 mM sodium phosphate, 250 mM glycerol, pH 7.5 pH 5.5: 1.33 mM citric acid monohydrate; 3.67 mM citrate, trisodium; 52 mg/ml trehalose; 15 mg/ml D-mannose; 0.73 mg/ml L-methionine; 0.05 mg/ml polysorbate 80, pH 5.5

The formulation procedure was for practical reasons slightly different for pH 6.5 formulations compared to formulations of other pH targets.

Formulations at pH 6.5: The lyophilized peptide was dissolved in a pH 7.4 buffer (8 mM sodium phosphate, 250 mM glycerol, pH 7.4) to a nominal concentration of 20-50% above the target peptide concentration and pH was adjusted to pH 6.5 using 0.2N NaOH, or 0.2N HCl. The actual peptide concentration was determined using CAD (Method F, CAD02) and a volume of a pH 6.5 buffer (8 mM sodium phosphate, 250 mM glycerol, pH 6.5) was added to reach a nominal concentration corresponding to the target peptide concentration and pH was adjusted to pH 6.5 using 0.2N NaOH, or 0.2N HCl. The actual peptide concentration was determined using CAD (Method F, CAD02). The formulation was sterile filtered (0.22 μm), the final peptide concentration was determined using CAD (Method F, CAD02) and the formulation was filled into sterile containers.

Formulations at pH 4.0, pH 6.0, pH 7.4 and pH 7.5: The lyophilized peptide was dissolved in a formulation buffer with a composition corresponding to the composition of the final formulation (specified in Example 9 to Example 15) to a nominal concentration of 20-50% above the target peptide concentration and pH was adjusted to target using 0.2 N NaOH, or 0.2 N HCl. The actual peptide concentration was determined using CAD (Method F, CAD02) and a volume of the same formulation buffer was added to reach a nominal concentration corresponding to the target peptide concentration and pH was adjusted to target using 0.2 N NaOH, or 0.2 N HCl. The actual peptide concentration was determined using CAD (Method F, CAD02). The formulation was sterile filtered (0.22 μm), the final peptide concentration was determined using CAD (Method F, CAD02) and the formulation was filled into sterile containers.

Example 1—Synthesis of CNP Compounds

CNP compounds were synthesized and characterized according to the general methods of preparation described above. The exemplified CNP compounds and their constituents are summarised in Table 1. The protractor and linker elements, of Table 1, together form up the modifying group of the CNP compounds.

TABLE 1

Summary of exemplified compounds Chem. 1-148

| Chem. No. | Compound ID | Protractor (Chem A) | Linker (Chem B-C) | CNP37 sequence modifications | SEQ ID |
| --- | --- | --- | --- | --- | --- |
| 1 | 0065 | | | des1-15 (CNP22) | 1 |
| 2 | 1510 | | | (CNP37) | 2 |
| 3 | 0312 | C18d | gGlu-2xOEG | des1-4, 5Q, 13Q, 32Nle | 3 |
| 4 | 0776 | C18d | gGlu-2xOEG | des1-5, 13Q, 27E, 32L | 4 |
| 5 | 1235 | C18d | gGlu-2xOEG | des1-8, 9E, 10H, 13Q, 32L | 5 |
| 6 | 0262 | C18d | 6xgGlu | des1-8, 32Nle | 6 |
| 7 | 0296 | C18d | 6xgGlu | des1-4, 15S, 19S, 32Nle | 7 |
| 8 | 0313 | C18d | 5xgGlu | des1-10, 32Nle | 8 |
| 9 | 0334 | C18d | 5xgGlu | des1-10, 13Q, 32Nle | 9 |

TABLE 1-continued

Summary of exemplified compounds Chem. 1-148

| Chem. No. | Compound ID | Protractor (Chem A) | Linker (Chem B-C) | CNP37 sequence modifications | SEQ ID |
|---|---|---|---|---|---|
| 10 | 1221 | C18d | gGlu-2xOEG | des1-8, 10E, 13Q, 32L | 10 |
| 11 | 1222 | C18d | gGlu-2xOEG | des1-8, 9E, 10E, 13Q, 32L | 11 |
| 12 | 1223 | C18d | gGlu-2xOEG | des1-8, 10E, 13Q, 14E, 32L | 12 |
| 13 | 1224 | C18d | gGlu-2xOEG | des1-8, 10E, 13Q, 19S, 32L | 13 |
| 14 | 1225 | C18d | gGlu-2xOEG | des1-8, 10E, 13Q, 25P, 32L | 14 |
| 15 | 1226 | C18d | gGlu-2xOEG | des1-8, 10E, 13Q, 14E, 25P, 32L | 15 |
| 16 | 1227 | C18d | gGlu-2xOEG | des1-8, 10E, 13Q, 19S, 25P, 32L | 16 |
| 17 | 1228 | C18d | gGlu-2xOEG | des1-8, 10E, 13Q, 14E, 19S, 25P, 32L | 17 |
| 18 | 1229 | C18d | gGlu-2xOEG | des1-8, 9E, 13Q, 14E, 32L | 18 |
| 19 | 1230 | C18d | gGlu-2xOEG | des1-8, 9E, 13Q, 14E, 19S, 32L | 19 |
| 20 | 1231 | C18d | gGlu-2xOEG | des1-8, 9E, 10Q, 13Q, 14E, 32L | 20 |
| 21 | 1232 | C18d | gGlu-2xOEG | des1-8, 13Q, 14E, 32L | 21 |
| 22 | 1233 | C18d | gGlu-2xOEG | des1-8, 13Q, 19S, 25P, 32L | 22 |
| 23 | 1236 | C18d | gGlu-2xOEG | des1-8, 9E, 10H, 13Q, 14E, 32L | 23 |
| 24 | 1237 | C18d | gGlu-2xOEG | des1-8, 10H, 13Q, 14E, 32L | 24 |
| 25 | 1240 | C18d | gGlu-2xOEG | des1-8, 10H, 13Q, 14E, 25P, 32L | 25 |
| 26 | 1241 | C18d | gGlu-2xOEG | des1-8, 10H, 13Q, 19S, 25P, 32L | 26 |
| 27 | 1242 | C18d | gGlu-2xOEG | des1-8, 10H, 13Q, 14E, 19S, 25P, 32L | 27 |
| 28 | 1274 | C18d | gGlu-2xOEG | des1-8, 10E, 13E, 19Q, 25P, 32L | 28 |
| 29 | 1287 | C18d | gGlu-2xOEG | des1-9, 10E, 13Q, 14E, 19S, 25P, 32L | 29 |
| 30 | 1288 | C18d | gGlu-2xOEG | des1-9, 10E, 13Q, 15E, 19S, 25P, 32L | 30 |
| 31 | 1289 | C18d | gGlu-2xOEG | des1-8, 10E, 13Q, 15E, 19S, 25P, 32L | 31 |
| 32 | 1290 | C18d | 2xgGlu-2xOEG | des1-8, 10E, 13Q, 19S, 25P, 32L | 16 |
| 33 | 1302 | C18d | gGlu-2xOEG | des1-8, 10H, 13Q, 15T, 19S, 25P, 32L | 32 |
| 34 | 1303 | C18d | gGlu-2xOEG | des1-8, 10H, 13Q, 15T, 17V, 19S, 25P, 32L | 33 |
| 35 | 1304 | C18d | gGlu-2xOEG | des1-8, 10H, 13Q, 14H, 15T, 19S, 25P, 32L | 34 |
| 36 | 1305 | C18d | gGlu-2xOEG | des1-8, 13Q, 14H, 15T, 19S, 25P, 32L | 35 |
| 37 | 1309 | C18d | gGlu-2xOEG | des1-8, 9E, 10H, 13Q, 25P, 32L | 36 |
| 38 | 1310 | C18d | gGlu-2xOEG | des1-8, 9E, 10H, 13Q, 19S, 25P, 32L | 37 |
| 39 | 1311 | C18d | gGlu-2xOEG | des1-8, 9E, 10H, 13Q, 17V, 19S, 25P, 32L | 38 |
| 40 | 1312 | C18d | gGlu-2xOEG | des1-8, 9E, 10H, 13Q, 15T, 17V, 19S, 25P, 32L | 39 |
| 41 | 1322 | C18d | gGlu-2xOEG | des1-8, 10H, 13Q, 14H, 15H, 27E, 32L | 40 |
| 42 | 1323 | C18d | 2xgGlu-2xOEG | des1-8, 10H, 13Q, 14H, 15H, 27E, 32L | 40 |
| 43 | 1324 | C18d | 2xgGlu-2xOEG | des1-8, 13Q, 14H, 15H, 19Q, 27E, 32L | 41 |
| 44 | 1338 | C18d | gGlu-2xOEG | des1-8, 10E, 13Q, 19S, 25P, 27E, 32L | 42 |
| 45 | 1339 | C18d | gGlu-2xOEG | des1-9, 10E, 13Q, 19S, 25P, 32L | 43 |
| 46 | 1340 | C18d | gGlu-2xOEG | des1-8, 13Q, 14H, 15H, 19Q, 32L | 44 |
| 47 | 1341 | C18d | gGlu-2xOEG | des1-8, 13Q, 14H, 15H, 19Q, 25P, 32L | 45 |
| 48 | 1345 | C18d | gGlu-2xOEG | des1-8, 10H, 13Q, 14H, 15H, 32L | 46 |
| 49 | 1346 | C18d | gGlu-2xOEG | des1-8, 10H, 13Q, 14H, 15H, 25P, 32L | 47 |
| 50 | 1347 | C18d | gGlu-2xOEG | des1-10, 13Q, 19H, 25P, 32L | 48 |
| 51 | 1348 | C18d | gGlu-2xOEG | des1-10, 13Q, 18H, 19S, 25P, 32L | 49 |
| 52 | 1350 | C18d | gGlu-2xOEG | des1-5, 10H, 13Q, 14H, 15T, 19S, 25P, 32L | 50 |
| 53 | 1351 | C18d | gGlu-2xOEG | des1-5, 10H, 13Q, 14H, 15T, 17V, 19S, 25P, 32L | 51 |
| 54 | 1352 | C18d | gGlu-3xOEG | des1-8, 10H, 13Q, 15T, 17V, 19S, 25P, 32L | 33 |
| 55 | 1353 | C18d | gGlu-3xOEG | des1-8, 9E, 10H, 13Q, 25P, 32L | 36 |
| 56 | 1354 | C18d | 2xgGlu-2xOEG | des1-5, 10H, 13Q, 15T, 17V, 19S, 25P, 32L | 52 |
| 57 | 1355 | C18d | gGlu-3xOEG | des1-8, 13Q, 19S, 25P, 32L | 22 |
| 58 | 1356 | C18d | 2xgGlu-3xOEG | des1-8, 13Q, 19S, 25P, 32L | 22 |

TABLE 1-continued

Summary of exemplified compounds Chem. 1-148

| Chem. No. | Compound ID | Protractor (Chem A) | Linker (Chem B-C) | CNP37 sequence modifications | SEQ ID |
|---|---|---|---|---|---|
| 59 | 1357 | C18d | 2xgGlu-3xOEG | des1-8, 9E, 10H, 13Q, 32L | 5 |
| 60 | 1359 | C18d | gGlu-2xOEG | des1-5, 9E, 10H, 13Q, 15T, 17V, 19S, 25P, 32L | 53 |
| 61 | 1360 | C18d | gGlu-2xOEG | des1-5, 9E, 10H, 13Q, 14H, 15T, 17V, 19S, 25P, 32L | 54 |
| 62 | 1375 | C18d | gGlu-4xOEG | des1-8, 10E, 13Q, 25P, 32L | 14 |
| 63 | 1376 | C20d | gGlu-2xOEG | des1-8, 10E, 13Q, 25P, 32L | 14 |
| 64 | 1377 | C18d | gGlu-2xOEG | des1-8, 10E, 13Q, 17G, 25P, 32L | 55 |
| 65 | 1378 | C18d | gGlu-2xOEG | des1-8, 10E, 13Q, 19S, 25P, 32L | 56 |
| 66 | 1379 | C18d | gGlu-2xOEG | 5Q, 8S, 10E, 13Q, 19S, 25P, 32L | 57 |
| 67 | 1380 | C18d | gGlu-2xOEG | 5E, 8S, 10E, 13Q, 19S, 25P, 32L | 58 |
| 68 | 1381 | C18d | gGlu-2xOEG | 5Q, 7H, 10H, 13Q, 14H, 15H, 17S, 19Q, 25P, 32L | 59 |
| 69 | 1382 | C18d | 3xgGlu-2xOEG | 5Q, 7H, 13Q, 19Q, 25P, 32L | 60 |
| 70 | 1383 | C18d | 2xgGlu-2xOEG | 5Q, 7H, 10H, 13Q, 15H, 17S, 19Q, 25P, 32L | 61 |
| 71 | 9384 | C18d | gGlu-2xOEG | des1-10, 13Q, 17S, 19S, 25P, 32L | 62 |
| 72 | 1385 | C18d | 4xgGlu | des1-5, 10E, 13Q, 25P, 32L | 63 |
| 73 | 1386 | C18d | 4xgGlu | des1-5, 13Q, 19S, 25P, 32L | 64 |
| 74 | 1387 | C18d | 4xgGlu-GGG | des1-8, 13Q, 19S, 25P, 32L | 65 |
| 75 | 1388 | C18d | 4xgGlu-GGG | des1-8, 13Q, 25P, 32L | 66 |
| 76 | 1389 | C18d | 4xgGlu | 5Q, 13Q, 19S, 25P, 32L | 67 |
| 77 | 1390 | C18d | 4xgGlu | 5Q, 10E, 13Q, 19S, 25P, 32L | 68 |
| 78 | 1391 | C18d | gGlu-4xOEG | des1-8, 10E, 13Q, 17G, 25P, 32L | 55 |
| 79 | 1392 | C18d | gGlu-4xOEG | des1-8, 10E, 13Q, 19S, 25P, 32L | 16 |
| 80 | 1393 | C18d | gGlu-4xOEG | des1-8, 10E, 13Q, 19Q, 25P, 32L | 69 |
| 81 | 1394 | C18d | gGlu-2xOEG | 5Q, 10E, 13Q, 19Q, 25P, 32L | 70 |
| 82 | 1395 | C18d | gGlu-2xOEG | 5Q, 7A, 10E, 13Q, 19Q, 25P, 32L | 71 |
| 83 | 1396 | C18d | 2xgGlu-2xOEG | 5Q, 10E, 13Q, 19Q, 25P, 32L | 70 |
| 84 | 1398 | C18d | 4xgGlu-2xOEG | 5Q, 8H, 13Q, 17S, 19Q, 25P, 32L | 72 |
| 85 | 1399 | C20d | 4xgGlu-2xOEG | 5Q, 8H, 13Q, 17S, 19Q, 25P, 32L | 72 |
| 86 | 1400 | C18d | 4xgGlu-2xOEG | 5Q, 7H, 13Q, 17G, 19Q, 25P, 32L | 73 |
| 87 | 1401 | C18d | 8xgGlu-2xOEG | 5Q, 13Q, 32L | 74 |
| 88 | 1402 | C18d | 6xgGlu-2xOEG | 5Q, 13Q, 19Q, 25P, 32L | 75 |
| 89 | 1403 | C18d | 6xgGlu-2xOEG | 5Q, 13Q, 17G, 19Q, 25P, 32L | 76 |
| 90 | 1404 | C18d | 6xgGlu-4xOEG | 5Q, 13Q, 19Q, 25P, 32L | 75 |
| 91 | 1405 | C20d | 6xgGlu-2xOEG | 5Q, 13Q, 19Q, 25P, 32L | 75 |
| 92 | 1406 | C18d | 5xgGlu-4xOEG | 5Q, 13Q, 19Q, 25P, 32L | 75 |
| 93 | 9407 | C18d | 5xgGlu-4xOEG | des1-5, 13Q, 19Q, 25P, 32L | 77 |
| 94 | 1419 | C18d | 2xgGlu-2xOEG | des1-5, 10H, 13Q, 14H, 15T, 17V, 19S, 25P, 32L | 51 |
| 95 | 1420 | C18d | 3xgGlu-2xOEG | des1-5, 10H, 13Q, 14H, 15T, 17V, 25P, 32L | 78 |
| 96 | 1421 | C18d | 3xgGlu-2xOEG | des1-5, 13Q, 15T, 17V, 19S, 25P, 32L | 79 |
| 97 | 1422 | C18d | 3xgGlu-2xOEG | des1-5, 10H, 13Q, 17V, 19S, 25P, 32L | 80 |
| 98 | 1423 | C18d | 3xgGlu-2xOEG | des1-5, 10H, 13Q, 15T, 17V, 25P, 32L | 81 |
| 99 | 1424 | C18d | 4xgGlu-2xOEG | des1-5, 13Q, 15T, 17V, 25P, 32L | 82 |
| 100 | 1425 | C18d | 2xgGlu-4xOEG | des1-8, 10H, 13Q, 15T, 17V, 25P, 32L | 83 |
| 101 | 1426 | Tetrazole-C18 | 2xgGlu-2xOEG | des1-5, 10H, 13Q, 15S, 19Q, 25P, 32L | 84 |
| 102 | 1431 | C18d | gGlu-4xOEG | des1-8, 10E, 13Q, 17G, 19H, 25P, 32L | 85 |
| 103 | 1432 | C18d | 2xgGlu-4xOEG | des1-5, 10E, 13Q, 14H, 17G, 19Q, 25P, 32L | 86 |
| 104 | 1434 | C18d | 2xgGlu-4xOEG | des1-8, 10H, 13Q, 17G, 19Q, 25P, 32L | 87 |
| 105 | 9435 | C18d | 2xgGlu-4xOEG | des1-8, 13Q, 17G, 19Q, 25P, 32L | 88 |
| 106 | 1436 | C18d | 2xgGlu-4xOEG | des1-8, 13Q, 17V, 19Q, 25P, 32L | 89 |
| 107 | 1437 | C18d | 2xgGlu-4xOEG | des1-8, 10H, 13Q, 17V, 19Q, 25P, 32L | 90 |
| 108 | 1448 | C18d | 4xgGlu | 5Q, 10E, 13Q, 25P, 32L | 91 |
| 109 | 1449 | C18d | 3xgGlu-2xOEG | des1-5, 10H, 13Q, 14H, 15T, 17V, 19S, 25P, 32L | 51 |

TABLE 1-continued

Summary of exemplified compounds Chem. 1-148

| Chem. No. | Compound ID | Protractor (Chem A) | Linker (Chem B-C) | CNP37 sequence modifications | SEQ ID |
|---|---|---|---|---|---|
| 110 | 1450 | C18d | 3xgGlu-2xOEG | des1-5, 10H, 13Q, 15T, 17V, 19S, 25P, 32L | 52 |
| 111 | 1451 | C18d | 3xgGlu-2xOEG | des1-5, 10H, 13Q, 17V, 19S, 25P, 27E, 32L | 92 |
| 112 | 1452 | C18d | 5xgGlu-3xOEG | des1-5, 13Q, 19Q, 25P, 32L | 77 |
| 113 | 1453 | C18d | 5xgGlu-2xOEG | des1-5, 13Q, 19Q, 25P, 32L | 77 |
| 114 | 1454 | C18d | 4xgGlu-4xOEG | des1-5, 13Q, 19Q, 25P, 32L | 77 |
| 115 | 1455 | C18d | 4xgGlu-3xOEG | des1-5, 13Q, 19Q, 25P, 32L | 77 |
| 116 | 1456 | C18d | 4xgGlu-2xOEG | des1-5, 13Q, 19Q, 25P, 32L | 77 |
| 117 | 1457 | C18d | gGlu-2xOEG | des1-10, 13Q, 19Q, 25P, 32L | 93 |
| 118 | 1458 | C18d | gGlu-2xOEG | des1-10, 13Q, 17S, 19Q, 25P, 32L | 94 |
| 119 | 1459 | C18d | 4xgGlu-2xOEG | des1-5, 13Q, 17S, 19Q, 25P, 32L | 95 |
| 120 | 1460 | C18d | 6xgGlu-2xOEG | des1-5, 13Q, 25P, 32L | 96 |
| 121 | 1461 | C18d | 2xgGlu-4xOEG | des1-8, 10H, 13Q, 19Q, 25P, 32L | 97 |
| 122 | 1462 | C18d | 5xgGlu-4xOEG | des1-5, 13Q, 25P, 32L | 96 |
| 123 | 1463 | C18d | 5xgGlu-4xOEG | des1-5, 13Q, 19Q, 32L | 98 |
| 124 | 1464 | C18d | 5xgGlu-4xOEG | des1-5, 19Q, 25P, 32L | 99 |
| 125 | 1465 | C18d | 5xgGlu-4xOEG | des1-5, 13Q, 19Q, 25P | 100 |
| 126 | 1470 | C18d | 5xgGlu-2xOEG | des1-5, 13Q, 25P, 32L | 96 |
| 127 | 1471 | C18d | 5xgGlu-2xOEG | 5Q, 13Q, 19Q, 25P, 32L | 75 |
| 128 | 1472 | C18d | 4xgGlu-2xOEG | 5Q, 13Q, 19Q, 25P, 32L | 75 |
| 129 | 1473 | C18d | 4xgGlu-2xOEG | 5Q, 13Q, 19S, 25P, 32L | 67 |
| 130 | 1474 | C18d | 5xgGlu-2xOEG | 5Q, 13Q, 25P, 32L | 101 |
| 131 | 1475 | C18d | 5xGlu-4xOEG | des1-5, 13Q, 19Q, 25P, 32L | 77 |
| 132 | 1476 | C18d | 4x(Glu-Gly)-Glu-2xOEG | des1-5, 13Q, 19Q, 25P, 32L | 77 |
| 133 | 1477 | C18d | 5xgGlu-4xOEG | des1-5, 13Q, 19Q, 25P, 27E, 32L | 102 |
| 134 | 1478 | C18d | 2xgGlu-4xOEG | des1-8, 13Q, 19Q, 25P, 32L | 103 |
| 135 | 9480 | C18d | 3xgGlu-4xOEG | des1-8, 13Q, 19Q, 25P, 32L | 103 |
| 136 | 1481 | C18d | 3xGlu-4xOEG | des1-8, 13Q, 19Q, 25P, 32L | 103 |
| 137 | 9482 | C18d | 5xgGlu | 5Q, 13Q, 19S, 25P, 32L | 67 |
| 138 | 9483 | C18d | 4xgGlu | 5Q, 13Q, 19S, 25P, 27E, 32L | 104 |
| 139 | 1484 | C18d | gGlu-2xOEG | des1-10, 13Q, 19Q, 25P, 32L | 105 |
| 140 | 1486 | C18d | gGlu-2xOEG | des1-10, 13Q, 17S, 19Q, 25P, 27E, 32L | 106 |
| 141 | 1487 | C18d | gGlu-2xOEG | des1-10, 13Q, 19Q, 25P, 32L | 107 |
| 142 | 1488 | C18d | gGlu-3xGQAP | des1-10, 13Q, 19Q, 25P, 32L | 107 |
| 143 | 1489 | C18d | 2xgGlu-4xOEG | des1-8, 13Q, 17G, 19Q, 25P, 27E, 32L | 108 |
| 144 | 1493 | C18d | 2xgGlu-4xOEG | des1-8, 13Q, 19Q, 25P, 27E, 32L | 109 |
| 145 | 1511 | C18d | Glu-2xOEG | des1-10, 13Q, 17S, 19Q, 25P, 32L | 62 |
| 146 | 1512 | C18d | 2xGlu-4xOEG | des1-8, 13Q, 17G, 19Q, 25P, 32L | 88 |
| 147 | 1513 | C18d | 5xGlu | 5Q, 13Q, 19S, 25P, 32L | 110 |
| 148 | 1514 | C18d | 4xGlu | 5Q, 13Q, 19S, 25P, 27E, 32L | 111 |
| 149 | 1265 | C18d | DgGlu-2xOEG | des1-5, 6a, 7r, 8k, 9y, 10k, 12a, 13q, 14k, 15k, 17l, 18s, 19k, 21c, 22f, 24l, 25k, 26l, 27e, 28r, 29i, 31s, 32l, 33s, 35l, 37c | 233 |
| 150 | 0106 |  |  | -2P, -1G | 234 |
| 151 | 0089 | C18d | gGlu-2xOEG | des1-15 | 1 |
| 152 | 0230 | C18d | gGlu-2xOEG | GQAPGQAPGQAPGQAPGQAP, des1-15 | 235 |
| 153 | 0231 | C18d | gGlu-8xOEG | des1-15 | 1 |

Chem. 1; Compound ID 0065; SEQ ID NO: 1 hCNP22

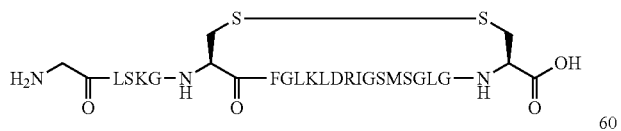

Molecular weight: 2197.6008. LCMS34: m/3 calcd: 733.5336; m/3 found: 733.7000; m/4 calcd: 550.4002; m/4 found: 550.2800.

Chem. 2; Compound ID 1510; SEQ ID NO: 2
hCNP37

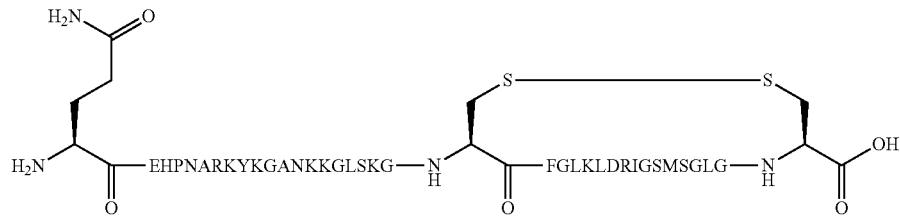

Molecular weight: 3948.5589. UPLC107UPLC107: m/3 calcd: 1317.1863

Chem. 3; Compound ID 0312; SEQ ID NO: 3

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), des1-4, 5Q, 13Q, 32Nle]-hCNP37

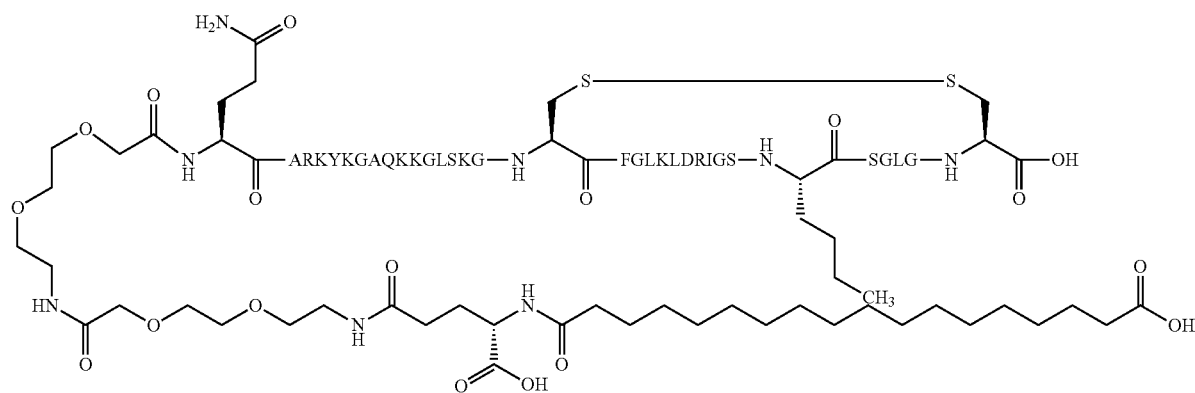

Molecular weight: 4182.9477. LCMS34LCMS34: m/3 calcd: 1395.3159; m/3 found: 1395.1200; m/4 calcd: 1046.7369; m/4 found: 1046.600.

Chem. 4; Compound ID 0776; SEQ ID NO: 4

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), des1-5, 13O, 27E, 32L]-hCNP37

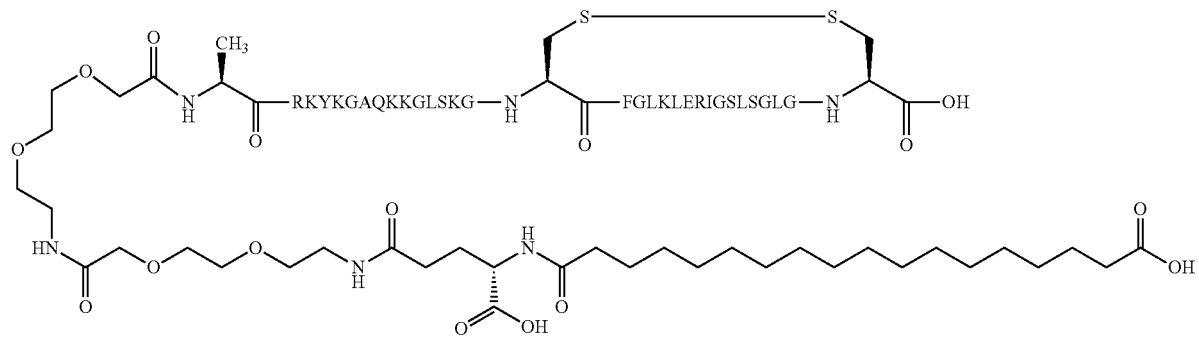

Molecular weight: 4068.8451. LCMS34LCMS34: m/3 calcd: 1357.2817; m/3 found: 1357.2694; m/4 calcd: 1018.2113; m/4 found: 1018.2089.

Chem. 5; Compound ID 1235; SEQ ID NO: 5

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), des1-8, 9E, 10H, 13Q, 32L]-hCNP37

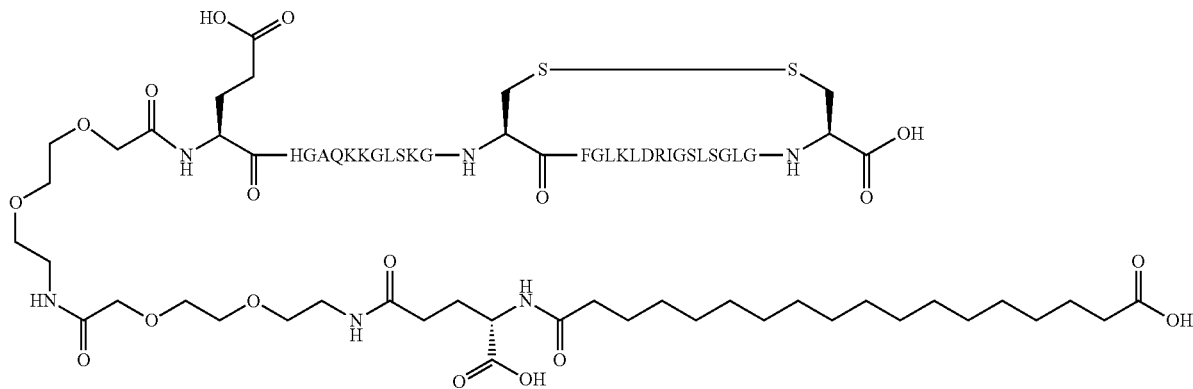

Molecular weight: 3674.2904. UPLC107: m/3 calcd: 1225.7635; m/3 found: 1225.5700.

Chem. 6; Compound ID 0262; SEQ ID NO: 6

[N-terminal([(4S)-4-carboxy-4-[[(4S)-4-carboxy-4-[[(4S)-4-carboxy-4-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]butanoyl]amino]butanoyl]amino]butanoyl]), des1-8, 32Nle]-hCNP37

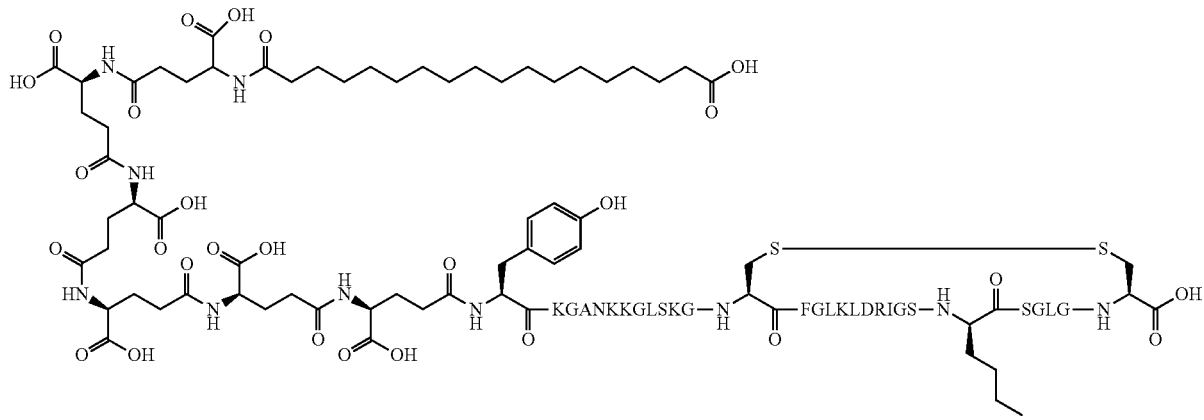

Molecular weight: 4040.6131. LCMS34LCMS34: m/3 calcd: 1347.8710; m/3 found: 1347.7200; m/4 calcd: 1011.1533; m/4 found: 1010.7900.

Chem. 7; Compound ID 0296; SEQ ID NO: 7

[N-terminal([(4S)-4-carboxy-4-[[(4S)-4-carboxy-4-[[(4S)-4-carboxy-4-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]butanoyl]amino]butanoyl]amino]butanoyl]), des1-4, 15S, 19S, 32Nle]-hCNP37

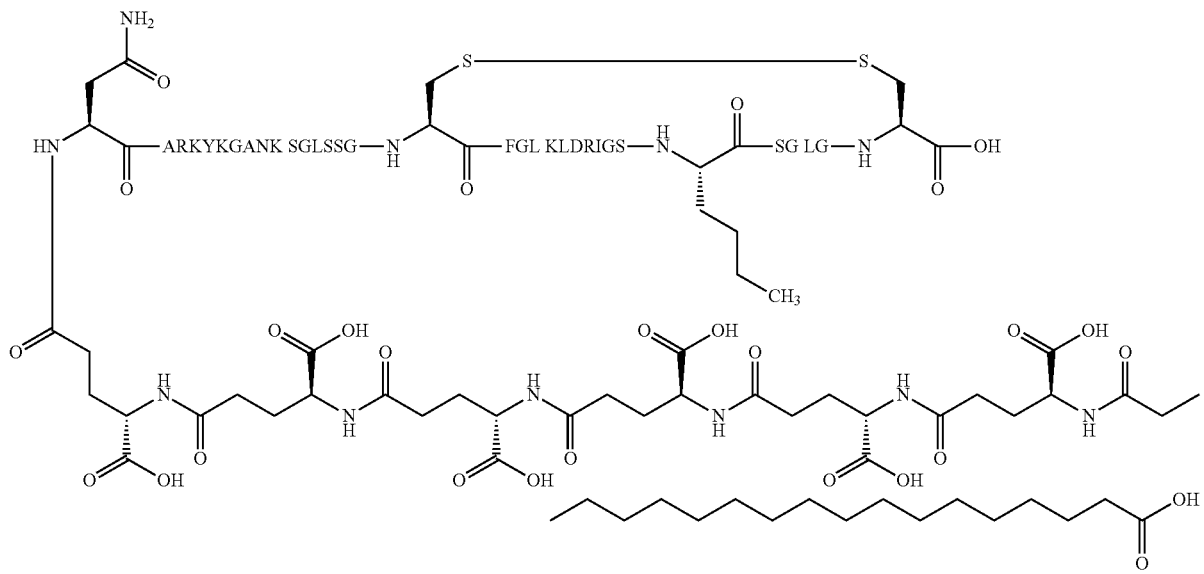

Molecular weight: 4427.9616. LCMS34LCMS34: m/3 calcd: 1476.9872; m/3 found: 1476.9200; m/4 calcd: 1107.9904; m/4 found: 1108.1700.

Chem. 8; Compound ID 0313; SEQ ID NO: 8

[N-terminal([(4S)-4-carboxy-4-[[(4S)-4-carboxy-4-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]butanoyl]amino]butanoyl]), des1-10, 32Nle]-hCNP37

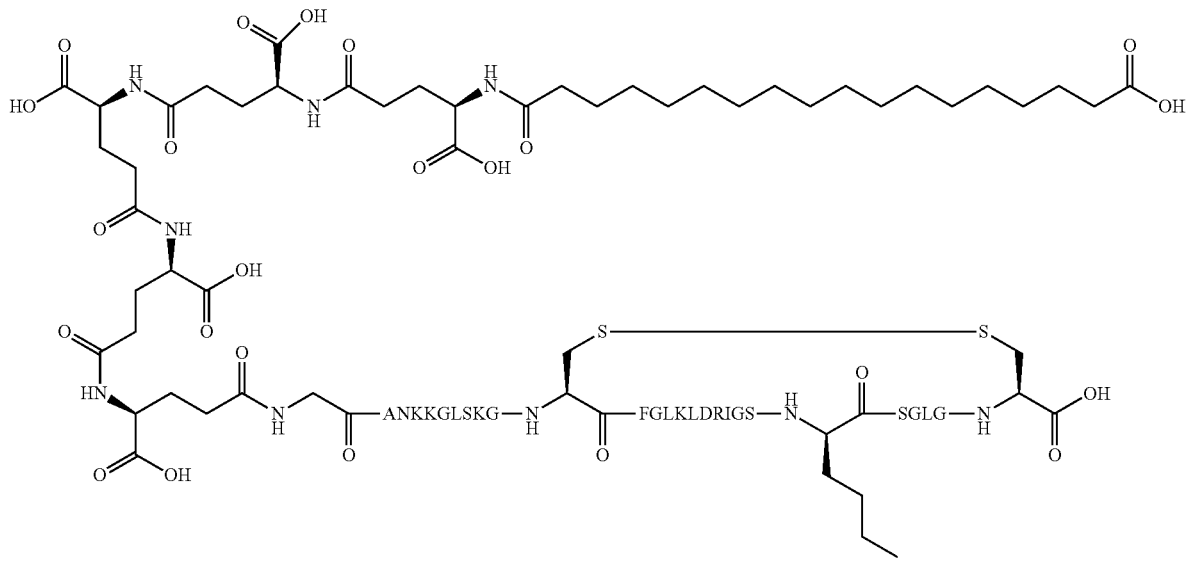

Molecular weight: 3620.1536. LCMS34: m/3 calcd: 1207.7179; m/3 found: 1207.6400; m/4.
calcd: 906.0384; m/4 found: 905.9900.
Chem. 9; Compound ID 0334; SEQ ID NO: 9

[N-terminal([[(4S)-4-carboxy-4-[[(4S)-4-carboxy-4-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]butanoyl]amino]butanoyl]), des1-10, 13Q, 32Nle]-hCNP37

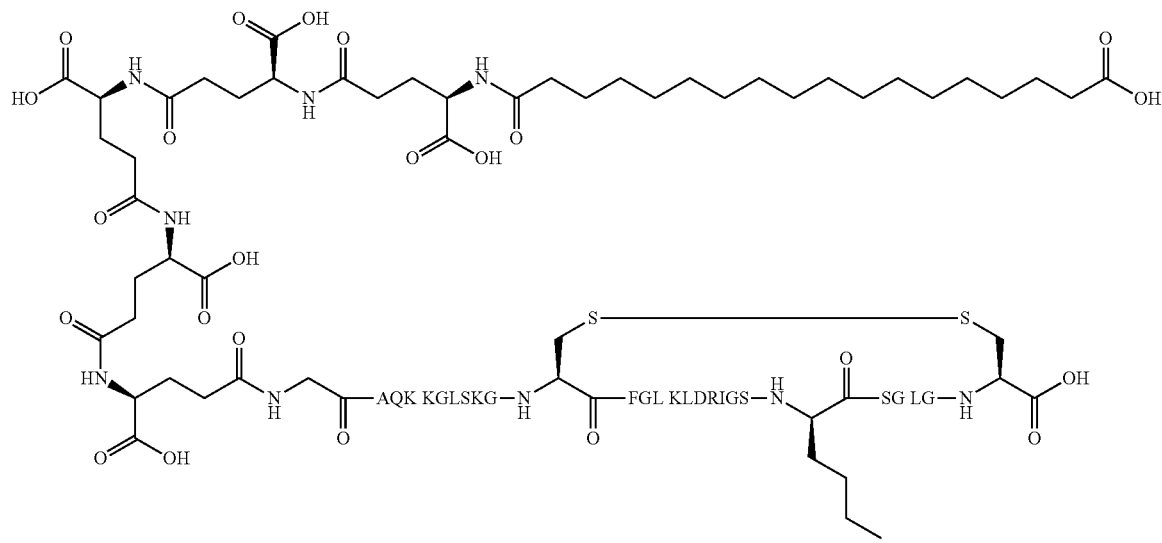

Molecular weight: 3634.1801. LCMS34: m/3 calcd: 1212.3934; m/3 found: 1212.3100; m/4.
calcd: 909.5450; m/4 found: 909.2400.
Chem. 10; Compound ID 1221; SEQ ID NO: 10

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), des1-8, 10E, 13Q, 32L]-hCNP37

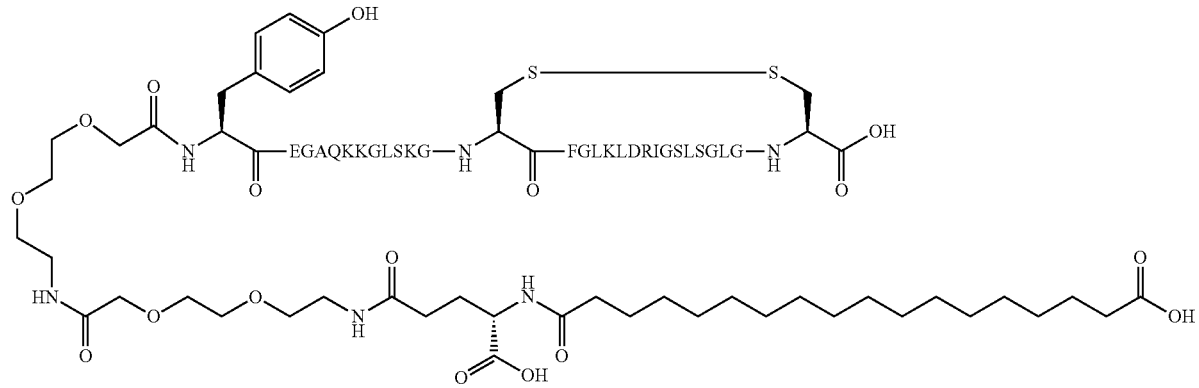

Molecular weight: 3700.3243. UPLC107: m/3 calcd: 1234.4414; m/3 found: 1234.2700.
Chem. 11; Compound ID 1222; SEQ ID NO: 11

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), des1-8, 9E, 10E, 13Q, 32L]-hCNP37

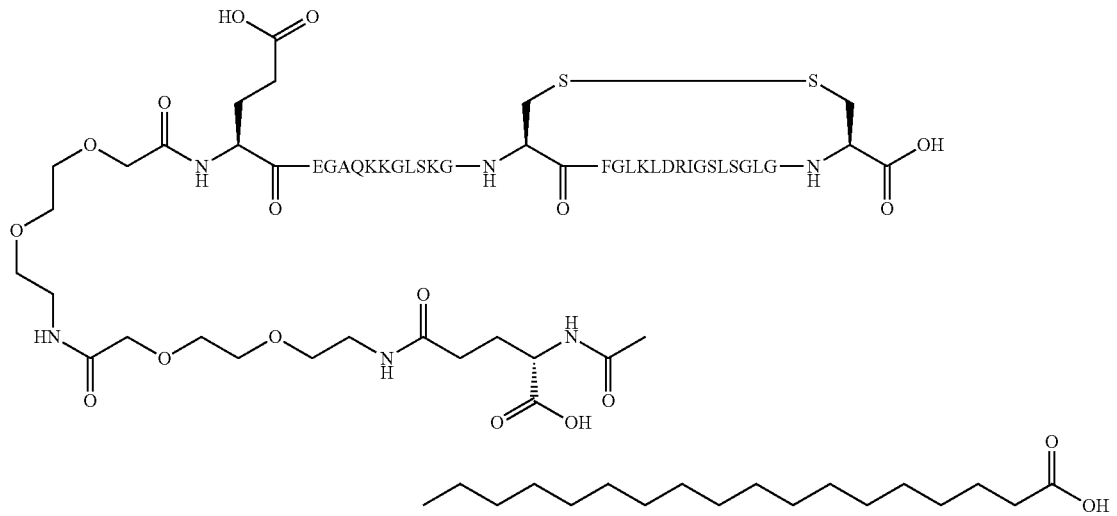

Molecular weight: 3666.2651. LCMS34: m/3 calcd: 1223.0884; m/3 found: 1222.9000.
Chem. 12; Compound ID 1223; SEQ ID NO: 12

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), des1-8, 10E, 13Q, 14E, 32L]-hCNP37

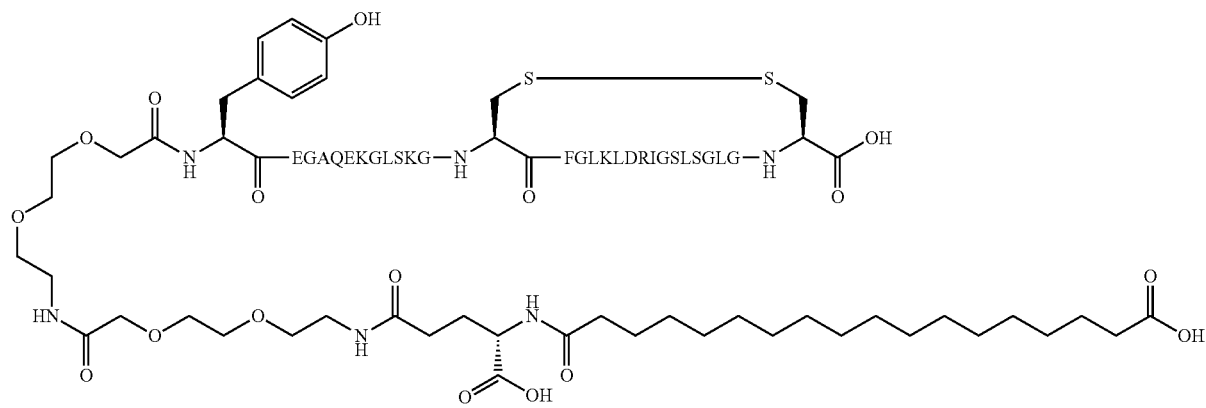

Molecular weight: 3701.266. LCMS34: m/3 calcd: 1234.7553; m/3 found: 1234.5800.
Chem. 13; Compound ID 1224; SEQ ID NO: 13

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), des1-8, 10E, 13Q, 19S, 32L]-hCNP37

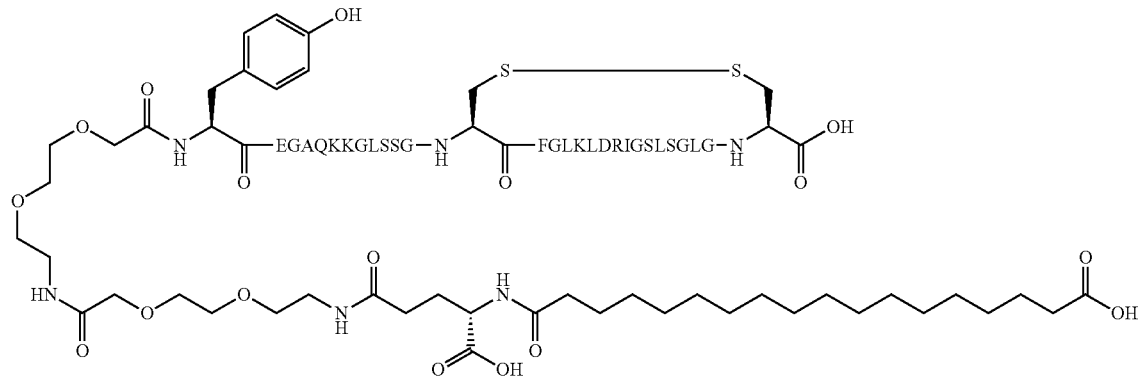

Molecular weight: 3659.2294. LCMS34: m/3 calcd: 1220.7431; m/3 found: 1220.3212; m/4 calcd: 915.8074; m/4 found: 915.7400.

Chem. 14; Compound ID 1225; SEQ ID NO: 14

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), des1-8, 10E, 13Q, 25P, 32L]-hCNP37

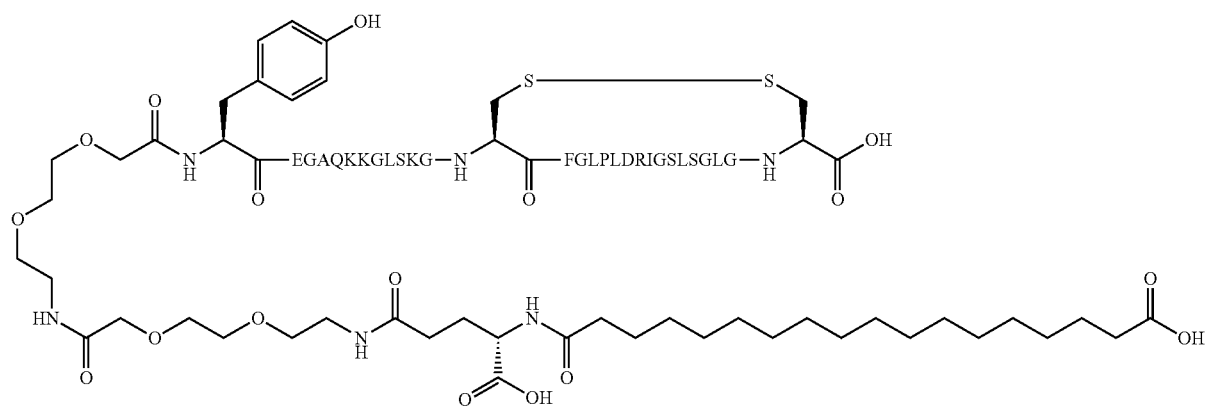

Molecular weight: 3669.2672. UPLC107: m/3 calcd: 1224.0891; m/3 found: 1223.9400.

Chem. 15; Compound ID 1226; SEQ ID NO: 15

[N-terminal([2-[2-[2-[[2-[2-[2-[[(4S)-4-carboxy-4-
(17-carboxyheptadecanoylamino)butanoyl]amino]
ethoxy]ethoxy]acetyl]amino]ethoxy]ethoxy]acet
yl]), des1-8, 10E, 13Q, 14E, 25P, 32L]-hCNP37

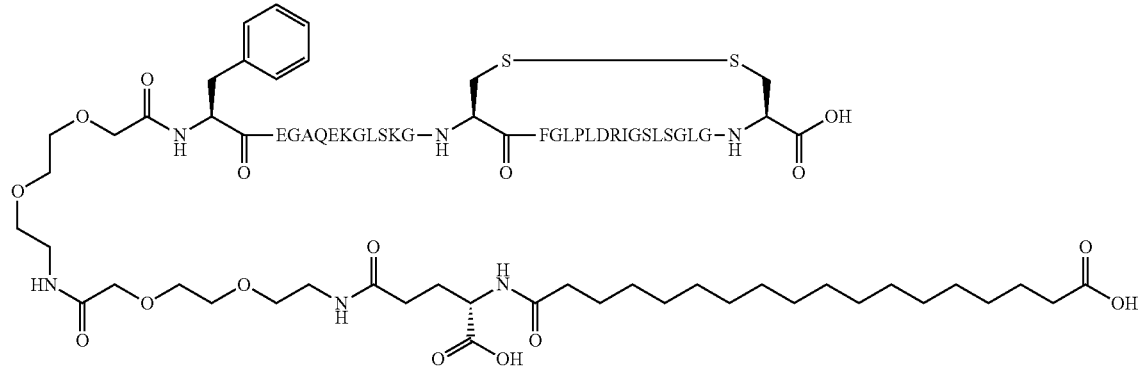

Molecular weight: 3670.2089. UPLC107: m/3 calcd: 1224.4030; m/3 found: 1224.2000.
Chem. 16; Compound ID 1227; SEQ ID NO: 16

[N-terminal([2-[2-[2-[[2-[2-[2-[[(4S)-4-carboxy-4-
(17-carboxyheptadecanoylamino)butanoyl]amino]
ethoxy]ethoxy]acetyl]amino]ethoxy]ethoxy]acet
yl]), des1-8, 10E, 13Q, 19S, 25P, 32L]-hCNP37

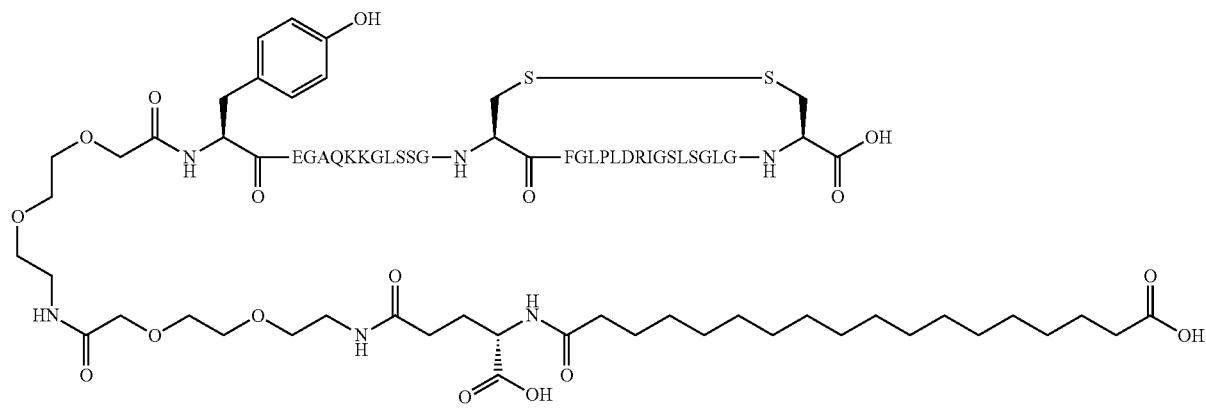

Molecular weight: 3628.1723. LCMS34: m/3 calcd: 1210.3908; m/3 found: 1210.4200; m/4.
calcd: 908.0431; m/4 found: 908.0900.
Chem. 17; Compound ID 1228; SEQ ID NO: 17

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), des1-8, 10E, 13Q, 14E, 19S, 25P, 32L]-hCNP37

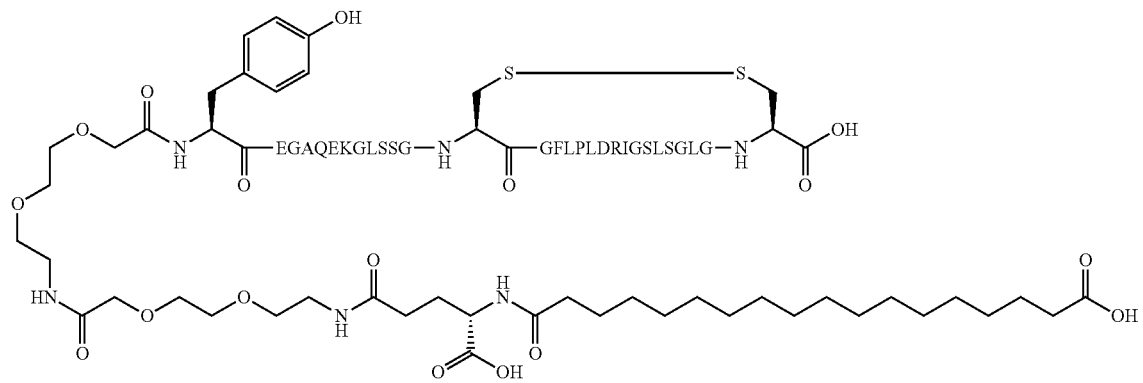

Molecular weight: 3629.114. LCMS34: m/3 calcd: 1210.7047; m/3 found: 1210.5790; m/4. calcd: 908.2785; m/4 found: 908.1400.

Chem. 18; Compound ID 1229; SEQ ID NO: 18

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), des1-8, 9E, 13Q, 14E, 32L]-hCNP37

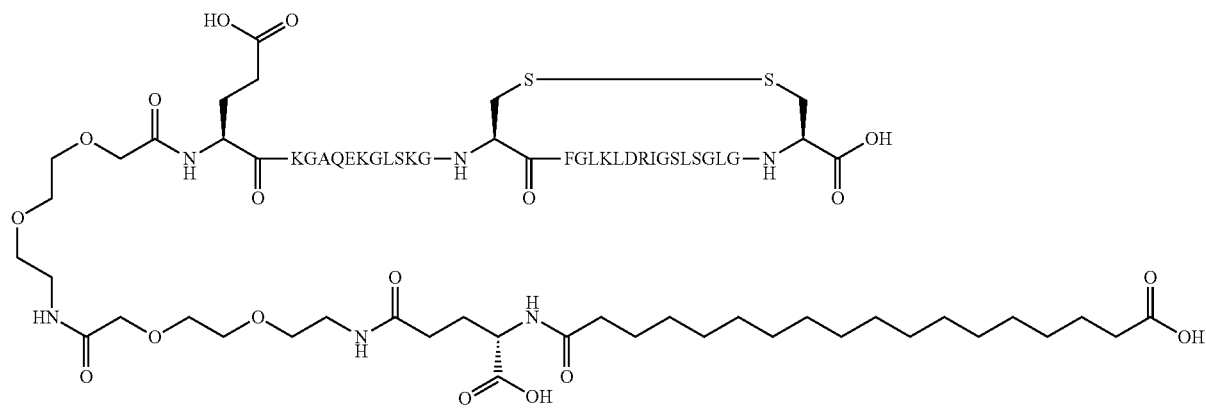

Molecular weight: 3666.2651. UPLC107: m/3 calcd: 1223.0884; m/3 found: 1222.9300.

Chem. 19; Compound ID 1230; SEQ ID NO: 19

[N-terminal([2-[2-[2-[[2-[2-[2-[[(4S)-4-carboxy-4-
(17-carboxyheptadecanoylamino)butanoyl]amino]
ethoxy]ethoxy]acetyl]amino]ethoxy]ethoxy]acet
yl]), des1-8, 9E, 13Q, 14E, 19S, 32L]-hCNP37

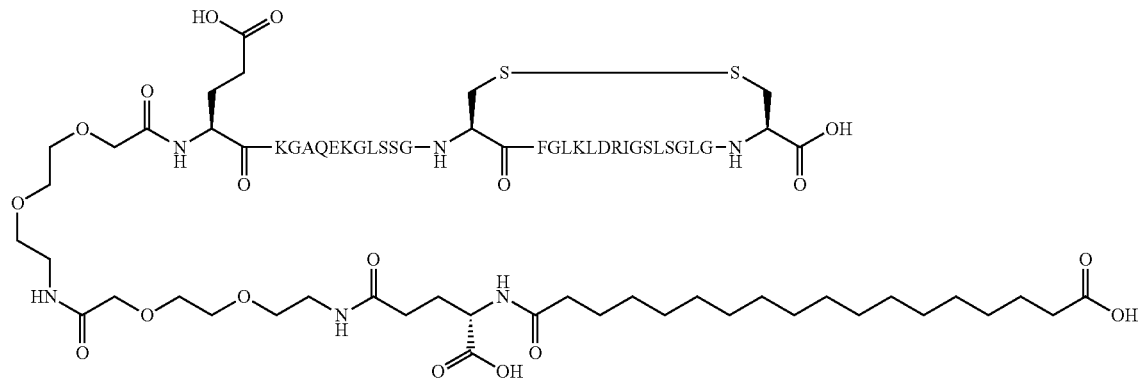

Molecular weight: 3625.1701. UPLC107: m/3 calcd: 1209.3900; m/3 found: 1209.2800.

Chem. 20; Compound ID 1231; SEQ ID NO: 20

[N-terminal([2-[2-[2-[[2-[2-[2-[[(4S)-4-carboxy-4-
(17-carboxyheptadecanoylamino)butanoyl]amino]
ethoxy]ethoxy]acetyl]amino]ethoxy]ethoxy]acet
yl]), des1-8, 9E, 10Q, 13Q, 14E, 32L]-hCNP37

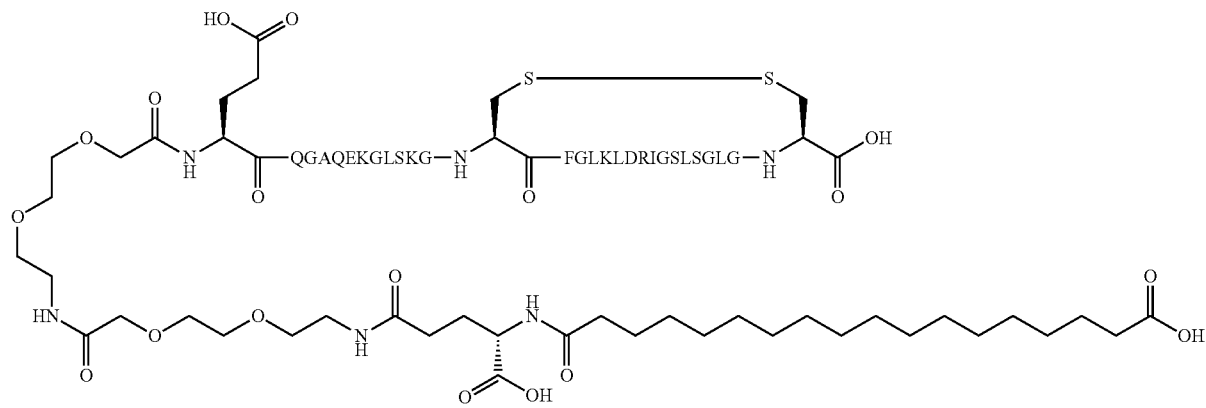

Molecular weight: 3666.222. UPLC107: m/3 calcd: 1223.0740; m/3 found: 1222.9700.

Chem. 21; Compound ID 1232; SEQ ID NO: 21

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), des1-8, 13Q, 14E, 32L]-hCNP37

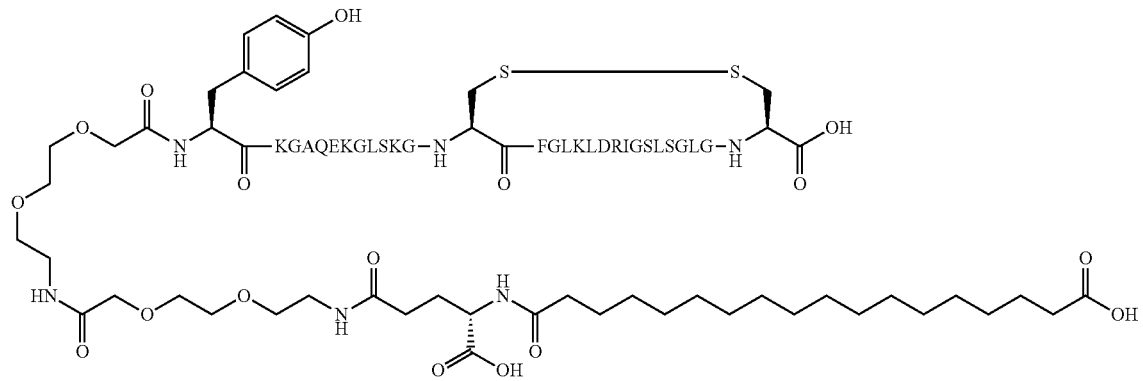

Molecular weight: 3700.3243. UPLC107: m/3 calcd: 1234.4414; m/3 found: 1234.2100.
Chem. 22; Compound ID 1233; SEQ ID NO: 22

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), des1-8, 13Q, 19S, 25P, 32L]-hCNP37

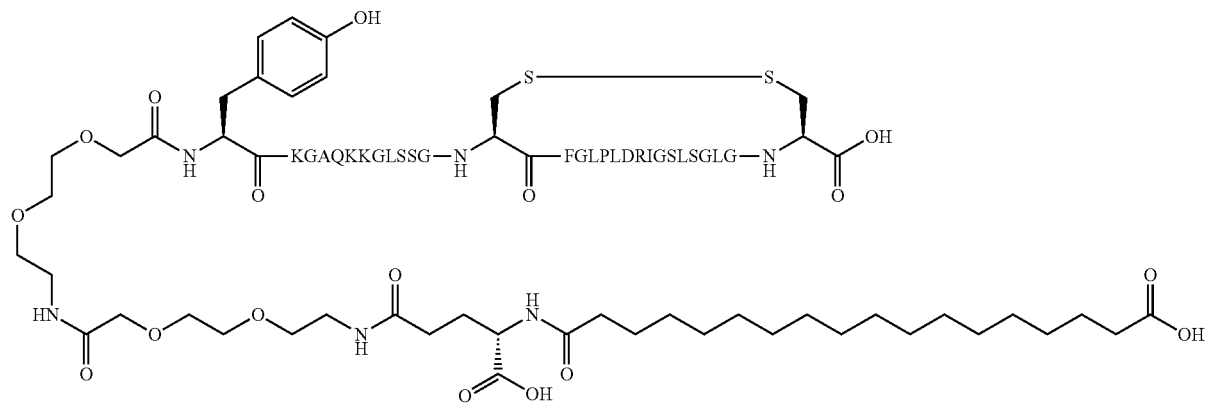

Molecular weight: 3627.2306. UPLC107: m/3 calcd: 1210.0769; m/3 found: 1209.9600.
Chem. 23; Compound ID 1236; SEQ ID NO: 23

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), des1-8, 9E, 10H, 13Q, 14E, 32L]-hCNP37

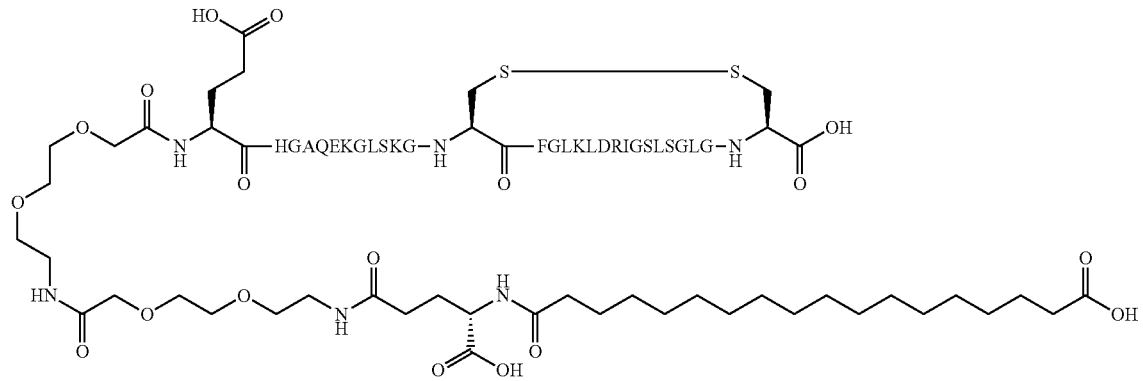

Molecular weight: 3675.2321. LCMS34: m/3 calcd: 1226.0774; m/3 found: 1225.8900.

Chem. 24; Compound ID 1237; SEQ ID NO: 24

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), des1-8, 10H, 13Q, 14E, 32L]-hCNP37

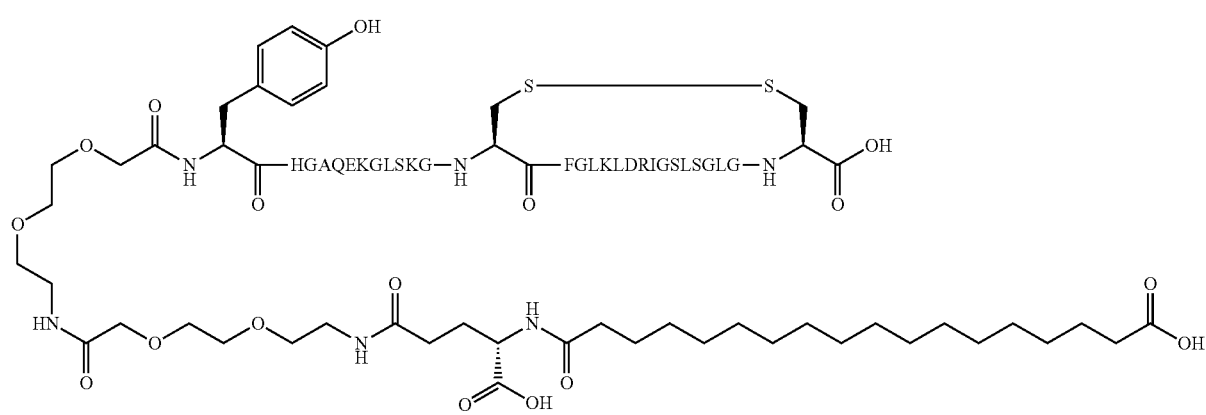

Molecular weight: 3709.2913. UPLC107: m/3 calcd: 1237.4304; m/3 found: 1237.3400.

Chem. 25; Compound ID 1240; SEQ ID NO: 25

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), des1-8, 10H, 13Q, 14E, 25P, 32L]-hCNP37

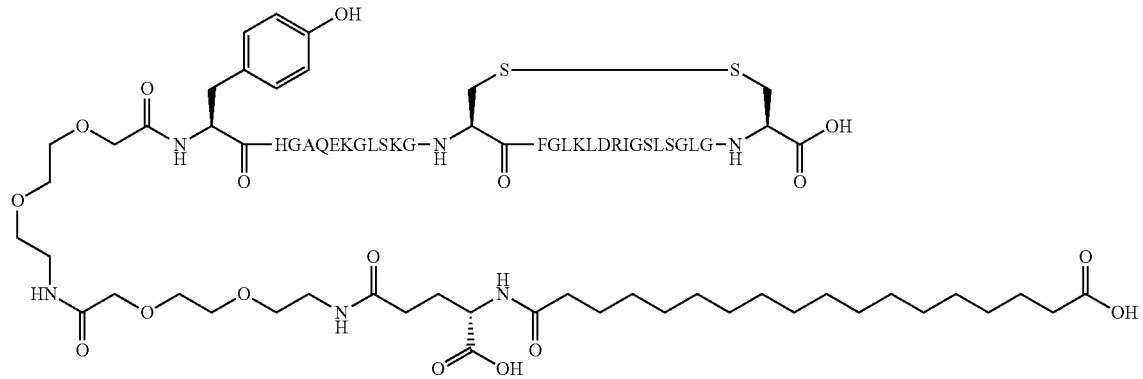

Molecular weight: 3678.2342. UPLC107: m/3 calcd: 1227.0781; m/3 found: 1226.9500.

Chem. 26; Compound ID 1241; SEQ ID NO: 26

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), des1-8, 10H, 13Q, 19S, 25P, 32L]-hCNP37

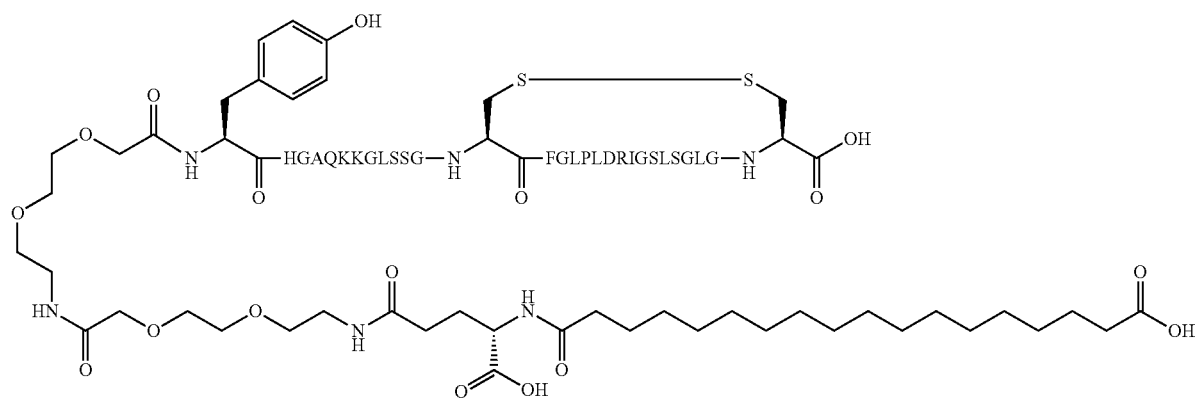

Molecular weight: 3636.1976. LCMS34: m/3 calcd: 1213.0659; m/3 found: 1213.1011; m/4.

calcd: 910.0494; m/4 found: 910.0900.

Chem. 27; Compound ID 1242; SEQ ID NO: 27

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), des1-8, 10H, 13Q, 14E, 19S, 25P, 32L]-hCNP37

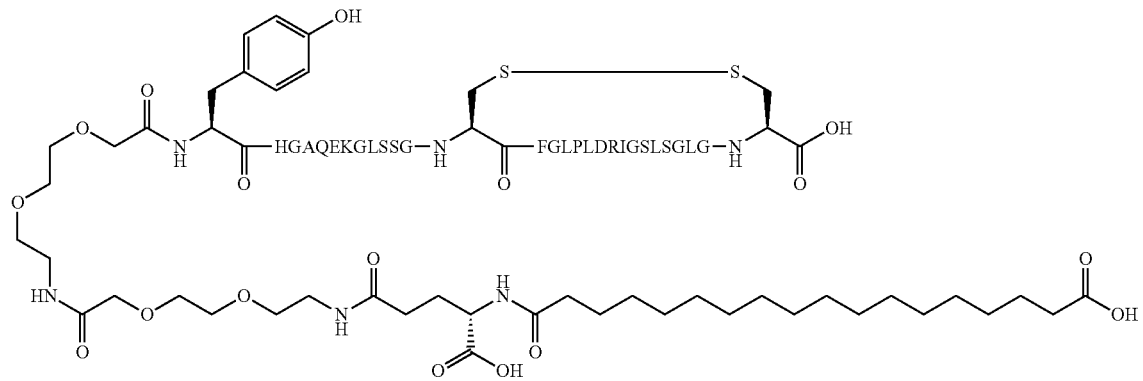

Molecular weight: 3637.1393. UPLC107: m/3 calcd: 1213.3798; m/3 found: 1213.2100.

Chem. 28; Compound ID 1274; SEQ ID NO: 28

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), des1-8, 10E, 13E, 19Q, 25P, 32L]-hCNP37

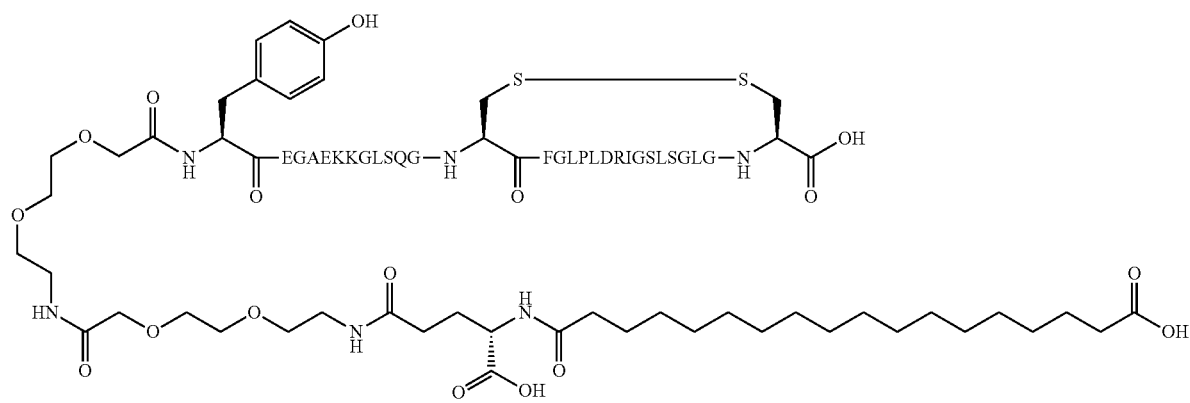

Molecular weight: 3670.2089. LCMS34: m/3 calcd: 1224.4030; m/3 found: 1224.3150; m/4. calcd: 918.5522; m/4 found: 918.4840.

Chem. 29; Compound ID 1287; SEQ ID NO: 29

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), des1-9, 10E, 13Q, 14E, 19S, 25P, 32L]-hCNP37

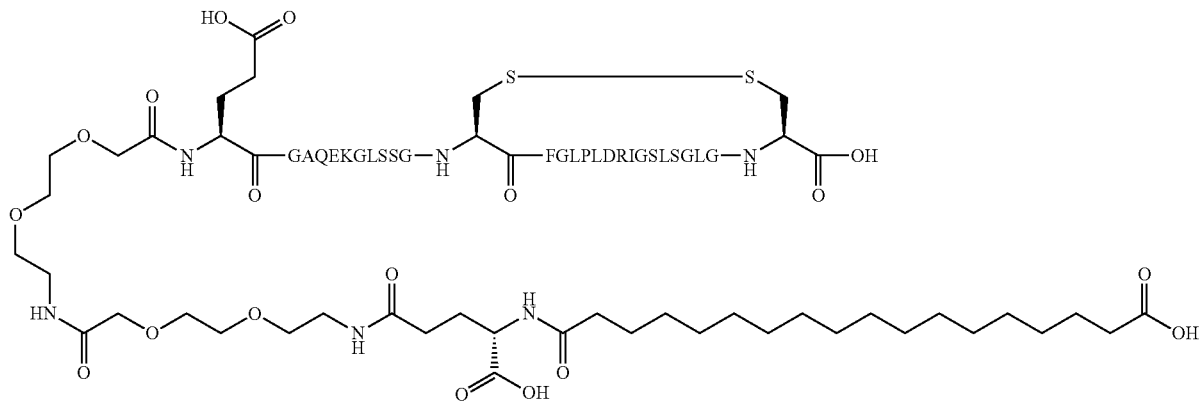

Molecular weight: 3465.9407. LCMS34: m/3 calcd: 1156.3136; m/3 found: 1156.5100; m/4.
calcd: 867.4852; m/4 found: 867.3800.

Chem. 30; Compound ID 1288; SEQ ID NO: 30

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), des1-9, 10E, 13Q, 15E, 19S, 25P, 32L]-hCNP37

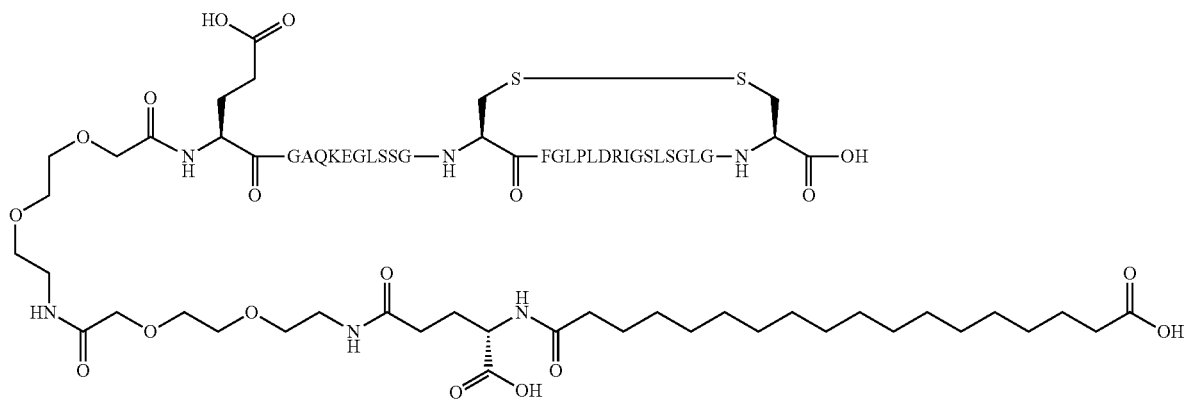

Molecular weight: 3465.9407. LCMS34: m/3 calcd: 1156.3136; m/3 found: 1155.8400; m/4.
calcd: 867.4852; m/4 found: 867.3800.

Chem. 31; Compound ID 1289; SEQ ID NO: 31

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), des1-8, 10E, 13Q, 15E, 19S, 25P, 32L]-hCNP37

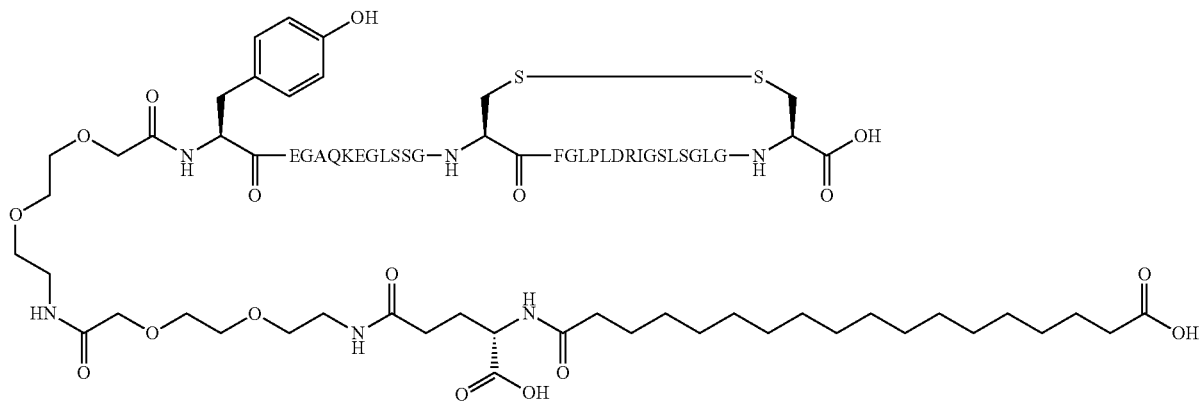

Molecular weight: 3629.114. LCMS34: m/3 calcd: 1210.7047; m/3 found: 1210.5500; m/4.
calcd: 908.2785; m/4 found: 908.1600.
Chem. 32; Compound ID 1290; SEQ ID NO: 16

[N-terminal([2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]), des1-8, 10E, 13Q, 19S, 25P, 32L]-hCNP37

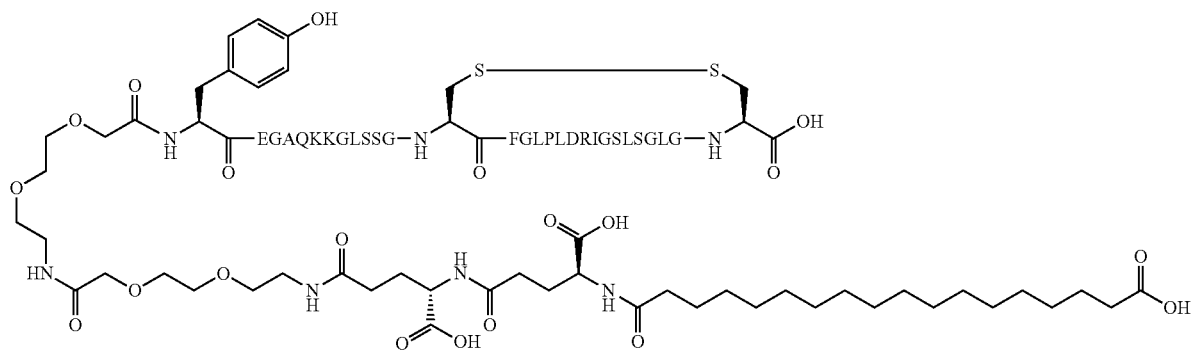

Molecular weight: 3757.2862. LCMS34: m/3 calcd: 1253.4287; m/3 found: 1253.5700; m/4.
calcd: 940.3216; m/4 found: 940.1700.
Chem. 33; Compound ID 1302; SEQ ID NO: 32

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), des1-8, 10H, 13Q, 15T, 19S, 25P, 32L]-hCNP37

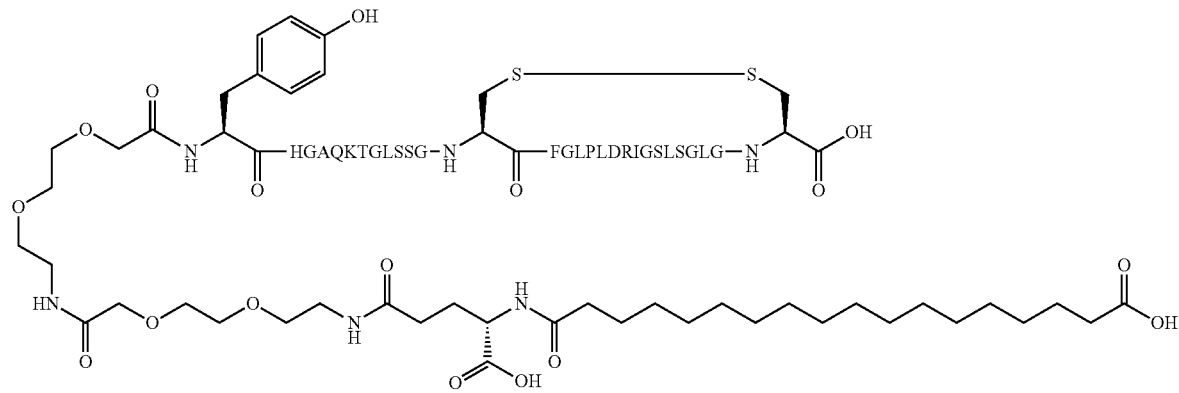

Molecular weight: 3609.1292. LCMS34: m/3 calcd: 1204.0431; m/3 found: 1203.7523; m/4.
calcd: 903.2823; m/4 found: 903.3355.

Chem. 34; Compound ID 1303; SEQ ID NO: 33

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), des1-8, 10H, 13Q, 15T, 17V, 19S, 25P, 32L]-hCNP37

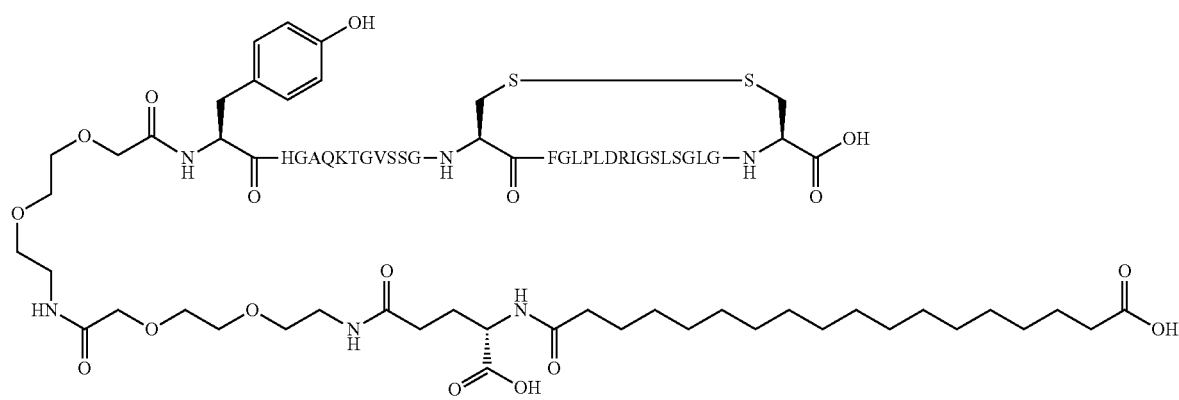

Molecular weight: 3595.1026. LCMS34: m/3 calcd: 1199.3675; m/3 found: 1199.3210; m/4.
calcd: 899.7757; m/4 found: 899.7320.

Chem. 35; Compound ID 1304; SEQ ID NO: 34

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), des1-8, 10H, 13Q, 14H, 15T, 19S, 25P, 32L]-hCNP37

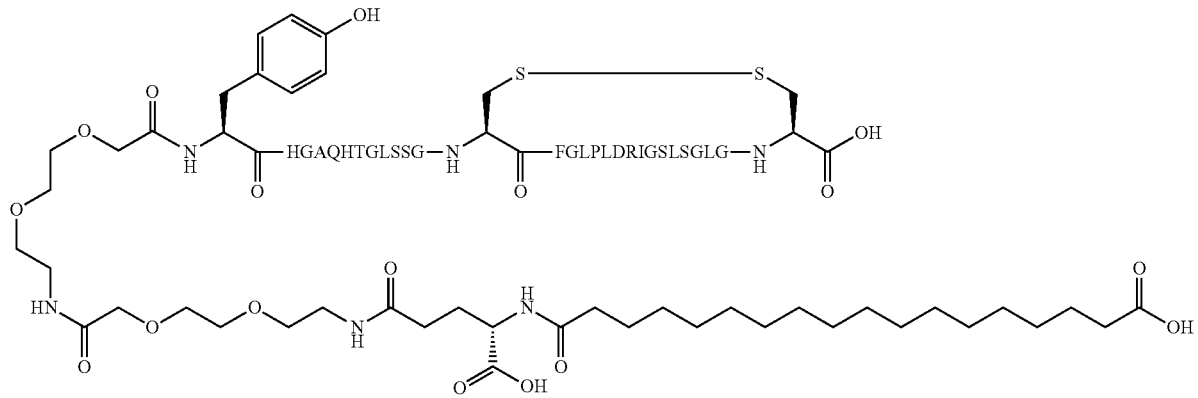

Molecular weight: 3618.0962. LCMS34: m/3 calcd: 1207.0321; m/3 found: 1206.7366; m/4.
calcd: 905.5241; m/4 found: 905.5760.
Chem. 36; Compound ID 1305; SEQ ID NO: 35

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), des1-8, 13Q, 14H, 15T, 19S, 25P, 32L]-hCNP37

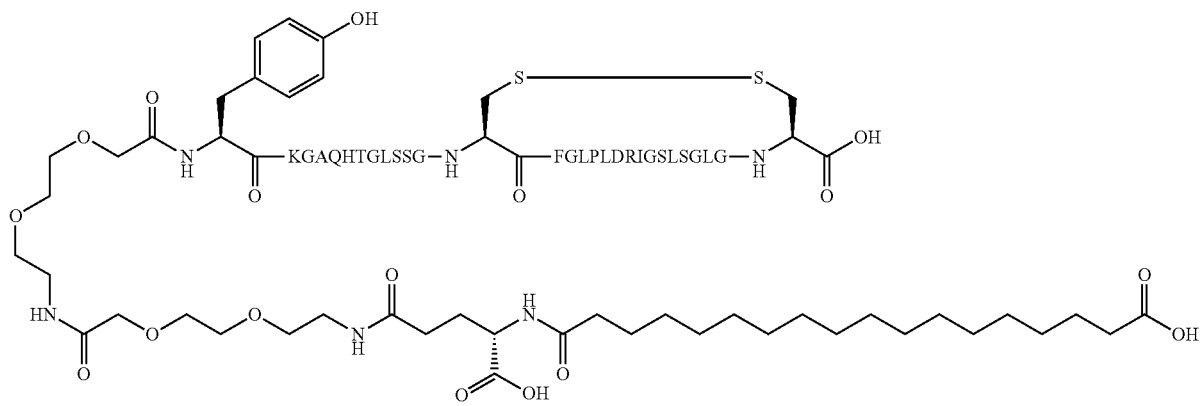

Molecular weight: 3609.1292. LCMS34: m/3 calcd: 1204.0431; m/3 found: 1204.0040; m/4.
calcd: 903.2823; m/4 found: 903.2470.
Chem. 37; Compound ID 1309; SEQ ID NO: 36

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), des1-8, 9E, 10H, 13Q, 25P, 32L]-hCNP37

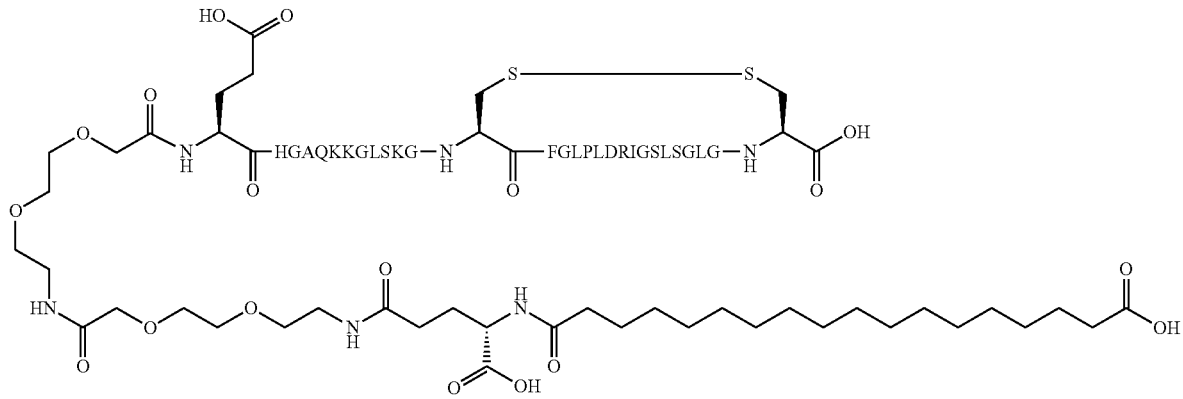

Molecular weight: 3643.2333. LCMS34: m/3 calcd: 1215.4111; m/3 found: 1215.4546; m/4. calcd: 911.8083; m/4 found: 911.8567.

Chem. 38; Compound ID 1310; SEQ ID NO: 37

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), des1-8, 9E, 10H, 13Q, 19S, 25P, 32L]-hCNP37

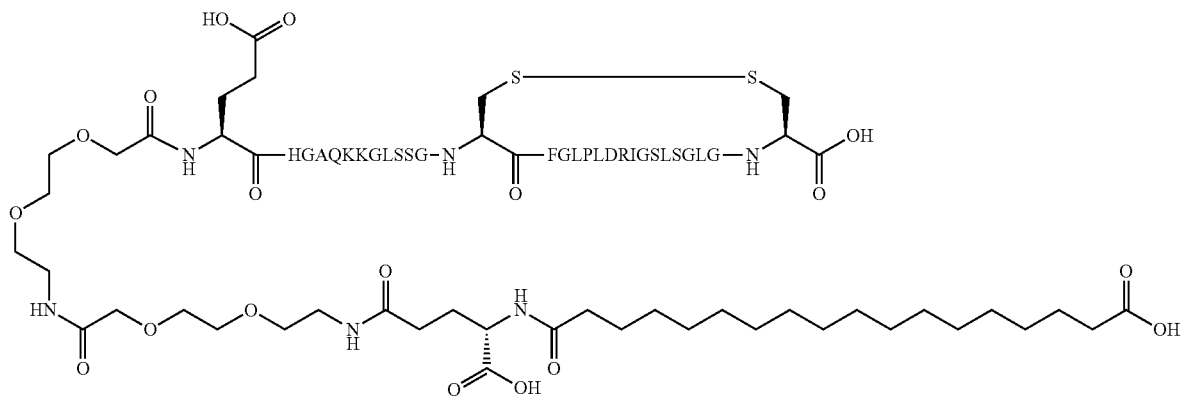

Molecular weight: 3602.1383. LCMS34: m/3 calcd: 1201.7128; m/3 found: 1201.7507; m/4. calcd: 901.5346; m/4 found: 901.5770.

Chem. 39; Compound ID 1311; SEQ ID NO: 38

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), des1-8, 9E, 10H, 13Q, 17V, 19S, 25P, 32L]-hCNP37

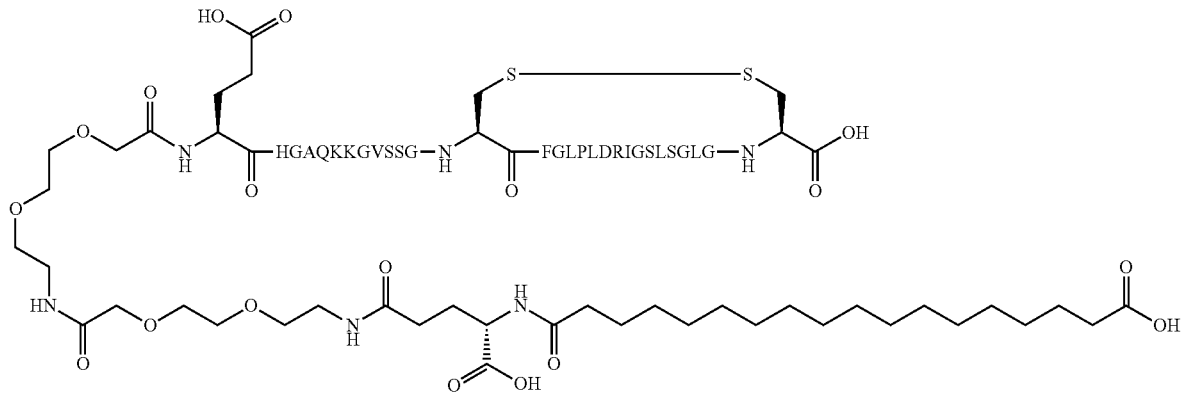

Molecular weight: 3588.1117. LCMS34: m/3 calcd: 1197.0372; m/3 found: 1197.0725; m/4.
calcd: 898.0279; m/4 found: 898.0776.
Chem. 40; Compound ID 1312; SEQ ID NO: 39

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), des1-8, 9E, 10H, 13Q, 15T, 17V, 19S, 25P, 32L]-hCNP37

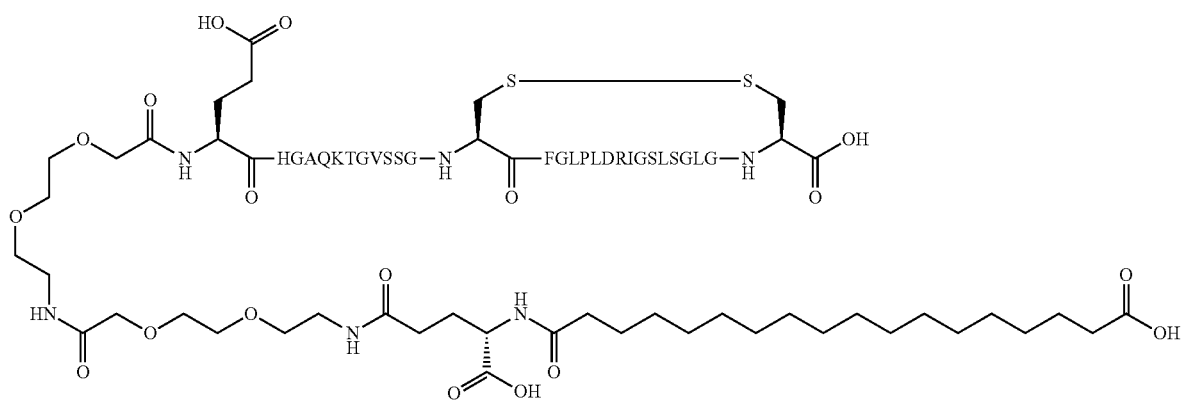

Molecular weight: 3561.0433. LCMS34: m/3 calcd: 1188.0144; m/3 found: 1187.9800; m/4.
calcd: 891.2608; m/4 found: 891.2320.
Chem. 41; Compound ID 1322; SEQ ID NO: 40

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), des1-8, 10H, 13Q, 14H, 15H, 27E, 32L]-hCNP37

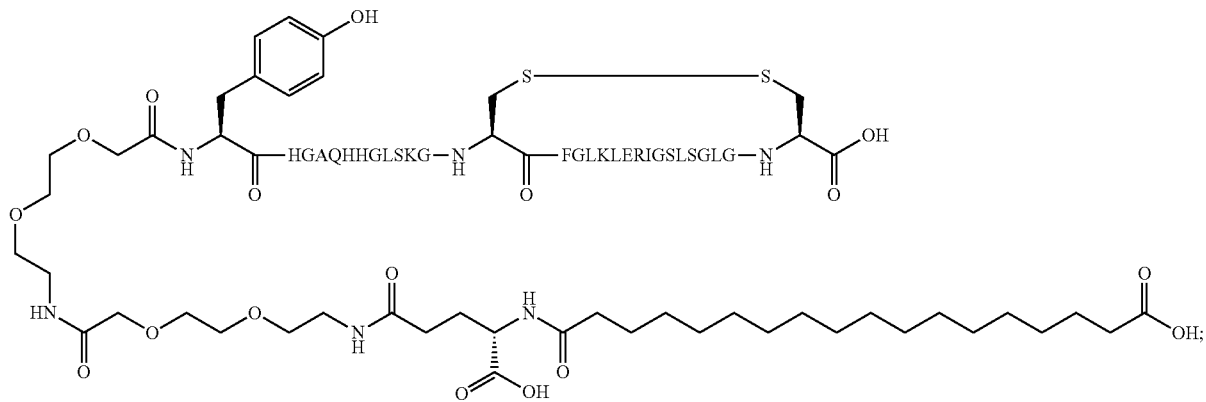

Molecular weight: 3740.3102. LCMS34: m/3 calcd: 1247.7701; m/3 found: 1247.6970; m/4.
calcd: 936.0776; m/4 found: 936.0280.

Chem. 42; Compound ID 1323; SEQ ID NO: 40

[N-terminal([2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]), des1-8, 10H, 13Q, 14H, 15H, 27E, 32L]-hCNP37

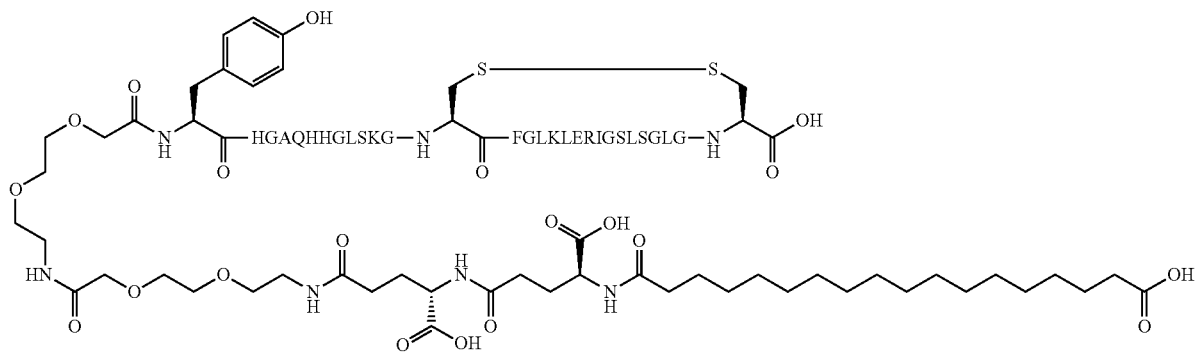

Molecular weight: 3869.4242. LCMS34: m/3 calcd: 1290.8081; m/3 found: 1290.7130; m/4.
calcd: 968.3561; m/4 found: 968.2840.

Chem. 43; Compound ID 1324; SEQ ID NO: 41

[N-terminal([2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]), des1-8, 13Q, 14H, 15H, 19Q, 27E, 32L]-hCNP37

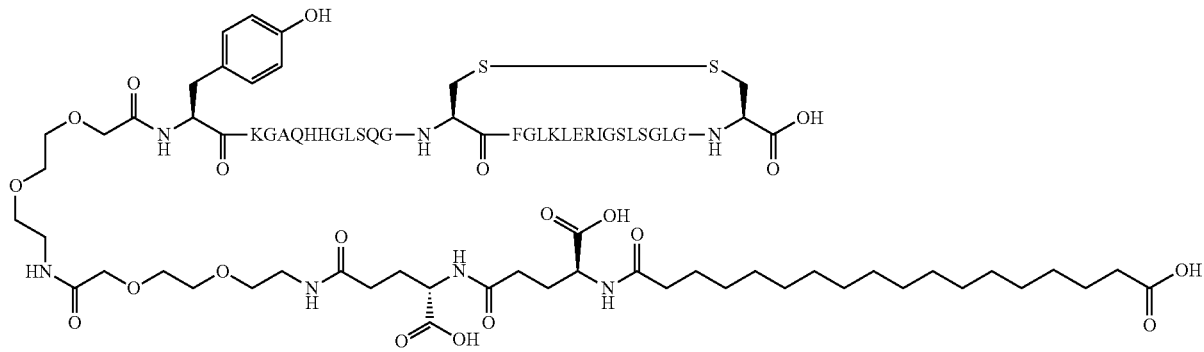

Molecular weight: 3860.4141. LCMS34: m/3 calcd: 1287.8047; m/3 found: 1287.7150; m/4. calcd: 966.1035; m/4 found: 966.0310.
Chem. 44; Compound ID 1338; SEQ ID NO: 42

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), des1-8, 10E, 13Q, 19S, 25P, 27E, 32L]-hCNP37

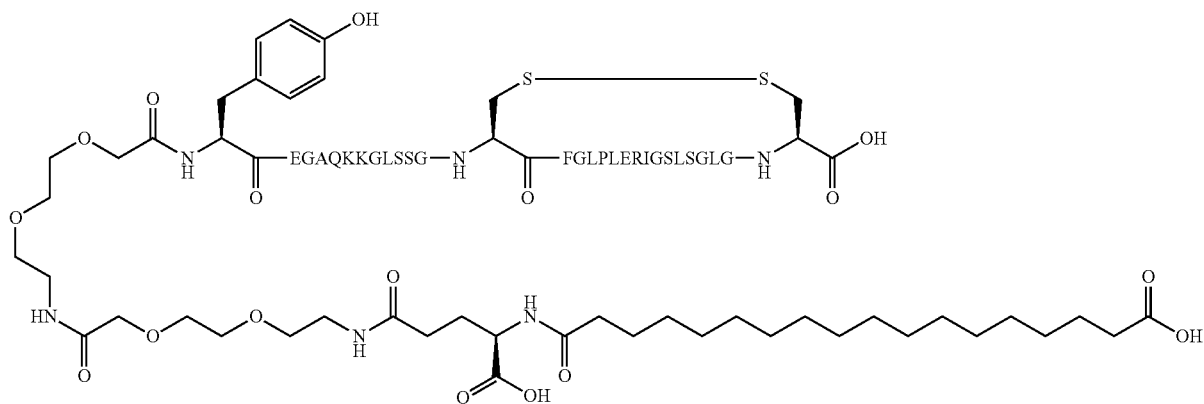

Molecular weight: 3642.1988. LCMS34: m/3 calcd: 1215.0663; m/3 found: 1214.9827; m/4. calcd: 911.5497; m/4 found: 911.2273.
Chem. 45; Compound ID 1339; SEQ ID NO: 43

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), des1-9, 10E, 13Q, 19S, 25P, 32L]-hCNP37

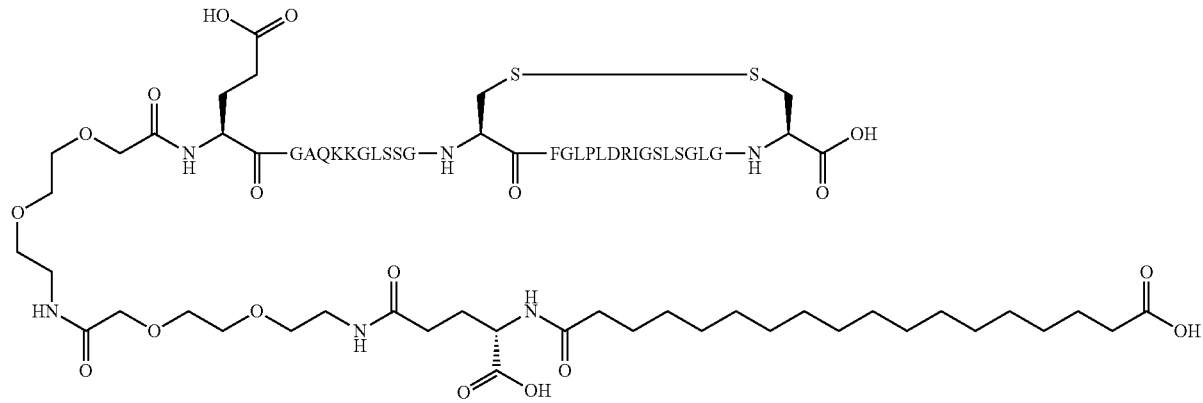

Molecular weight: 3464.999. LCMS34: m/3 calcd: 1155.9997; m/3 found: 1155.9600; m/4.
calcd: 867.2498; m/4 found: 866.9667.
Chem. 46; Compound ID 1340; SEQ ID NO: 44

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), des1-8, 13Q, 14H, 15H, 19Q, 32L]-hCNP37

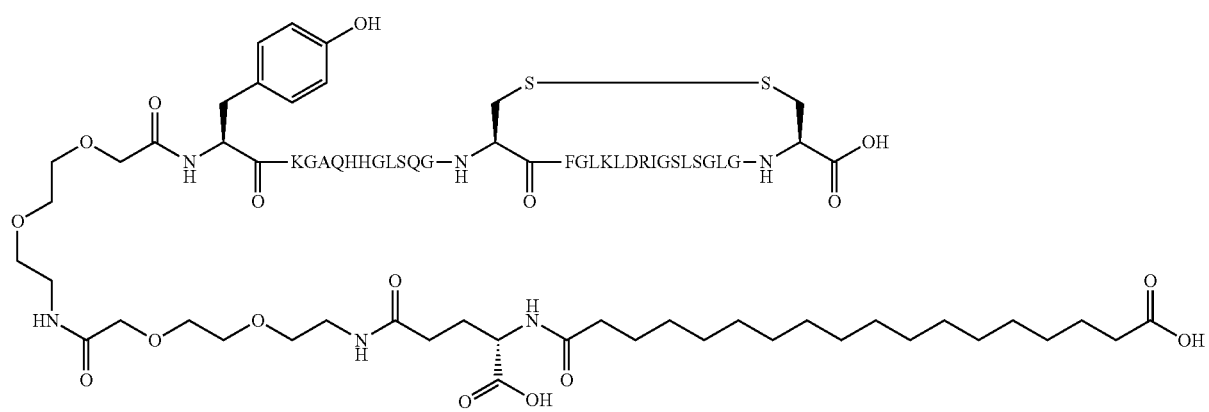

Molecular weight: 3717.2736. LCMS34: m/3 calcd: 1240.0912; m/3 found: 1240.0320; m/4.
calcd: 930.3184; m/4 found: 930.2630.
Chem. 47; Compound ID 1341; SEQ ID NO: 45

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), des1-8, 13Q, 14H, 15H, 19Q, 25P, 32L]-hCNP37

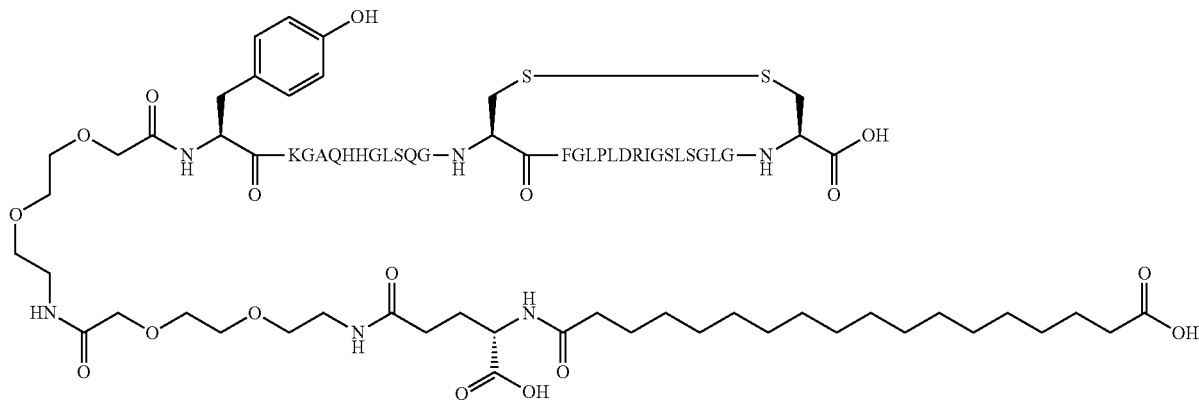

Molecular weight: 3686.2165. LCMS34: m/3 calcd: 1229.7388; m/3 found: 1229.6760; m/4. calcd: 922.5541; m/4 found: 922.5020.

Chem. 48; Compound ID 1345; SEQ ID NO: 46

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), des1-8, 10H, 13Q, 14H, 15H, 32L]-hCNP37

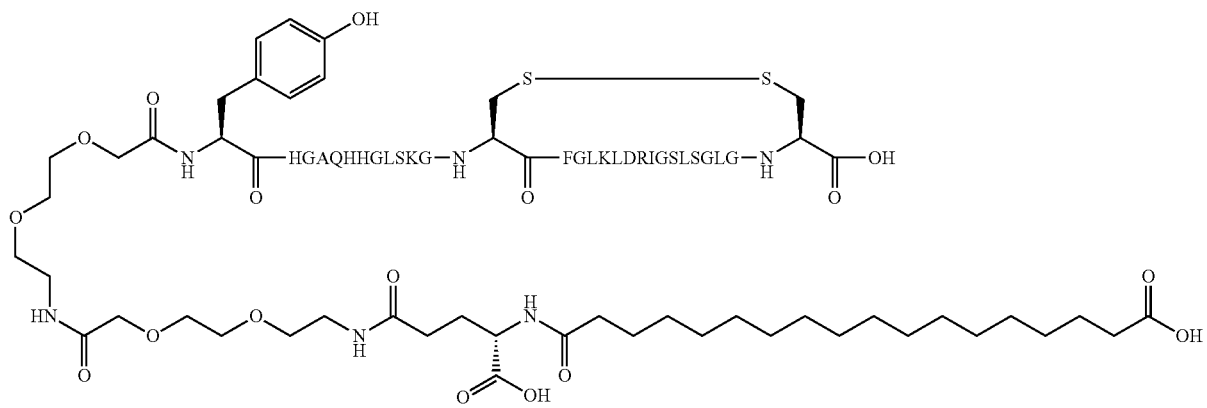

Molecular weight: 3726.2836. LCMS34: m/3 calcd: 1243.0945; m/3 found: 1243.0310; m/4. calcd: 932.5709; m/4 found: 932.5240.

Chem. 49; Compound ID 1346; SEQ ID NO: 47

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), des1-8, 10H, 13Q, 14H, 15H, 25P, 32L]-hCNP37

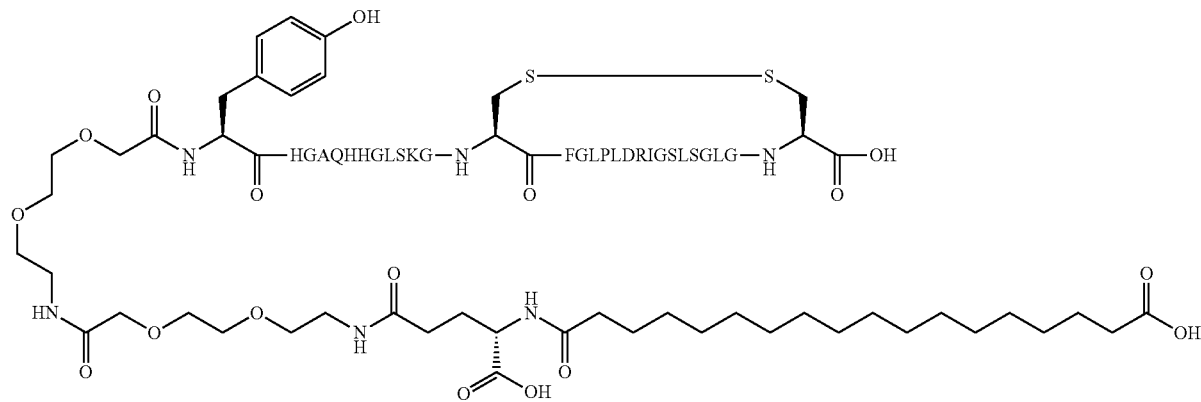

Molecular weight: 3695.2265. LCMS34: m/3 calcd: 1232.7422; m/3 found: 1232.6930; m/4.
calcd: 924.8066; m/4 found: 924.7340.
Chem. 50; Compound ID 1347; SEQ ID NO: 48

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), des1-10, 13Q, 19H, 25P, 32L]-hCNP37

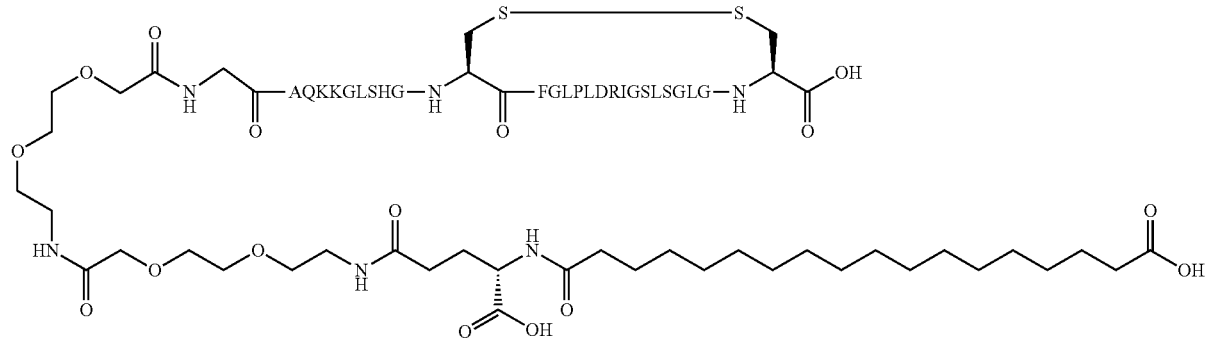

Molecular weight: 3385.947. LCMS34: m/3 calcd: 1129.6490; m/3 found: 1129.2775; m/4.
calcd: 847.4868; m/4 found: 847.2063.
Chem. 51; Compound ID 1348; SEQ ID NO: 49

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), des1-10, 13Q, 18H, 19S, 25P, 32L]-hCNP37

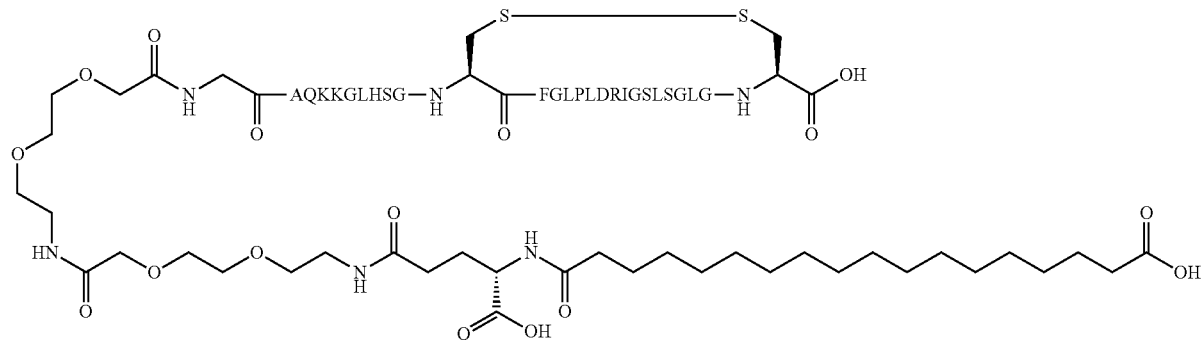

Molecular weight: 3385.947. LCMS34: m/3 calcd: 1129.6490; m/3 found: 1129.2775; m/4.
calcd: 847.4868; m/4 found: 847.4684.
Chem. 52; Compound ID 1350; SEQ ID NO: 50

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), des1-5, 10H, 13Q, 14H, 15T, 19S, 25P, 32L]-hCNP37

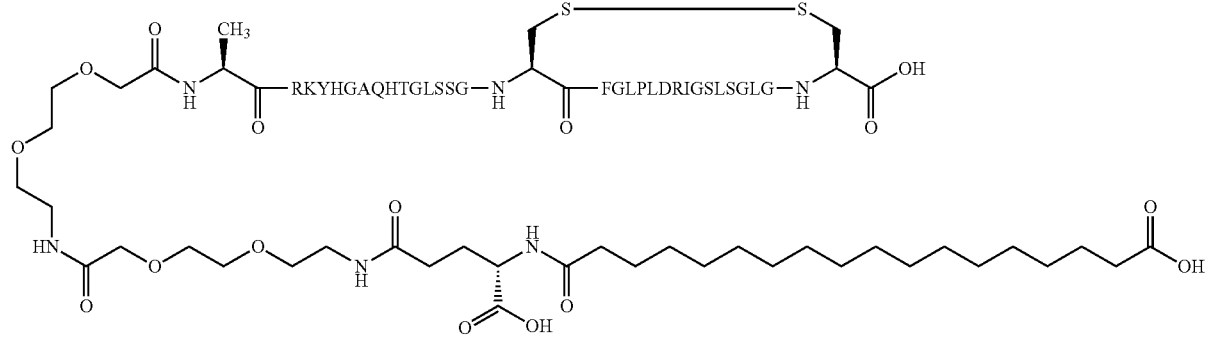

Molecular weight: 3973.532. LCMS34: m/3 calcd: 1325.5107; m/3 found: 1325.3463; m/4.
calcd: 994.3830; m/4 found: 994.2843.
Chem. 53; Compound ID 1351; SEQ ID NO: 51

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), des1-5, 10H, 13Q, 14H, 15T, 17V, 19S, 25P, 32L]-hCNP37

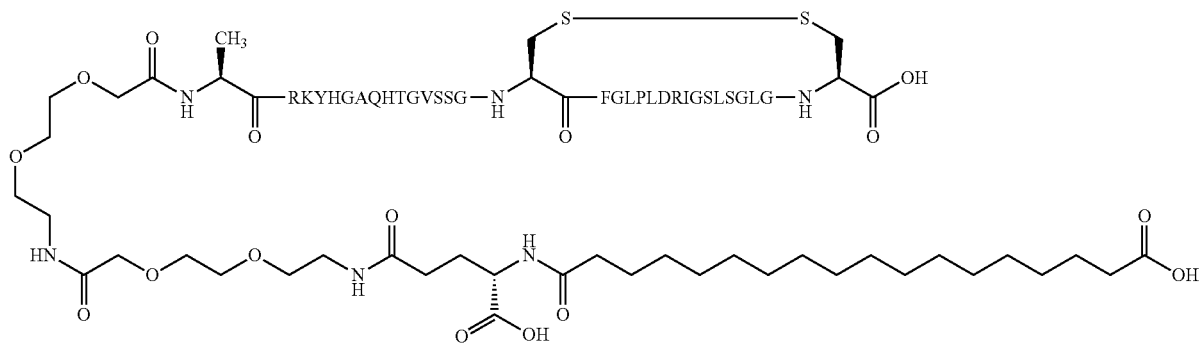

Molecular weight: 3959.5054. LCMS34: m/3 calcd: 1320.8351; m/3 found: 1320.6271; m/4. calcd: 990.8764; m/4 found: 990.7383.
Chem. 54; Compound ID 1352; SEQ ID NO: 33

[N-terminal([2-[2-[2-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]ethoxy]ethoxy]acetyl]), des1-8, 10H, 13Q, 15T, 17V, 19S, 25P, 32L]-hCNP37

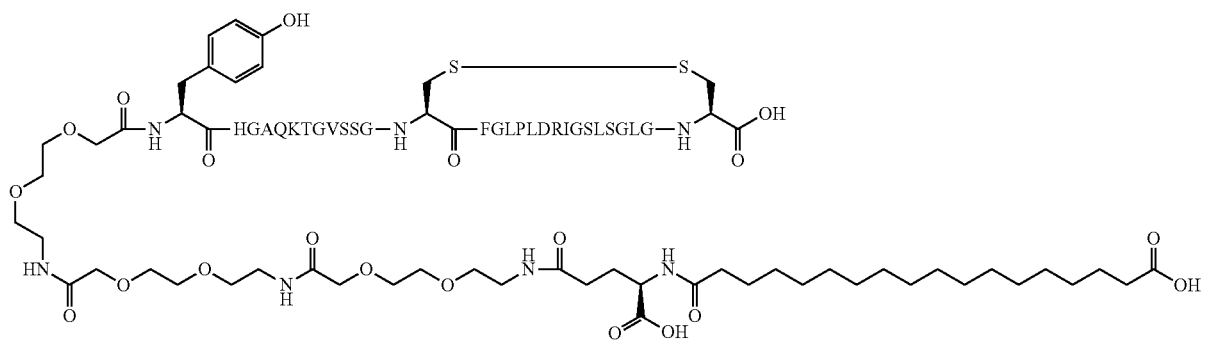

Molecular weight: 3740.259. LCMS34: m/3 calcd: 1247.7530; m/3 found: 1247.3048; m/4. calcd: 936.0648; m/4 found: 935.9911.
Chem. 55; Compound ID 1353; SEQ ID NO: 36

[N-terminal([2-[2-[2-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]ethoxy]ethoxy]acetyl]), des1-8, 9E, 10H, 13Q, 25P, 32L]-hCNP37

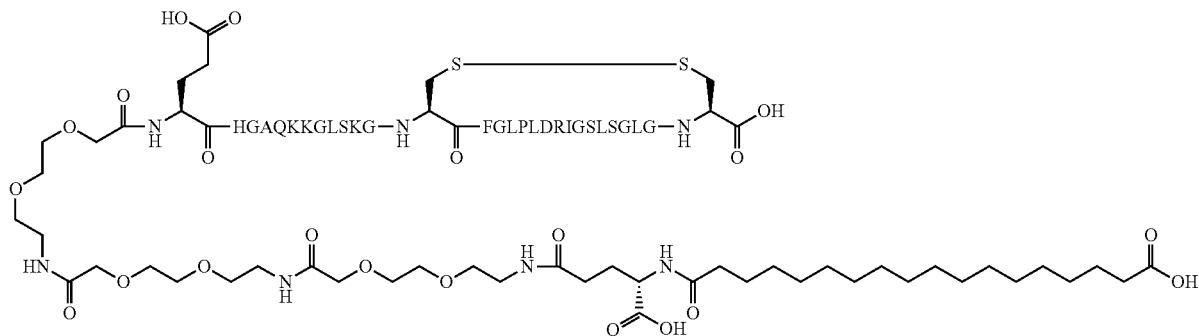

Molecular weight: 3788.3897. LCMS34: m/3 calcd: 1263.7966; m/3 found: 1263.6780; m/4. calcd: 948.0974; m/4 found: 947.7735.

Chem. 56; Compound ID 1354; SEQ ID NO: 52

[N-terminal([2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]), des1-5, 10H, 13Q, 15T, 17V, 19S, 25P, 32L]-hCNP37

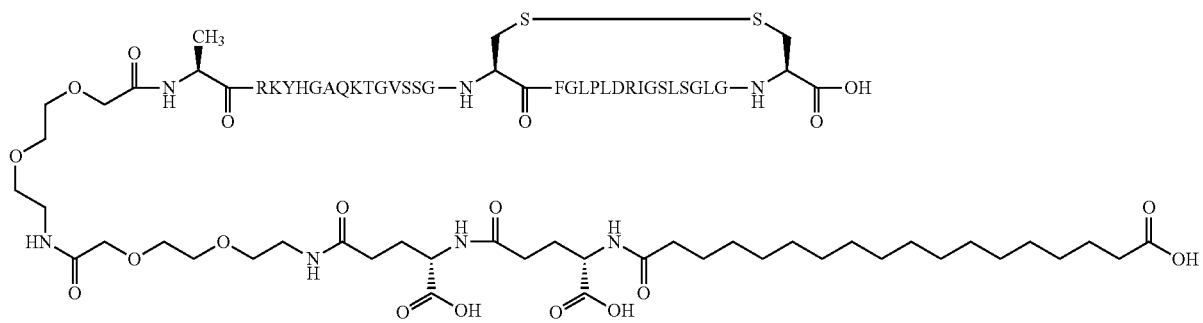

Molecular weight: 4079.6524. LCMS34: m/3 calcd: 1360.8841; m/3 found: 1360.7530; m/4. calcd: 1020.9131; m/4 found: 1020.8160.

Chem. 57; Compound ID 1355; SEQ ID NO: 22

[N-terminal([2-[2-[2-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]ethoxy]ethoxy]acetyl]), des1-8, 13Q, 19S, 25P, 32L]-hCNP37

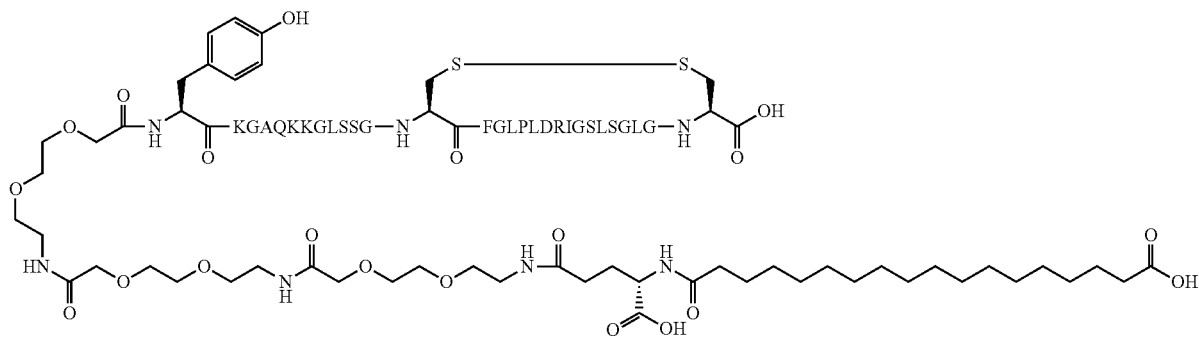

Molecular weight: 3772.387. LCMS34: m/3 calcd: 1258.4623; m/3 found: 1258.3439; m/4.
calcd: 944.0968; m/4 found: 944.0223.
Chem. 58; Compound ID 1356; SEQ ID NO: 22

[N-terminal([2-[2-[2-[[2-[2-[2-[[2-[2-[2-[[(4S)-4-carboxy-4-[[(4S)-4- carboxy-4-(17-carboxyheptadecanoylamino)butanoyl]amino]butanoyl]amino]ethoxy]ethoxy]acetyl]amino]ethoxy]ethoxy]acetyl]amino]ethoxy]ethoxy]acetyl]), des1-8, 13Q, 19S, 25P, 32L]-hCNP37

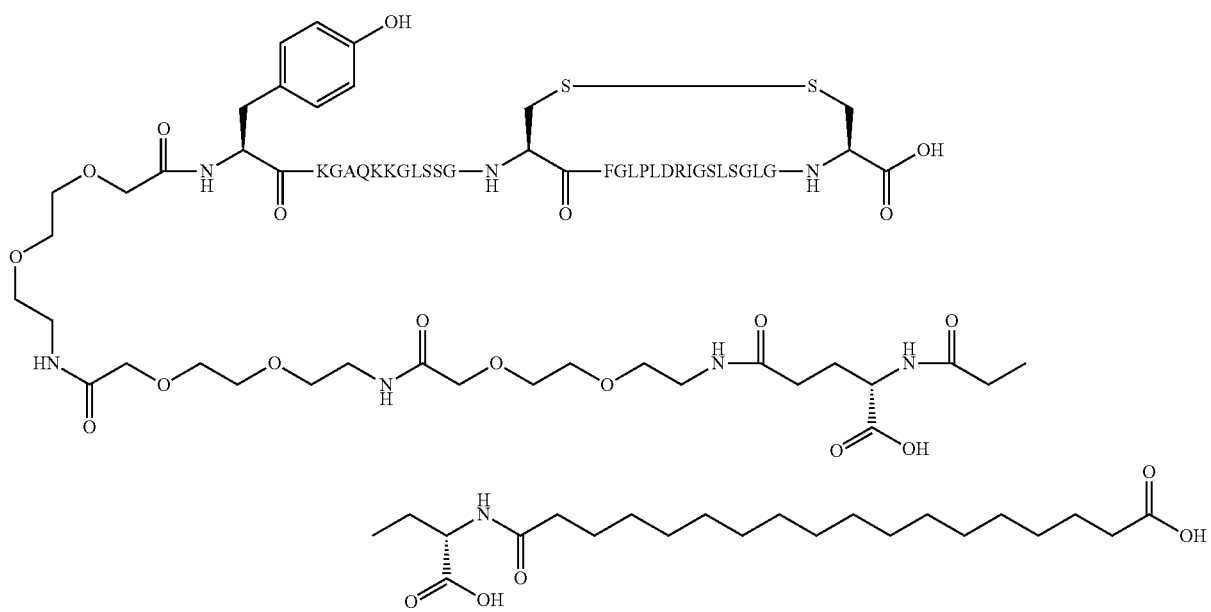

Molecular weight: 3901.501. LCMS34: m/3 calcd: 1301.5003; m/3 found: 1301.3470; m/4.
calcd: 976.3753; m/4 found: 976.2725.
Chem. 59; Compound ID 1357; SEQ ID NO: 5

[N-terminal([2-[2-[2-[[2-[2-[2-[[2-[2-[2-[[(4S)-4-carboxy-4-[[(4S)-4- carboxy-4-(17-carboxyheptade-canoylamino)butanoyl]amino]butanoyl]amino]eth-oxy]ethoxy]acetyl]amino]eth oxy]ethoxy]acetyl]amino]ethoxy]ethoxy]acetyl]), des1-8, 9E, 10H, 13Q, 32L]-hCNP37

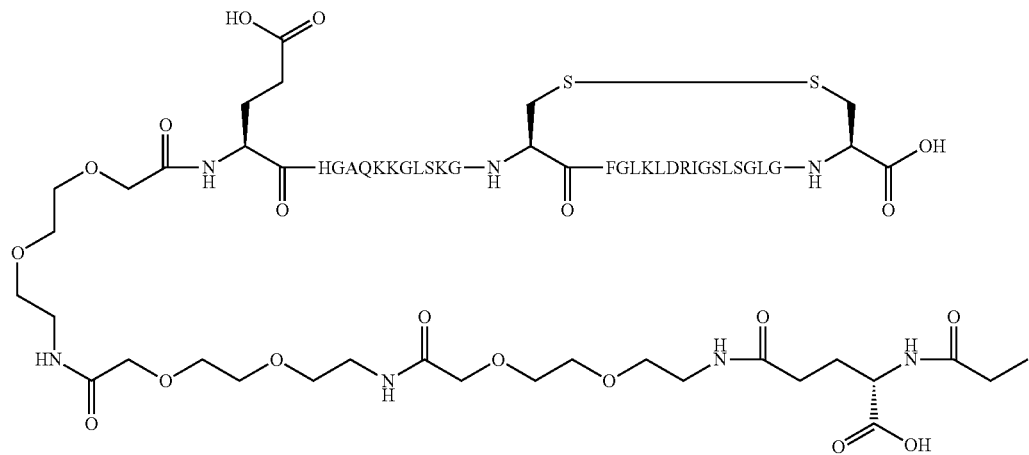

Molecular weight: 3948.5608. LCMS34: m/3 calcd: 1317.1869; m/3 found: 1317.0300; m/4.
calcd: 988.1402; m/4 found: 988.0348.
Chem. 60; Compound ID 1359; SEQ ID NO: 53

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), des1-5, 9E, 10H, 13Q, 15T, 17V, 19S, 25P, 32L]-hCNP37

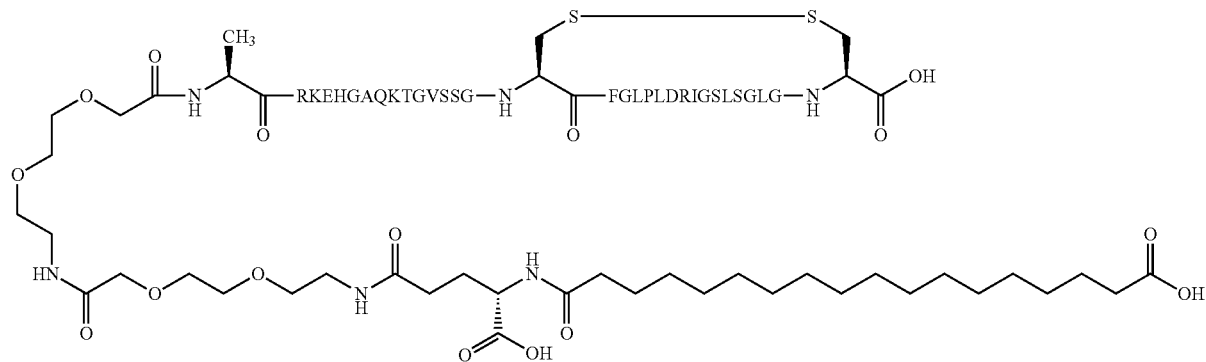

Molecular weight: 3916.4792. LCMS34: m/3 calcd: 1306.4931; m/3 found: 1306.0170; m/4.
calcd: 980.1198; m/4 found: 979.7797.
Chem. 61; Compound ID 1360; SEQ ID NO: 54

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), des1-5, 9E, 10H, 13Q, 14H, 15T, 17V, 19S, 25P, 32L]-hCNP37

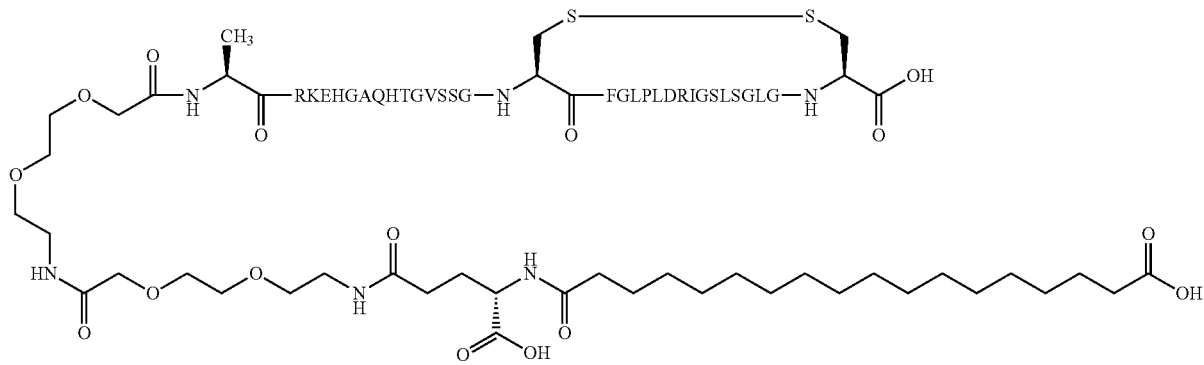

Molecular weight: 3925.4462. LCMS34: m/3 calcd: 1309.4821; m/3 found: 1309.3323; m/4. calcd: 982.3616; m/4 found: 982.2667.

Chem. 62; Compound ID 1375; SEQ ID NO: 14

[N-terminal([2-[2-[2-[[2-[2-[2-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]ethoxy]ethoxy]acetyl]amino]ethoxy]ethoxy]acetyl]), des1-8, 10E, 13Q, 25P, 32L]-hCNP37

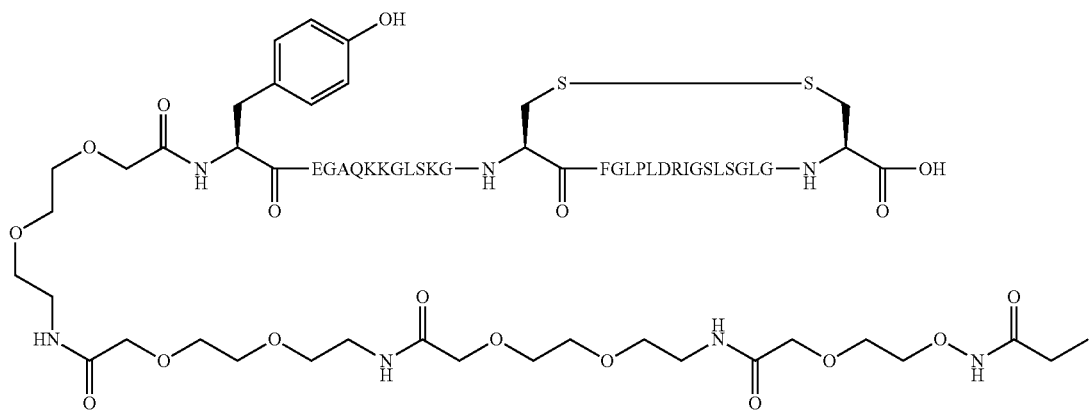

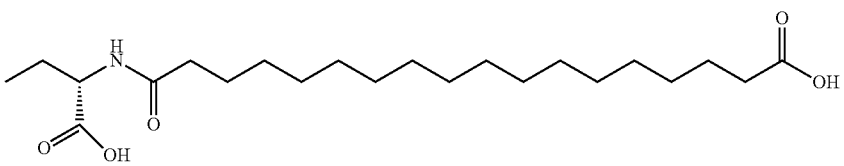

Molecular weight: 3959.5801. LCMS34: m/3 calcd: 1320.8600; m/3 found: 1320.7200; m/4. calcd: 990.8950; m/4 found: 990.5400.

Chem. 63; Compound ID 1376; SEQ ID NO: 14

[N-terminal([2-[2-[2-[[2-[2-[2-[[(4S)-4-carboxy-4-(19-carboxynonadecanoylamino)butanoyl]amino]ethoxy]ethoxy]acetyl]amino]ethoxy]ethoxy]acetyl]), des1-8, 10E, 13Q, 25P, 32L]-hCNP37

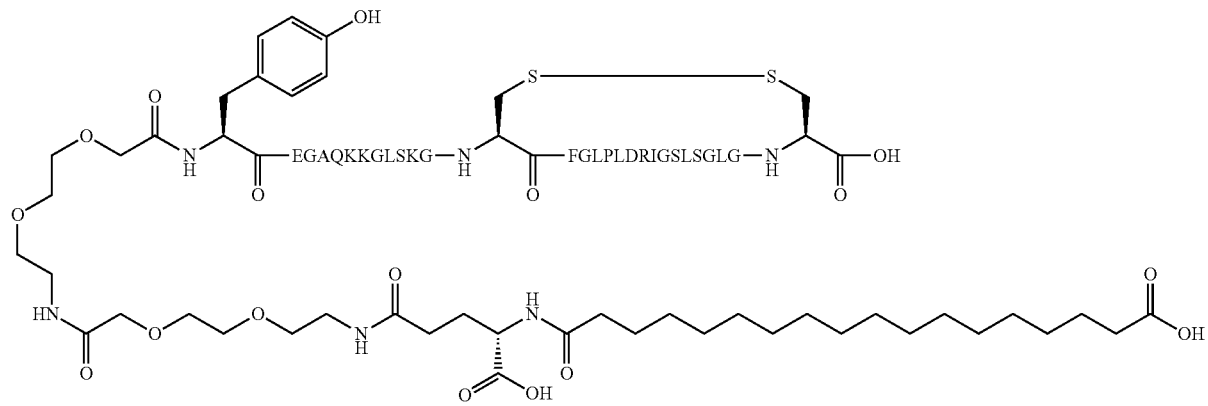

Molecular weight: 3697.3204. LCMS34: m/3 calcd: 1233.4401; m/3 found: 1233.3500; m/4. calcd: 925.3301; m/4 found: 925.2600.
Chem. 64; Compound ID 1377; SEQ ID NO: 55

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), des1-8, 10E, 13Q, 17G, 25P, 32L]-hCNP37

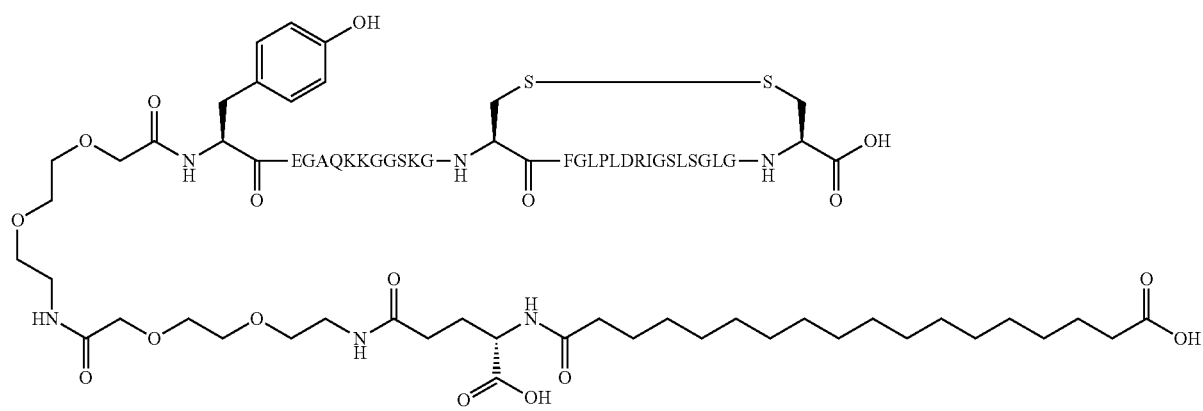

Molecular weight: 3613.1609. LCMS34: m/3 calcd: 1205.3870; m/3 found: 1205.3100; m/4. calcd: 904.2902; m/4 found: 903.9800.
Chem. 65; Compound ID 1378; SEQ ID NO: 56

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), des1-5, 6G, 7G, 8G, 10E, 13Q, 19S, 25P, 32L]-hCNP37

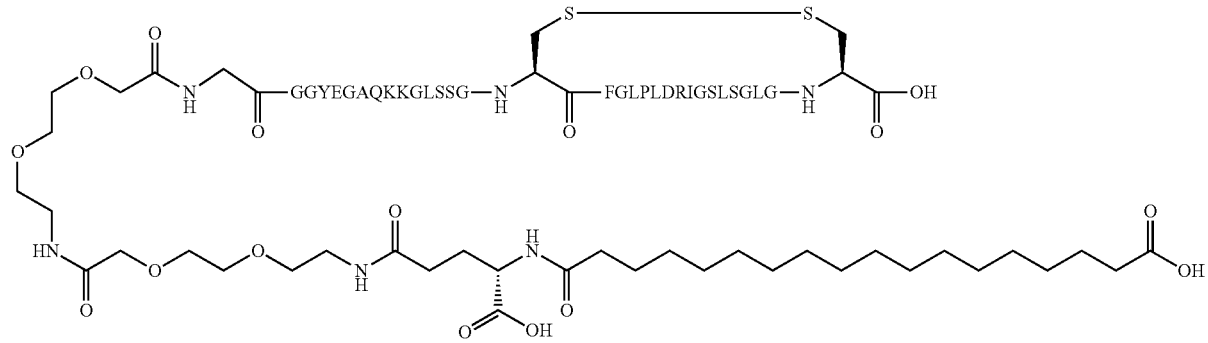

Molecular weight: 3799.3262. LCMS34: m/3 calcd: 1267.4421; m/3 found: 1267.3470; m/4.
calcd: 950.8316; m/4 found: 950.7240.
Chem. 66; Compound ID 1379; SEQ ID NO: 57

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), 5Q, 8S, 10E, 13Q, 19S, 25P, 32L]-hCNP37

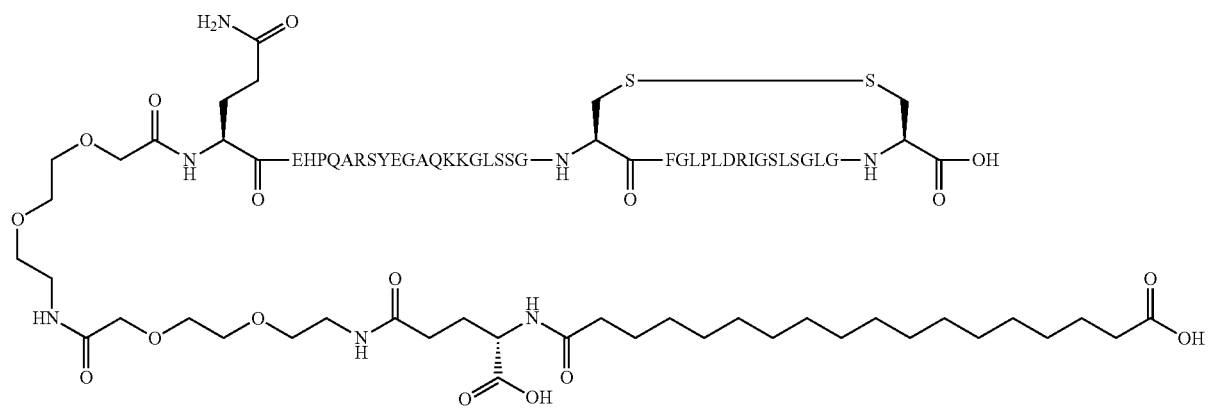

Molecular weight: 4562.14. LCMS34: m/3 calcd: 1521.7133; m/3 found: 1521.3220; m/4.
calcd: 1141.5350; m/4 found: 1141.2370.
Chem. 67; Compound ID 1380; SEQ ID NO: 58

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), 5E, 8S, 10E, 13Q, 19S, 25P, 32L]-hCNP37

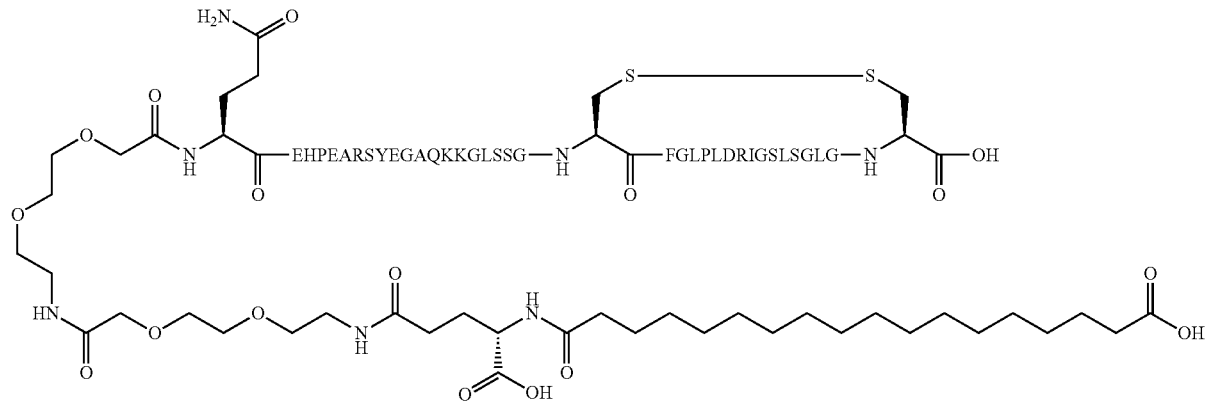

Molecular weight: 4563.1248. LCMS34: m/3 calcd: 1522.0416; m/3 found: 1521.8490; m/4.
calcd: 1141.7812; m/4 found: 1141.6240.
Chem. 68; Compound ID 1381; SEQ ID NO: 59

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), 5Q, 7H, 10H, 13O, 14H, 15H, 17S, 19Q, 25P, 32L]-hCNP37

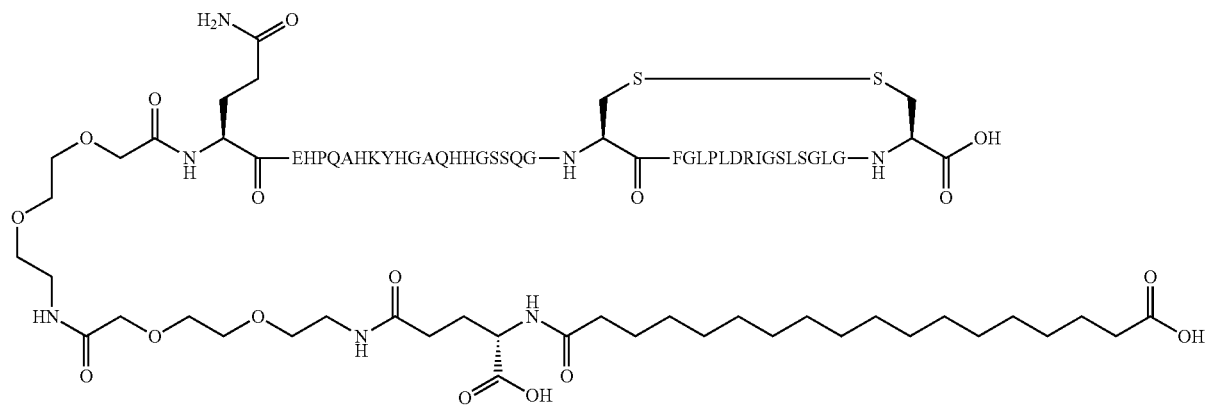

Molecular weight: 4625.1195. LCMS34: m/3 calcd: 1542.7065; m/3 found: 1542.3070; m/4.
calcd: 1157.2799; m/4 found: 1156.9700.
Chem. 69; Compound ID 1382; SEQ ID NO: 60

[N-terminal([2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]), 5Q, 7H, 13Q, 19Q, 25P, 32L]-hCNP37

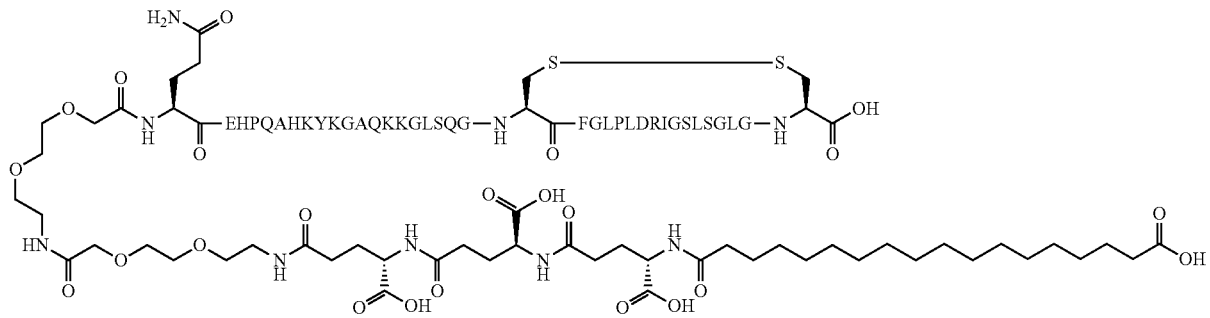

Molecular weight: 4882.5268. LCMS34: m/3 calcd: 1628.5089; m/3 found: 1628.2280; m/4.
calcd: 1221.6317; m/4 found: 1221.2810.
Chem. 70; Compound ID 1383; SEQ ID NO: 61

[N-terminal([2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]), 5Q, 7H, 10H, 13Q, 15H, 17S, 19Q, 25P, 32L]-hCNP37

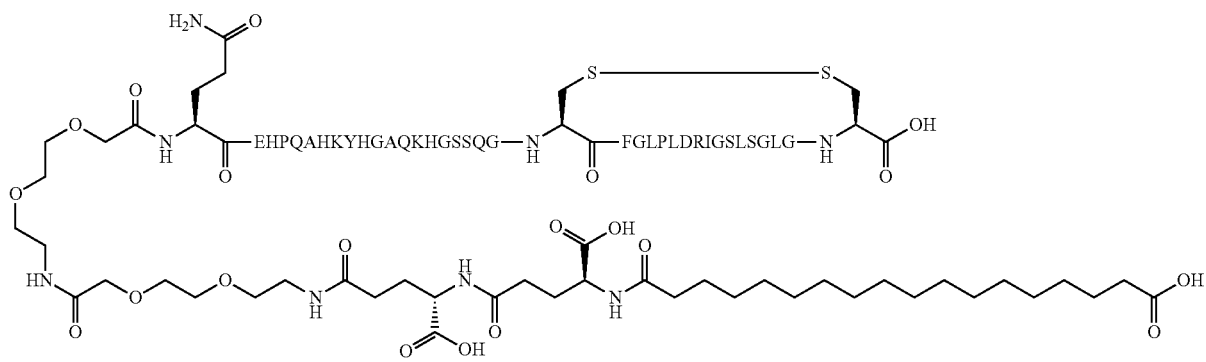

Molecular weight: 4745.2665. LCMS34: m/3 calcd: 1582.7555; m/3 found: 1582.5080; m/4.
calcd: 1187.3166; m/4 found: 1186.9970.
Chem. 71; Compound ID 9384; SEQ ID NO: 62

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), des1-6, 7G, 8Q, 9A, 10P, 13Q, 17S, 19Q, 25P, 32L]-hCNP37

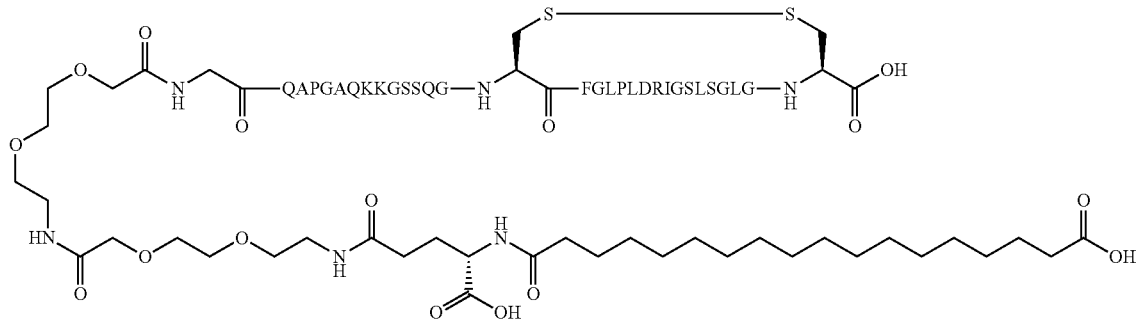

Molecular weight: 3704.2302. LCMS34: m/3 calcd: 1235.7434; m/3 found: 1235.5400; m/4.
calcd: 927.0576; m/4 found: 926.9010.
Chem. 72; Compound ID 1385; SEQ ID NO: 63

[N-terminal([(4S)-4-carboxy-4-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]butanoyl]), des1-5, 10E, 13Q, 25P, 32L]-hCNP37

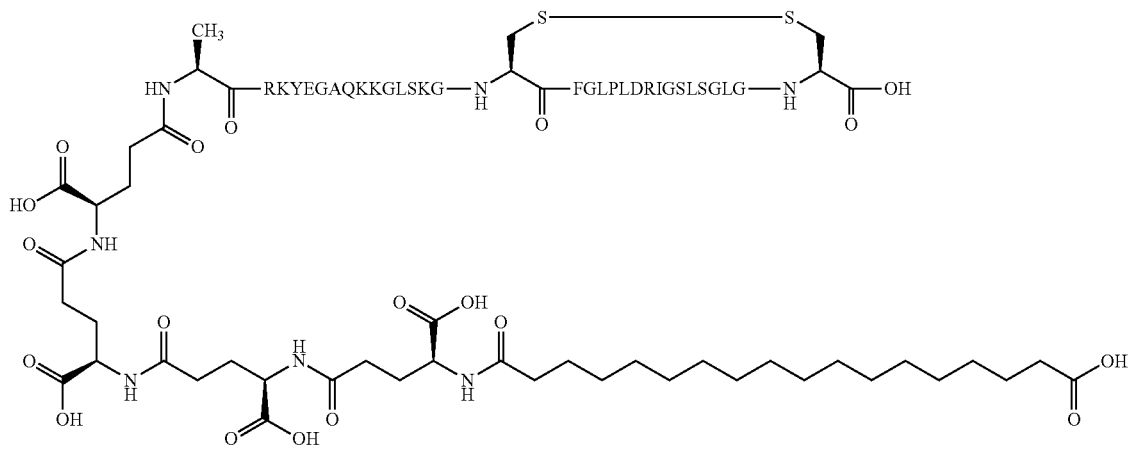

Molecular weight: 4121.7322. LCMS34: m/3 calcd: 1374.9107; m/3 found: 1374.6120; m/4.
calcd: 1031.4331; m/4 found: 1031.2130.
Chem. 73; Compound ID 1386; SEQ ID NO: 64

[N-terminal([(4S)-4-carboxy-4-[[(4S)-4-carboxy-4-[[(4S)-4-carboxy-4-[[(4S)-4-carboxy-4-(17-carboxy-heptadecanoylamino)butanoyl]amino]butanoyl]amino]butanoyl]amino]butanoyl]), des1-5, 13Q, 19S, 25P, 32L]-hCNP37

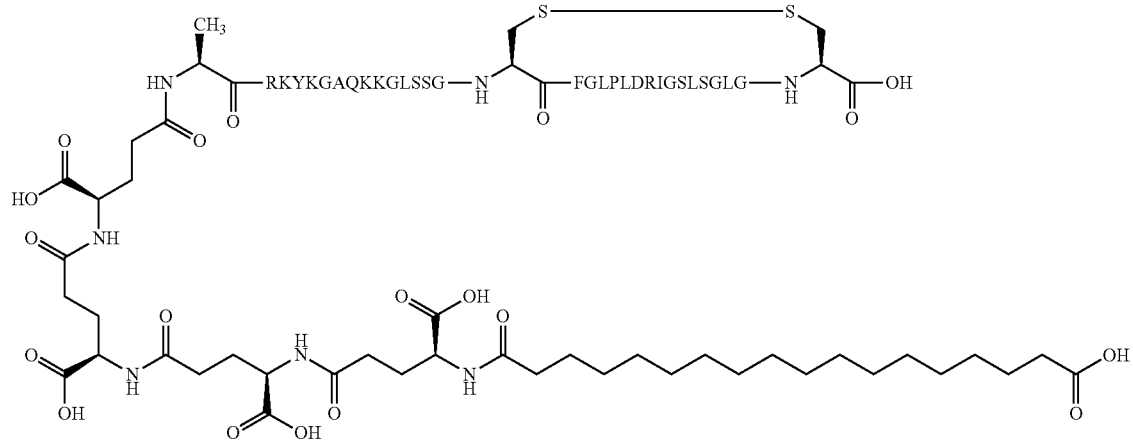

Molecular weight: 4079.6955. LCMS34: m/3 calcd: 1360.8985; m/3 found: 1360.7680; m/4.
calcd: 1020.9239; m/4 found: 1020.8160.
Chem. 74; Compound ID 1387; SEQ ID NO: 65

[N-terminal([(4S)-4-carboxy-4-[[(4S)-4-carboxy-4-[[(4S)-4-carboxy-4-[[(4S)-4-carboxy-4-(17-carboxy-heptadecanoylamino)butanoyl]amino]butanoyl]amino]butanoyl]amino]butanoyl]), des1-5, 6G, 7G, 8G, 13Q, 19S, 25P, 32L]-hCNP37

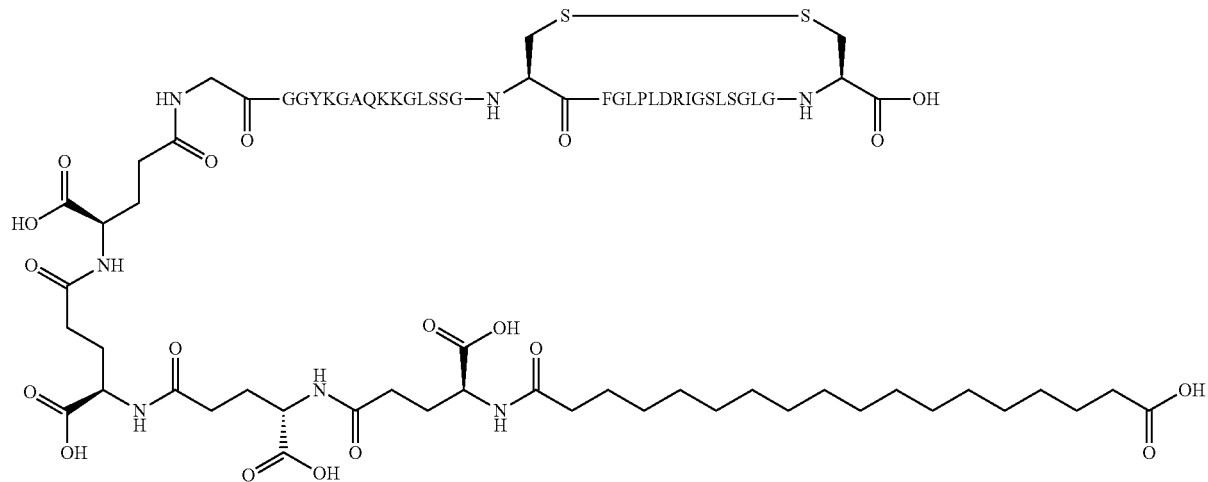

Molecular weight: 3895.4136. LCMS34: m/3 calcd: 1299.4712; m/3 found: 1299.3300; m/4.
calcd: 974.8534; m/4 found: 974.7500.
Chem. 75; Compound ID 1388; SEQ ID NO: 66

[N-terminal([[(4S)-4-carboxy-4-[[(4S)-4-carboxy-4-[[(4S)-4-carboxy-4-[[(4S)-4-carboxy-4-(17-carboxy-heptadecanoylamino)butanoyl]amino]butanoyl]amino]butanoyl]amino]butanoyl]), des1-5, 6G, 7G, 8G, 13Q, 25P, 32L]-hCNP37

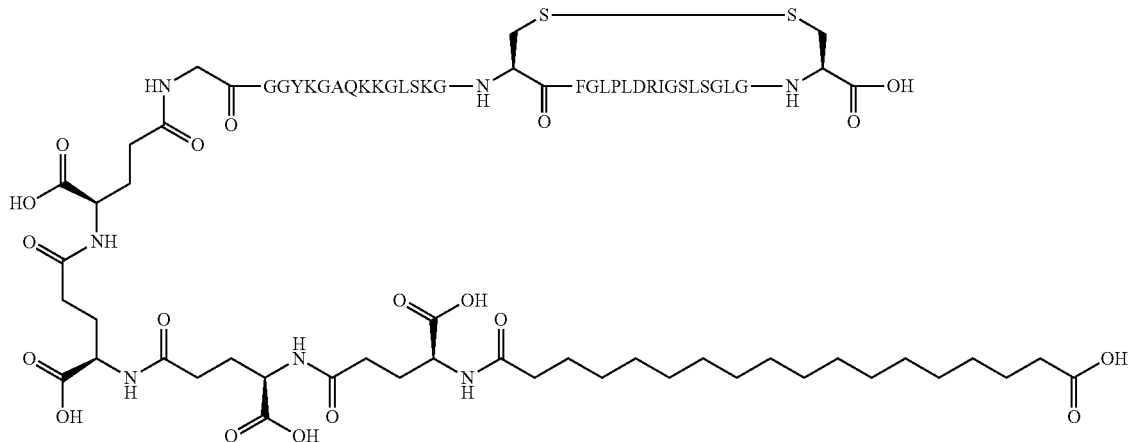

Molecular weight: 3936.5086. LCMS34: m/3 calcd: 1313.1695; m/3 found: 1313.0250; m/4 calcd: 985.1272; m/4 found: 985.2870.

Chem. 76; Compound ID 1389; SEQ ID NO: 67

[N-terminal([[(4S)-4-carboxy-4-[[(4S)-4-carboxy-4-[[(4S)-4-carboxy-4-[[(4S)-4-carboxy-4-(17-carboxy-heptadecanoylamino)butanoyl]amino]butanoyl]amino]butanoyl]amino]butanoyl]), 5Q, 13Q, 19S, 25P, 32L]-hCNP37

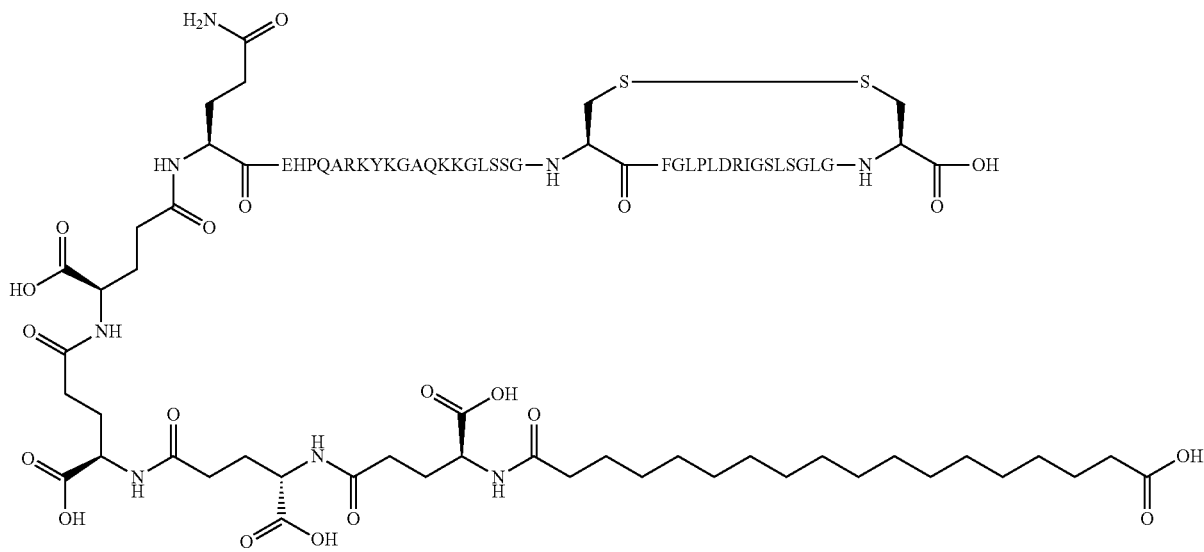

Molecular weight: 4699.3224. LCMS34: m/3 calcd: 1567.4408; m/3 found: 1567.4835; m/4 calcd: 1175.8306; m/4 found: 1176.1075.

Chem. 77; Compound ID 1390; SEQ ID NO: 68

[N-terminal([[(4S)-4-carboxy-4-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]butanoyl]), 5Q, 10E, 13Q, 19S, 25P, 32L]-hCNP37

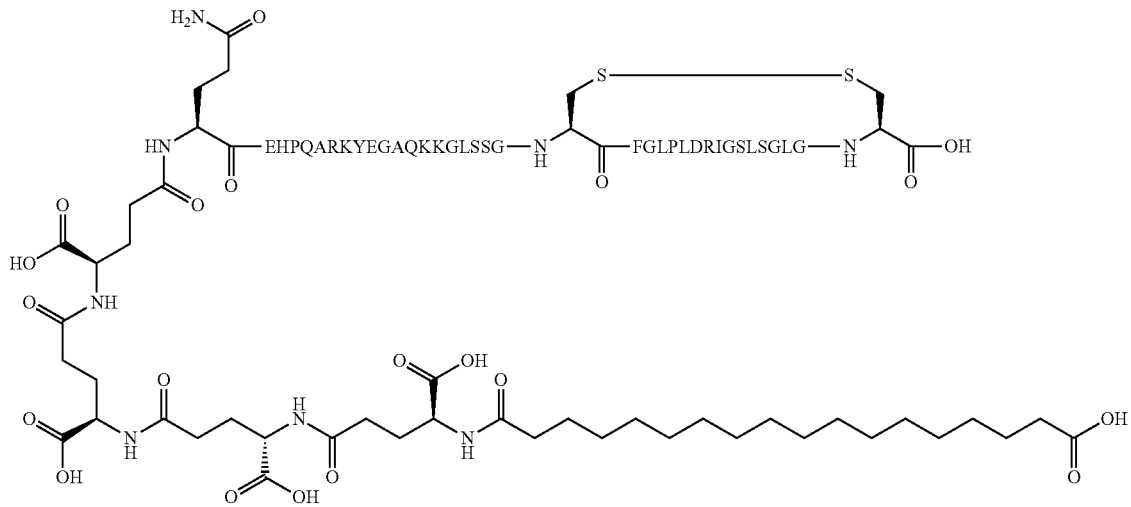

Molecular weight: 4700.2641. LCMS34: m/3 calcd: 1567.7547; m/3 found: 1567.5480; m/4. calcd: 1176.0660; m/4 found: 1175.8970.

Chem. 78; Compound ID 1391; SEQ ID NO: 55

[N-terminal([2-[2-[2-[[2-[2-[2-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]ethoxy]ethoxy]acetyl]amino]ethoxy]ethoxy]acetyl]), des1-8, 10E, 13Q, 17G, 25P, 32L]-hCNP37

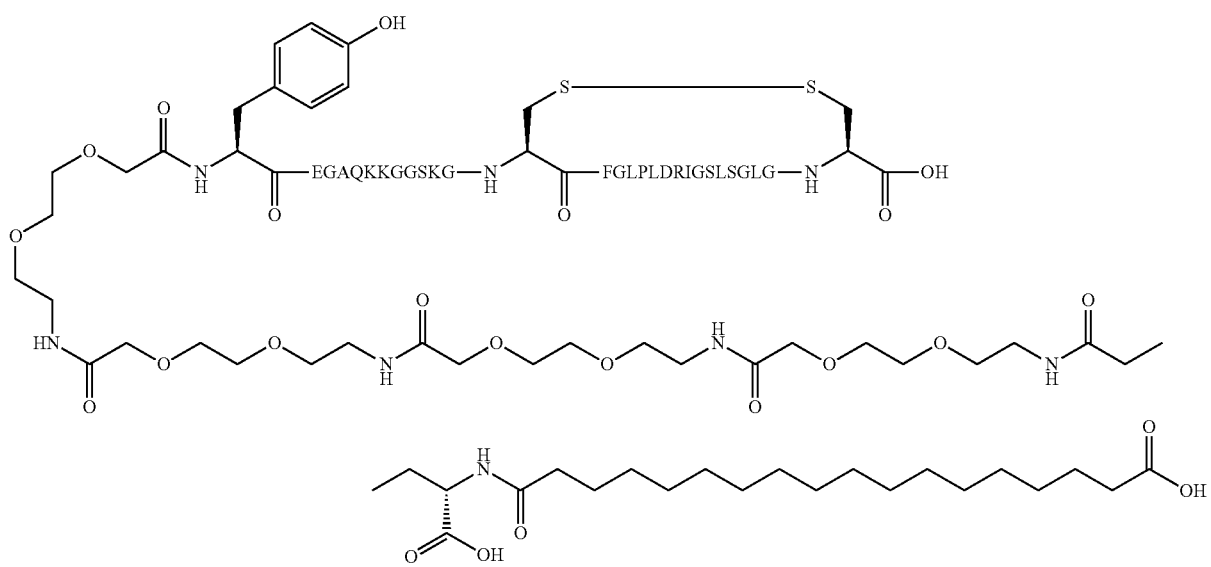

Molecular weight: 3903.4738. LCMS34: m/3 calcd: 1302.1579; m/3 found: 1302.0100; m/4. calcd: 976.8685; m/4 found: 976.5200.

Chem. 79; Compound ID 1392; SEQ ID NO: 16

[N-terminal([2-[2-[2-[[2-[2-[2-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acet yl]amino]ethoxy]ethoxy]acetyl]amino]ethoxy]ethoxy]acetyl]), des1-8, 10E, 13Q, 19S, 25P, 32L]-hCNP37

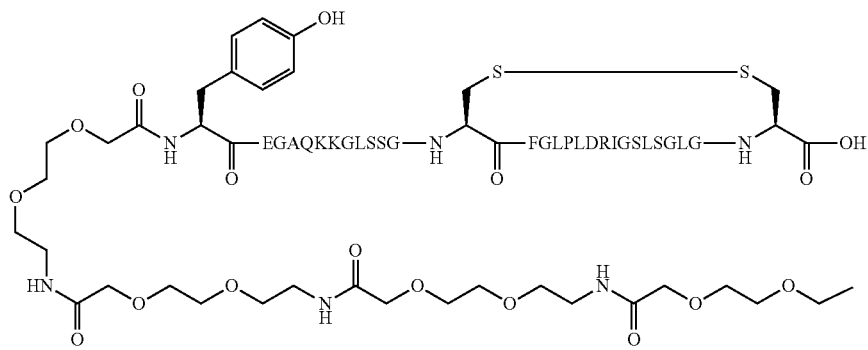

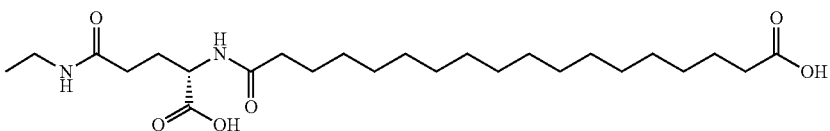

Molecular weight: 3918.4851. LCMS34: m/3 calcd: 1307.1617; m/3 found: 1307.3500; m/4.
calcd: 980.6213; m/4 found: 980.5300.
Chem. 80; Compound ID 1393; SEQ ID NO: 69

[N-terminal([2-[2-[2-[[2-[2-[2-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acet yl]amino]ethoxy]ethoxy]acetyl]amino]ethoxy]ethoxy]acetyl]), des1-8, 10E, 13Q, 19Q, 25P, 32L]-hCNP37

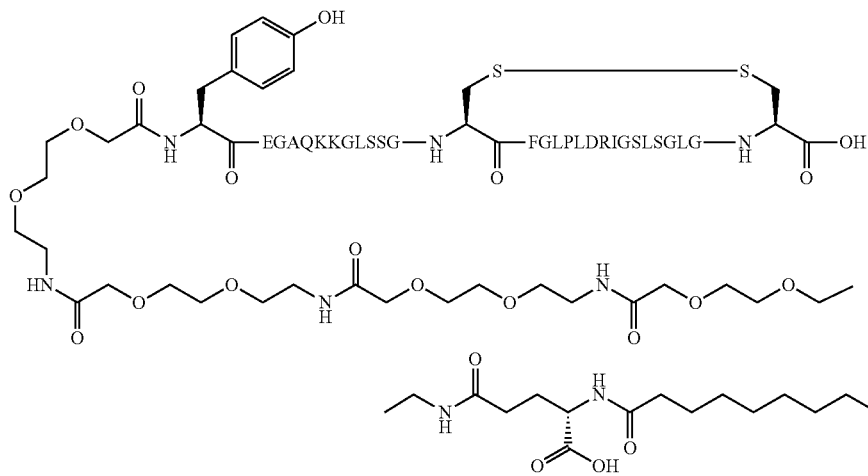

Molecular weight: 3959.5371. LCMS34: m/3 calcd: 1320.8457; m/3 found: 1321.0300; m/4.
calcd: 990.8843; m/4 found: 990.7800.
Chem. 81; Compound ID 1394; SEQ ID NO: 70

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), 5Q, 10E, 13Q, 19Q, 25P, 32L]-hCNP37

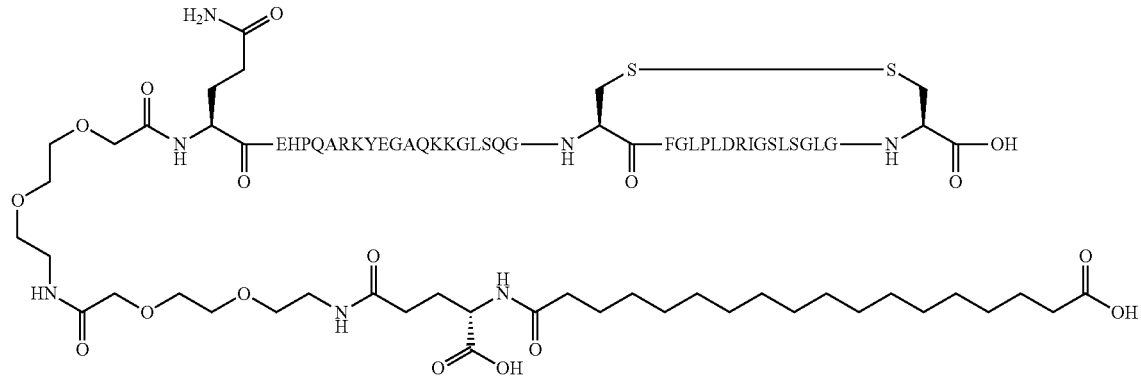

Molecular weight: 4644.2869. LCMS34: m/3 calcd: 1549.0956; m/3 found: 1548.7900; m/4.
calcd: 1162.0717; m/4 found: 1161.8500.
Chem. 82; Compound ID 1395; SEQ ID NO: 71

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), 5Q, 7A, 10E, 13Q, 19Q, 25P, 32L]-hCNP37

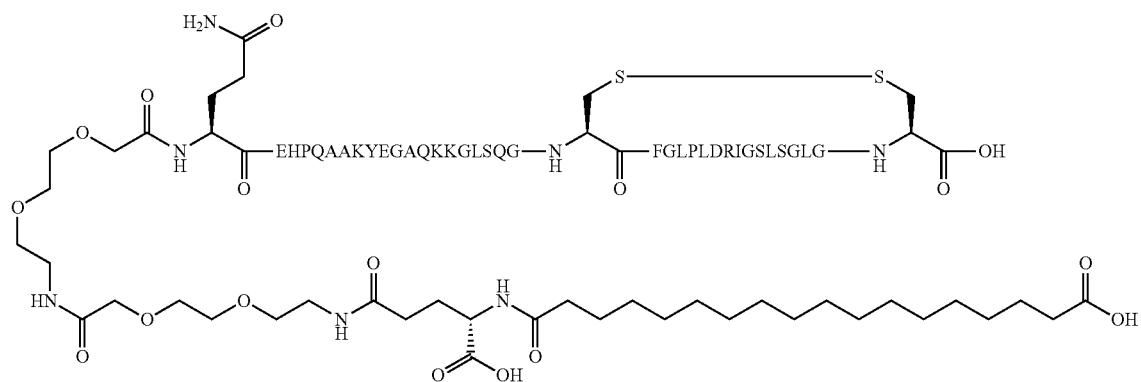

Molecular weight: 4559.1791. LCMS34: m/3 calcd: 1520.7264; m/3 found: 1520.4600; m/4.
calcd: 1140.7948; m/4 found: 1140.600.
Chem. 83; Compound ID 1396; SEQ ID NO: 70

[N-terminal([2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]), 5Q, 10E, 13Q, 19Q, 25P, 32L]-hCNP37

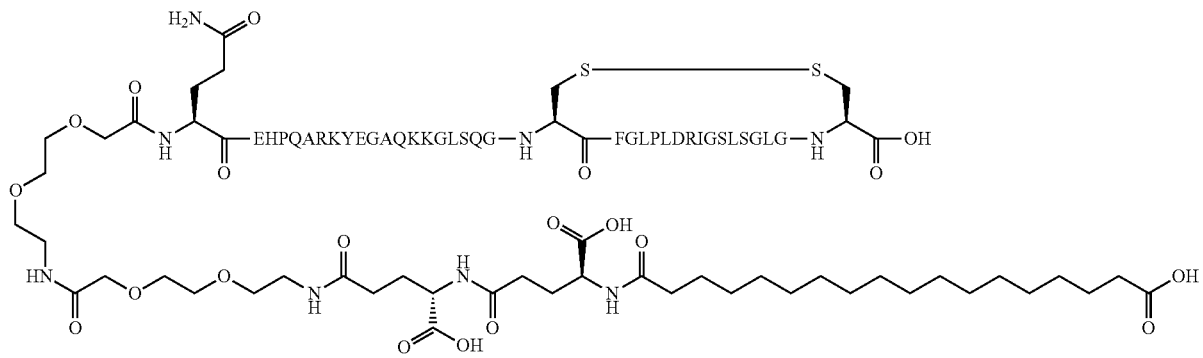

Molecular weight: 4773.4009. LCMS34: m/3 calcd: 1592.1336; m/3 found: 1592.1600; m/4 calcd: 1194.3502; m/4 found: 1194.3700.

Chem. 84; Compound ID 1398; SEQ ID NO: 72

[N-terminal([2-[2-[2-[[2-[2-[2-[[(4S)-4-carboxy-4-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]butanoyl]amino]ethoxy]ethoxy]acetyl]amino]ethoxy]ethoxy]acetyl]), 5Q, 8H, 13Q, 17S, 19Q, 25P, 32L]-hCNP37

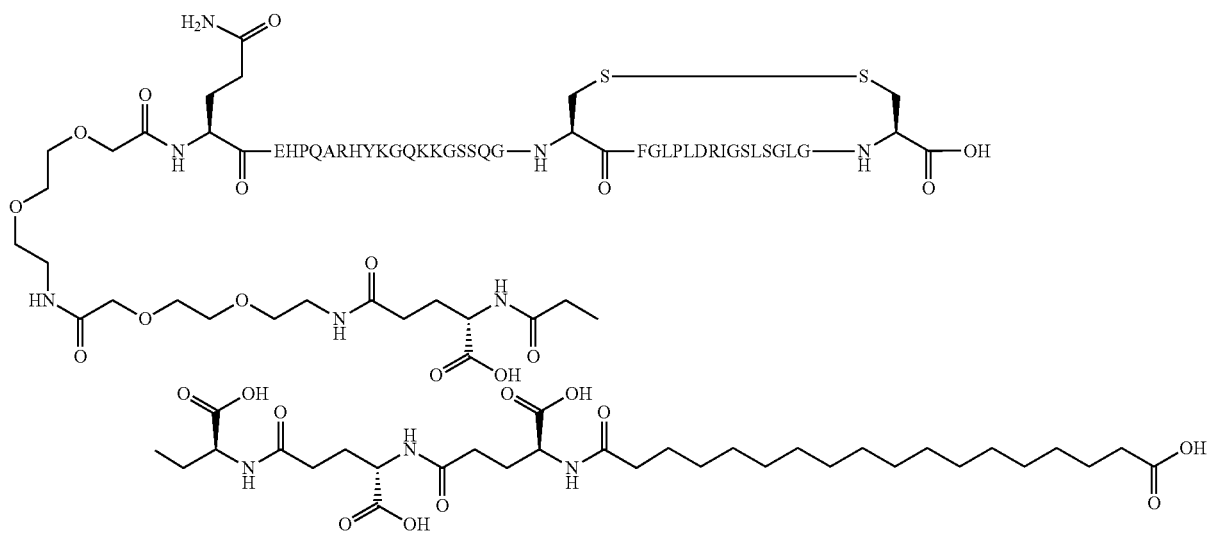

Molecular weight: 5013.5738. LCMS34: m/3 calcd: 1672.1913; m/3 found: 1672.1528; m/4 calcd: 1254.3935; m/4 found: 1254.1224.

Chem. 85; Compound ID 1399; SEQ ID NO: 72

[N-terminal([2-[2-[2-[[2-[2-[2-[[(4S)-4-carboxy-4-[[(4S)-4-carboxy-4-[[(4S)-4- carboxy-4-[[(4S)-4-carboxy-4-(19-carboxynonadecanoylamino)bu-tanoyl]amino]butanoyl]amino]butanoyl]amino]butanoyl]amino]ethoxy]ethoxy]acetyl]amino]ethoxy]ethoxy]acetyl]), 5Q, 8H, 13Q, 17S, 19Q, 25P, 32L]-hCNP37

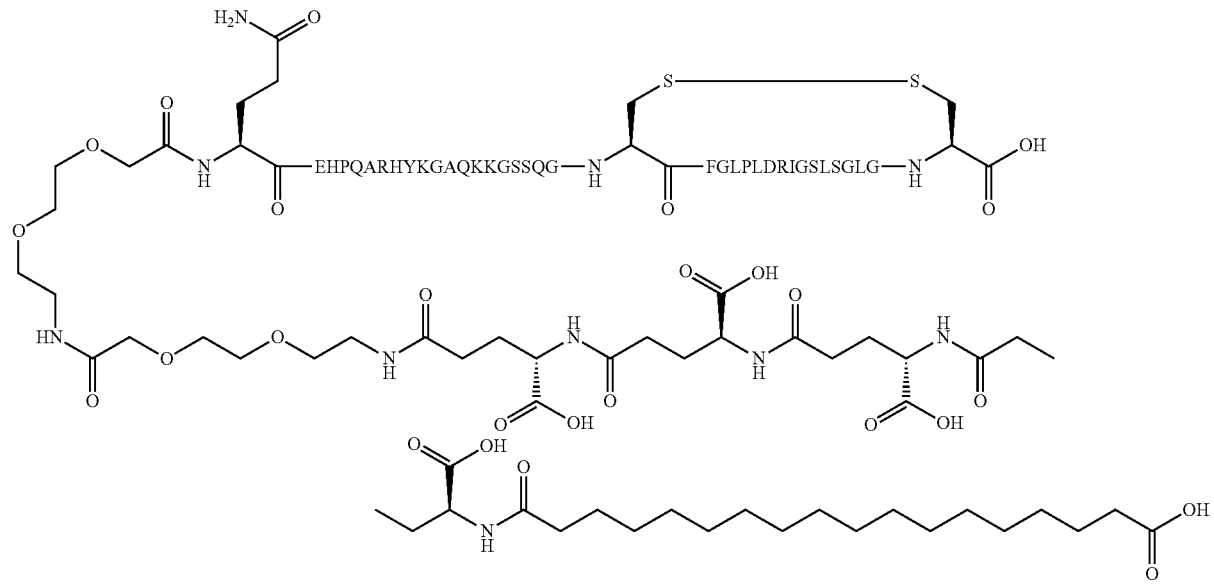

Molecular weight: 5041.627. LCMS34: m/3 calcd: 1681.5423; m/3 found: 1681.5050; m/4.
calcd: 1261.4068; m/4 found: 1261.1331.
Chem. 86; Compound ID 1400; SEQ ID NO: 73

[N-terminal([2-[2-[2-[[2-[2-[2-[[(4S)-4-carboxy-4-[[(4S)-4-carboxy-4-[[(4S)-4- carboxy-4-[[(4S)-4-carboxy-4-(17-carboxyheptadecanoylamino)bu-tanoyl]amino]butanoyl]amino]butanoyl]amino]ethoxy]ethoxy]acetyl]amino]ethoxy]ethoxy]acetyl]), 5Q, 7H, 13Q, 17G, 19Q, 25P, 32L]-hCNP37

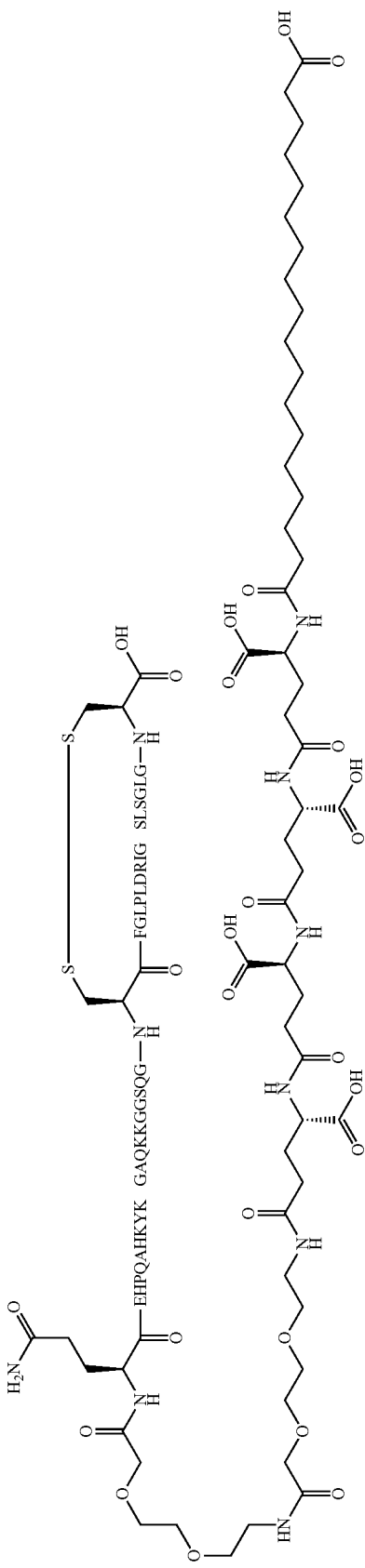

Molecular weight: 4955.5344. LCMS34: m/3 calcd: 1652.8448; m/3 found: 1652.8279; m/4.
calcd: 1239.8836; m/4 found: 1239.8716.

Chem. 87; Compound ID 1401; SEQ ID NO: 74

[N-terminal([2-[2-[2-[[2-[2-[2-[[(4S)-4-carboxy-4-[[(4S)-4-carboxy-4-[[(4S)-4- carboxy-4-[[(4S)-4-carboxy-4-[[(4S)-4-carboxy-4-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]butanoyl]amino]butanoyl]amino]butanoyl]amino]butanoyl]amino]ethoxy]ethoxy]acetyl]amino]ethoxy]ethoxy]acetyl]), 5Q, 13Q, 32L]-hCNP37

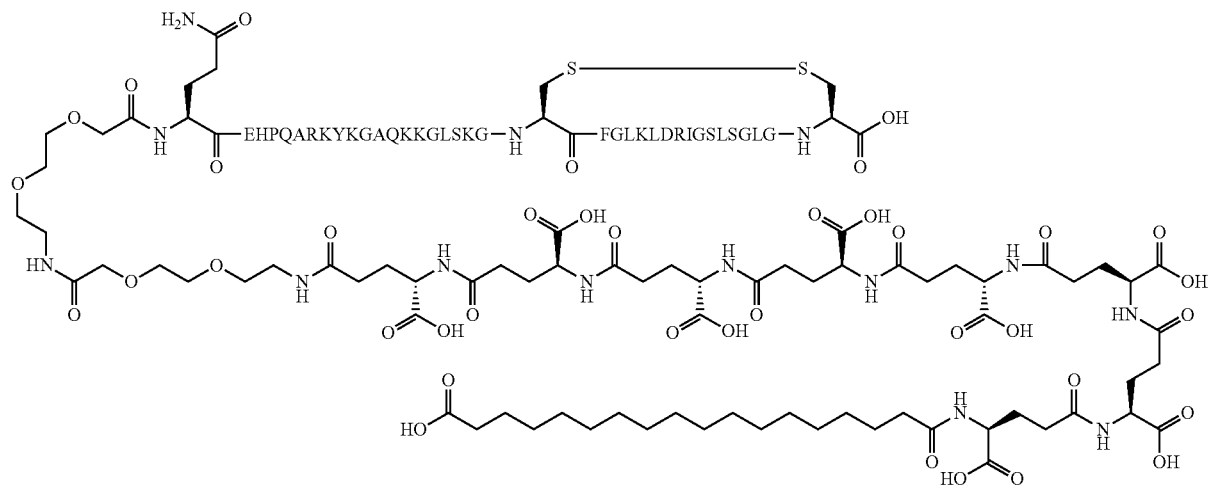

Molecular weight: 5578.2432. LCMS34: m/3 calcd: 1860.4144; m/3 found: 1860.2654; m/4.
calcd: 1395.5608; m/4 found: 1395.4623.

Chem. 88; Compound ID 1402; SEQ ID NO: 75

[N-terminal([2-[2-[2-[[2-[2-[2-[[(4S)-4-carboxy-4-[[(4S)-4-carboxy-4-[[(4S)-4- carboxy-4-[[(4S)-4-carboxy-4-[[(4S)-4-carboxy-4-(17-carboxyheptadecanoylamino)butanoyl]amino]butanoyl]amino]butanoyl]amino]butanoyl]amino]butanoyl]amino]ethoxy]ethoxy]acetyl]amino]ethoxy]ethoxy]acetyl]), 5Q, 13Q, 19Q, 25P, 32L]-hCNP37

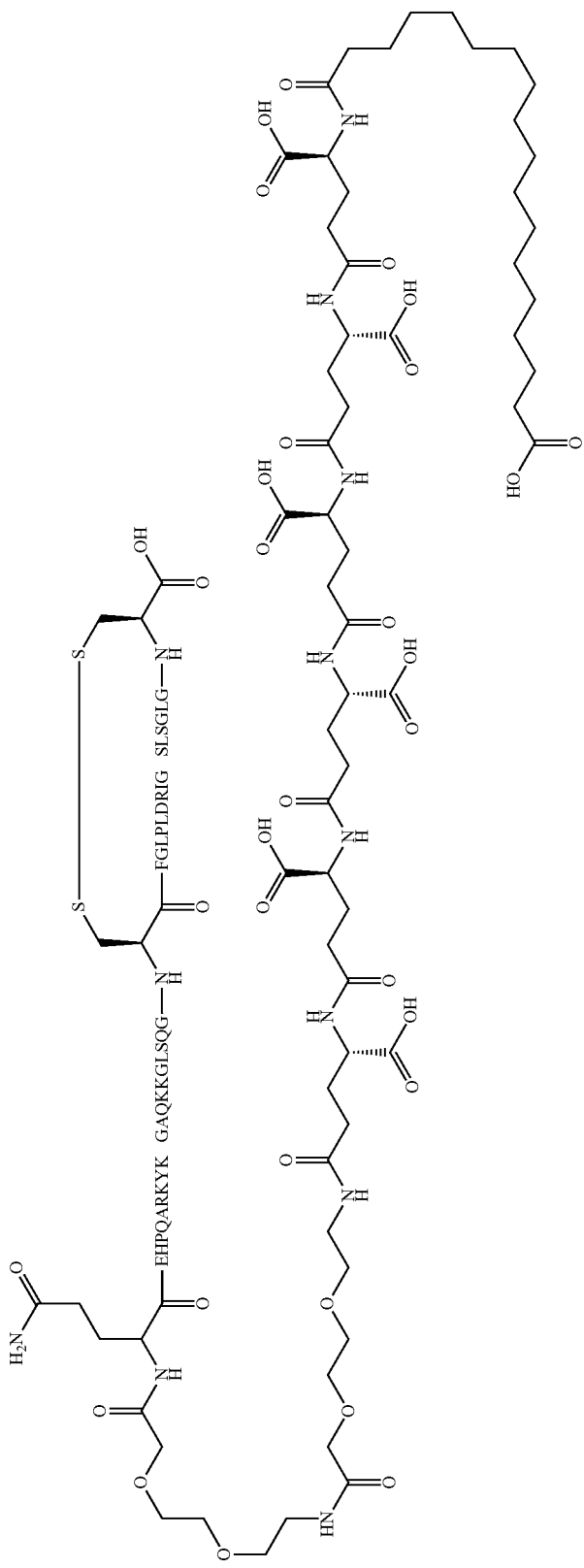

Molecular weight: 5288.9151. LCMS34: m/3 calcd: 1763.9717; m/3 found: 1763.8729; m/4. calcd: 1323.2288; m/4 found: 1323.1718.

Chem. 89; Compound ID 1403; SEQ ID NO: 76

[N-terminal([2-[2-[2-[[2-[2-[2-[[(4S)-4-carboxy-4-[[(4S)-4-carboxy-4-[[(4S)-4- carboxy-4-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]butanoyl]amino]butanoyl]amino]ethoxy]ethoxy]acetyl]amino]ethoxy]ethoxy]acetyl]), 5Q, 13Q, 17G, 19Q, 25P, 32L]-hCNP37

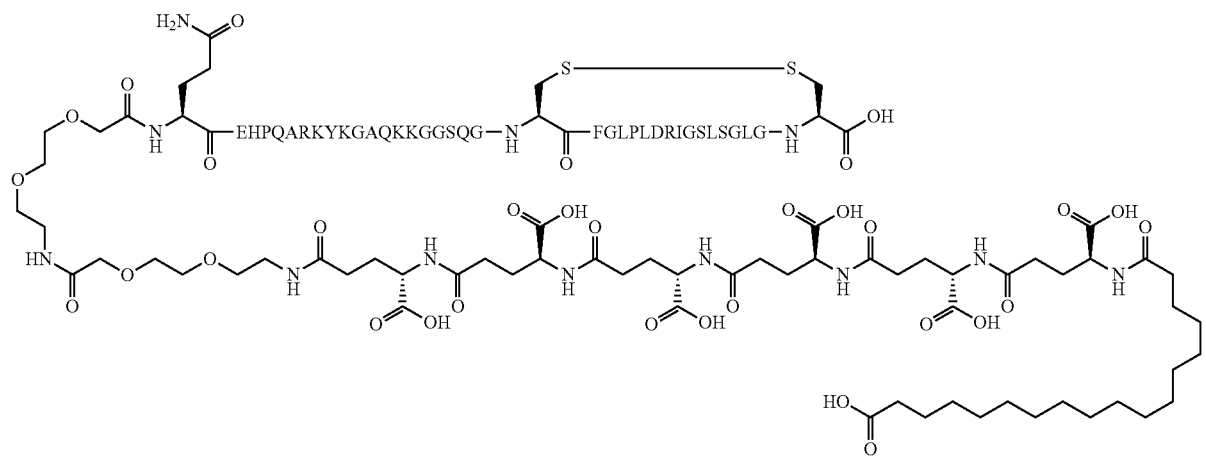

Molecular weight: 5232.8088. LCMS34: m/3 calcd: 1745.2696; m/3 found: 1744.8611; m/4. calcd: 1309.2022; m/4 found: 1309.1547.

Chem. 90; Compound ID 1404; SEQ ID NO: 75

[N-terminal([2-[2-[2-[[2-[2-[2-[[2-[2-[2-[[2-[2-[2-[[(4S)-4-carboxy-4-[[(4S)-4-carboxy-4-[[(4S)-4-carboxy-4-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]butanoyl]amino]butanoyl]amino]ethoxy]ethoxy]acetyl]amino]ethoxy]ethoxy]acetyl]amino]ethoxy]ethoxy]acetyl]amino]ethoxy]ethoxy]acetyl]), 5Q, 13Q, 19Q, 25P, 32L]-hCNP37

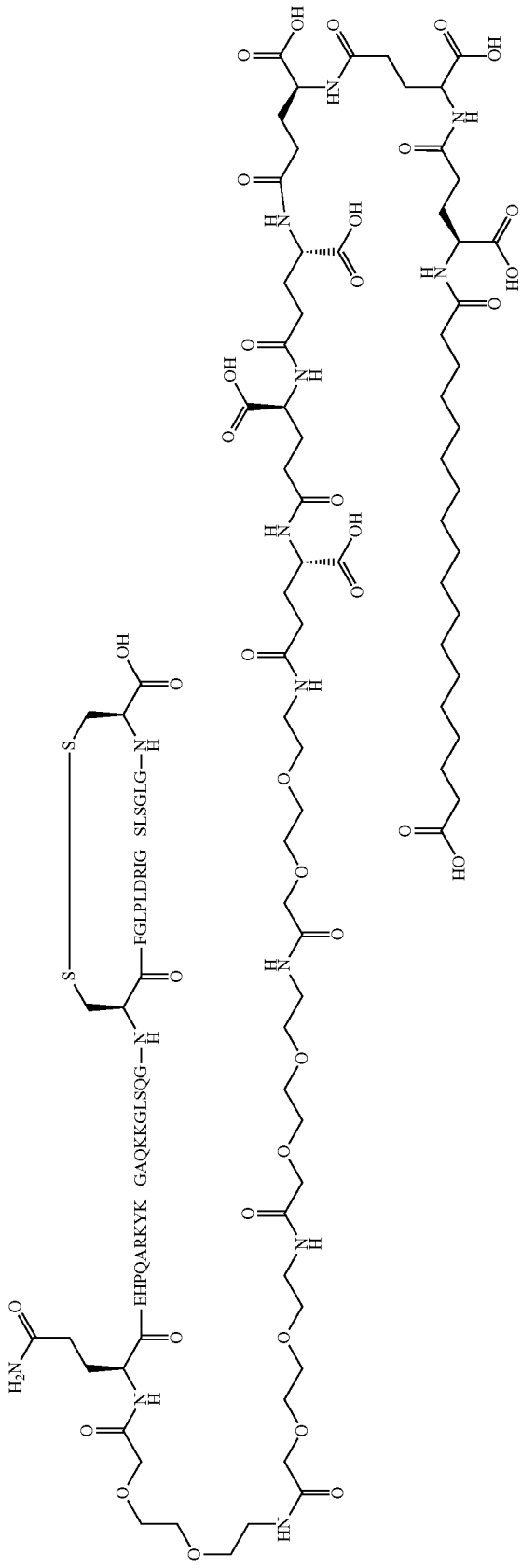

Molecular weight: 5579.228. LCMS34: m/3 calcd: 1860.7427; m/3 found: 1860.6008; m/4. calcd: 1395.8070; m/4 found: 1395.7069.

Chem. 91; Compound ID 1405; SEQ ID NO: 75

[N-terminal([2-[2-[2-[[2-[2-[2-[[(4S)-4-carboxy-4-[[(4S)-4-carboxy-4-[[(4S)-4- carboxy-4-[[(4S)-4-carboxy-4-[[(4S)-4-carboxy-4-[[(4S)-4-carboxy-4-(19-carboxynonadecanoylamino)butanoyl]amino]butanoyl]amino]butanoyl]amino]butanoyl]amino]butanoyl]amino]ethoxy]ethoxy]acetyl]amino]ethoxy]ethoxy]acetyl]), 5Q, 13Q, 19Q, 25P, 32L]-hCNP37

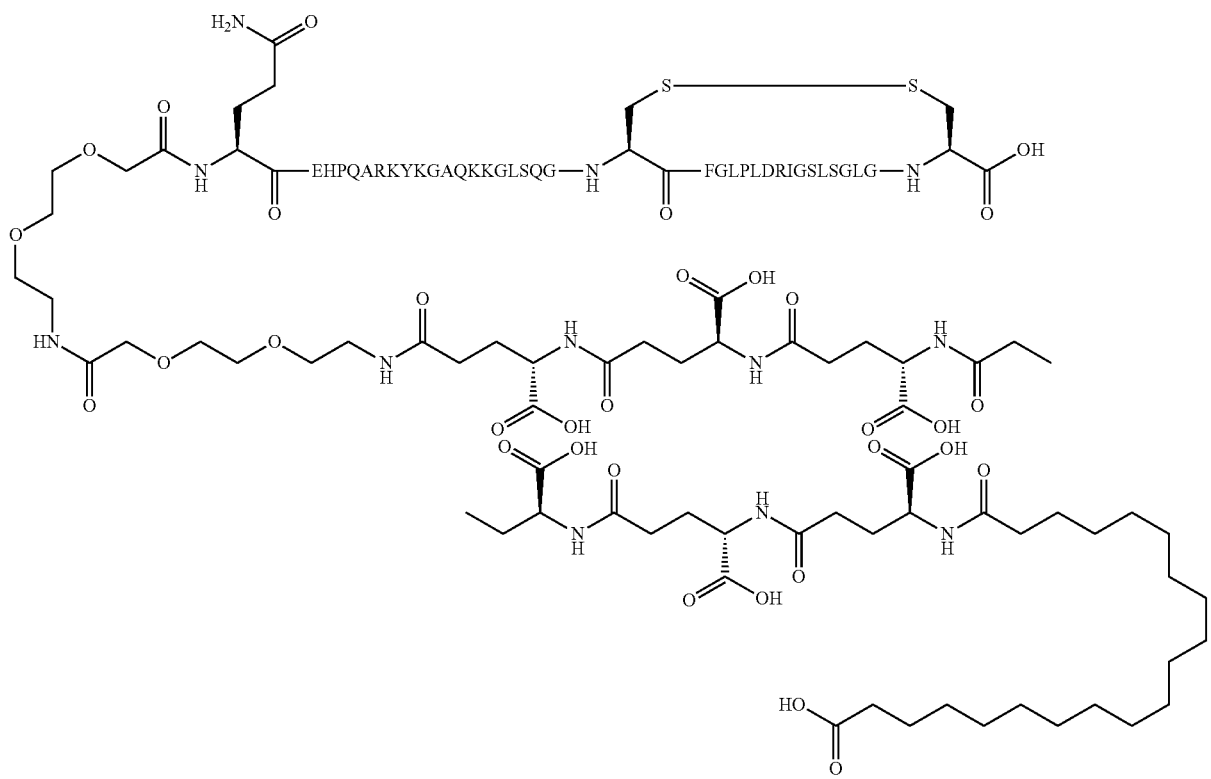

Molecular weight: 5316.9683. LCMS34: m/3 calcd: 1773.3228; m/3 found: 1773.2192; m/4. calcd: 1330.2421; m/4 found: 1330.1785.

Chem. 92; Compound ID 1406; SEQ ID NO: 75

[N-terminal([2-[2-[2-[[2-[2-[2-[[2-[2-[2-[[2-[2-[2-[[(4S)-4-carboxy-4-[[(4S)-4-carboxy-4-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]butanoyl]amino]ethoxy]ethoxy]acetyl]amino]ethoxy]ethoxy]acetyl]amino]ethoxy]ethoxy]acetyl]amino]ethoxy]ethoxy]acetyl]), 5Q, 13Q, 19Q, 25P, 32L]-hCNP37

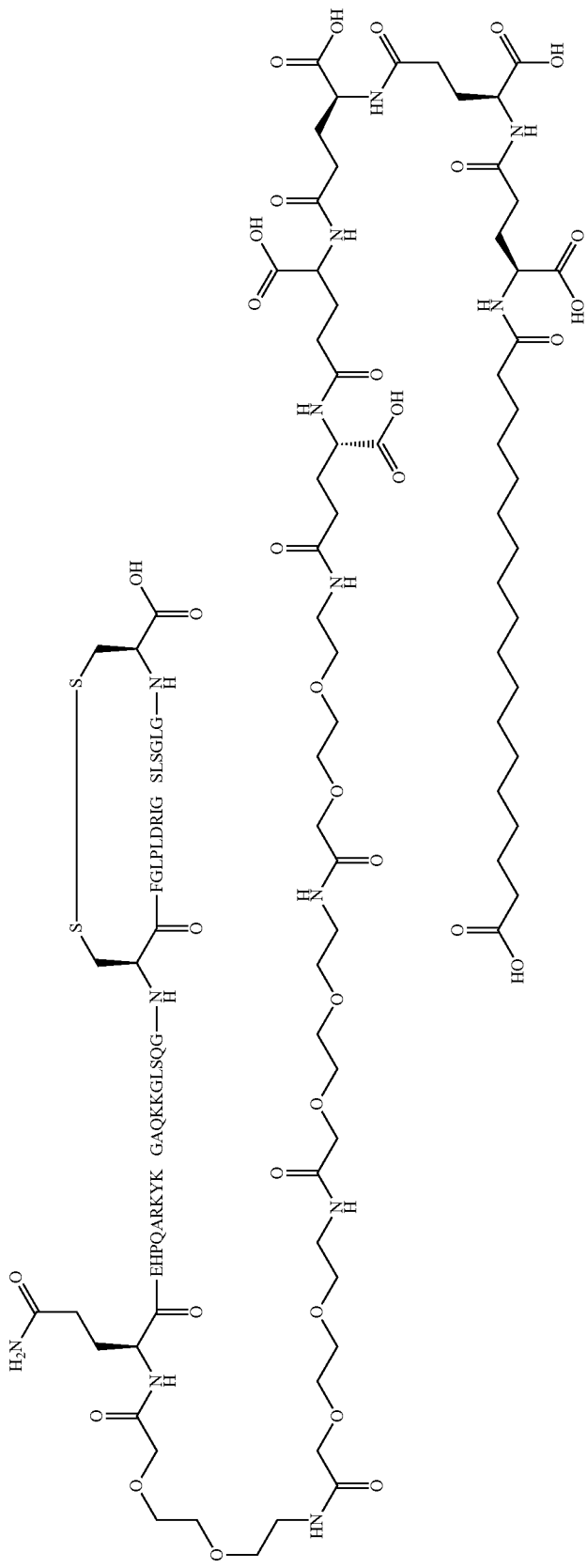

Molecular weight: 5450.114. LCMS34: m/3 calcd: 1817.7047; m/3 found: 1817.5808; m/4.
calcd: 1363.5285; m/4 found: 1363.4484.

Chem. 93; Compound ID 9407; SEQ ID NO: 77

[N-terminal([2-[2-[2-[[2-[2-[2-[[2-[2-[2-[[2-[2-[2-[[(4S)-4-carboxy-4-[[(4S)-4-carboxy-4-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]butanoyl]amino]ethoxy]ethoxy]acetyl]amino]ethoxy]ethoxy]acetyl]amino]ethoxy]ethoxy]acetyl]amino]ethoxy]ethoxy]acetyl]), des1-5, 13Q, 19Q, 25P, 32L]-hCNP37

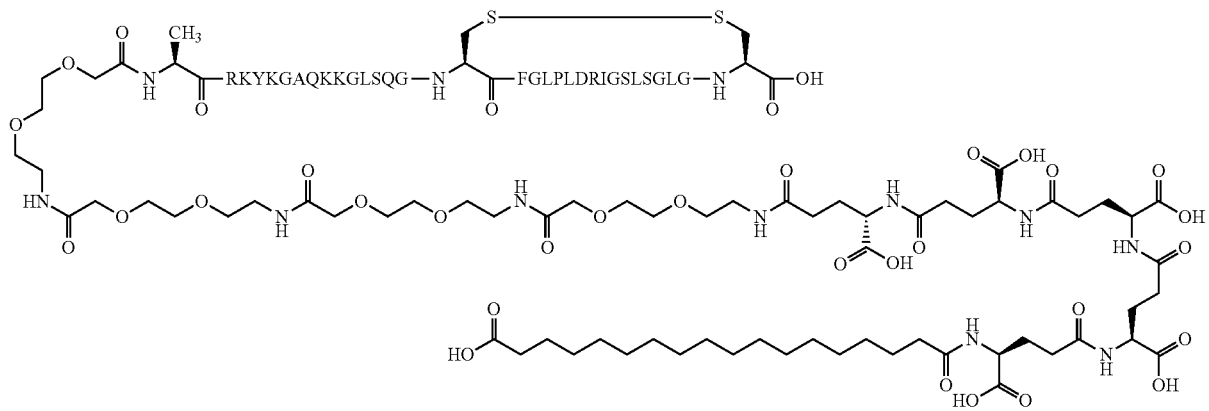

Molecular weight: 4830.4871. LCMS34: m/3 calcd: 1611.1624; m/3 found: 1610.8330; m/4.
calcd: 1208.6218; m/4 found: 1208.3823.

Chem. 94; Compound ID 1419; SEQ ID NO: 51

[N-terminal([2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]), des1-5, 10H, 13Q, 14H, 15T, 17V, 19S, 25P, 32L]-hCNP37

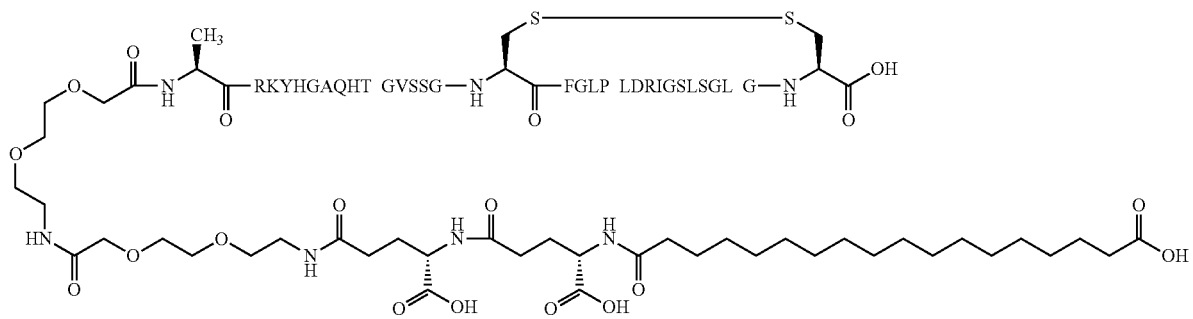

Molecular weight: 4088.6194. LCMS34: m/3 calcd: 1363.8731; m/3 found: 1363.6902; m/4.
calcd: 1023.1549; m/4 found: 1023.0371.

Chem. 95; Compound ID 1420; SEQ ID NO: 78

[N-terminal([2-[2-[2-[[2-[2-[2-[[(4S)-4-carboxy-4-[[(4S)-4-carboxy-4-[[(4S)-4- carboxy-4-(17-carboxyheptadecanoylamino)butanoyl]amino]butanoyl]amino]butanoyl]amino]ethoxy]ethoxy]acetyl]amino]ethoxy]ethoxy]acetyl]), des1-5, 10H, 13Q, 14H, 15T, 17V, 25P, 32L]-hCNP37

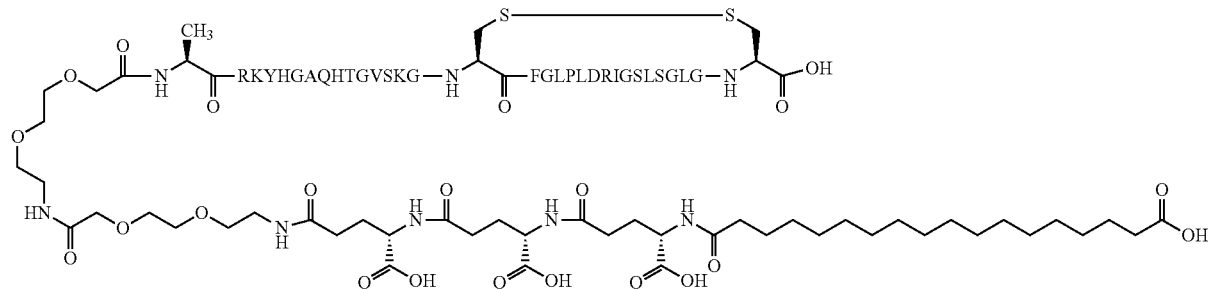

Molecular weight: 4258.8284. LCMS34: m/3 calcd: 1420.6095; m/3 found: 1420.3875; m/4.
calcd: 1065.7071; m/4 found: 1065.5448.
Chem. 96; Compound ID 1421; SEQ ID NO: 79

[N-terminal([2-[2-[2-[[2-[2-[2-[[(4S)-4-carboxy-4-[[(4S)-4-carboxy-4-[[(4S)-4- carboxy-4-(17-carboxyheptadecanoylamino)butanoyl]amino]butanoyl]amino]butanoyl]amino]ethoxy]ethoxy]acetyl]amino]ethoxy]ethoxy]acetyl]), des1-5, 13Q, 15T, 17V, 19S, 25P, 32L]-hCNP37

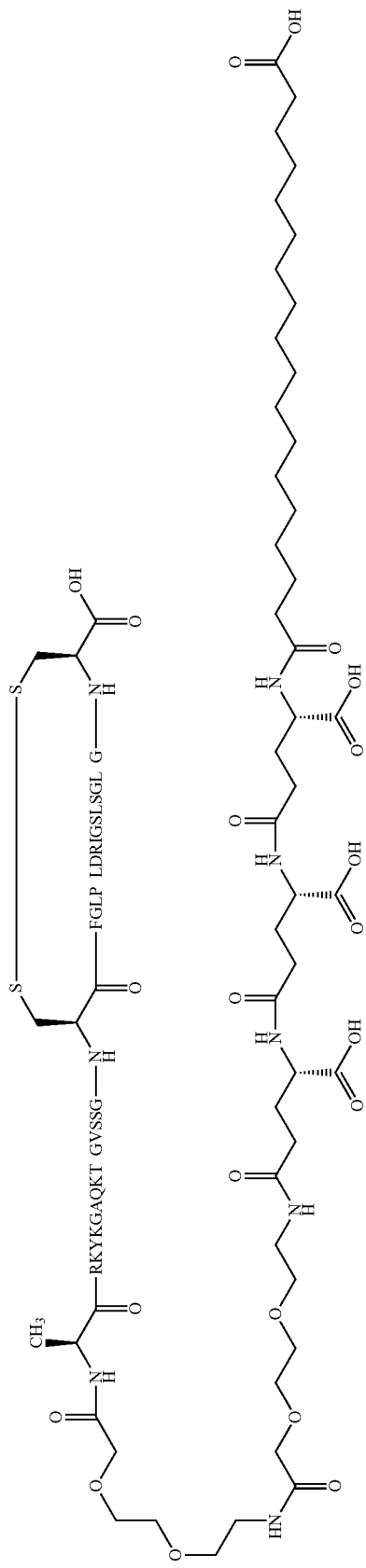

Molecular weight: 4199.7994. LCMS34: m/3 calcd: 1400.9331; m/3 found: 1400.7268; m/4.
calcd: 1050.9499; m/4 found: 1050.8062.

Chem. 97; Compound ID 1422; SEQ ID NO: 80

[N-terminal([2-[2-[2-[[2-[2-[2-[[(4S)-4-carboxy-4-[[(4S)-4-carboxy-4-[[(4S)-4- carboxy-4-(17-carboxyheptadecanoylamino)butanoyl]amino]butanoyl]amino]butanoyl]amino]ethoxy]ethoxy]acetyl]amino]ethoxy]ethoxy]acetyl]), des1-5, 10H, 13Q, 17V, 19S, 25P, 32L]-hCNP37

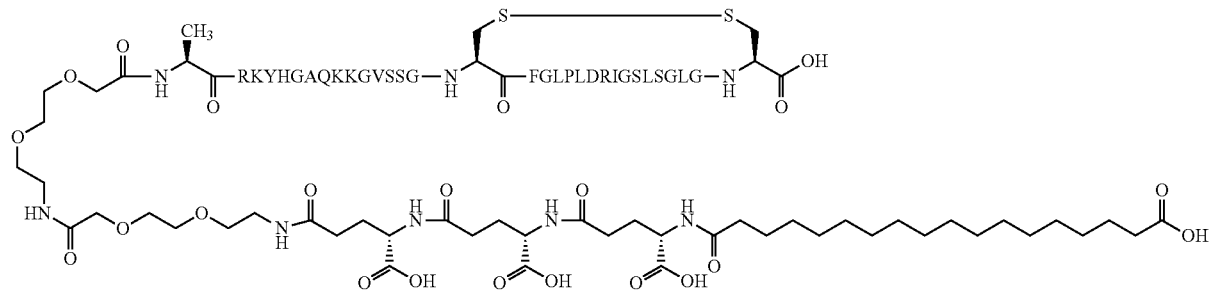

Molecular weight: 4235.8348. LCMS34: m/3 calcd: 1412.9449; m/3 found: 1412.7313; m/4.
calcd: 1059.9587; m/4 found: 1059.8075.

Chem. 98; Compound ID 1423; SEQ ID NO: 81

[N-terminal([2-[2-[2-[[2-[2-[2-[[(4S)-4-carboxy-4-[[(4S)-4-carboxy-4-[[(4S)-4- carboxy-4-(17-carboxyheptadecanoylamino)butanoyl]amino]butanoyl]amino]butanoyl]amino]ethoxy]ethoxy]acetyl]amino]ethoxy]ethoxy]acetyl]), des1-5, 10H, 13Q, 15T, 17V, 25P, 32L]-hCNP37

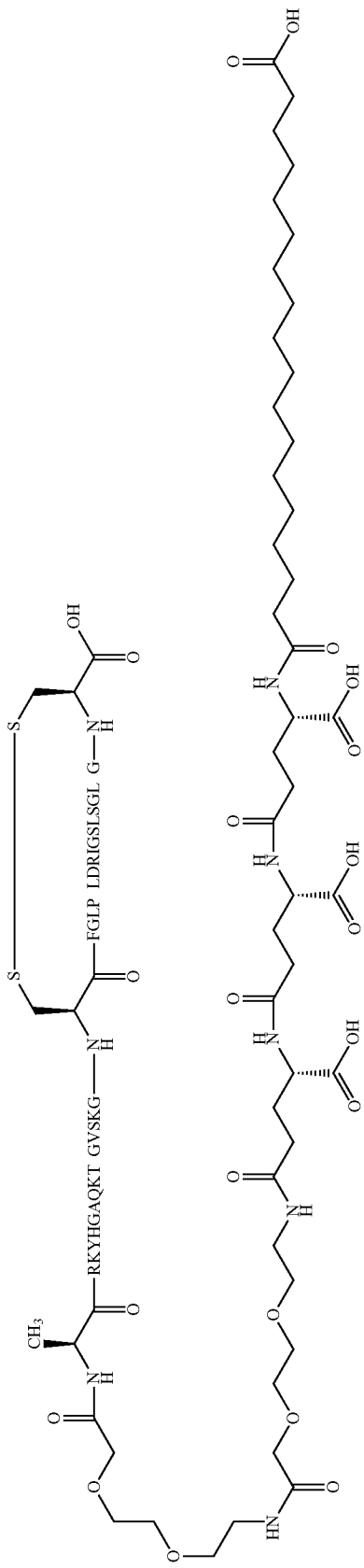

Molecular weight: 4249.8614. LCMS34: m/3 calcd: 1417.6205; m/3 found: 1417.3965; m/4.
calcd: 1063.4654; m/4 found: 1063.3148.

Chem. 99; Compound ID 1424; SEQ ID NO: 82

[N-terminal([2-[2-[2-[[2-[2-[2-[[(4S)-4-carboxy-4-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]butanoyl]amino]ethoxy]ethoxy]acetyl]amino]ethoxy]ethoxy]acetyl]), des1-5, 13Q, 15T, 17V, 25P, 32L]-hCNP37

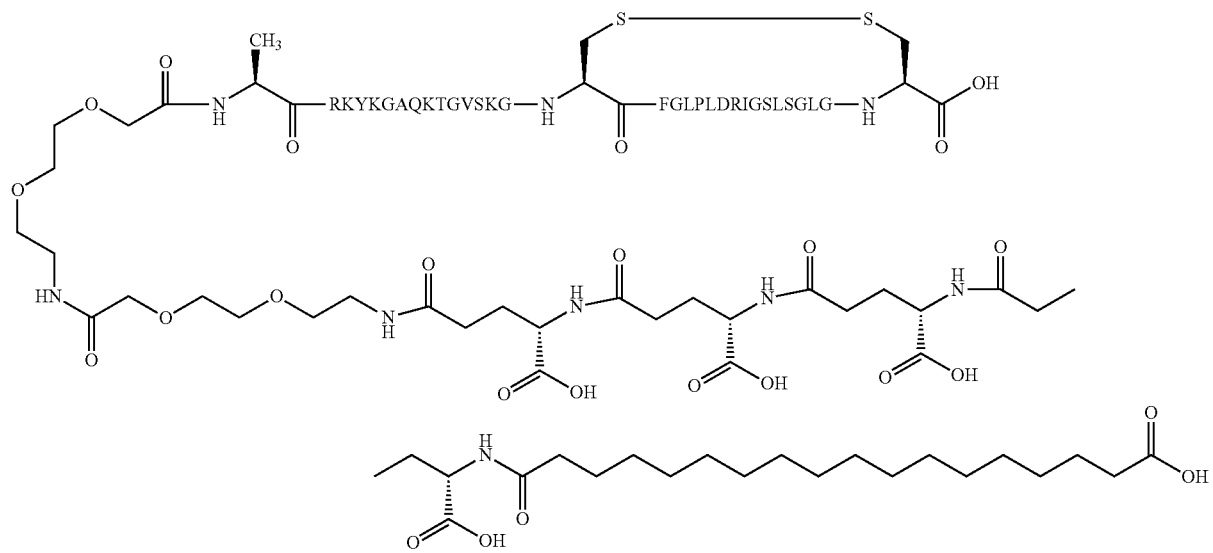

Molecular weight: 4370.0084. LCMS34: m/3 calcd: 1457.6695; m/3 found: 1457.4309; m/4.
calcd: 1093.5021; m/4 found: 1093.5833.

Chem. 100; Compound ID 1425; SEQ ID NO: 83

[N-terminal([2-[2-[2-[[2-[2-[2-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]eth oxy]ethoxy]acetyl]amino]ethoxy]ethoxy]acetyl]amino]ethoxy]ethoxy]acetyl]), des1-8, 10H, 13Q, 15T, 17V, 25P, 32L]-hCNP37

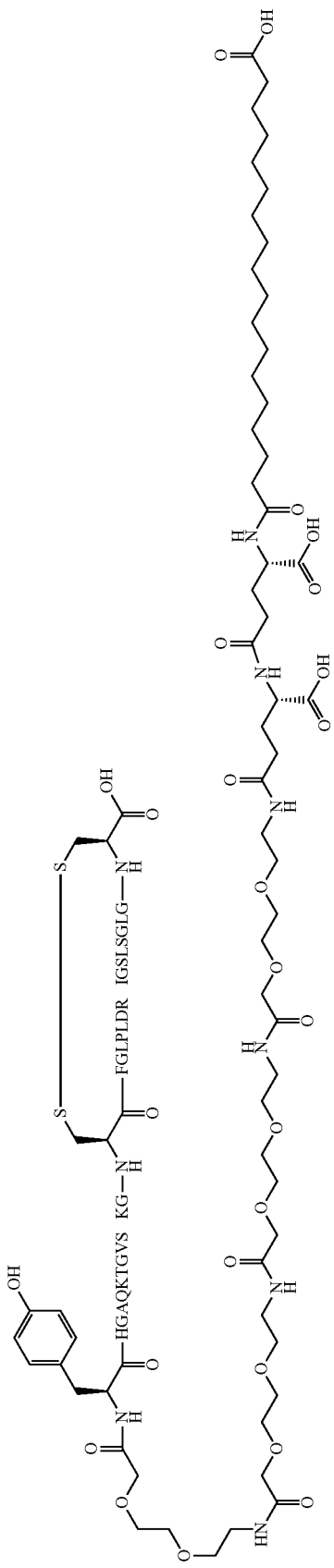

Molecular weight: 4055.6244. LCMS34: m/3 calcd: 1352.8748; m/3 found: 1352.6941; m/4.
calcd: 1014.9061; m/4 found: 1014.5325.

Chem. 101; Compound ID 1426; SEQ ID NO: 84

[N-terminal([2-[2-[2-[[2-[2-[2-[[(4S)-4-carboxy-4-[[(4S)-4-carboxy-4-[17-(1H- tetrazol-5-yl)heptadecanoylamino]butanoyl]amino]butanoyl]amino]ethoxy]ethoxy]acetyl]amino]ethoxy]et hoxy]acetyl]), des1-5, 10H, 13Q, 15S, 19Q, 25P, 32L]-hCNP37

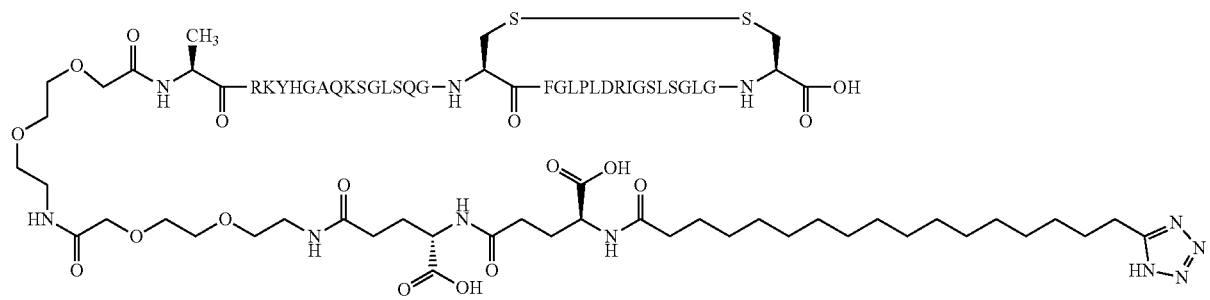

Molecular weight: 4144.7323. LCMS34: m/3 calcd: 1382.5774; m/3 found: 1382.3732; m/4.
calcd: 1037.1831; m/4 found: 1037.0341.

Chem. 102; Compound ID 1431; SEQ ID NO: 85

[N-terminal([2-[2-[2-[[2-[2-[2-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acet yl]amino]ethoxy]ethoxy] acetyl]amino]ethoxy]ethoxy]acetyl]), des1-8, 10E, 13Q, 17G, 19H, 25P, 32L]-hCNP37

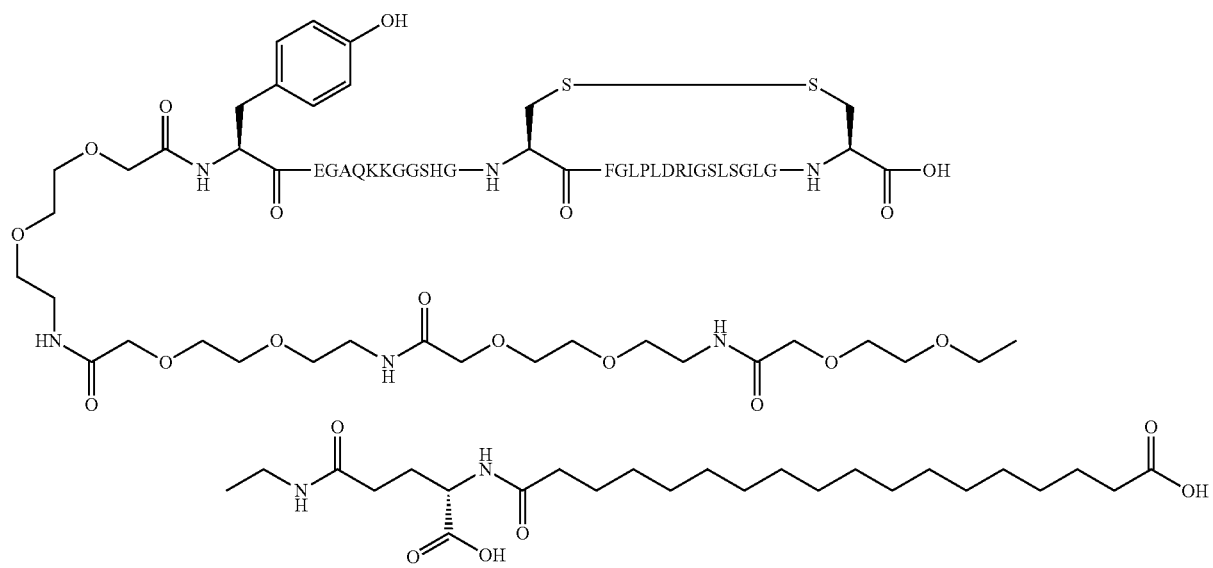

Molecular weight: 3912.4408. LCMS34: m/3 calcd: 1305.1469; m/3 found: 1304.9080; m/4.
calcd: 979.1102; m/4 found: 978.9250.

Chem. 103; Compound ID 1432; SEQ ID NO: 86

[N-terminal([2-[2-[2-[[2-[2-[2-[[2-[2-[2-[[2-[2-[2-[[(4S)-4-carboxy-4-[[(4S)-4-carboxy-4-(17-carboxy-heptadecanoylamino)butanoyl]amino]butanoyl]amino]ethoxy]ethoxy]acetyl]amino]eth oxy]ethoxy]acetyl]amino]ethoxy]ethoxy]acetyl]amino]ethoxy]ethoxy]acetyl]), des1-5, 10E, 13Q, 14H, 17G, 19Q, 25P, 32L]-hCNP37

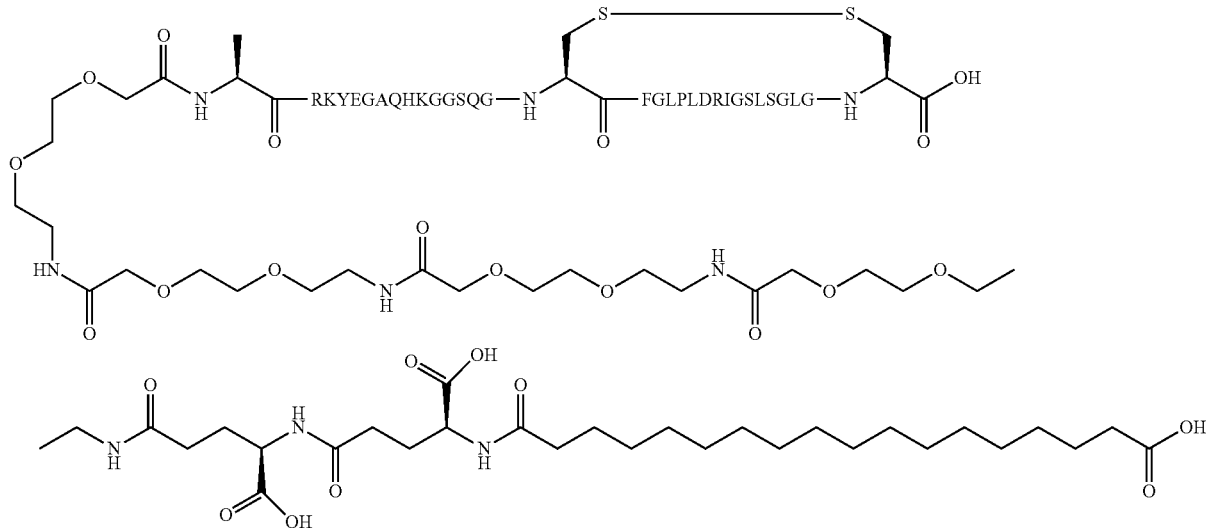

Molecular weight: 4396.9476. LCMS34: m/3 calcd: 1466.6492; m/3 found: 1466.3500; m/4. calcd: 1100.2369; m/4 found: 1100.0354.
Chem. 104; Compound ID 1434; SEQ ID NO: 87

[N-terminal([2-[2-[2-[[2-[2-[2-[[2-[2-[2-[[2-[2-[2-[[(4S)-4-carboxy-4-[[(4S)-4-carboxy-4-(17-carboxy-heptadecanoylamino)butanoyl]amino]butanoyl]amino]ethoxy]ethoxy]acetyl]amino]eth oxy]ethoxy]acetyl]amino]ethoxy]ethoxy]acetyl]amino]ethoxy]ethoxy]acetyl]), des1-8, 10H, 13Q, 17G, 19Q, 25P, 32L]-hCNP37

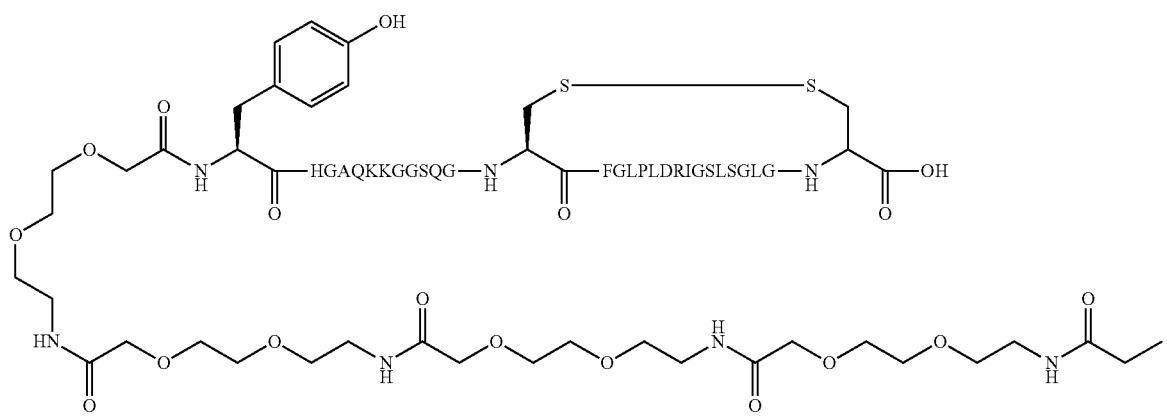

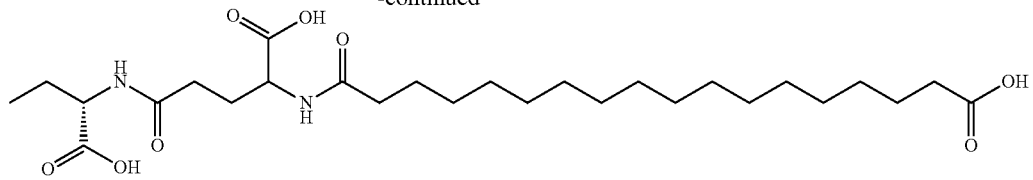

Molecular weight: 4040.57. LCMS34: m/3 calcd: 1347.8567; m/3 found: 1347.9714; m/4.
calcd: 1011.1425; m/4 found: 1011.2499.
Chem. 105; Compound ID 9435; SEQ ID NO: 88

[N-terminal([2-[2-[2-[[2-[2-[2-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]eth oxy]ethoxy]acetyl]amino]ethoxy]ethoxy]acetyl]amino]ethoxy]ethoxy]acetyl]), des1-8, 13Q, 17G, 19Q, 25P, 32L]-hCNP37

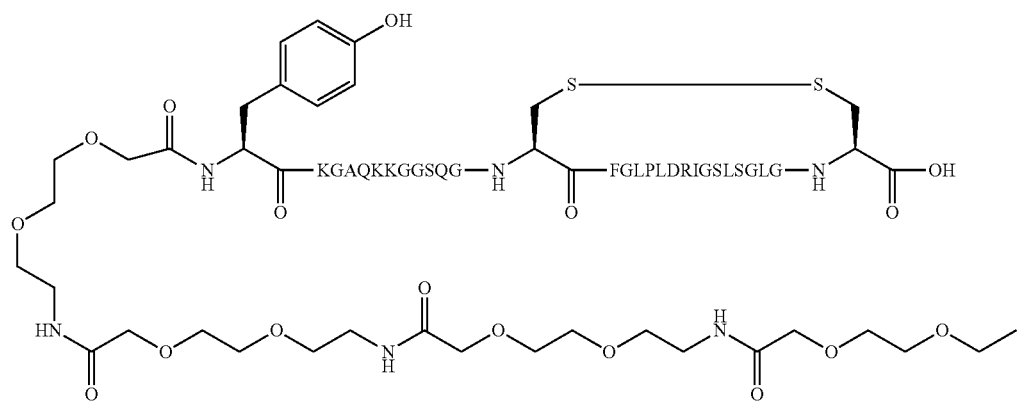

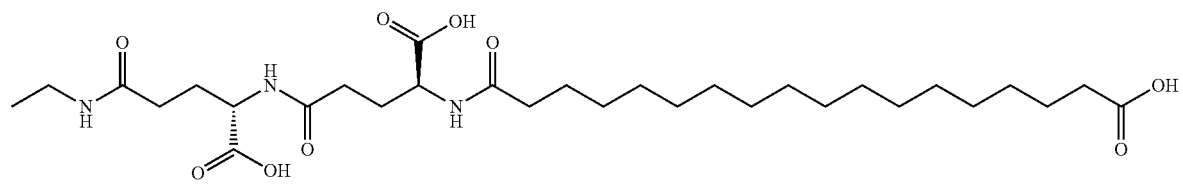

Molecular weight: 4031.603. LCMS34: m/3 calcd: 1344.8677; m/3 found: 1344.7600; m/4.
calcd: 1008.9008; m/4 found: 1008.8210.
Chem. 106; Compound ID 1436; SEQ ID NO: 89

[N-terminal([2-[2-[2-[[2-[2-[2-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]ethoxy]ethoxy]acetyl]amino]ethoxy]ethoxy]acetyl]), des1-8, 13Q, 17V, 19Q, 25P, 32L]-hCNP37

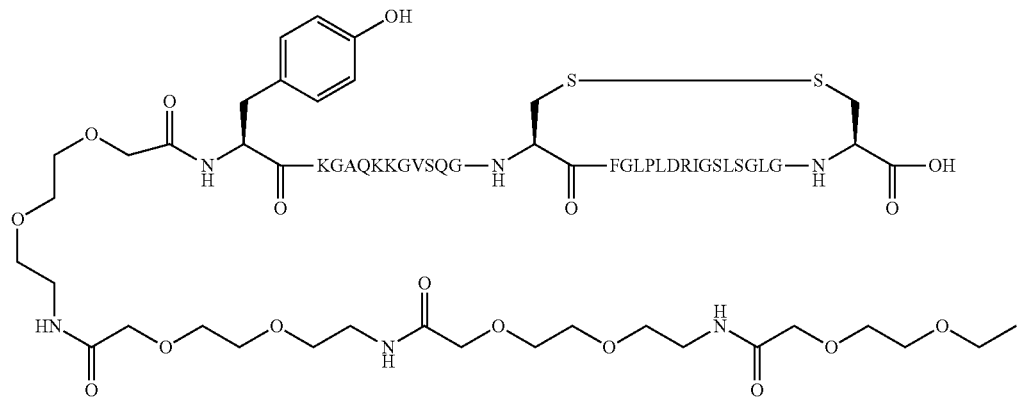

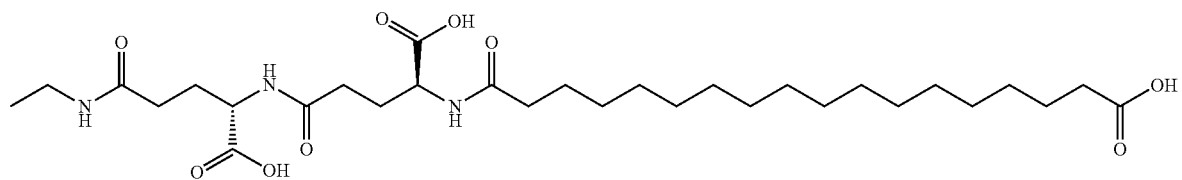

Molecular weight: 4073.6828. LCMS34: m/3 calcd: 1358.8943; m/3 found: 1358.6617; m/4.
calcd: 1019.4207; m/4 found: 1019.2703.
Chem. 107; Compound ID 1437; SEQ ID NO: 90

[N-terminal([2-[2-[2-[[2-[2-[2-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]ethoxy]ethoxy]acetyl]amino]ethoxy]ethoxy]acetyl]), des1-8, 10H, 13Q, 17V, 19Q, 25P, 32L]-hCNP37

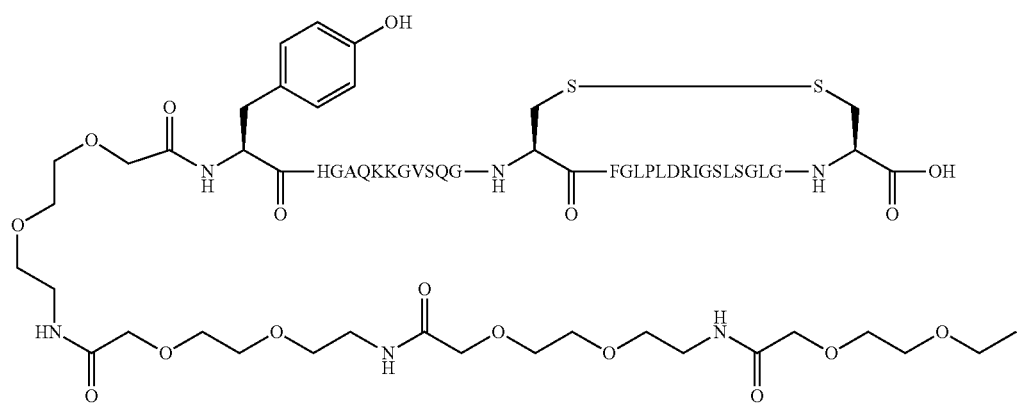

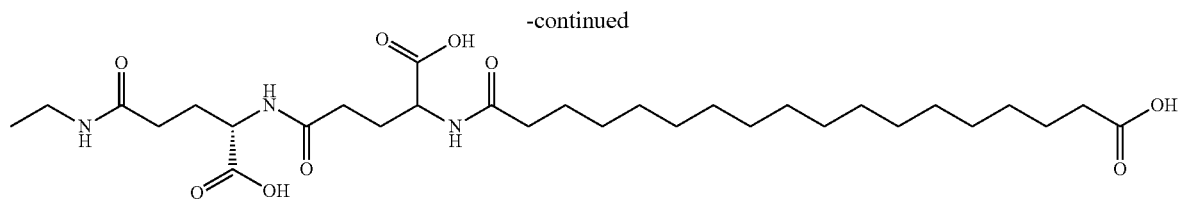
Molecular weight: 4082.6498. LCMS34: m/3 calcd: 1361.8833; m/3 found: 1361.7580; m/4.
 calcd: 1021.6625; m/4 found: 1021.5750.
Chem. 108; Compound ID 1448; SEQ ID NO: 91
[N-terminal([[(4S)-4-carboxy-4-[[(4S)-4-carboxy-4-[[(4S)-4-carboxy-4-[[(4S)-4-carboxy-4-(17-carboxy-heptadecanoylamino)butanoyl]amino]butanoyl]amino]butanoyl]amino]butanoyl]), 5Q, 10E, 13Q, 25P, 32L]-hCNP37
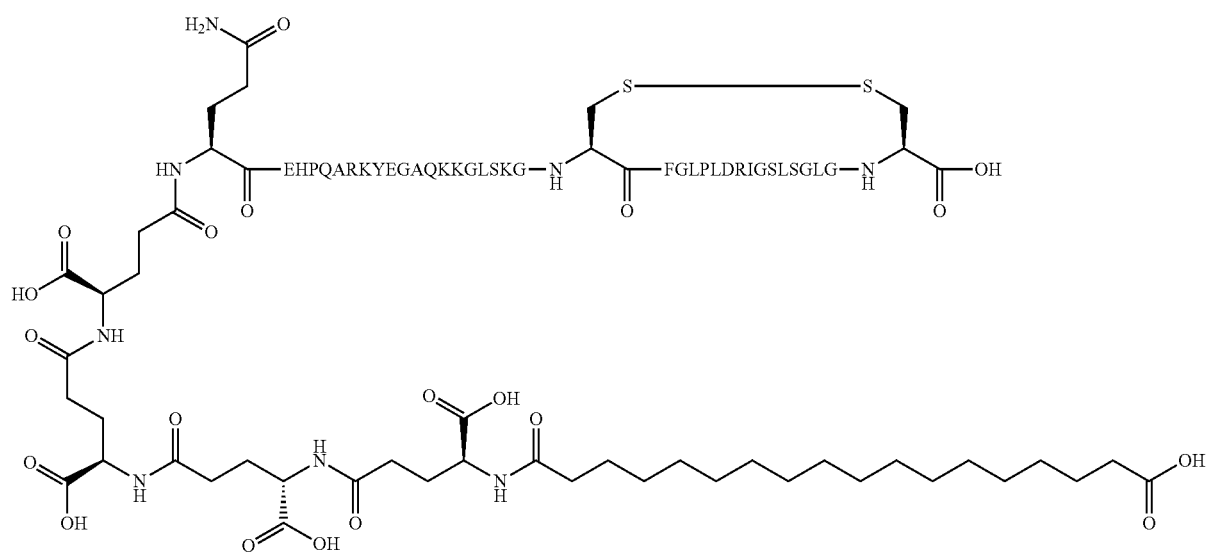
Molecular weight: 4741.359. LCMS34: m/3 calcd: 1581.4530; m/3 found: 1581.2060; m/4.
 calcd: 1186.3398; m/4 found: 1186.0240.
Chem. 109; Compound ID 1449; SEQ ID NO: 51

[N-terminal([2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]), des1-5, 10H, 13Q, 14H, 15T, 17V, 19S, 25P, 32L]-hCNP37

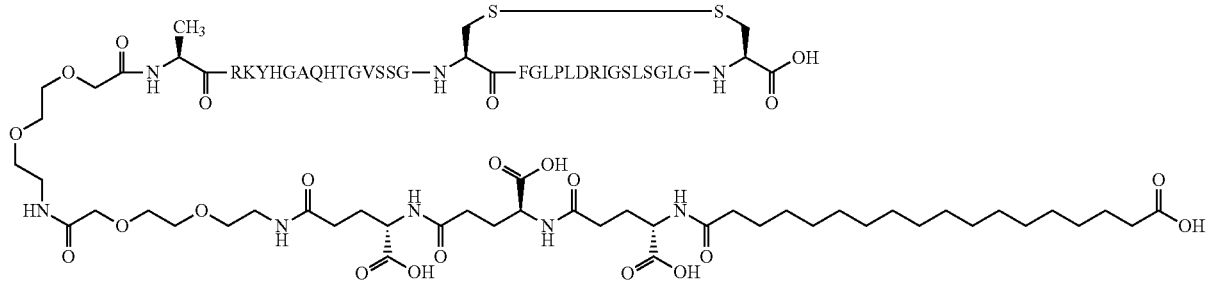

Molecular weight: 4217.7334. LCMS34: m/3 calcd: 1406.9111; m/3 found: 9407.0500; m/4.
calcd: 1055.4334; m/4 found: 1055.300.
Chem. 110; Compound ID 1450; SEQ ID NO: 52

[N-terminal([2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]), des1-5, 10H, 13Q, 15T, 17V, 19S, 25P, 32L]-hCNP37

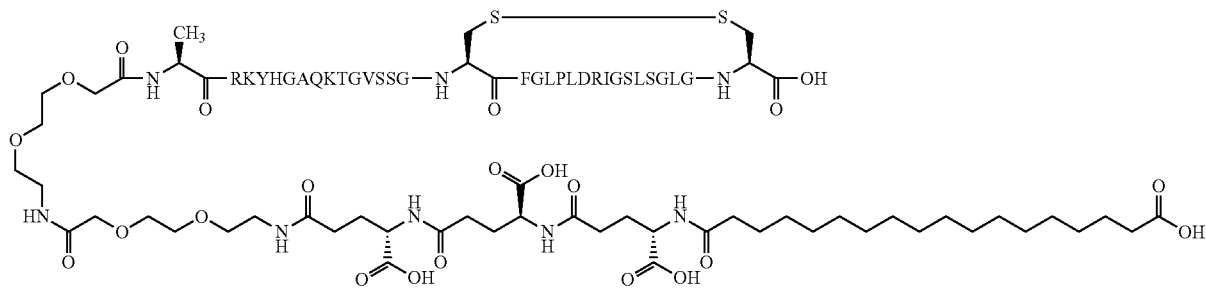

Molecular weight: 4208.7664. LCMS34: m/3 calcd: 1403.9221; m/3 found: 1403.7330; m/4.
calcd: 1053.1916; m/4 found: 1053.0130.
Chem. 111; Compound ID 1451; SEQ ID NO: 92

[N-terminal([2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]), des1-5, 10H, 13Q, 17V, 19S, 25P, 27E, 32L]-hCNP37

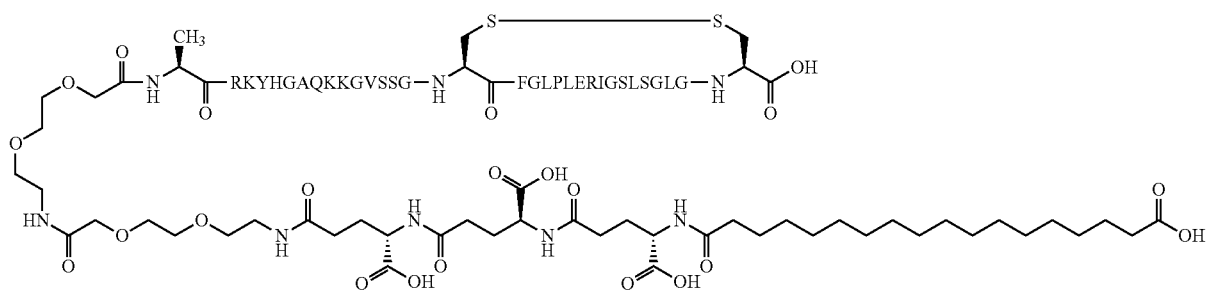

Molecular weight: 4249.8614. LCMS34: m/3 calcd: 1417.6205; m/3 found: 1417.4290; m/4. calcd: 1063.4654; m/4 found: 1063.3310.

Chem. 112; Compound ID 1452; SEQ ID NO: 77

[N-terminal([2-[2-[2-[[2-[2-[2-[[2-[2-[2-[[(4S)-4-carboxy-4-[[(4S)-4- carboxy-4-[[(4S)-4-carboxy-4-[[(4S)-4-carboxy-4-[[(4S)-4-carboxy-4-(17-carboxy-heptadecanoylamino)butanoyl]amino]butanoyl]amino]butanoyl]amino]butanoyl]amino]ethoxy]ethoxy]acetyl]amino]ethoxy]ethoxy]acetyl]amino]ethoxy]ethoxy]acetyl]), des1-5, 13Q, 19Q, 25P, 32L]-hCNP37

Molecular weight: 4685.3307. LCMS34: m/3 calcd: 1562.7769; m/3 found: 1562.3981; m/4. calcd: 1172.3327; m/4 found: 1172.3179.

Chem. 113; Compound ID 1453; SEQ ID NO: 77

[N-terminal([2-[2-[2-[[2-[2-[2-[[(4S)-4-carboxy-4-[[(4S)-4-carboxy-4-[[(4S)-4- carboxy-4-[[(4S)-4-carboxy-4-[[(4S)-4-carboxy-4-(17-carboxyheptade-canoylamino)butanoyl]amino]butanoyl]amino]butanoyl]amino]butanoyl]amino ]butanoyl]amino]ethoxy]ethoxy]acetyl]amino]ethoxy]ethoxy]acetyl]), des1-5, 13Q, 19Q, 25P, 32L]-hCNP37

Molecular weight: 4540.1743. LCMS34: m/3 calcd: 1514.3914; m/3 found: 1514.0494; m/4. calcd: 1136.0436; m/4 found: 1135.8064.

Chem. 114; Compound ID 1454; SEQ ID NO: 77

[N-terminal([2-[2-[2-[[2-[2-[2-[[2-[2-[2-[[2-[2-[2-[[(4S)-4-carboxy-4-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]butanoyl]amino]ethoxy]ethoxy]acetyl]amino]ethoxy]ethoxy]acetyl]amino]ethoxy]ethoxy]acetyl]amino]ethoxy]ethoxy]acetyl]), des1-5, 13Q, 19Q, 25P, 32L]-hCNP37

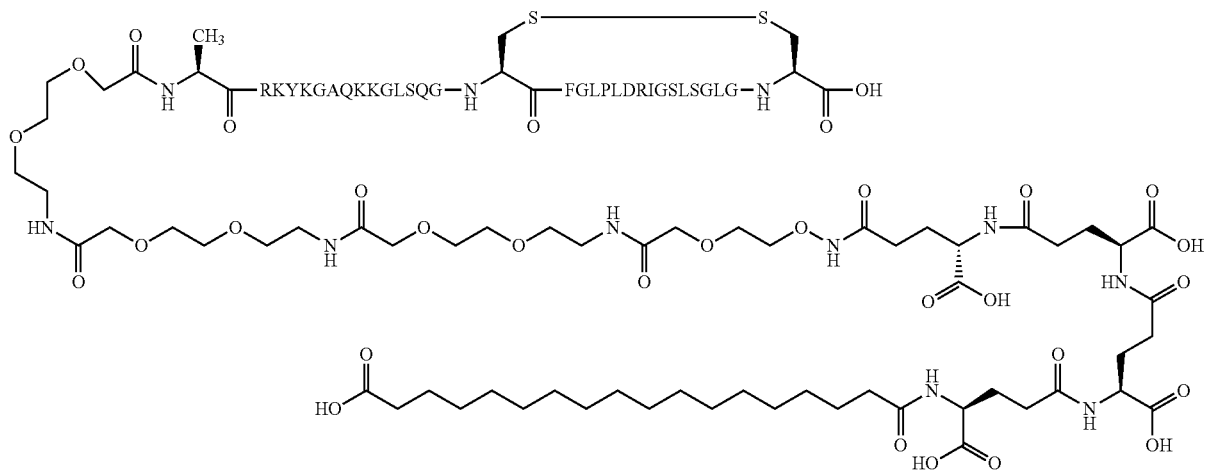

Molecular weight: 4701.3732. LCMS34: m/3 calcd: 1568.1244; m/3 found: 1567.7415; m/4.
calcd: 1176.3433; m/4 found: 1176.0765.
Chem. 115; Compound ID 1455; SEQ ID NO: 77

[N-terminal([2-[2-[2-[[2-[2-[2-[[2-[2-[2-[[(4S)-4-carboxy-4-[[(4S)-4- carboxy-4-[[(4S)-4-carboxy-4-[[(4S)-4-carboxy-4-(17-carboxyheptadecanoylamino)butanoyl]amino]butanoyl]amino]butanoyl]amino]butanoyl]amino ]ethoxy]ethoxy]acetyl]amino]ethoxy]ethoxy]acetyl]amino]ethoxy]ethoxy]acetyl]), des1-5, 13Q, 19Q, 25P, 32L]-hCNP37

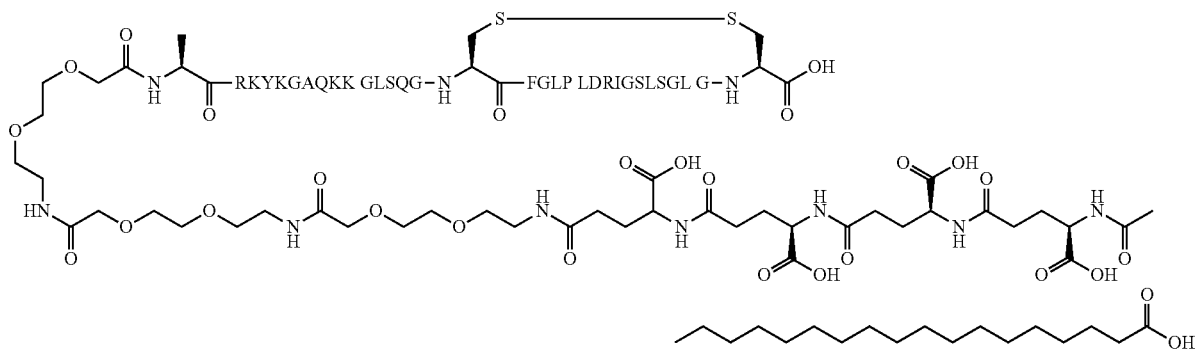

Molecular weight: 4556.2167. LCMS34: m/3 calcd: 1519.7389; m/3 found: 1519.3893; m/4.
calcd: 1140.0542; m/4 found: 1139.8102.
Chem. 116; Compound ID 1456; SEQ ID NO: 77

[N-terminal([2-[2-[2-[[2-[2-[2-[[(4S)-4-carboxy-4-[[(4S)-4-carboxy-4-[[(4S)-4- carboxy-4-[[(4S)-4-carboxy-4-(17-carboxyheptadecanoylamino)butanoyl]amino]butanoyl]amino]butanoyl]amino]butanoyl]amino]ethoxy]ethoxy]acetyl]amino]ethoxy]ethoxy]acetyl]), des1-5, 13Q, 19Q, 25P, 32L]-hCNP37

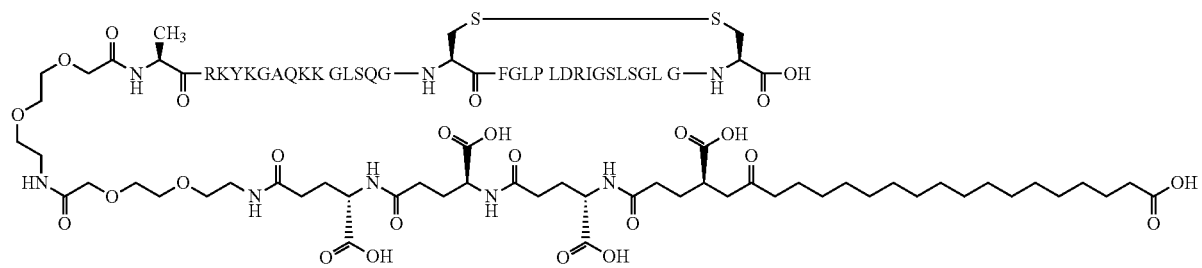

Molecular weight: 4411.0603. LCMS34: m/3 calcd: 1471.3534; m/3 found: 1471.0409; m/4.
calcd: 1103.7651; m/4 found: 1103.5541.
Chem. 117; Compound ID 1457; SEQ ID NO: 93

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), −2G, −1Q, 2P, 3G, 4Q, 5A, 6P, 7G, 8Q, 9A, 10P, 13Q, 19Q, 25P, 32L]-hCNP37

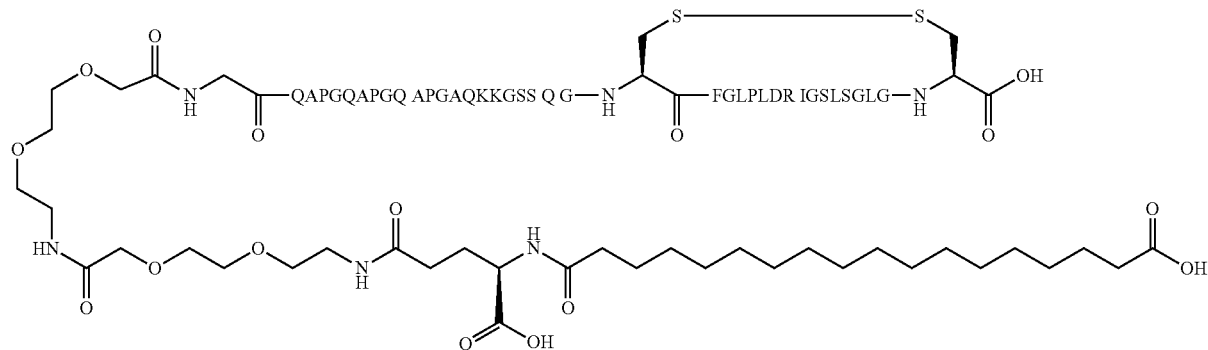

Molecular weight: 4410.9775. LCMS34: m/3 calcd: 1471.3258; m/3 found: 1471.0251; m/4.
calcd: 1103.7444; m/4 found: 1103.7853.
Chem. 118; Compound ID 1458; SEQ ID NO: 94

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), des1-2, 3G, 4Q, 5A, 6P, 7G, 8Q, 9A, 10P, 13Q, 17S, 19Q, 25P, 32L]-hCNP37

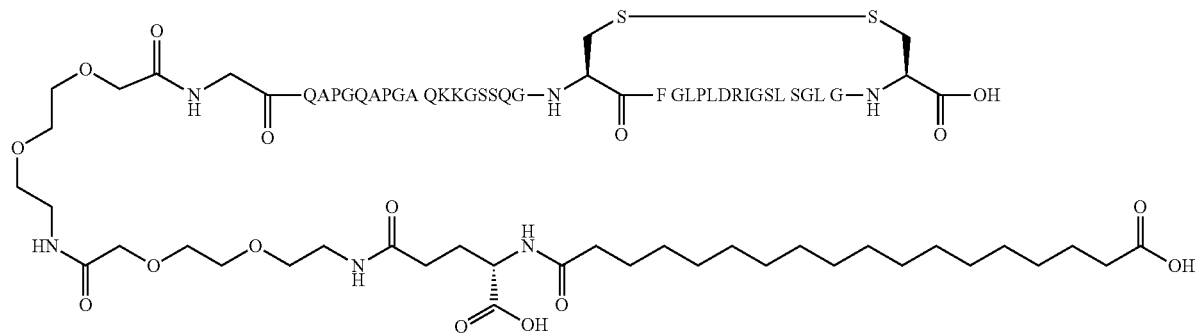

Molecular weight: 4057.6038. LCMS34: m/3 calcd: 1353.5346; m/3 found: 1353.3113; m/4.
calcd: 1015.4010; m/4 found: 1015.2496.
Chem. 119; Compound ID 1459; SEQ ID NO: 95

[N-terminal([2-[2-[2-[[2-[2-[2-[[(4S)-4-carboxy-4-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]butanoyl]amino]ethoxy]ethoxy]acetyl]amino]ethoxy]ethoxy]acetyl]), des1, 2G, 3Q, 4A, 5P, 13Q, 17S, 19Q, 25P, 32L]-hCNP37

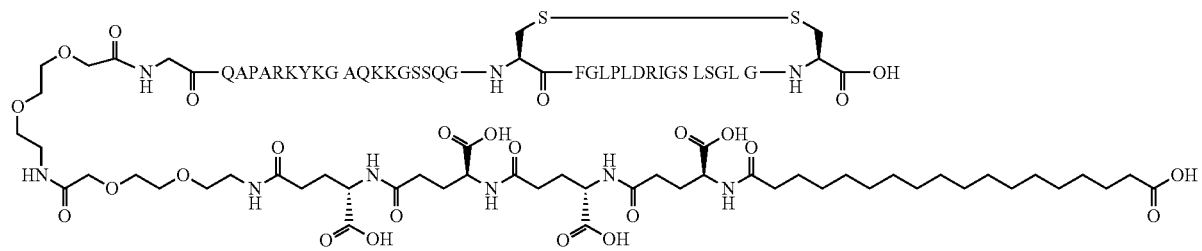

Molecular weight: 4738.3536. LCMS34: m/3 calcd: 1580.4512; m/3 found: 1580.0658; m/4.
calcd: 1185.5884; m/4 found: 1185.5701.
Chem. 120; Compound ID 1460; SEQ ID NO: 96

[N-terminal([2-[2-[2-[[2-[2-[2-[[(4S)-4-carboxy-4-[[(4S)-4-carboxy-4-[[(4S)-4-carboxy-4-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]butanoyl]amino]butanoyl]amino]ethoxy]ethoxy]acetyl]amino]ethoxy]ethoxy]acetyl]), des1-5, 13Q, 25P, 32L]-hCNP37

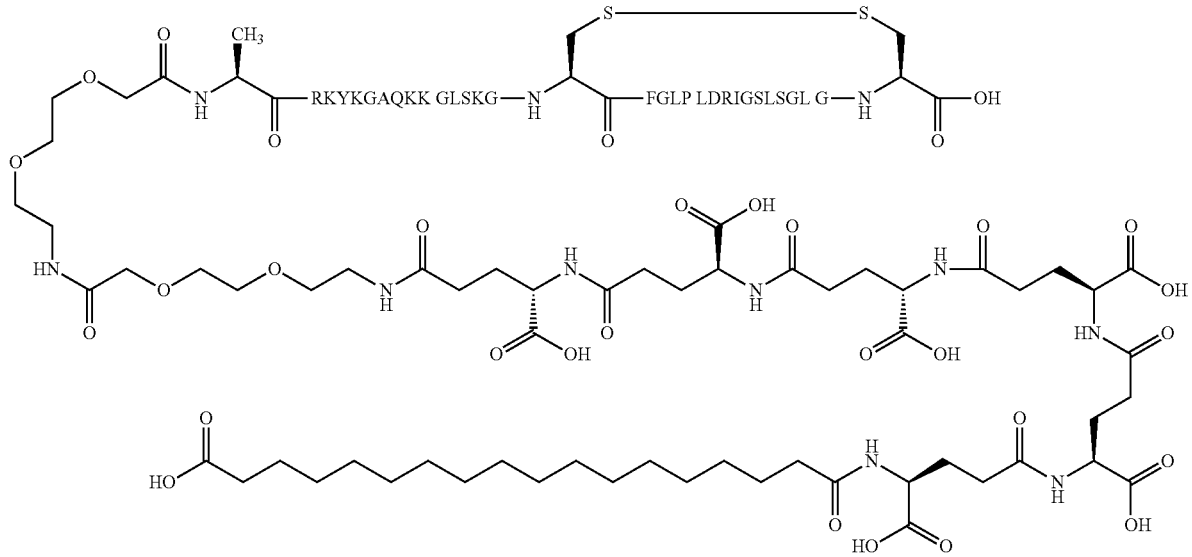

Molecular weight: 4669.3313. LCMS34: m/3 calcd: 1557.4438; m/3 found: 1557.4031; m/4. calcd: 1168.3328; m/4 found: 1168.0756.
Chem. 121; Compound ID 1461; SEQ ID NO: 97

[N-terminal([2-[2-[2-[[2-[2-[2-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]eth oxy]ethoxy]acetyl]amino]ethoxy]ethoxy]acetyl]amino]ethoxy]ethoxy]acetyl]), des1-8, 10H, 13Q, 19Q, 25P, 32L]-hCNP37

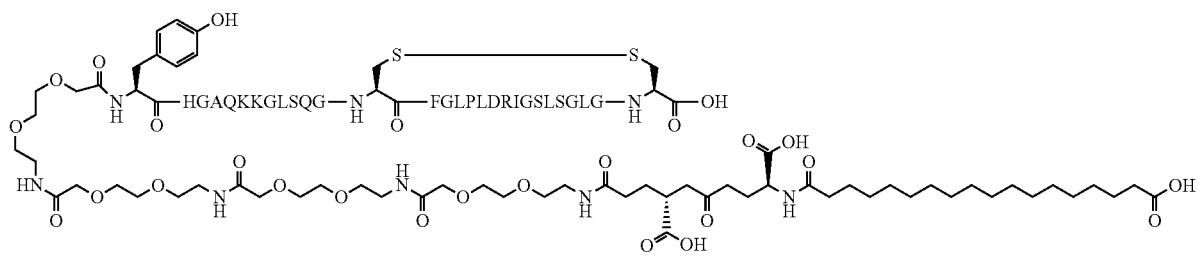

Molecular weight: 4096.6763. LCMS34: m/3 calcd: 1366.5588; m/3 found: 1366.3214; m/4. calcd: 1025.1691; m/4 found: 1025.0148.
Chem. 122; Compound ID 1462; SEQ ID NO: 96

[N-terminal([2-[2-[2-[[2-[2-[2-[[2-[2-[2-[[2-[2-[2-[[(4S)-4-carboxy-4-[[(4S)-4-carboxy-4-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]butanoyl]amino]ethoxy]ethoxy]acetyl]amino]ethoxy]ethoxy]acetyl]amino]ethoxy]ethoxy]acetyl]amino]ethoxy]ethoxy]acetyl]), des1-5, 13Q, 25P, 32L]-hCNP37

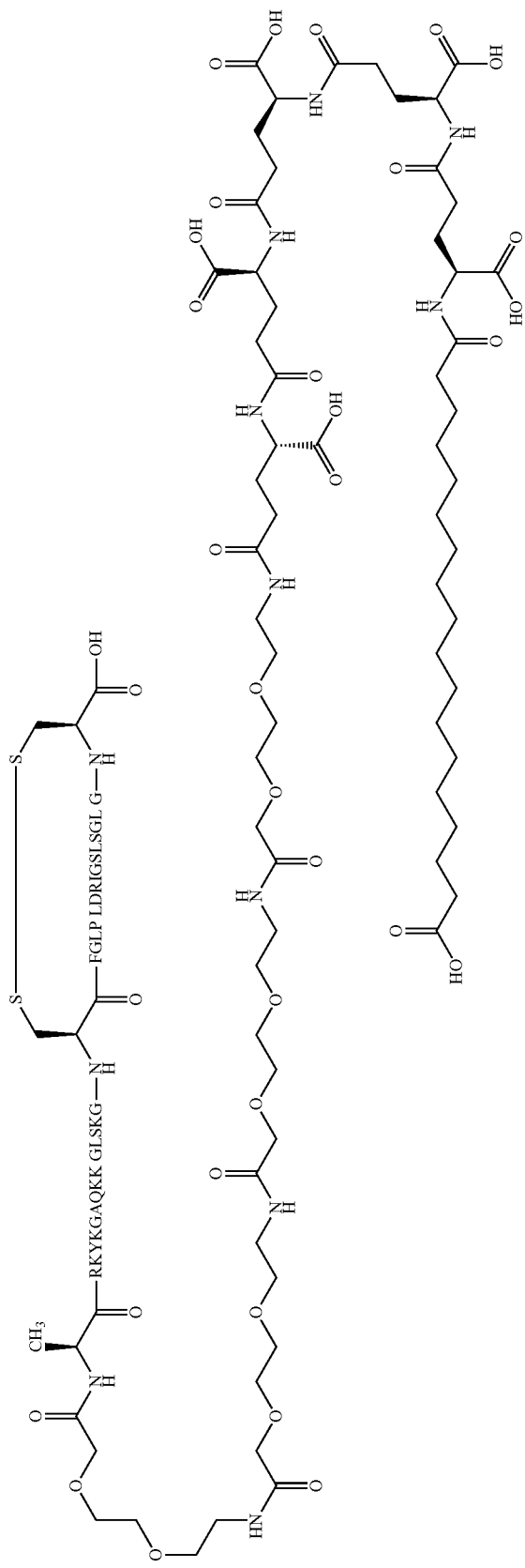

Molecular weight: 4830.5302. LCMS34: m/3 calcd: 1611.1767; m/3 found: 1611.1900; m/4. calcd: 1208.6326; m/4 found: 1208.6500.

Chem. 123; Compound ID 1463; SEQ ID NO: 98

[N-terminal([2-[2-[2-[[2-[2-[2-[[2-[2-[2-[[2-[2-[2-[[(4S)-4-carboxy-4-[[(4S)-4-carboxy-4-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]butanoyl]amino]ethoxy]ethoxy]acetyl]amino]ethoxy]ethoxy]acetyl]amino]ethoxy]ethoxy]acetyl]amino]ethoxy]ethoxy]acetyl]), des1-5, 13Q, 19Q, 32L]-hCNP37

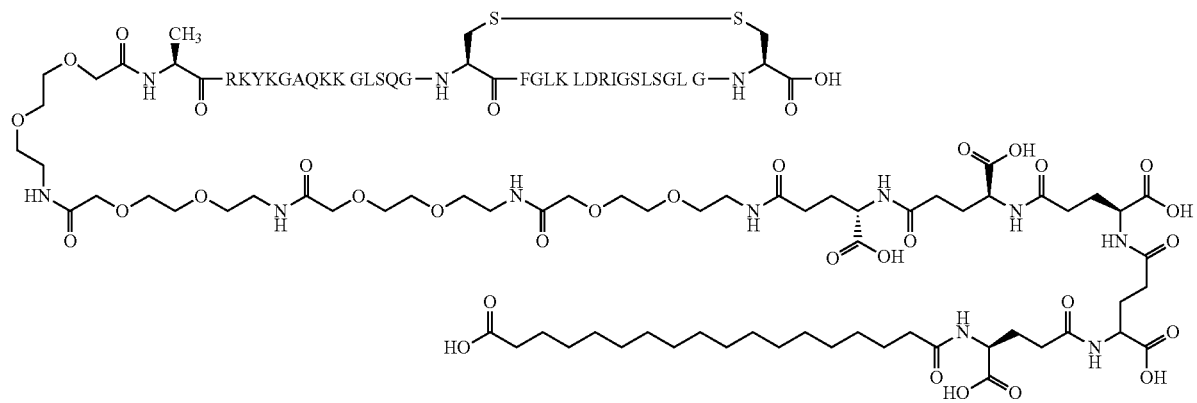

Molecular weight: 4861.5442. LCMS34: m/3 calcd: 1621.5147; m/3 found: 1621.1760; m/4. calcd: 1216.3861; m/4 found: 1216.1420.

Chem. 124; Compound ID 1464; SEQ ID NO: 99

[N-terminal([2-[2-[2-[[2-[2-[2-[[2-[2-[2-[[2-[2-[2-[[(4S)-4-carboxy-4-[[(4S)-4-carboxy-4-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]butanoyl]amino]ethoxy]ethoxy]acetyl]amino]ethoxy]ethoxy]acetyl]amino]ethoxy]ethoxy]acetyl]amino]ethoxy]ethoxy]acetyl]), des1-5, 19Q, 25P, 32L]-hCNP37

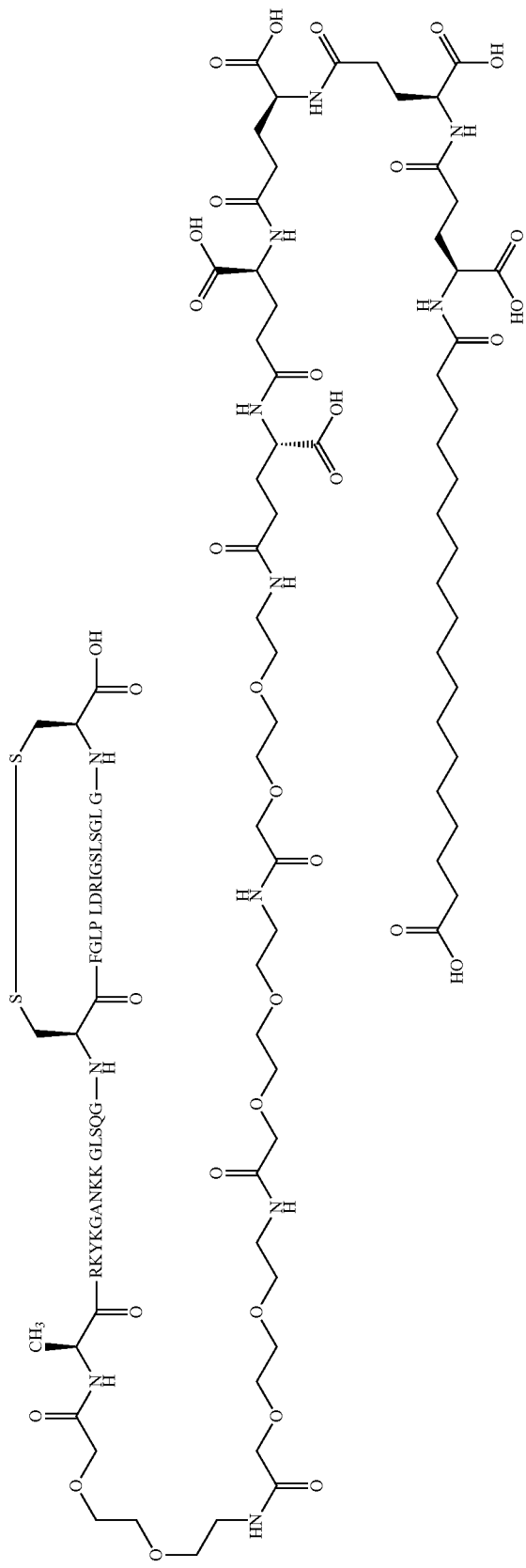

Molecular weight: 4816.4606. LCMS34: m/3 calcd: 1606.4869; m/3 found: 1606.1700; m/4. calcd: 1205.1152; m/4 found: 1204.8820.

Chem. 125; Compound ID 1465; SEQ ID NO: 100

[N-terminal([2-[2-[2-[[2-[2-[2-[[2-[2-[2-[[2-[2-[2-[[(4S)-4-carboxy-4-[[(4S)-4-carboxy-4-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]butanoyl]amino]ethoxy]ethoxy]acetyl]amino]ethoxy]ethoxy]acetyl]amino]ethoxy]ethoxy]acetyl]amino]ethoxy]ethoxy]acetyl]), des1-5, 13Q, 19Q, 25P]-hCNP37

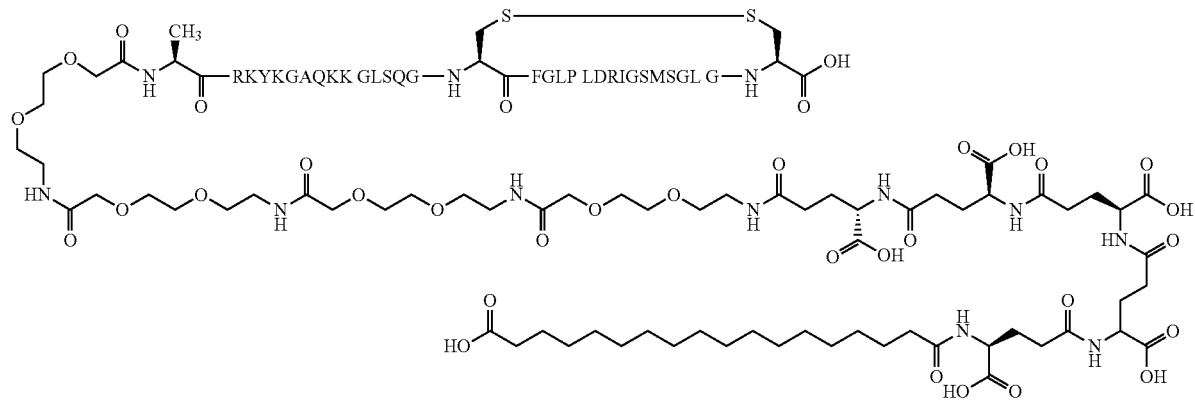

Molecular weight: 4848.5256. LCMS34: m/3 calcd: 1617.1752; m/3 found: 1616.8130; m/4. calcd: 1213.1314; m/4 found: 1212.8620.

Chem. 126; Compound ID 1470; SEQ ID NO: 96

[N-terminal([2-[2-[2-[[2-[2-[2-[[(4S)-4-carboxy-4-[[(4S)-4-carboxy-4-[[(4S)-4- carboxy-4-[[(4S)-4-carboxy-4-[[(4S)-4-carboxy-4-(17-carboxyheptadecanoylamino)butanoyl]amino]butanoyl]amino]butanoyl]amino]butanoyl]amino]ethoxy]ethoxy]acetyl]amino]ethoxy]ethoxy]acetyl]), des1-5, 13Q, 25P, 32L]-hCNP37

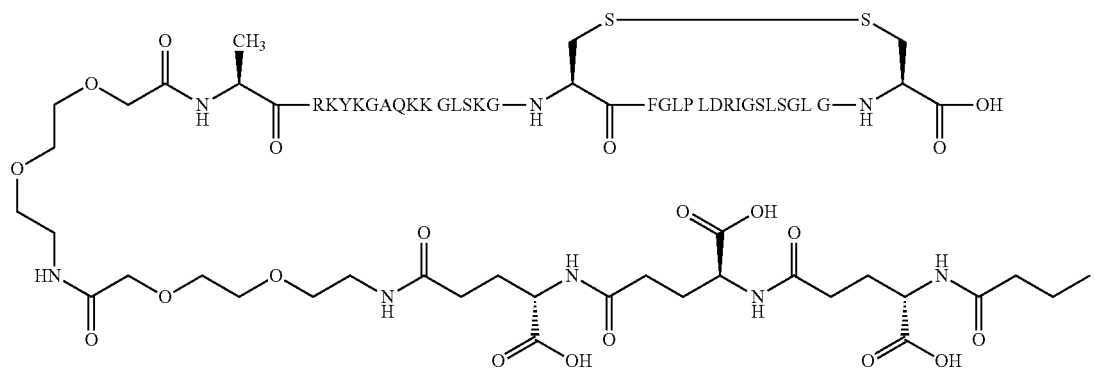

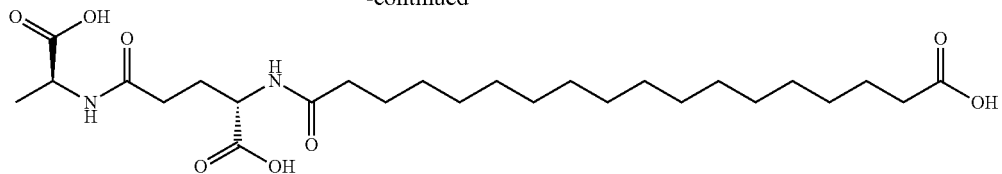

Molecular weight: 4540.2173. LCMS34: m/3 calcd: 1514.4058; m/3 found: 1514.1500; m/4.
calcd: 1136.0543; m/4 found: 1135.8500.
Chem. 127; Compound ID 1471; SEQ ID NO: 75

[N-terminal([2-[2-[2-[[2-[2-[2-[[(4S)-4-carboxy-4-[[(4S)-4-carboxy-4-[[(4S)-4- carboxy-4-[[(4S)-4-carboxy-4-[[(4S)-4-carboxy-4-(17-carboxyheptadecanoylamino)butanoyl]amino]butanoyl]amino]butanoyl]amino]butanoyl]amino]butanoyl]amino]ethoxy]ethoxy]acetyl]amino]ethoxy]ethoxy]acetyl]), 5Q, 13Q, 19Q, 25P, 32L]-hCNP37

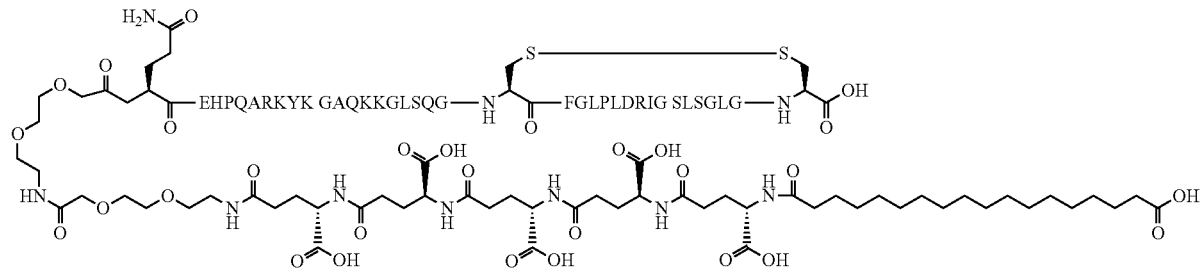

Molecular weight: 5159.8011. LCMS34: m/3 calcd: 1720.9337; m/3 found: 1720.8900; m/4.
calcd: 1290.9503; m/4 found: 1290.9200.
Chem. 128; Compound ID 1472; SEQ ID NO: 75

[N-terminal([2-[2-[2-[[2-[2-[2-[[(4S)-4-carboxy-4-[[(4S)-4-carboxy-4-[[(4S)-4- carboxy-4-[[(4S)-4-carboxy-4-(17-carboxyheptadecanoylamino)butanoyl]amino]butanoyl]amino]butanoyl]amino]butanoyl]amino]ethoxy]ethoxy]acetyl]amino]ethoxy]ethoxy]acetyl]), 5Q, 13Q, 19Q, 25P, 32L]-hCNP37

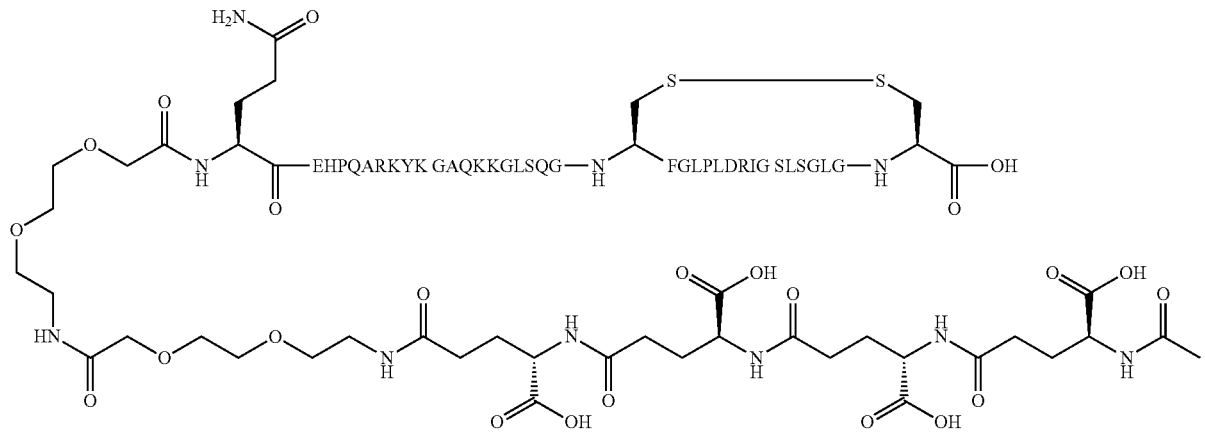

-continued

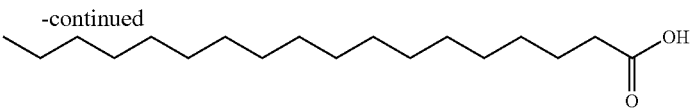

Molecular weight: 5030.6872. LCMS34: m/3 calcd: 1677.8957; m/3 found: 1677.8700; m/4.
calcd: 1258.6718; m/4 found: 1258.6600.

Chem. 129; Compound ID 1473; SEQ ID NO: 67

[N-terminal([2-[2-[2-[[2-[2-[2-[[(4S)-4-carboxy-4-[[(4S)-4-carboxy-4-[[(4S)-4- carboxy-4-[[(4S)-4-carboxy-4-(17-carboxyheptadecanoylamino)butanoyl]amino]butanoyl]amino]butanoyl]amino]butanoyl]amino]ethoxy]ethoxy]acetyl]amino]ethoxy]ethoxy]acetyl]), 5Q, 13Q, 19S, 25P, 32L]-hCNP37

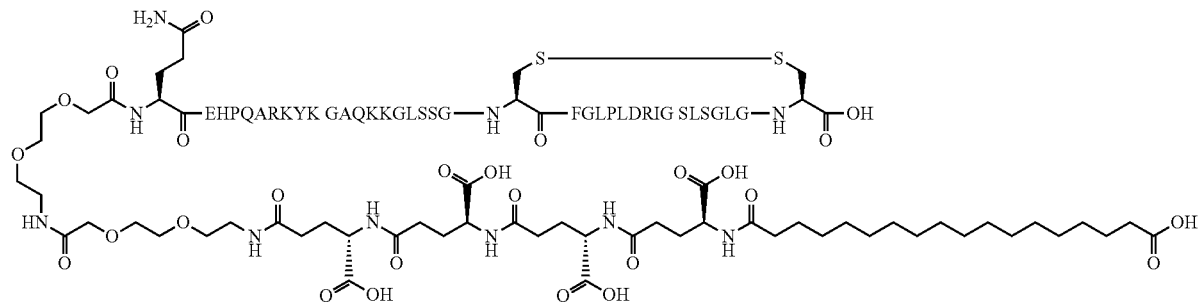

Molecular weight: 4989.6352. LCMS34: m/3 calcd: 1664.2117; m/3 found: 1664.2000; m/4.
calcd: 1248.4088; m/4 found: 1248.400.

Chem. 130; Compound ID 1474; SEQ ID NO: 101

[N-terminal([2-[2-[2-[[2-[2-[2-[[(4S)-4-carboxy-4-[[(4S)-4-carboxy-4-[[(4S)-4- carboxy-4-[[(4S)-4-carboxy-4-[[(4S)-4-carboxy-4-(17-carboxyheptadecanoylamino)butanoyl]amino]butanoyl]amino]butanoyl]amino]butanoyl]amino]butanoyl]amino]ethoxy]ethoxy]acetyl]amino]ethoxy]ethoxy]acetyl]), 5Q, 13Q, 25P, 32L]-hCNP37

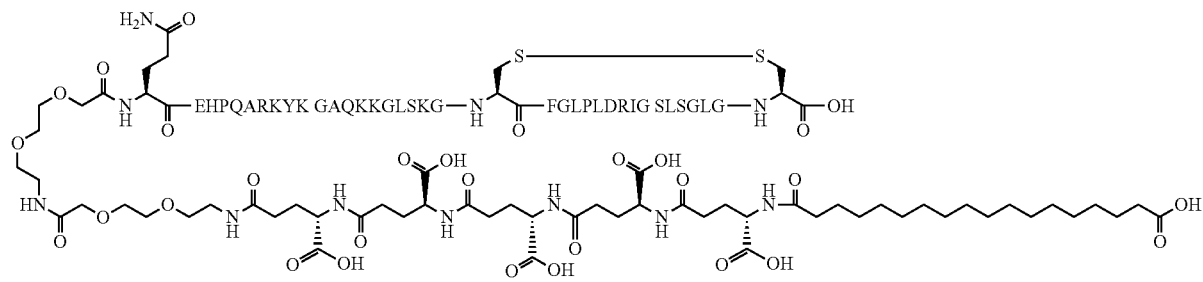

Molecular weight: 5159.8442. LCMS34: m/3 calcd: 1720.9481; m/3 found: 1720.8900; m/4.
calcd: 1290.9611; m/4 found: 1290.9200.

Chem. 131; Compound ID 1475; SEQ ID NO: 77

[N-terminal([2-[2-[2-[[2-[2-[2-[[2-[2-[2-[[2-[2-[2-[[(2S)-4-carboxy-2-[[(2S)-4-carboxy-2-[[(2S)-4-carboxy-2-[[(2S)-4-carboxy-2-[[(2S)-4-carboxy-2-(17-carboxyheptadecanoylamino)butanoyl]amino]butanoyl]amino]butanoyl]amino]butanoyl]amino]ethoxy]ethoxy]acetyl]amino]ethoxy]ethoxy]acetyl]amino]ethoxy]ethoxy]acetyl]), des1-5, 13Q, 19Q, 25P, 32L]-hCNP37
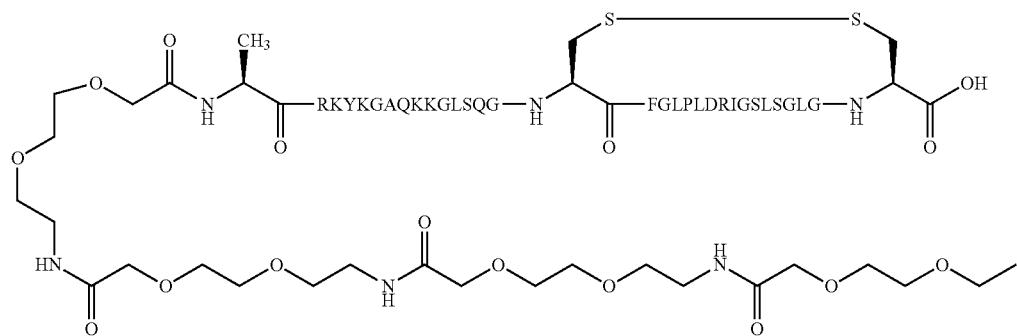
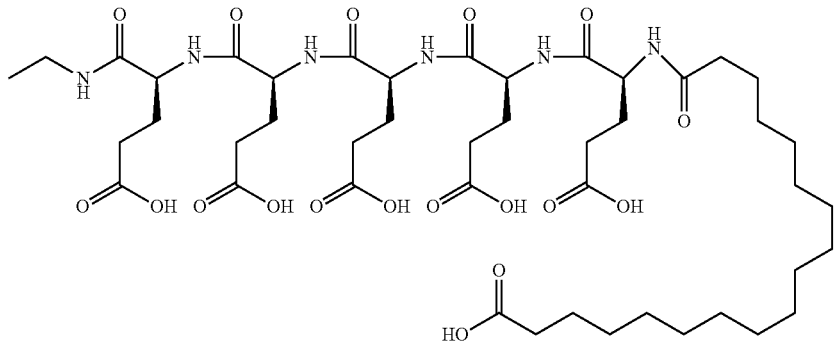
Molecular weight: 4830.4871. LCMS34: m/3 calcd: 1611.1624; m/3 found: 1610.7510; m/4. calcd: 1208.6218; m/4 found: 1208.5814.
Chem. 132; Compound ID 1476; SEQ ID NO: 77

[N-terminal([2-[2-[2-[[2-[2-[2-[[(2S)-4-carboxy-2-[[2-[[(2S)-4-carboxy-2-[[2-[[(2S)-4-carboxy-2-[[2-[[(2S)-4-carboxy-2-[[2-[[(2S)-4-carboxy-2-(17-carboxyheptadecanoylamino)butanoyl]amino]acetyl]amino]butanoyl]amino]acetyl]amino]buta noyl]amino]acetyl]amino]butanoyl]amino]acetyl]amino]butanoyl]amino]ethoxy]ethoxy]acetyl]a mino]ethoxy]ethoxy]acetyl]), des1-5, 13Q, 19Q, 25P, 32L]-hCNP37

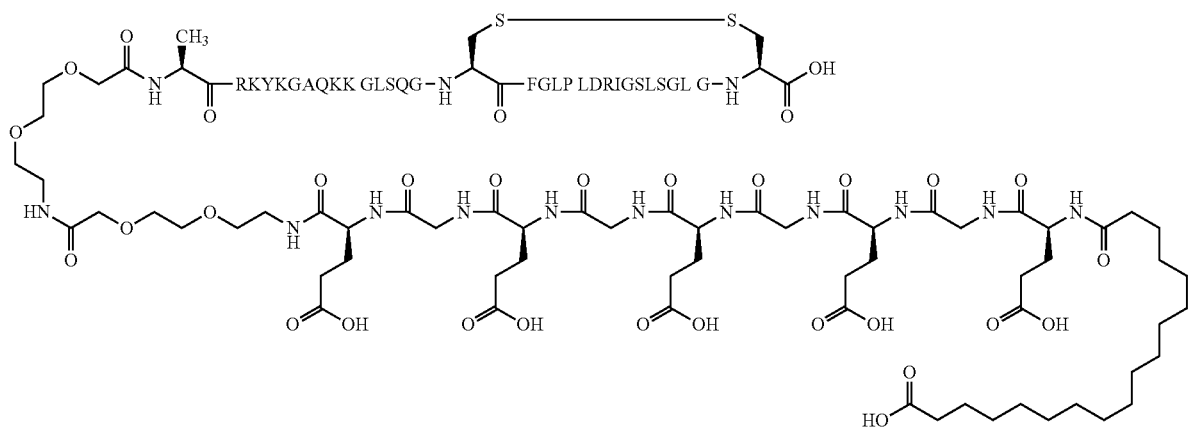

Molecular weight: 4768.3795. LCMS34: m/3 calcd: 1590.4598; m/3 found: 1590.4137; m/4.
calcd: 1193.0949; m/4 found: 1193.0793.
Chem. 133; Compound ID 1477; SEQ ID NO: 102

[N-terminal([2-[2-[2-[[2-[2-[2-[[2-[2-[2-[[2-[2-[2-[[(4S)-4-carboxy-4-[[(4S)-4-carboxy-4-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]butanoyl]amino]butanoyl]amino]ethoxy]ethoxy]acetyl]amino]ethoxy]ethoxy]acetyl]amino]ethoxy]ethoxy]acetyl]amino]ethoxy]ethoxy]acetyl]), des1-5, 13Q, 19Q, 25P, 27E, 32L]-hCNP37

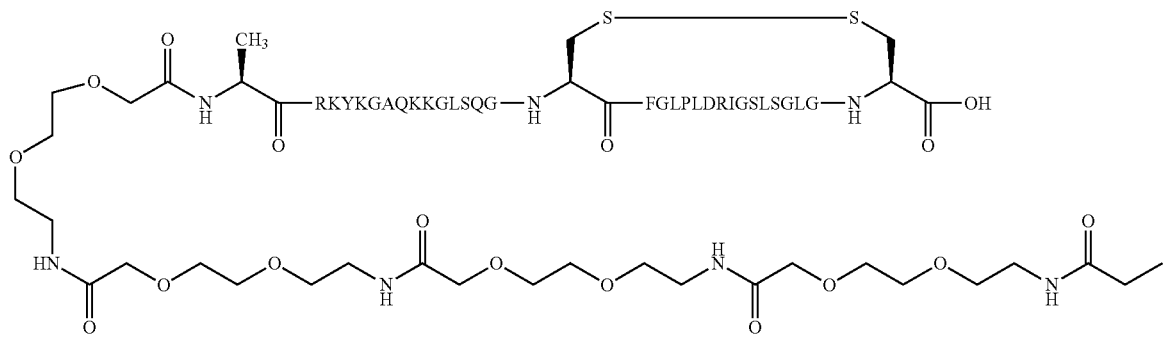

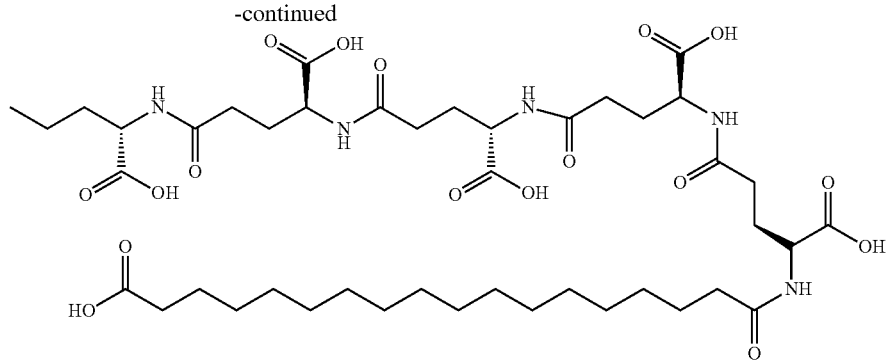

Molecular weight: 4844.5137. LCMS34: m/3 calcd: 1615.8379; m/3 found: 1615.4194; m/4. calcd: 1212.1284; m/4 found: 1212.0844.

Chem. 134; Compound ID 1478; SEQ ID NO: 103

[N-terminal([2-[2-[2-[[2-[2-[2-[[2-[2-[2-[[2-[2-[2-[[(4S)-4-carboxy-4-[[(4S)-4-carboxy-4-(17-carboxy-heptadecanoylamino)butanoyl]amino]butanoyl]amino]ethoxy]ethoxy]acetyl]amino]eth oxy]ethoxy]acetyl]amino]ethoxy]ethoxy]acetyl]amino]ethoxy]ethoxy]acetyl]), des1-8, 13Q, 19Q, 25P, 32L]-hCNP37

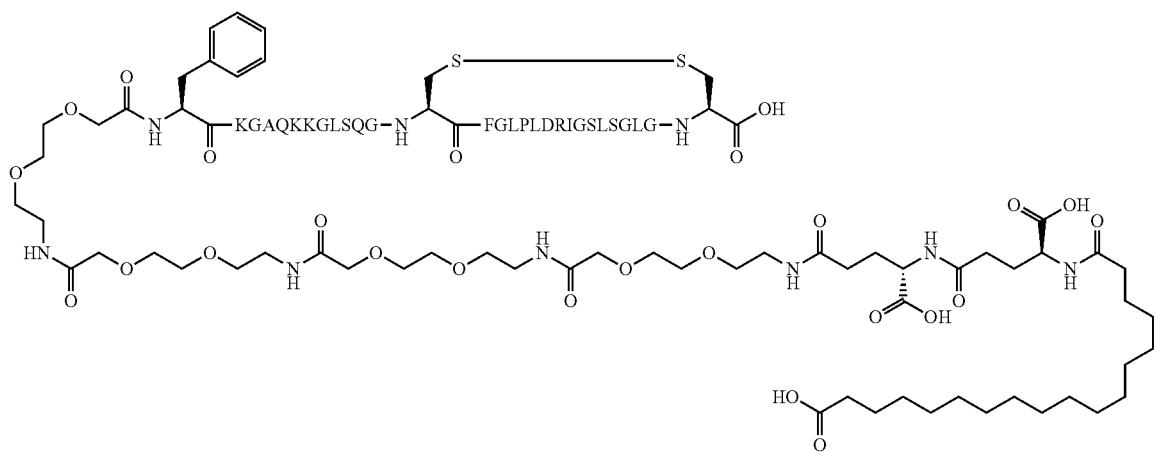

Molecular weight: 4087.7093. LCMS34: m/3 calcd: 1363.5698; m/3 found: 1363.3427; m/4. calcd: 1022.9273; m/4 found: 1022.7753.

Chem. 135; Compound ID 9480; SEQ ID NO: 103

[N-terminal([2-[2-[2-[[2-[2-[2-[[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]amino]ethoxy]ethoxy]acetyl]amino]ethoxy]ethoxy]acetyl]), des1-8, 13Q, 19Q, 25P, 32L]-hCNP37

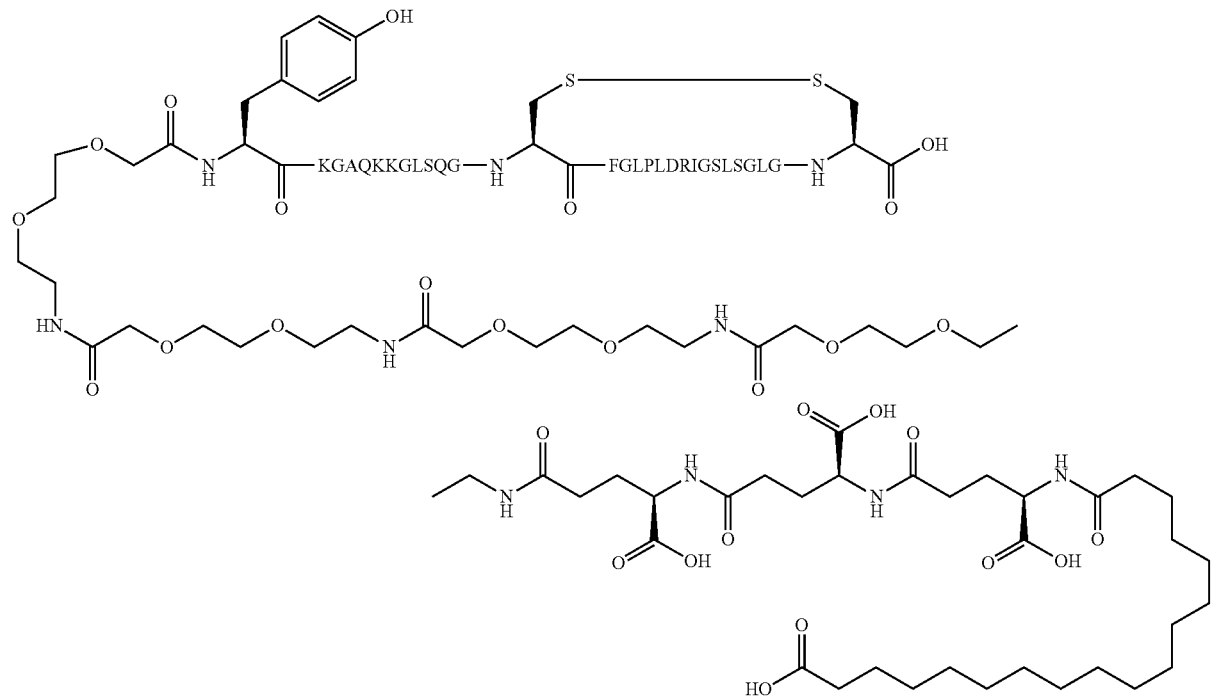

Molecular weight: 4216.8233. LCMS34: m/3 calcd: 1406.6078; m/3 found: 1406.6766; m/4. calcd: 1055.2058; m/4 found: 1055.0295.
Chem. 136; Compound ID 1481; SEQ ID NO: 103

[N-terminal([2-[2-[2-[[2-[2-[2-[[2-[2-[2-[[2-[2-[2-[[(2S)-4-carboxy-2-[[(2S)-4-carboxy-2-[[(2S)-4-carboxy-2-(17-carboxyheptadecanoylamino)butanoyl]amino]butanoyl]amino]butanoyl]amino]ethoxy]ethoxy]acetyl]amino]ethoxy]ethoxy]acetyl]amino]ethoxy]ethoxy]acetyl]amino]ethoxy]ethoxy]acetyl]), des1-8, 13Q, 19Q, 25P, 32L]-hCNP37

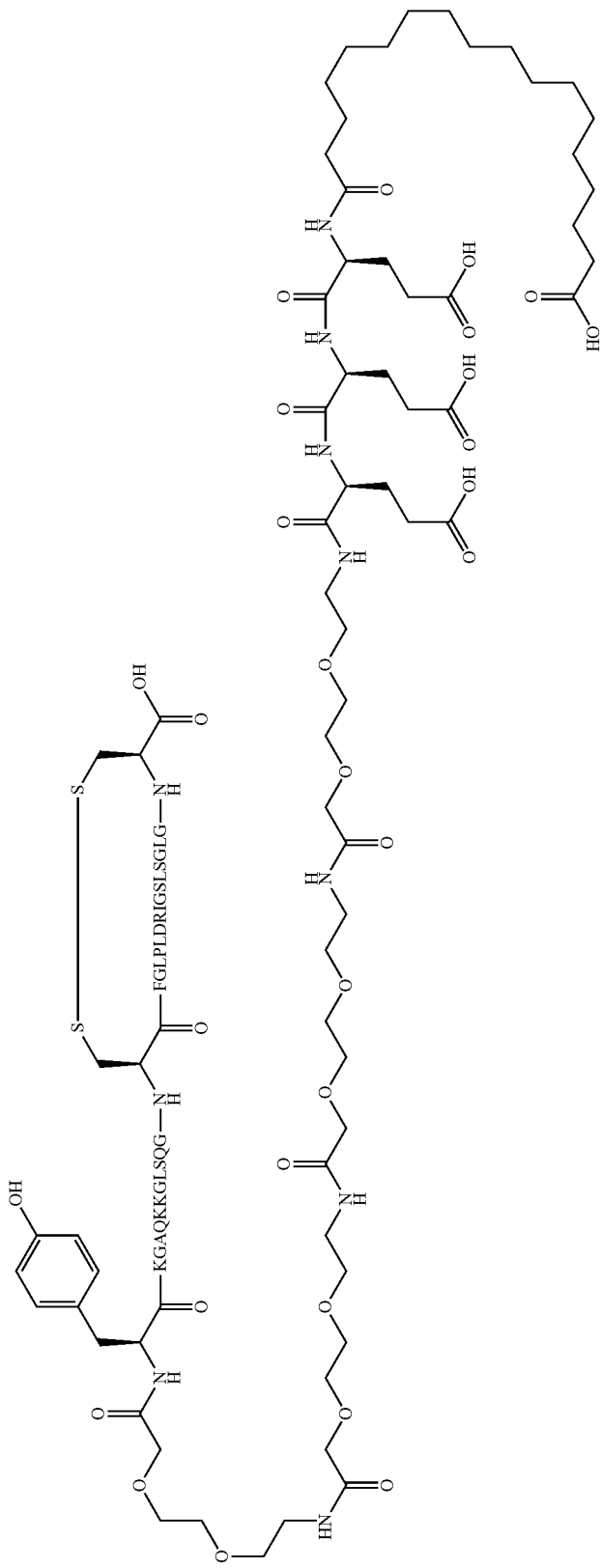

Molecular weight: 4216.8233. LCMS34: m/3 calcd: 1406.6078; m/3 found: 1406.3542; m/4.
calcd: 1055.2058; m/4 found: 1055.0295.

Chem. 137; Compound ID 9482; SEQ ID NO: 67

[N-terminal([[(4S)-4-carboxy-4-[[(4S)-4-carboxy-4-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]butanoyl]amino]butanoyl]), 5Q, 13Q, 19S, 25P, 32L]-hCNP37

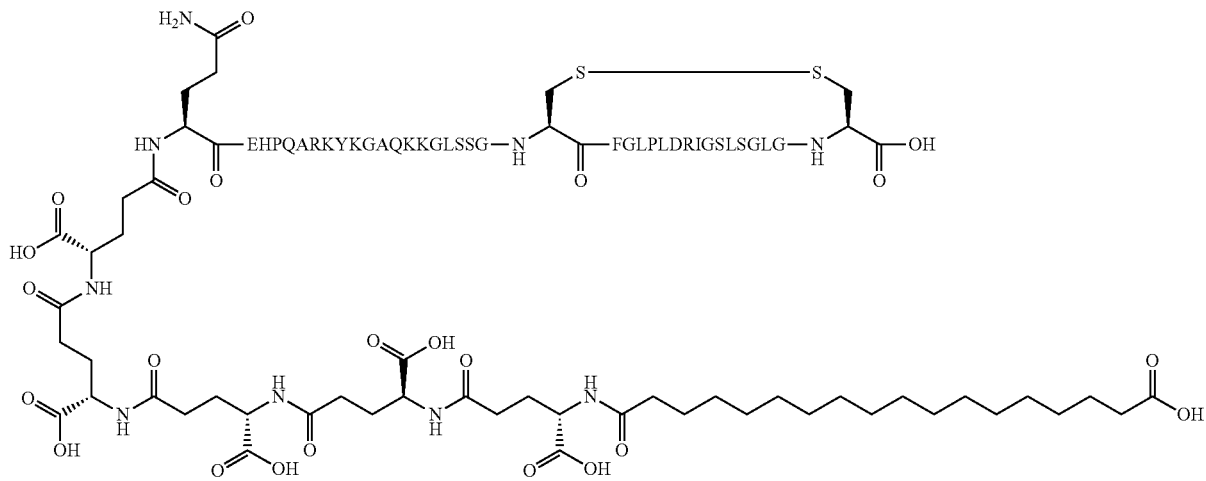

Molecular weight: 4828.4363. LCMS34: m/3 calcd: 1610.4788; m/3 found: 1610.4060; m/4.
calcd: 1208.1091; m/4 found: 1207.8275.

Chem. 138; Compound ID 9483; SEQ ID NO: 104

[N-terminal([[(4S)-4-carboxy-4-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]butanoyl]), 5Q, 13Q, 19S, 25P, 27E, 32L]-hCNP37

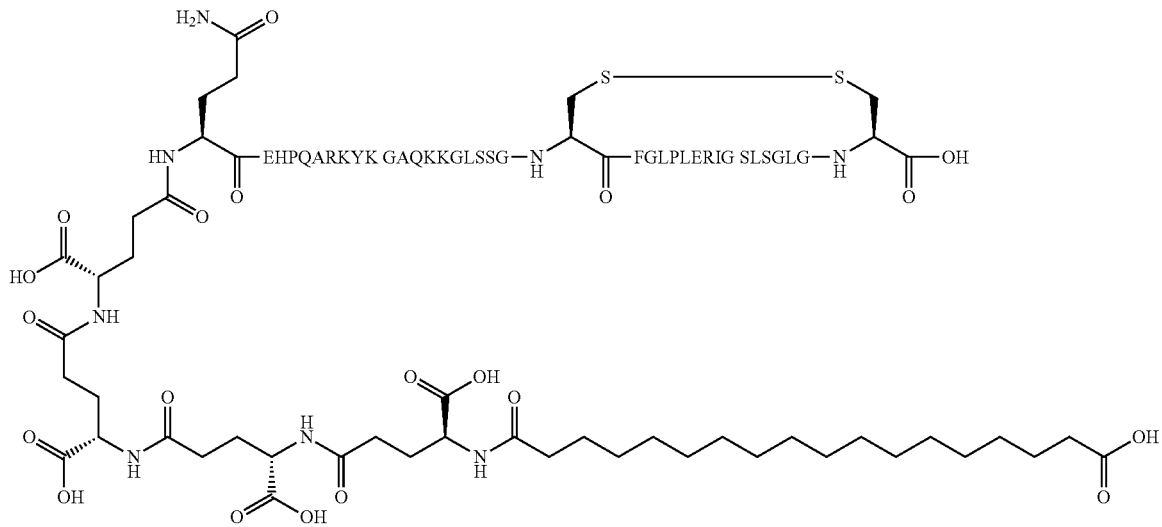

Molecular weight: 4713.3489. LCMS34: m/3 calcd: 1572.1163; m/3 found: 1572.1500; m/4.
calcd: 1179.3372; m/4 found: 1179.1200.

Chem. 139; Compound ID 1484; SEQ ID NO: 105

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), des1-6, 7G, 8Q, 9A, 10P, 13Q, 19Q, 25P, 32L]-hCNP37

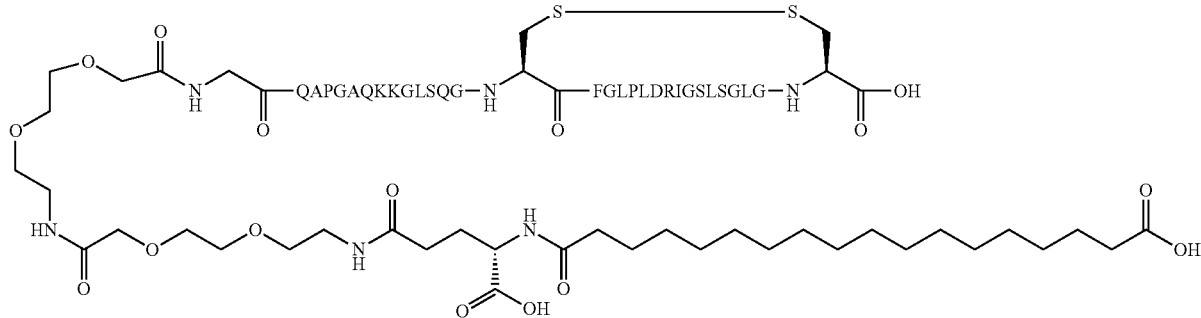

Molecular weight: 3730.3106. LCMS34: m/3 calcd: 1244.4369; m/3 found: 1244.7042; m/4.
calcd: 933.5777; m/4 found: 933.5259.

Chem. 140; Compound ID 1486; SEQ ID NO: 106

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), des1-6, 7G, 8Q, 9A, 10P, 13Q, 17S, 19Q, 25P, 27E, 32L]-hCNP37

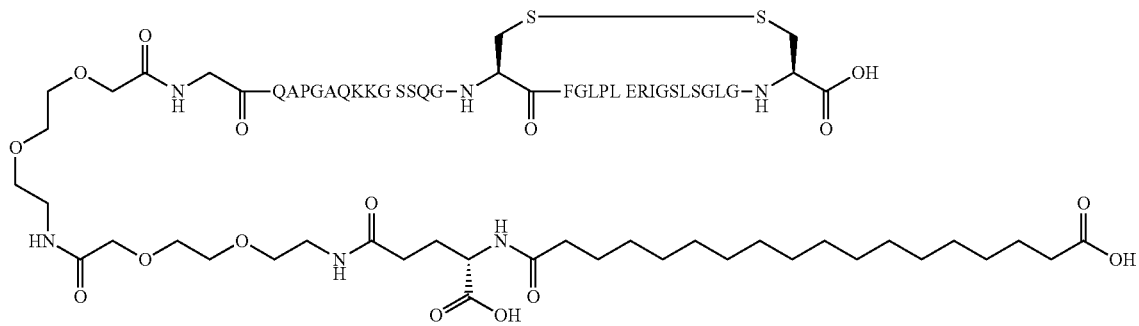

Molecular weight: 3718.2568. LCMS34: m/3 calcd: 1240.4189; m/3 found: 1240.3220; m/4.
calcd: 930.5642; m/4 found: 930.4920.

Chem. 141; Compound ID 1487; SEQ ID NO: 107

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), -2G, -1Q, 2P, 3G, 4Q, 5A, 6P, 7G, 8Q, 9A, 10P, 13Q, 19Q, 25P, 32L]-hCNP37

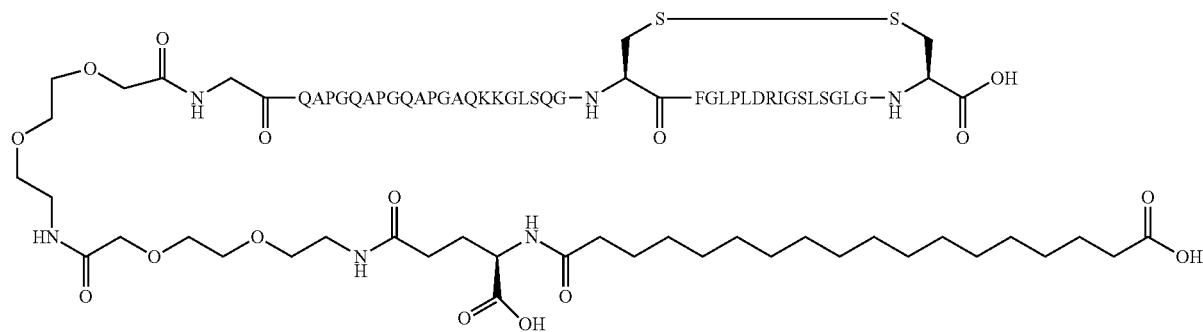

Molecular weight: 4437.0578. LCMS34: m/3 calcd: 9480.0193; m/3 found: 1479.8291; m/4.
calcd: 1110.2645; m/4 found: 1110.3766.
Chem. 142; Compound ID 1488; SEQ ID NO: 107

[N-terminal([[(4S)-4-carboxy-4-(17-carboxyheptadecanoylamino)butanoyl]), -2G, -1Q, 2P, 3G, 4Q, 5A, 6P, 7G, 8Q, 9A, 10P, 13Q, 19Q, 25P, 32L]-hCNP37

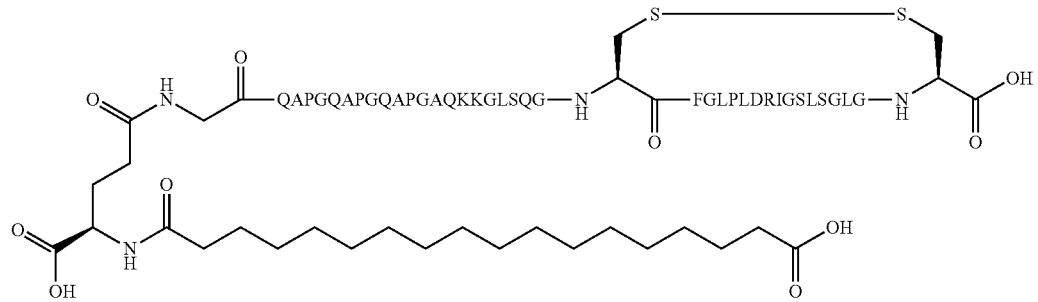

Molecular weight: 4146.7449. LCMS34: m/3 calcd: 1383.2483; m/3 found: 1383.4402; m/4.
calcd: 1037.6862; m/4 found: 1037.5803.
Chem. 143; Compound ID 1489; SEQ ID NO: 108

[N-terminal([2-[2-[2-[[2-[2-[2-[[2-[2-[2-[[2-[2-[2-[[(4S)-4-carboxy-4-[[(4S)-4-carboxy-4-(17-carboxy-heptadecanoylamino)butanoyl]amino]butanoyl]amino]ethoxy]ethoxy]acetyl]amino]eth oxy]ethoxy]acetyl]amino]ethoxy]ethoxy]acetyl]amino]ethoxy]ethoxy]acetyl]), des1-8, 13Q, 17G, 19Q, 25P, 27E, 32L]-hCNP37

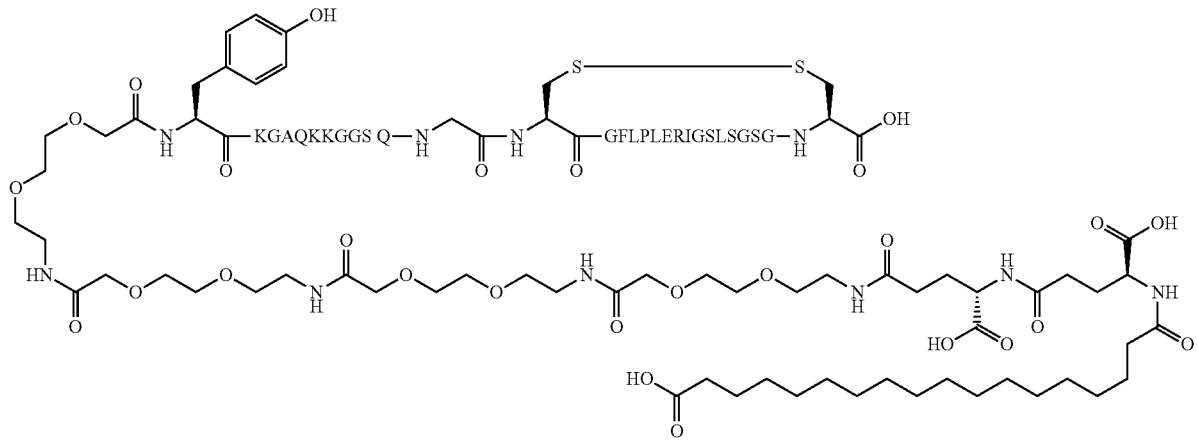

Molecular weight: 4045.6296. LCMS34: m/3 calcd: 1349.5432; m/3 found: 1349.3710; m/4.
calcd: 1012.4074; m/4 found: 1012.2860.
Chem. 144; Compound ID 1493; SEQ ID NO: 109

[N-terminal([2-[2-[2-[[2-[2-[2-[[2-[2-[2-[[2-[2-[2-[[(4S)-4-carboxy-4-[[(4S)-4-carboxy-4-(17-carboxy-heptadecanoylamino)butanoyl]amino]butanoyl]amino]ethoxy]ethoxy]acetyl]amino]eth oxy]ethoxy]acetyl]amino]ethoxy]ethoxy]acetyl]amino]ethoxy]ethoxy]acetyl]), des1-8, 13Q, 19Q, 25P, 27E, 32L]-hCNP37

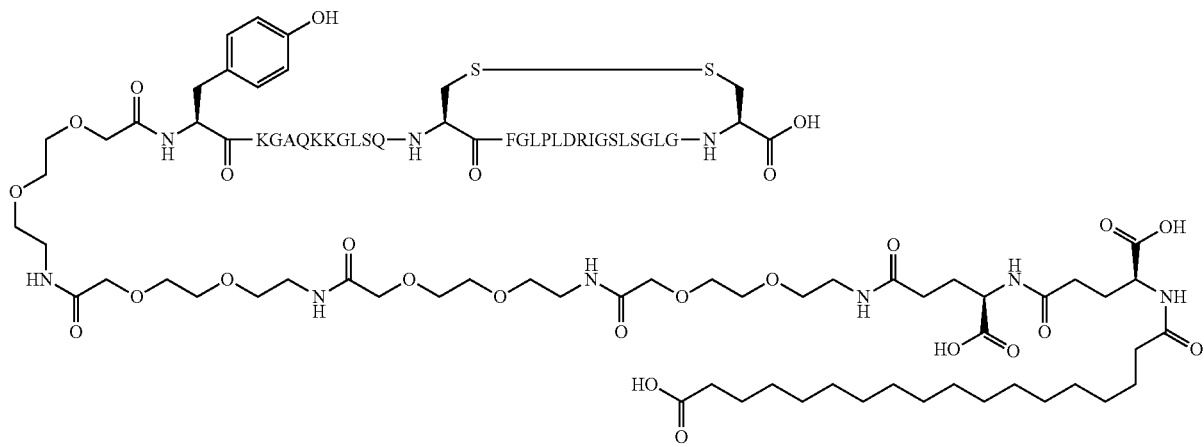

Molecular weight: 4101.7359. LCMS34: m/3 calcd: 1368.2453; m/3 found: 1368.0680; m/4.
calcd: 1026.4340; m/4 found: 1026.3130.
Chem. 145; Compound ID 1511; SEQ ID NO: 62

[N-terminal([2-[2-[2-[[2-[2-[2-[[(2S)-4-carboxy-2-(17-carboxyheptadecanoylamino)butanoyl]amino]ethoxy]ethoxy]acetyl]amino]ethoxy]ethoxy]acetyl]), des1-6, 7G, 8Q, 9A, 10P, 13Q, 17S, 19Q, 25P, 32L]-hCNP37

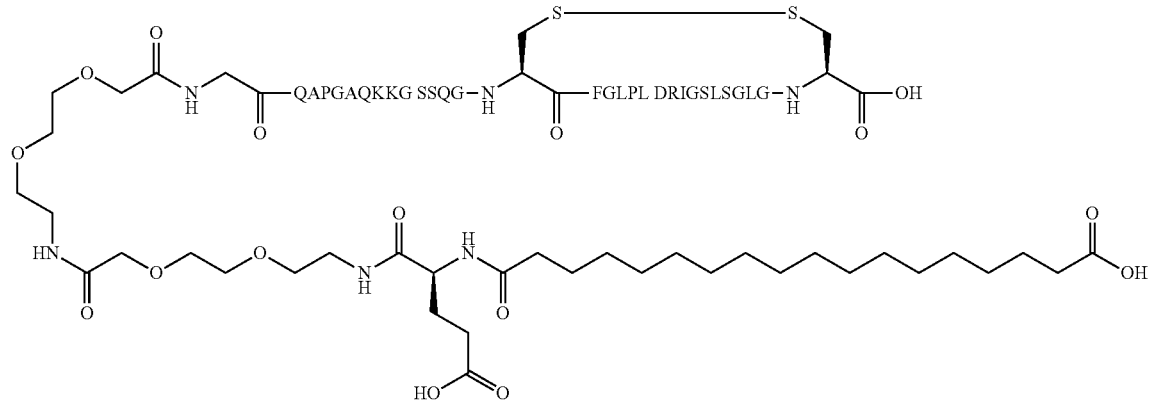

Molecular weight: 3704.2302. LCMS34: m/3 calcd: 1235.7434; m/3 found: 1235.6700; m/4.
calcd: 927.0576; m/4 found: 927.0010.
Chem. 146; Compound ID 1512; SEQ ID NO: 88

[N-terminal([2-[2-[2-[[2-[2-[2-[[2-[2-[2-[[2-[2-[2-[[(2S)-4-carboxy-2-[[(2S)-4-carboxy-2-(17-carboxy-heptadecanoylamino)butanoyl]amino]butanoyl]amino]ethoxy]ethoxy]acetyl]amino]ethoxy]ethoxy]acetyl]amino]ethoxy]ethoxy]acetyl]amino]ethoxy]ethoxy]acetyl]), des1-8, 13Q, 17G, 19Q, 25P, 32L]-hCNP37

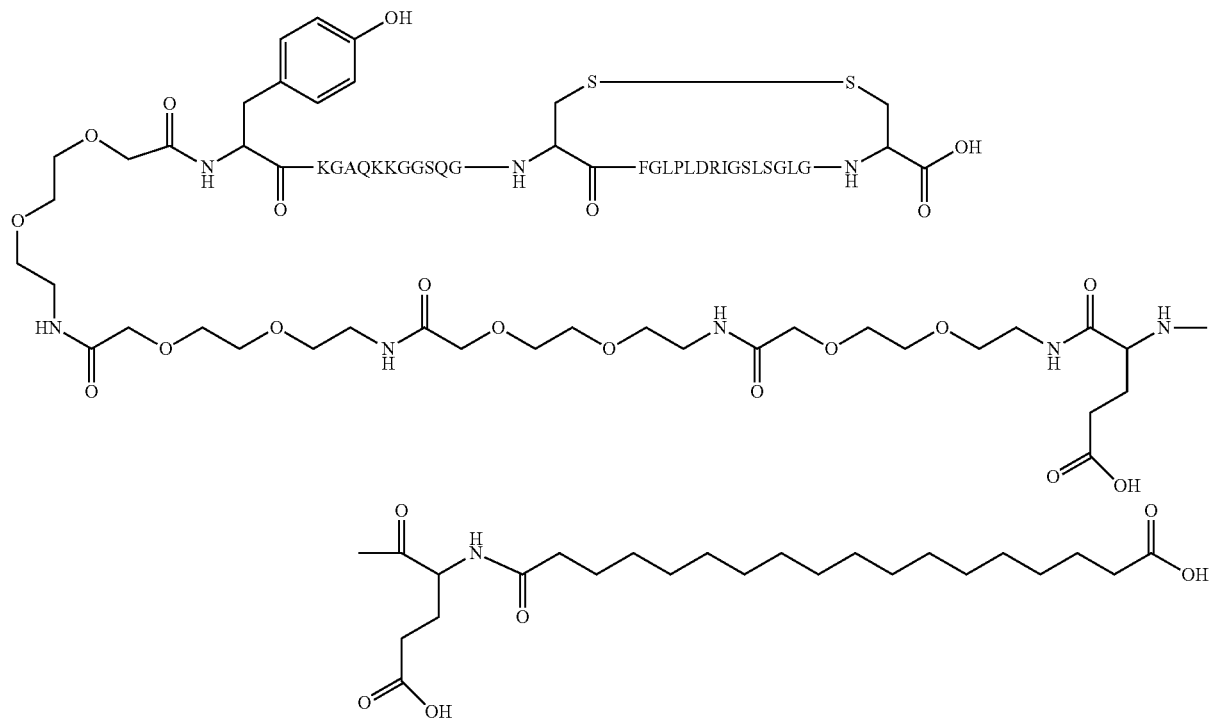

Molecular weight: 4031.603. LCMS34: m/3 calcd: 1344.8677; m/3 found: 1344.7600; m/4.
calcd: 1008.9008; m/4 found: 1008.8080.
Chem. 147; Compound ID 1513; SEQ ID NO: 110
[N-terminal(17-carboxyheptadecanoyl), -5E, -4E, -3E, -2E, -1E, 5Q, 13Q, 19S, 25P, 32L]-hCNP37
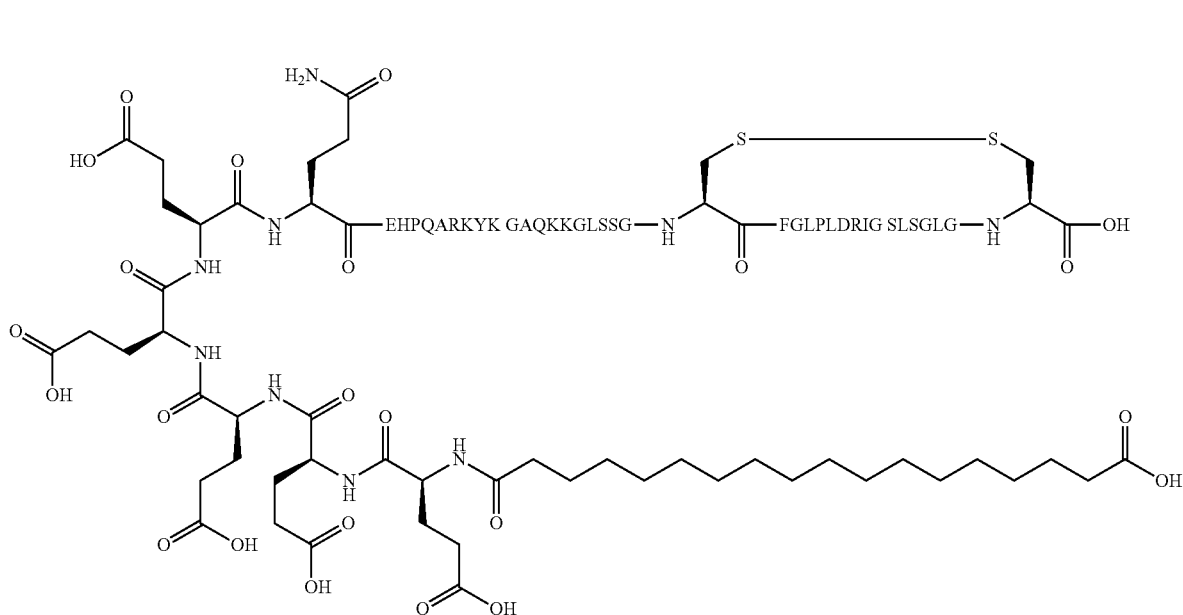
Molecular weight: 4828.4363. LCMS34: m/3 calcd: 1610.4788; m/3 found: 1610.2260; m/4.
calcd: 1208.1091; m/4 found: 1207.9160.
Chem. 148; Compound ID 1514; SEQ ID NO: 111
[N-terminal(17-carboxyheptadecanoyl), -4E, -3E, -2E, -1E, 5Q, 13Q, 19S, 25P, 27E, 32L]-hCNP37
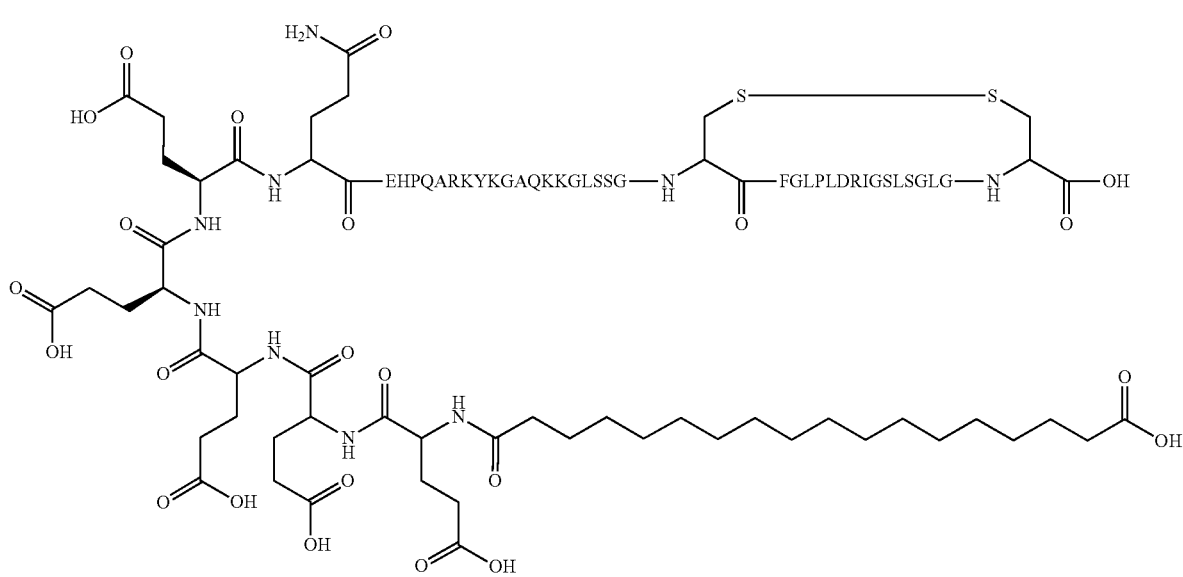
Molecular weight: 4713.3489. LCMS34: m/3 calcd: 1572.1163; m/3 found: 1571.8940; m/4.
calcd: 1179.3372; m/4 found: 1179.1550.
Chem. 149; Compound ID 1265; SEQ ID NO: 233

[N-terminal([2-[2-[2-[[2-[2-[2-[[(4R)-4-carboxy-4-(17-carboxyheptadecanoylamino) butanoyl]amino]ethoxy]ethoxy]acetyl]amino]ethoxy]ethoxy]acetyl]), des1-5, 6a, 7r, 8k, 9y, 10k, 12a, 13q, 14k, 15k, 17l, 18s, 19k, 21c, 22f, 24l, 25k, 26l, 27e, 28r, 29i, 31s, 32l, 33s, 35l, 37c]-hCNP37

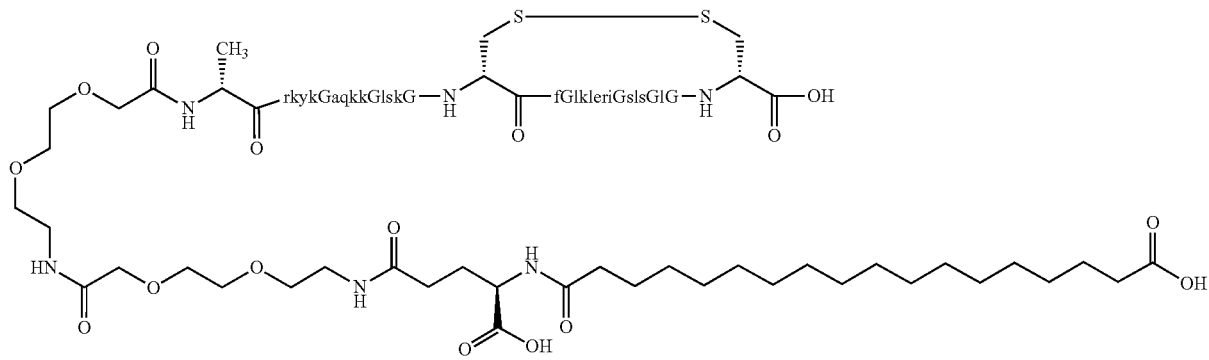

Molecular weight: 4068.8451. LCMS34: m/4 calcd: 1018.2113; m/4 found: 1018.1958.
Chem. 150; Compound ID 0106; SEQ ID NO: 234

[−2P, −1G]-hCNP37

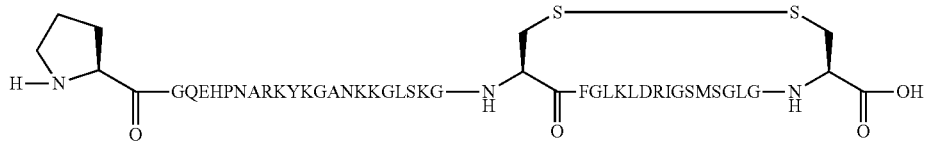

Molecular weight: 4102.7254. LCMS34: m/3 calcd: 1368.5751; m/3 found: 1368.362; m/4.
calcd: 1026.6814; m/4 found: 1026.529.
Chem. 151; Compound ID 0089; SEQ ID NO: 1

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl])]-hCNP22

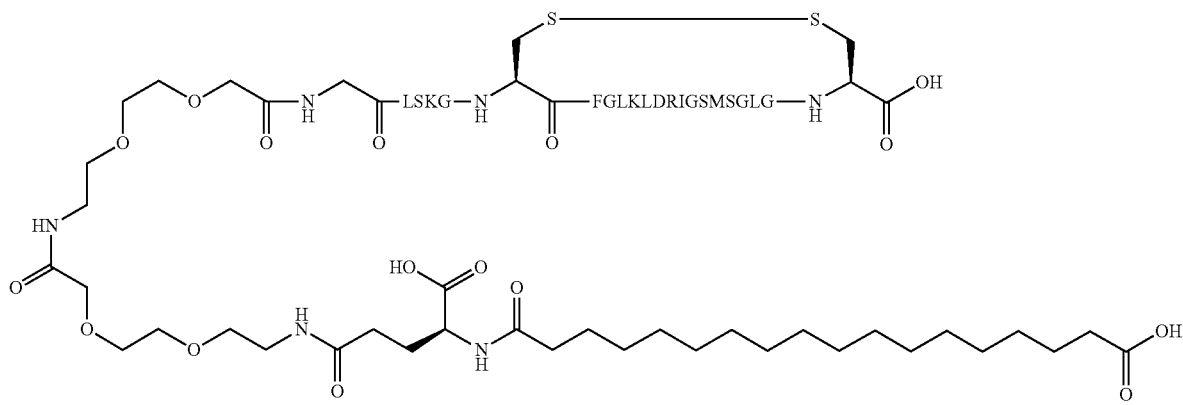

Molecular weight: 2913.4725. LCMS34: m/3 calcd: 972.1575; m/3 found: 971.844; m/4 calcd: 729.3681; m/4 found: 729.131.
Chem. 152; Compound ID 0230; SEQ ID NO: 235

[N-terminal([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]), -5G, -4Q, -3A, -2P, -1G, 2A, 3P, 4G, 5Q, 7P, 8G, 9Q, 10A, 11P, 12G, 13Q, 14A, 15P]-hCNP37

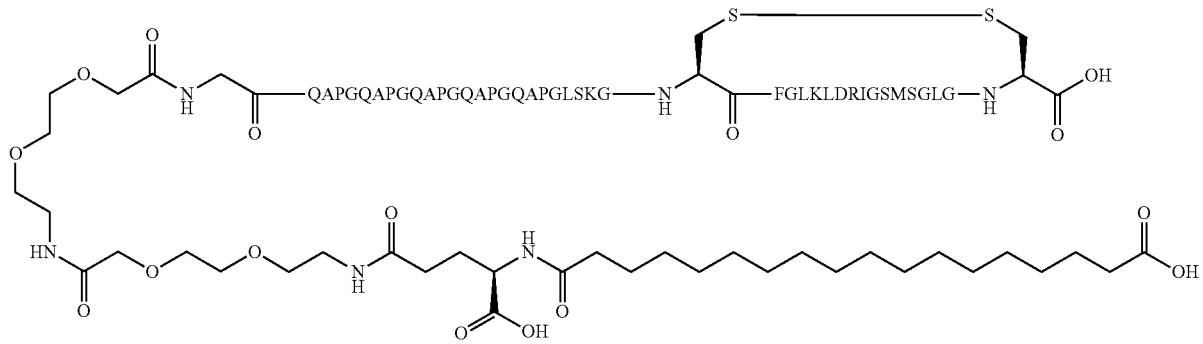

Molecular weight: 4680.3406. LCMS34: m/3 calcd: 1561.11; m/3 found: 1560.773; m/4 calcd: 1171.0852; m/4 found: 1170.834.
Chem. 153; Compound ID 0231; SEQ ID NO: 1

[N-terminal([2-[2-[2-[[2-[2-[2-[[2-[2-[2-[[2-[2-[2-[[2-[2-[2-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl])]-hCNP22

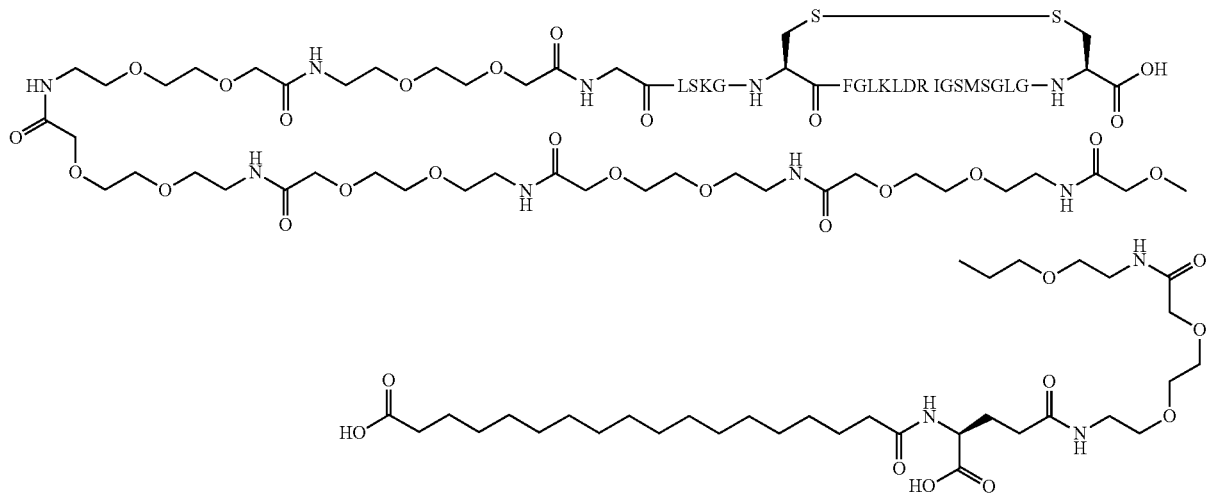

Molecular weight: 3784.4112. LCMS34: m/3 calcd: 1262.4704; m/3 found: 1262.303; m/4. calcd: 947.1028; m/4 found: 946.995.

Example 2—In Vitro hNPR2 Activity Assay

To evaluate the in vitro activity of CNP22 (0065; Chem. 1) and CNP compounds of the invention, they were tested for their ability to induce production of cyclic guanosine monophosphate (cGMP) in reporter cells expressing the human natriuretic peptide receptor 2 (hNPR2).

Cell culture: To produce the reporter cell line, HEK293 (ATCC® CRL-1573™) cells were stably transfected with the pGloSensor-42F reporter plasmid (GloSensor cGMP reporter—luciferase, Promega) and an expression plasmid encoding the hNPR2 receptor. A single cell clone was isolated for the reporter cell line. When reporter cells are exposed to an hNPR2 activating compound, hNPR2 cause production of cGMP. GloSensor luciferase, produced from the pGloSensor-42F plasmid, binds cGMP and this binding induces a conformational shift of the GloSensor luciferase, activating the otherwise inactive enzyme. Active GloSensor luciferase is able to convert luciferin to oxyluciferin, a process that produces bioluminescence. Upon cell lysis and supply of luciferase substrate, luciferase activity can be quantified by detection of luminescence. Therefore, addition of an hNPR2 activating compound and subsequent addition of detection reagent to reporter cells causes generation of luminescence in a dose dependent manner. By testing a number of different concentrations of hNPR2 activating compound, a half maximal effective concentration (EC50) can be determined. This measure, also referred to as in vitro potency, is reported for all compounds tested. In all the in vitro activity experiments, CNP22 was used as a positive in-plate control for hNPR2 activation. To reduce inter-assay variation, we also report the potency of each compound relative to the potency of the CNP22 control on each plate.

Procedure: HEK293-hNPR2/GloSensor clone 35 cells were continuously cultured in selection medium (DMEM containing 10% FCS, 1% P/S, 200 µg/mL G418 and 100 µg/mL hygromycin). To perform the assay, cells were detached with TrypLE Express (Gibco #12604013), put through a 70 µm cell strainer, counted and seeded in 30 µL/well assay medium (DMEM without phenol red and with 1% P/S) at 10,000 cells/well in white 384-well plates (Perkin Elmer #6007680) overnight. The following day, test compounds were serial diluted in dilution medium (DMEM without phenol red containing 1% OVA (Sigma #A5505 lot 04M7001V), 0.01% Tween20 (Roche #33766700) and 1% P/S) and 10 µL/well of diluted test compounds were subsequently added to the cells. For each compound, ten different concentrations in the range 0.25 µM-10 µM were tested. After 30 min of incubation at 37° C. and 5% $CO_2$, 40 µL/well Bright-Glo detection reagent (Promega #E2650) was added. Immediately thereafter or after 15 min, luminescence was detected by an EnVision Multimode Plate Reader (PerkinElmer). To determine the in vitro potency or EC50 of each test compound, a four parameter logistic regression was done on the raw data for each test compound using the Python package SciPy optimize. The average EC50 values are listed as "hNPR2 0% HSA. [EC50 (nM)]" in Table 2. A relative potency was calculated by the following expression: EC50 (CNP22 in-plate control)/EC50 (test compound)*100, shown as "hNPR2 0% HSA. [EC50% rel CNP]" in Table 2. A minimum of two replicates was measured for each test compound. The reported values are averages of the replicates and listed in Table 2.

TABLE 2

In vitro human NPR2 potencies of CNP compounds:

| Compound ID (Chem ref.) | hNPR2 0% HSA. [EC50 (nM)] | hNPR2 0% HSA. [EC50% rel CNP] |
|---|---|---|
| 0065 (CNP22, chem. 1) | 0.28 | 100.0 |
| 1510 | 0.05 | 139.2 |
| 0312 | 0.47 | 80.0 |
| 0776 | 0.58 | 33.2 |
| 1235 | 1.17 | 27.2 |
| 0262 | 15.44 | 1.8 |
| 0296 | 5.50 | 3.6 |
| 0313 | 48.37 | 0.7 |
| 0334 | 124.43 | 2.0 |
| 1221 | 1.17 | 35.9 |

TABLE 2-continued

In vitro human NPR2 potencies of CNP compounds:

| Compound ID (Chem ref.) | hNPR2 0% HSA. [EC50 (nM)] | hNPR2 0% HSA. [EC50% rel CNP] |
|---|---|---|
| 1222 | 2.94 | 14.3 |
| 1223 | 1.05 | 6.77 |
| 1224 | 0.86 | 16.9 |
| 1225 | 2.23 | 29.4 |
| 1226 | 2.95 | 7.5 |
| 1227 | 1.01 | 38.2 |
| 1228 | 11.03 | 12.3 |
| 1229 | 4.44 | 5.3 |
| 1230 | 6.98 | 4.2 |
| 1231 | 5.62 | 4.1 |
| 1232 | 1.63 | 16.0 |
| 1233 | 0.81 | 49.7 |
| 1236 | 3.40 | 6.1 |
| 1237 | 1.95 | 11.8 |
| 1240 | 4.01 | 11.2 |
| 1241 | 1.35 | 30.5 |
| 1242 | 6.58 | 5.4 |
| 1274 | 7.66 | 13.2 |
| 1287 | 12.78 | 2.9 |
| 1288 | 12.42 | 3.0 |
| 1289 | 12.97 | 2.9 |
| 1290 | 5.30 | 7.0 |
| 1302 | 2.80 | 26.5 |
| 1303 | 1.48 | 25.5 |
| 1304 | 2.91 | 20.7 |
| 1305 | 6.98 | 8.7 |
| 1309 | 1.35 | 33.3 |
| 1310 | 6.88 | 10.4 |
| 1311 | 6.79 | 12.7 |
| 1312 | 7.82 | 9.0 |
| 1322 | 4.73 | 1.9 |
| 1323 | 11.24 | 0.8 |
| 1324 | 5.51 | 1.6 |
| 1338 | 6.77 | 1.3 |
| 1339 | 1.03 | 15.5 |
| 1340 | 0.18 | 44.4 |
| 1341 | 0.48 | 16.7 |
| 1345 | 0.38 | 21.1 |
| 1346 | 0.47 | 17.0 |
| 1347 | 0.52 | 15.4 |
| 1348 | 0.35 | 31.4 |
| 1350 | 0.39 | 41.0 |
| 1351 | 0.29 | 55.2 |
| 1352 | 0.39 | 38.6 |
| 1353 | 1.22 | 9.0 |
| 1354 | 0.40 | 27.5 |
| 1355 | 0.39 | 28.2 |
| 1356 | 0.49 | 22.4 |
| 1357 | 2.53 | 4.3 |
| 1359 | 0.39 | 28.2 |
| 1360 | 0.73 | 15.1 |
| 1375 | 0.68 | 16.2 |
| 1376 | 0.12 | 91.7 |
| 1377 | 0.39 | 28.2 |
| 1378 | 0.33 | 28.6 |
| 1379 | 0.35 | 33.5 |
| 1380 | 0.72 | 15.7 |
| 1381 | 0.25 | 38.7 |
| 1382 | 0.23 | 43.8 |
| 1383 | 0.25 | 43.1 |
| 9384 | 0.10 | 53.7 |
| 1385 | 0.35 | 30.7 |
| 1386 | 0.29 | 36.9 |
| 1387 | 0.46 | 20.6 |
| 1388 | 0.41 | 23.5 |
| 1389 | 0.13 | 52.3 |
| 1390 | 0.33 | 84.6 |
| 1391 | 0.35 | 37.9 |
| 1392 | 0.45 | 29.5 |
| 1393 | 0.42 | 27.8 |
| 1394 | 0.21 | 93.9 |
| 1395 | 0.04 | 60.2 |
| 1396 | 0.07 | 43.1 |
| 1398 | 0.14 | 55.6 |
| 1399 | 0.13 | 137.0 |

TABLE 2-continued

In vitro human NPR2 potencies of CNP compounds:

| Compound ID (Chem ref.) | hNPR2 0% HSA. [EC50 (nM)] | hNPR2 0% HSA. [EC50% rel CNP] |
|---|---|---|
| 1400 | 0.26 | 85.3 |
| 1401 | 0.56 | 19.7 |
| 1402 | 0.24 | 57.6 |
| 1403 | 0.25 | 87.1 |
| 1404 | 0.31 | 81.3 |
| 1405 | 0.31 | 62.3 |
| 1406 | 0.28 | 59.1 |
| 9407 | 0.16 | 38.6 |
| 1419 | 0.33 | 37.2 |
| 1420 | 0.08 | 87.5 |
| 1421 | 0.14 | 50.0 |
| 1422 | 0.28 | 75.3 |
| 1423 | 0.31 | 37.7 |
| 1424 | 0.19 | 36.2 |
| 1425 | 0.25 | 26.4 |
| 1426 | 0.19 | 76.2 |
| 1431 | 1.11 | 14.3 |
| 1432 | 0.43 | 26.0 |
| 1434 | 0.46 | 29.0 |
| 9435 | 0.07 | 73.6 |
| 1436 | 0.23 | 30.2 |
| 1437 | 0.35 | 19.9 |
| 1448 | 0.24 | 33.3 |
| 1449 | 0.16 | 110.0 |
| 1450 | 0.24 | 84.2 |
| 1451 | 0.72 | 47.5 |
| 1452 | 0.03 | 57.6 |
| 1453 | 0.04 | 33.5 |
| 1454 | 0.02 | 63.6 |
| 1455 | 0.03 | 43.4 |
| 1456 | 0.03 | 50.4 |
| 1457 | 0.02 | 79.4 |
| 1458 | 0.02 | 93.6 |
| 1459 | 0.02 | 76.1 |
| 1460 | 0.04 | 32.4 |
| 1461 | 0.20 | 28.9 |
| 1462 | 0.01 | 106.6 |
| 1463 | 0.30 | 20.0 |
| 1464 | 0.12 | 48.8 |
| 1465 | 0.25 | 24.0 |
| 1470 | 0.06 | 23.9 |
| 1471 | 0.03 | 40.2 |
| 1472 | 0.03 | 52.0 |
| 1473 | 0.01 | 107.7 |
| 1474 | 0.03 | 62.5 |
| 1475 | 0.13 | 46.5 |
| 1476 | 0.12 | 48.4 |
| 1477 | 0.13 | 10.3 |
| 1478 | 0.05 | 26.6 |
| 9480 | 0.05 | 45.2 |
| 1481 | 0.02 | 35.1 |
| 9482 | 0.06 | 39.4 |
| 9483 | 0.30 | 10.2 |
| 1484 | 0.03 | 27.9 |
| 1486 | 0.14 | 6.0 |
| 1487 | 0.04 | 22.0 |
| 1488 | 0.03 | 29.3 |
| 1489 | 0.22 | 3.7 |
| 1493 | 0.80 | 11.5 |
| 1265 | >1000 | N/A |
| 0106 | 0.18 | 201.1 |
| 0089 | 12.25 | 3.1 |
| 0230 | 29.23 | 0.4 |
| 0231 | 14.53 | 0.8 |

These data demonstrate that the tested CNP compounds span a broad range of NPR2 in vitro activation levels and that negatively charged CNP compounds commonly show reduced in vitro NPR2 potency relative to positively charged CNP compounds.

Example 3—In Vitro Neprilysin Stability of CNP-Compounds

It has been reported that native CNP can be metabolised by neprilysin (neutral endopeptidase, NEP), which is a protease that is widely present in the body. Therefore, an in vitro neprilysin stability assay was set up to test the neprilysin mediated degradation of selected CNP compounds.

Procedure: In short, the assay buffer consisted of PBS-buffer (pH 7.4, ThermoFisher Scientific) with a final concentration of 0.005% v/v tween 20 (Sigma-Aldrich). Recombinant human neprilysin (rhNEP; R&D Systems) and the CNP compounds were dissolved in assay buffer. Native CNP22 (0065, Chem. 1) was included as positive control on each day of incubation. Initially, the CNP compound (the final concentration was 1000 nM) was pre-incubated in assay buffer for 10 min at 37° C. The assay was started by adding either rhNEP (final concentration was 2 µg protein per mL) or assay buffer (adsorption experiment) and the incubation was conducted at 37° C. The reaction was terminated at selected time points (0.5; 5; 15; 30; 60: 90 and 120 min) by adding one volume of incubation mixture to three volumes of ethanol (containing 1% v/v of formic acid). The mixture was centrifuged at 13000 rpm at 4° C. for 20 minutes. After centrifugation, one volume of supernatant was mixed with one volume of Milli-Q water.

Analysis by LCMS: The mixture was analysed by LCMS using an Acquity UPLC Peptide CSH C18 analytical column from Waters (130 Å, 1.7 µm, 1*50 mm) operated at 60° C. A gradient elution was conducted with a Nexera UHPLC system (Shimadzu) using mobile phase A (consisting of Milli-Q water with 0.1% formic acid) and mobile phase B (consisting of acetonitrile with 0.1% formic acid). The flow was 0.3 ml/min. A zenoTOF 7600 mass spectrometer (Sciex) was used as detector and operated in positive electrospray ionisation mode. Data was recorded in full scan mode (m/z 300-1700).

Calibration curves were prepared in assay buffer and treated as study samples. These samples were used for calculating the concentration of the relevant CNP compound in the in vitro samples. Quality control samples were included. For at least 75% of the standards and QCs, the deviation between nominal and calculated concentration was below 20%.

All incubations were conducted in duplicate. Data was reported as percent remaining at 90 min (based on calculated concentrations) compared to the average concentration in the 0.5-minute time point samples. An example of seven compounds and CNP22 (0065, Chem. 1) is shown in Table 3.

TABLE 3

Percent remaining of CNP-compounds upon incubation with rhNEP for 90 minutes

| Compound | Remaining of parent after 90 min (%) |
|---|---|
| 0065* (CNP22) | 1.7 |
| 0106 | 95.1 |
| 9384 | 87.8 |
| 9407 | 96.6 |
| 9435 | 93.2 |
| 9480 | 98.3 |
| 9482 | 96.3 |
| 9483 | 105.6 |

*Run as positive control within each experiment

These data demonstrate that the CNP compounds of the present invention are substantially stable in the presence of recombinant human neprilysin in comparison to CNP22 which is rapidly degraded.

Example 4—Peptide Net Charge Calculation

The charge of an ionizable group in a peptide at a given pH can be calculated using the Henderson-Hasselbalch equation using empirically determined acid dissociation constants (pKa) for each amino acid residue or modifying group as is well known in the art, for example as by the method described by B. Skoog and A. Wichman (Trends in Analytical Chemistry, 1986, vol. 5, pp. 82-83.) and L. Kozlowski (Biology Direct, 2016, 11:55). This is shown for negatively charged amino acids or modifying groups in Equation 1 and for positively charged amino acids and modifying groups in Equation 2, in which pKn is the pKa of the negatively charged group and pKp is the pKa of the positively charged group and where pH in the equation is the pH of interest. The net charge of a peptide at a given pH is then the sum of the negative and positive charges of all the ionizable groups in the peptide.

$$\sum_{i=1}^{n} \frac{-1}{1 + 10^{pKn - pH}} \quad \text{Equation 1}$$

$$\sum_{i=1}^{n} \frac{1}{1 + 10^{pH - pKp}} \quad \text{Equation 2}$$

For natural amino acid residues, tabulated pKa constants are used for free terminals and ionizable sites in side chains. pKa-values for modified amino acid and modifying groups were estimated by the ACD/Labs ver. 12 package and also shown in Table 4.

As an example, to calculate the net charge of compound 9482 at pH 7.4 the sum of negative charges carried by positions Cys37 (C-terminal acid), Asp27, Glu2, gGlu (1), gGlu (2), gGlu (3), gGlu (4), gGlu (5) and C18d fatty acid is minus 8.995 Fd when using the pKa values shown in Table 4. The sum of positive charges carried by positions Arg28, Lys15, Lys14, Lys10, Lys8, Arg7 and His3 is 6.162 Fd. The net charge is then the sum of the above which is minus 2.833.

Calculated charge values for selected pH (pH 7.4 and pH 6.5) using the above principle for CNP compounds of the present invention are shown in Table 5.

TABLE 4 pKa values for termini, sidechains of amino acids and modifying groups used when calculating pI and net charge of CNP compounds

| Residue | N-terminal | C-terminal | Side chain |
|---|---|---|---|
| Ala | 7.8 | 3.7 | N/A |
| Arg | 7.4 | 3.6 | 13.3 |
| Asn | 6.1 | 3.5 | N/A |
| Asp | 7.4 | 3.5 | 4.2 |
| Cys | 6.1 | 3.3 | 9.1 |
| Gln | 6.9 | 3.5 | N/A |
| Glu | 8.4 | 3.5 | 4.4 |
| Gly | 7.3 | 3.7 | N/A |
| His | 6.1 | 3.1 | 6.7 |
| Ile | 7.9 | 3.7 | N/A |
| Leu | 7.9 | 3.7 | N/A |
| Lys | 7.2 | 3.6 | 10.4 |
| Met | 6.9 | 3.5 | N/A |
| Phe | 7.0 | 3.6 | N/A |
| Pro | 8.9 | 3.4 | N/A |
| Ser | 6.3 | 3.3 | N/A |
| Thr | 6.3 | 3.3 | N/A |
| Trp | 7.7 | 3.7 | N/A |
| Tyr | 7.3 | 3.7 | 9.8 |
| Val | 7.9 | 3.7 | N/A |
| Cys in disulfide | 6.1 | 3.3 | N/A |
| C18d | N/A | N/A | 4.8 |
| C20d | N/A | N/A | 4.8 |
| Tetrazole-C18 | N/A | N/A | 5.1 |
| gGlu | N/A | N/A | 3.5 |

TABLE 5

Calculated values of net charge (Q) at pH 7.4 and net charge at 6.5 for CNP compounds

| Chem No | Compound ID | Q (pH = 7.4) | Q (pH = 6.5) |
|---|---|---|---|
| 1 | 0065 | 1.4 | 1.9 |
| 2 | 1510 | 5.4 | 6.4 |
| 3 | 0312 | 4.0 | 4.0 |
| 4 | 0776 | 4.0 | 4.0 |
| 5 | 1235 | 0.2 | 0.6 |
| 6 | 0262 | −3.0 | −3.0 |
| 7 | 0296 | −3.0 | −3.0 |
| 8 | 0313 | −3.0 | −3.0 |
| 9 | 0334 | −3.0 | −3.0 |
| 10 | 1221 | 0.0 | 0.0 |
| 11 | 1222 | −1.0 | −1.0 |
| 12 | 1223 | −2.0 | −2.0 |
| 13 | 1224 | −1.0 | −1.0 |
| 14 | 1225 | −1.0 | −1.0 |
| 15 | 1226 | −3.0 | −3.0 |
| 16 | 1227 | −2.0 | −2.0 |
| 17 | 1228 | −4.0 | −4.0 |
| 18 | 1229 | −1.0 | −1.0 |
| 19 | 1230 | −2.0 | −2.0 |
| 20 | 1231 | −2.0 | −2.0 |
| 21 | 1232 | 0.0 | 0.0 |
| 22 | 1233 | 0.0 | 0.0 |
| 23 | 1236 | −1.8 | −1.4 |
| 24 | 1237 | −0.8 | −0.4 |
| 25 | 1240 | −1.8 | −1.4 |
| 26 | 1241 | −0.8 | −0.4 |
| 27 | 1242 | −2.8 | −2.4 |
| 28 | 1274 | −3.0 | −3.0 |
| 29 | 1287 | −4.0 | −4.0 |
| 30 | 1288 | −4.0 | −4.0 |
| 31 | 1289 | −4.0 | −4.0 |
| 32 | 1290 | −3.0 | −3.0 |
| 33 | 1302 | −1.8 | −1.4 |
| 34 | 1303 | −1.8 | −1.4 |
| 35 | 1304 | −2.7 | −1.8 |
| 36 | 1305 | −1.8 | −1.4 |
| 37 | 1309 | −0.8 | −0.4 |
| 38 | 1310 | −1.8 | −1.4 |
| 39 | 1311 | −1.8 | −1.4 |
| 40 | 1312 | −2.8 | −2.4 |
| 41 | 1322 | −0.5 | 0.9 |
| 42 | 1323 | −1.5 | −0.2 |
| 43 | 1324 | −1.7 | −0.8 |
| 44 | 1338 | −2.0 | −2.0 |
| 45 | 1339 | −2.0 | −2.0 |
| 46 | 1340 | −0.7 | 0.2 |
| 47 | 1341 | −1.7 | −0.8 |
| 48 | 1345 | −0.5 | 0.9 |
| 49 | 1346 | −1.5 | −0.2 |
| 50 | 1347 | −0.8 | −0.4 |

TABLE 5-continued

Calculated values of net charge (Q) at pH 7.4 and net charge at 6.5 for CNP compounds

| Chem No | Compound ID | Q (pH = 7.4) | Q (pH = 6.5) |
|---|---|---|---|
| 51 | 1348 | −0.8 | −0.4 |
| 52 | 1350 | −0.7 | 0.2 |
| 53 | 1351 | −0.7 | 0.2 |
| 54 | 1352 | −1.8 | −1.4 |
| 55 | 1353 | −0.8 | −0.4 |
| 56 | 1354 | −0.8 | −0.4 |
| 57 | 1355 | 0.0 | 0.0 |
| 58 | 1356 | −1.0 | −1.0 |
| 59 | 1357 | −0.8 | −0.4 |
| 60 | 1359 | −0.8 | −0.4 |
| 61 | 1360 | −1.7 | −0.8 |
| 62 | 1375 | −1.0 | −1.0 |
| 63 | 1376 | −1.0 | −1.0 |
| 64 | 1377 | −1.0 | −1.0 |
| 65 | 1378 | −2.0 | −2.0 |
| 66 | 1379 | −1.8 | −1.4 |
| 67 | 1380 | −2.8 | −2.3 |
| 68 | 1381 | −2.2 | 0.1 |
| 69 | 1382 | −1.7 | −0.8 |
| 70 | 1383 | −2.4 | −0.5 |
| 71 | 9384 | −1.0 | −1.0 |
| 72 | 1385 | −2.0 | −2.0 |
| 73 | 1386 | −1.0 | −1.0 |
| 74 | 1387 | −3.0 | −3.0 |
| 75 | 1388 | −2.0 | −2.0 |
| 76 | 1389 | −1.8 | −1.4 |
| 77 | 1390 | −3.8 | −3.4 |
| 78 | 1391 | −1.0 | −1.0 |
| 79 | 1392 | −2.0 | −2.0 |
| 80 | 1393 | −2.0 | −2.0 |
| 81 | 1394 | −0.8 | −0.4 |
| 82 | 1395 | −1.8 | −1.4 |
| 83 | 1396 | −1.8 | −1.4 |
| 84 | 1398 | −2.7 | −1.8 |
| 85 | 1399 | −2.7 | −1.8 |
| 86 | 1400 | −2.7 | −1.8 |
| 87 | 1401 | −3.8 | −3.4 |
| 88 | 1402 | −3.8 | −3.4 |
| 89 | 1403 | −3.8 | −3.4 |
| 90 | 1404 | −3.8 | −3.4 |
| 91 | 1405 | −3.8 | −3.4 |
| 92 | 1406 | −2.8 | −2.4 |
| 93 | 9407 | −2.0 | −2.0 |
| 94 | 1419 | −1.7 | −0.8 |
| 95 | 1420 | −1.7 | −0.8 |
| 96 | 1421 | −1.0 | −1.0 |
| 97 | 1422 | −0.8 | −0.4 |
| 98 | 1423 | −0.8 | −0.4 |
| 99 | 1424 | −1.0 | −1.0 |
| 100 | 1425 | −1.8 | −1.4 |
| 101 | 1426 | −0.8 | −0.4 |
| 102 | 1431 | −1.8 | −1.4 |
| 103 | 1432 | −1.8 | −1.4 |
| 104 | 1434 | −1.8 | −1.4 |
| 105 | 9435 | −1.0 | −1.0 |
| 106 | 1436 | −1.0 | −1.0 |
| 107 | 1437 | −1.8 | −1.4 |
| 108 | 1448 | −2.8 | −2.4 |
| 109 | 1449 | −2.7 | −1.8 |
| 110 | 1450 | −1.8 | −1.4 |
| 111 | 1451 | −0.8 | −0.4 |
| 112 | 1452 | −2.0 | −2.0 |
| 113 | 1453 | −2.0 | −2.0 |
| 114 | 1454 | −1.0 | −1.0 |
| 115 | 1455 | −1.0 | −1.0 |
| 116 | 1456 | −1.0 | −1.0 |
| 117 | 1457 | −1.0 | −1.0 |
| 118 | 1458 | −1.0 | −1.0 |
| 119 | 1459 | −1.0 | −1.0 |
| 120 | 1460 | −2.0 | −2.0 |
| 121 | 1461 | −1.8 | −1.4 |
| 122 | 1462 | −1.0 | −1.0 |
| 123 | 1463 | −1.0 | −1.0 |
| 124 | 1464 | −2.0 | −2.0 |
| 125 | 1465 | −2.0 | −2.0 |
| 126 | 1470 | −1.0 | −1.0 |
| 127 | 1471 | −2.8 | −2.4 |
| 128 | 1472 | −1.8 | −1.4 |
| 129 | 1473 | −1.8 | −1.4 |
| 130 | 1474 | −1.8 | −1.4 |
| 131 | 1475 | −2.0 | −1.9 |
| 132 | 1476 | −2.0 | −1.9 |
| 133 | 1477 | −2.0 | −2.0 |
| 134 | 1478 | −1.0 | −1.0 |
| 135 | 9480 | −2.0 | −2.0 |
| 136 | 1481 | −2.0 | −2.0 |
| 137 | 9482 | −2.8 | −2.4 |
| 138 | 9483 | −1.8 | −1.4 |
| 139 | 1484 | −1.0 | −1.0 |
| 140 | 1486 | −1.0 | −1.0 |
| 141 | 1487 | −1.0 | −1.0 |
| 142 | 1488 | −1.0 | −1.0 |
| 143 | 1489 | −1.0 | −1.0 |
| 144 | 1493 | −1.0 | −1.0 |
| 145 | 1511 | −1.0 | −1.0 |
| 146 | 1512 | −1.0 | −1.0 |
| 147 | 1513 | −2.8 | −2.3 |
| 148 | 1514 | −1.8 | −1.3 |
| 149 | 1265 | 4.0 | 4.0 |
| 150 | 0106 | 6.1 | 6.6 |
| 151 | 0089 | −1.0 | −1.0 |
| 152 | 0230 | −1.0 | −1.0 |
| 153 | 0231 | −1.0 | −1.0 |

Example 5—Solubility of CNP Compounds

In order to assess the suitability of CNP compounds for a soluble liquid formulation, the solubility of CNP compounds in pharmaceutically relevant buffers were measured. Solubility at two different pH-levels (pH 4.0 and pH 6.5) was examined as pH is expected to affect solubility.

Preparation of pH 4.0 samples: The pH 4.0 samples of the CNP compounds were prepared by mixing freeze dried peptide with a pH 4.0 5 mM sodium acetate, 250 mM glycerol buffer at room temperature to a nominal concentration of at least 4000-5000 nmol/mL. The pH of the samples was measured and adjusted to pH 4.0 and the samples were allowed to equilibrate at room temperature until next day if not fully dissolved.

Preparation of pH 6.5 samples: The pH 6.5 samples of the CNP compounds were prepared by dissolving the freeze dried peptide in water. While stirring, a part of the peptide solution was transferred to a buffer consisting of 41 mM sodium phosphate and 118 mg/mL glycerol, pH 7.5-8.0, followed by addition of diluted sodium hydroxide followed by another part of the peptide solution and further addition of diluted sodium hydroxide. This procedure was repeated until all of the peptide solution had been added where a nominal concentration of at least 4000-5000 nmol/mL had been reached and the buffer composition was 8 mM sodium phosphate, 23 mg/mL glycerol. The pH of the samples were measured and adjusted to pH 6.5 and the samples were allowed to equilibrate at room temperature until next day if not fully dissolved.

Procedure: Samples at pH 4.0 were prepared as described above and the compound concentration in the supernatant was determined using CAD (Method F, CAD02). The compound concentration at pH 4.0 represents the solubility at pH 4.0 and the measured values are given in Table 6.

TABLE 6

Solubility of CNP compounds formulated at pH 4.0

| Compound ID (chem. ref.) | Solubility at pH 4.0 (μM) |
|---|---|
| 1351 | 6168 |
| 1381 | 8995 |
| 1389 | 8896 |
| 1422 | 8286 |
| 1426 | 11242 |
| 9435 | 7416 |
| 1470 | 6476 |
| 1473 | 5832 |
| 1474 | 6376 |
| 1478 | 6507 |
| 9480 | 23 |
| 9482 | 99 |
| 9483 | 4964 |
| 1484 | 0 |
| 1489 | 5932 |

Samples at pH 6.5 were prepared as described above and peptide concentration in the supernatant was determined by CAD (Method F, CAD02). The peptide concentration at pH 6.5 represents the solubility at pH 6.5 and the measured values are given in Table 7.

TABLE 7

Solubility of CNP compound formulations at pH 6.5

| Compound ID | Solubility at pH 6.5 (μM) |
|---|---|
| 0745 | 872 |
| 1218 | 2160 |
| 1303 | 4840 |
| 1304 | 6661 |
| 1310 | 7610 |
| 1318 | 6100 |
| 1352 | 7727 |
| 1354 | 440 |
| 1375 | 3131 |
| 1377 | 443 |
| 1378 | 8923 |
| 1379 | 2674 |
| 1382 | 3175 |
| 9384 | 7559 |
| 1386 | 490 |
| 1389 | 426 |
| 1392 | 9877 |
| 1402 | 10021 |
| 1404 | 6883 |
| 1406 | 5670 |
| 9407 | 6687 |
| 1411 | 3296 (at pH 5.5) |
| 1417 | 1928 |
| 1419 | 318 |
| 1420 | 1409 |
| 1421 | 857 |
| 1432 | 9825 |
| 1434 | 8514 |
| 9435 | 2356 |
| 1453 | 7885 |
| 1457 | 8955 |
| 1470 | 595 |
| 1473 | 1764 |
| 1474 | 969 |
| 1477 | 5346 |
| 1478 | 2177 |
| 9480 | 6166 |
| 9482 | 5323 |
| 1484 | 2332 |

As a rule of thumb, only samples containing more than 4000 μM were subjected to further testing as described below.

These results demonstrate the CNP compounds of the present invention can be formulated in pharmaceutically relevant buffers at concentrations suitable for s.c. administration.

Example 6—Thioflavin T (ThT) Assay

The ThT assay was used to evaluate physical stability of the CNP compounds and their suitability for liquid formulation. Low physical stability of peptides may lead to amyloid fibril formation, which is observed as well-ordered, thread-like macromolecular structures in the sample eventually resulting in gel formation. This has traditionally been tested by visual inspection of the sample. However, that kind of measurement is very subjective and depending on the observer. Therefore, the application of a small molecule indicator probe is much more advantageous. Thioflavin T (ThT) is such a probe and has a distinct fluorescence signature when binding to fibrils [Naiki et al. (1989) Anal. Biochem. 177, 244-249; LeVine (1999) Methods. Enzymol. 09, 274-284].

Procedure: Thioflavin T was added to the supernatant samples from Example 5 (pH 4.0 and 6.5) using an aqueous ThT stock solution to a final concentration of about 1 μM in the samples. Sample aliquots of 150 μL were placed in a 96 well microtiter plate (Packard OptiPlate™-96, white polystyrene). Usually, two to three replicas of each sample were applied to the plate. The plate was sealed and placed in a fluorescence plate reader (Fluoroskan Ascent FL) and incubated at 37° C. with orbital shaking (960 rpm; 1 mm amplitude). Fluorescence measurements were performed every 20 minutes using excitation through a 444 nm filter and measurement of emission through a 485 nm filter. Between each measurement, the plate was shaken and heated as described above and the assay was terminated after 45 hours. Fluorescence measurements for each microtiter plate well were plotted against time and the lag-time (time until an increase in ThT fluorescence was observed) was estimated.

To assess loss of dissolved peptide following 45 h incubation, peptide recovery was measured as the ratio between total peak area after incubation vs. before incubation using the RP-UPLC method described below.

Measurement of LagTime and Peptide recovery % using RP-UPLC: RP-UPLC was conducted using an Acquity UPLC BEH C18 1.7 μm (2.1×30 mm) Waters column (Eluent A: 0.1% v/v % TFA in water; Eluent B: 0.1% v/v TFA in acetonitrile/water 4:1) with gradient elution (0 min: 95% A; 2 min: 20% A; 2.3 min: 20% A; 2.4 min: 95% A; 9 min: 95% A) in a flow rate of 0.9 mL/min and a column temperature of 30° C. UV-detection at 215 nm was used to assess the total peptide area.

Samples at pH 4.0 were prepared as described in Example 5 and subjected to the ThT assay as described above. LagTime and Peptide recovery values are given in Table 8.

TABLE 8

ThT assay lagtime and peptide recovery of CNP compounds at pH 4.0

| Compound ID | LagTime (h) at pH 4.0 | Peptide Recovery (%) at pH 4.0 |
|---|---|---|
| 1351 | 45 | 110 |
| 1381 | 45 | 112 |
| 1422 | 45 | 99 |
| 1426 | 0.33 | 0 |
| 1389 | 45 | 117 |

TABLE 8-continued

ThT assay lagtime and peptide recovery of CNP compounds at pH 4.0

| Compound ID | LagTime (h) at pH 4.0 | Peptide Recovery (%) at pH 4.0 |
|---|---|---|
| 9435 | 45 | 111 |
| 1473 | 45 | 118 |
| 1470 | 45 | 121 |
| 1474 | 45 | 161 |
| 1478 | 0.33 | 3 |
| 9483 | 45 | 74 |
| 1489 | 45 | 99 |

Samples at pH 6.5 were prepared as described in Example 5 and subjected to the ThT assay as described above. LagTime and Peptide recovery values are given in Table 9.

TABLE 9

ThT assay lagtime and peptide recovery of CNP compounds at pH 6.5

| Compound ID | LagTime (h) at pH 6.5 | Peptide Recovery (%) at pH 6.5 |
|---|---|---|
| 1318 | 45 | 105 |
| 1218 | 45 | 89 |
| 1303 | 5 | 16 |
| 1310 | 45 | 117 |
| 1375 | 45 | 88 |
| 1304 | 45 | 141 |
| 1352 | 23 | 0 |
| 9384 | 45 | 135 |
| 9407 | 45 | 128 |
| 1411 | 45 | 112 |
| 1417 | 45 | 119 |
| 1382 | 45 | 157 |
| 1432 | 45 | 188 |
| 1434 | 45 | 127 |
| 1378 | 2.5 | 23 |
| 1392 | 45 | 118 |
| 9435 | 45 | 99 |
| 1402 | 45 | 123 |
| 1404 | 45 | 148 |
| 1406 | 45 | 120 |
| 1453 | 45 | 109 |
| 1457 | 45 | 109 |
| 1477 | 23 | 16 |
| 1478 | 45 | 99 |
| 9480 | 45 | 104 |
| 9482 | 45 | 93 |
| 1484 | 4 | 98 |

In conclusion this experiment demonstrates that most CNP compounds of the invention can be formulated in pharmaceutically relevant buffers with low propensity towards fibril formation.

Example 7—Measurement of High-Molecular-Weight-Protein (HMWP)

In order to assess the propensity of CNP compounds to form covalent dimers or oligomers when formulated the High-Molecular-Weight-Protein content of CNP compound formulations at pH 4.0 and 6.5 were determined.

Procedure: The relative amount of covalent HMWP was assessed using SEC-UPLC. SEC-UPLC was conducted using a Waters UPLC Protein BEH SEC column, 125 Å, 4.6×150 mm, 1.7 μm, with isocratic elution (0.3 M NaCl, 10 mM $NaH_2PO_4$ and 5 mM $H_3PO_4$, 50% (v/v) isopropanol, pH 2.4) with a flow rate of 0.3 mL/min, a column temperature at 50° C. with UV-detection at 215 nm. The total area of peaks eluting prior to the monomeric main peak was termed HMWP and given on a percentage scale relative to the total peptide peak area.

Results: HMWP Formation Following 2-Weeks Quiescent Incubation at 37° C.: Samples at pH 4.0 were prepared as described in Example 5 and the amount of HMWP was determined as described above. Samples were incubated for two weeks at 37° C. and the amount of HMWP was determined again. The increase in HMWP over two weeks incubation at 37° C. are reported in Table 10 (in case the incubation period deviated from two weeks the increase in HMWP was normalized to two weeks assuming a constant formation rate).

TABLE 10

2-Week HMWP formation at pH 4.0 (%)

| Compound ID | % relative to total peak area |
|---|---|
| 1351 | 1.94 |
| 1381 | 0.84 |
| 1422 | 36 |
| 1389 | 1.43 |
| 9435 | 1.07 |
| 1473 | 0.9 |
| 1470 | 1.75 |
| 1473 | 1.26 |
| 1474 | 1.6 |
| 1478 | 1.98 |
| 9483 | 3.0 |
| 1489 | 2.12 |

Samples at pH 6.5 were prepared as described in Example 5 and the amount of HMWP was determined as described above. Samples were incubated for two weeks at 37° C. and the amount of HMWP was determined again. The increase in HMWP over two weeks incubation at 37° C. are reported in Table 11 (in case the incubation period deviated from two weeks the increase in HMWP was normalized to two weeks assuming a constant formation rate).

TABLE 11

2-Week HMWP formation at pH 6.5 (%)

| Compound ID | % relative to total peak area |
|---|---|
| 1318 | 1.18 |
| 1218 | 0.43 |
| 1310 | 0.87 |
| 1304 | 1.55 |
| 1352 | 0.82 |
| 9384 | 1.5 |
| 9407 | 12 |
| 1411 | 0.62 |
| 1417 | 3.19 |
| 1382 | 0 |
| 1432 | 2.89 |
| 1434 | 3.2 |
| 1378 | 6.67 |
| 1392 | 0.33 |
| 9435 | 1.93 |
| 1402 | 2.19 |
| 1404 | 1.8 |
| 1406 | 2.77 |
| 1453 | 3.94 |
| 1457 | 3.24 |
| 1477 | 1.83 |
| 9480 | 2.65 |
| 9482 | 1.96 |

In conclusion, this experiment demonstrates that CNP compounds of the invention can be formulated in pharmaceutically relevant buffers with low propensity towards HMWP formation.

Example 8—Accelerated Chemical Stability of CNP Compounds

In order to determine the chemical stability of CNP compounds in formulation, samples of CNP compounds in buffer were exposed to accelerated chemical degradation by heating. The stability of a given peptide was assessed by measuring recovery of intact peptide by quantification by RP-UPLC. To assess the chemical degradation pattern samples were also analysed by LC-MS.

Sample preparation: Samples for the 2 week study were prepared according to the principles described in Example 5.

Samples for the 6 week study were prepared by dissolving lyophilized peptide in buffer (8 mM phosphate, 250 mM glycerol, pH 7.4) to a nominal peptide concentration of 5000 nmol/ml followed by pH adjustment with 0.1 N HCl to pH 6.5.

Incubation: For the 2 week study a time-zero (TZ) sample was pulled and stored at −18° C. and the remaining volume was incubated at 37° C. Samples were pulled and stored at −18° C. after 2 weeks of incubation. Frozen samples were thawed, diluted to about 200 nmol/mL and the extent of chemical degradation was determined using LCMS as described.

For the 6 week study a time-zero (TZ) sample was pulled and stored at −18° C. and the remaining volume was incubated at 37° C. Samples were pulled on a weekly basis and stored at −18° C. until the last sampling time point at 6 weeks. Frozen samples were thawed, diluted to about 200 nmol/mL and the extent of chemical degradation was determined using RP-UPLC and LCMS as described.

Analysis of peptide recovery by RP-UPLC: The RP-UPLC method was performed on a Waters ACQUITY H-CLASS UPLC system fitted with a PDA detector. Separation was carried out on an ACQUITY UPLC BEH C8 Column (130 Å, 1.7 μm, 2.1 mm×150 mm) operating at a column temperature of 50° C. with eluent A (19.59 mM $NH_4H_2PO_4$ 41.71 mM $(NH_4)_2HPO_4$, pH 6.5 and MeCN 9:1 v:v) and eluent B (80% MeCN in water). UV-detection was carried out at 214 nm. The analysis was performed by injection of 3 μL of sample onto the column which was eluted with a 1-step linear gradient of eluents A and B from 27 to 30% B over 20 minutes followed by a wash at 95% B over 2 minutes followed by a re-equilibration phase for 7 minutes at a constant flow rate of 0.3 mL/min. This yielded an analysis time of 30 minutes per sample. The area of the peak corresponding to intact CNP compound was given on a percentage scale relative to the total peptide peak area.

Analysis of chemical degradation patterns by LCMS: Samples were analysed on a VANQUISH UPLC from Thermo Scientific, using a Waters Acquity C18 reversed-phase column, 300 Å, 1.7 μM particles 1 mm×150 mm. The compounds were separated by a linear gradient of solvent B from 5% to 55% over 48 minutes, using solvent A: water, 0.1% formic acid with 0.02% TFA and solvent B: acetonitrile, 0.1% formic acid with 0.02% TFA. Mass spectra were acquired by a Q Exactive Plus hybrid Quadrupole-Orbitrap mass spectrometer, BioPharma option (Thermo Scientific) interfaced with H-ESI II ion source. Data acquisitions were performed with a m/z 500 to 2000 scan range and a resolution of 30000.

The data list was aggregated into a summed table of the compounds. The table headers were defined as follows:

"Recovery": The compound peak (i.e. the main peak intensity at time zero possessing the compounds monoisotopic mass) recovery's are normalized to the compound peak at a given time point; "Isomers": as the summed intensity of peaks with isobaric masses to the main compound, which segregate in the RT dimension; "Loss of 18 amu": i.e., the summed intensity of peaks with masses 18 amu lower than the CNP compound peak, which segregate in the RT dimension; Fragments: the summed intensity of peaks with a mass 50 amu lower than the compound peak and peaks with a mass 18 amu higher than the compound mass, which segregate in the RT dimension and develop over time and assumed to be derived from hydrolytic peptide backbone cleavage; and finally "Others": contains the sum intensities of peaks with a 32 amu addition or dimers of the main peak, which develop over time.

Results: The results from LCMS analysis of a 2 week accelerated degradation study on several CNP compounds of the present invention are summarised in Table 12. The results from RP-UPLC and LCMS analysis of a 6 week accelerated degradation study on CNP compound 9482 (Chem. 137) is summarised in Table 13 and Table 14 respectively.

TABLE 12

Recovery and chemical degradation pattern of CNP compounds after 2 weeks incubation at 37° C.:

| Compound | Buffer | Recovery | | Isomers | | Loss of 18 amu | | Fragments | | Others | |
|---|---|---|---|---|---|---|---|---|---|---|---|
| | | TZ | 2 W | TZ | 2 W | TZ | 2 W | TZ | 2 W | TZ | 2 W |
| 9407 | 8 mM sodium phosphate, 250 mM glycerol pH 6.5 | 100 | 98.5 | 0 | 1.1 | 0 | 0 | 0 | 0.7 | 0.1 | 0.3 |
| 9435 | 5 mM sodium acetate, 250 mM glycerol, pH 4 | 100 | 92.9 | 0 | 0.6 | 0 | 4.1 | 0 | 0 | 0.0 | 0.0 |
| 9480 | 8 mM sodium phosphate, 250 mM glycerol, pH 6.5 | 100 | 100.5 | 0 | 0 | 0 | 0 | 0 | 0 | 0.0 | 0.6 |

TABLE 12-continued

Recovery and chemical degradation pattern of CNP compounds after 2 weeks incubation at 37° C.:

| Compound | Buffer | Recovery | | Isomers | | Loss of 18 amu | | Fragments | | Others | |
|---|---|---|---|---|---|---|---|---|---|---|---|
| | | TZ | 2 W | TZ | 2 W | TZ | 2 W | TZ | 2 W | TZ | 2 W |
| 9482 | 8 mM sodium phosphate. 250 mM glycerol, pH 6.5 | 100 | 99.6 | 0 | 0 | 0 | 0 | 0 | 0 | 0.0 | 0.3 |
| 9483 | 5 mM sodium acetate, 250 mM glycerol, pH 4 | 100 | 96.2 | 0 | 0 | 0 | 0 | 0 | 0 | 0.2 | 0.6 |

TABLE 13

RP-UPLC analysis of peptide recovery of CNP compound [9482] over 6 weeks:

| | % relative to total peak area | | | | | | |
|---|---|---|---|---|---|---|---|
| Compound | TZ | 1 Week | 2 Week | 3 Week | 4 Week | 5 Week | 6 Week |
| 9482 (Chem. 137) | 90.6 | 89.1 | 89.1 | 86.9 | 85.5 | 83.5 | 81.8 |

TABLE 14

LCMS analysis of recovery and chemical degradation pattern of CNP compound 9482 (Chem. 137) over 6 weeks:

| Compound no. | Time | | | | | | |
|---|---|---|---|---|---|---|---|
| 9482 | TZ | 1 W | 2 W | 3 W | 4 W | 5 W | 6 W |
| Recovery | 100.00 | 100.10 | 99.50 | 98.90 | 95.10 | 94.70 | 92.30 |
| Isomers | 0.00 | 0.00 | 0.60 | 1.20 | 1.70 | 2.40 | 3.90 |
| Loss of 18 amu | 0.00 | 0.00 | 0.10 | 0.10 | 0.20 | 0.20 | 0.30 |
| Fragments | 0.00 | 0.20 | 0.30 | 0.50 | 0.90 | 0.80 | 1.20 |
| Others | 0.20 | 0.30 | 0.30 | 0.30 | 0.50 | 0.40 | 0.50 |

These data show that a CNP compound according to the present invention display substantial chemical stability in formulation.

Example 9—Local Tolerance of CNP Compounds in Rats

The purpose of this study was to evaluate the local tissue reaction to subcutaneous injection of CNP compounds in rats.

Procedure: The CNP compounds were formulated according to the principles described in General Methods of Preparation—Method G. Each Sprague Dawley rat (male, 10-11 weeks of age at arrival, Janvier, France) was dosed s.c. with 250 or 350 uL of the same compound (formulation concentration of 1000 nmol/mL) 120 h prior to tissue collection resulting in a total of two injections for each animal (Table 15). Injection site (flank or neck) was alternated across animals within each group and time point.

TABLE 15

Experimental timeline for local tolerance study in rats

| Time point | Study activity |
|---|---|
| Day 0 | Shaving (e.g. neck) followed by $1^{st}$ dose into shaved area |
| Day 3 | Shaving (e.g. flank) |
| Day 4 | $2^{nd}$ dose into shaved area (e.g. flank) |
| Day 5 | Observation of skin, tissue collection and termination |

Animals had access to tap water and food (Altromin 1324) ad libitum. Group size was n=3 for vehicles and positive control, and n=4 for test compounds. Vehicles and compounds were formulated in either 5 mM sodium acetate, 250 mM glycerol, pH 4.0 or 8 mM sodium phosphate, 250 mM glycerol, pH 7.4 as shown in Table 16.

The animals were anesthetized with isoflurane. Via an electric shaving machine, a squared area of fur (2 cm×2 cm) was removed either from the rats' neck or flank area). For dosing, a new injection needle (25G canula, 1 ml syringe) was placed in the middle of the square border closest to the animal's head and the needle was inserted into the skin from the border towards the center of the square. Hence, the needle tip was located in the center of the square, the location was marked with a permanent pen and the formulation was inserted in the center of the square. On the day of tissue collection, the rats were deeply anaesthetized with isoflurane and euthanized by exsanguination. The injection sites were inspected and scored with regards to pathological lesions. The injection sites were evaluated, and any changes were noted (location, colour, shape and size), and sampled for histology preparation.

The injection sites were removed and fixed in 4% phosphate buffered neutral formaldehyde in sealed plastic containers.

Each injection site was subsequently cut into three sections 0.8 cm, 1.0 cm and 1.2 cm from the square border where the injection needle was placed, and, respectively, these sections represented the injection sites and the adjacent tissue. The tissue was processed, embedded in paraffin and cut in 2-4 µm thin sections, stained with the haematoxylin and eosin (H&E), and evaluated microscopically with a light microscope. Histopathological changes were graded on a 5-level scale (Minimal (Min), Mild (Mil), Moderate (Mod), Marked (Mar) and Severe (Sev)). The studies are summarised in Table 16.

TABLE 16

Overview of compound, timepoint for sampling, and formulations

| Compound ID | Dosing volume | Timepoint for sampling (days post injection) | Formulations |
|---|---|---|---|
| 1351 | 350 µl | 5 | pH = 4.01; 947 nmol/ml compound 1351; 8 mM phosphate; 250 mM glycerol |
| 9384 | 350 µl | 5 | pH = 7.39; 1032 nmol/ml 9384; 8 mM phosphate; 250 mM glycerol |
| 9407 | 350 µl | 5 | pH = 7.40; 1046 nmol/ml 9407; 8 mM phosphate; 250 mM glycerol |
| 1420 | 350 µl | 5 | pH = 3.98; 1021 nmol/ml compound 1420; 5 mM acetate; 250 mM glycerol |
| Inactive control: 1265 | 350 µL | 5 | pH = 4; 1042 nmol/ml 1265; 5 mM acetate; 250 mM glycerol |
| Positive net charge control: 0776 | 250 µl | 5 | pH = 4.02; 4417 nmol/ml 0776; 5 mM acetate; 240 mM propylene glycol |
| 0776 | 350 µl | 5 | pH = 4.02; 1019 nmol/ml compound 0776; 5 mM acetate; 250 mM glycerol |

Results: The results from the local tolerance study are summarised in Table 17.

TABLE 17

Severity and incidence of local subcutaneous reactions* 4 or 5 days after injection of different compounds in rats.

| Compound ID Severity grade | Number of injection sites evaluated | Number of injections by severity of necrosis | | | | | |
|---|---|---|---|---|---|---|---|
| | | NAD** | Min. | Mil. | Mod. | Mar. | Sev. |
| 1351 | 4 | 4 | | | | | |
| 9384 | 4 | 4 | | | | | |
| 9407 | 4 | 4 | | | | | |
| 1420 | 4 | 3 | | 1 | | | |
| 1265 | 2 | | | | | 2 | |
| Positive net charge control: 0776 | 3 | | | | | 3 | |
| | 3 | | | | 1 | 2 | |

*Necrosis was used as a marker for local subcutaneous reactions;
**NAD = No Abnormalities Detected Conclusions: The positive net charge control 0776 showed moderate to marked local subcutaneous necrosis 5 days after subcutaneous injections in the rat. In comparison the compounds 1351, 9384, 9407 and 1420 showed no or mild local subcutaneous necrosis 5 days after subcutaneous injections in the rat and were all assessed as acceptable for human subcutaneous administration.

Example 10—CNP Local Tolerance Study in LYD Pips

The purpose of this study was to evaluate the local tissue reaction response to subcutaneous injection of CNP compounds in pigs.

Procedure: In domestic pigs, the injection site was subjected to histopathologic examination after subcutaneous dosing. Injections were placed mid-back between the shoulder and hip on both sides of the dorsal midline, and one or two days before injection sites of 2×2 cm were shaved and marked by permanent ink under light anaesthesia.

Each injection consisted of 100 or 200 µl formulation with a concentration of approx. 4400 µM. CNP compound formulations were prepared according to the principles in General Methods of Preparation—Method G, and were either A) 8 mM sodium phosphate, 250 mM glycerol, pH 6.5, B) 5 mM sodium acetate, 250 mM glycerol, pH 4.0 or C) 5 mM sodium acetate, 240 mM propylene glycol, pH 4.0 and physiological saline was included as negative control.

On Day 1 the pigs were lightly anaesthetised. An insulin pen (NovoPen 4) and insulin needle (NovoTwist 32G/5 mm) were used for accurate deposition of the CNP formulations in the subcutaneous fat tissue with the needle perpendicular to the skin. On Day 5 (4 days post injection) or 6 (5 days post injection), the pigs were euthanised, and the injection sites were removed and fixed in 4% phosphate buffered neutral formaldehyde in sealed plastic containers. The tissue blocks were prefixed for 2-4 hours in 10% buffered formalin, cut into 2 mm thick slabs with a multi knife, examined for macroscopic changes and finally fixed overnight in cassettes. Two slabs of tissue were selected for light microscopic evaluation where the tissue reaction was maximal or alternatively in the central part of the injection site. Three to four 2-4 µm sections were cut from three levels at 100 µm distance, stained with haematoxylin and eosin (H&E) and evaluated in a light microscope. Histopathological changes were graded on a 5-level scale ((Minimal (Min), Mild (Mil), Moderate (Mod), Marked (Mar) and Severe (Sev)). The studies are summarised in Table 18.

TABLE 18

Overview of compound, timepoint for sampling and formulations:

| Compound ID | Timepoint for sampling (days post injection) | Formulations |
|---|---|---|
| 9384 | 5 | pH = 6.57; 3988 µM compound 9384; 8 mM phosphate; 250 mM glycerol (A) |
| 9407 | 5 | pH = 6.50; 4343 µM compound 9407; 8 mM phosphate; 250 mM glycerol (A) |
| 9435 | 5 | pH = 4.00; 4362 µM compound 9435; 5 mM acetate; 250 mM glycerol (B) |
| 9480 | 4 | pH = 6.46; 4362 µM compound 9480; 8 mM phosphate; 250 mM glycerol (A) |
| 9482 | 4 | pH = 6.49; 4383 µM compound 9482; 8 mM phosphate; 250 mM glycerol (A) |
| 9483 | 4 | pH = 3.96; 4385 µM compound 9483; 5 mM acetate; 250 mM glycerol (B) |
| 0106 | 5 | pH = 5.5; 4321 µM compound 0106; 1.33 mM citric acid monohydrate; 3.67 mM citrate, trisodium; 52 mg/ml trehalose; 15 mg/ml D-mannose; 0.73 mg/ml L-methionine; 0.05 mg/ml polysorbate 80 |

TABLE 18-continued

Overview of compound, timepoint for sampling and formulations:

| Compound ID | Timepoint for sampling (days post injection) | Formulations |
|---|---|---|
| Positive net charge control: 0776 | 5 | pH = 4.02; 4157 µM compound 0776; 5 mM acetate; 240 mM propylene glycol (C) |
| Positive net charge control: 1235 | 5 | pH = 4.05; 4528 µM compound 1235; 5 mM acetate; 250 mM glycerol (B) |

Results: The results are summarised in Table 19. * Necrosis was used as a marker for local subcutaneous reactions; **NAD: No Abnormalities Detected

TABLE 19

Severity and incidence of local subcutaneous reactions 4 or 5 days after injection of different compounds in pigs:

| Compound ID Severity grade | Number of injection sites evaluated | Number of injections by severity of necrosis | | | | |
|---|---|---|---|---|---|---|
| | | NAD* | Min. | Mild | Mod. | Mar. | Sev. |
| 9384 | 4 | 3 | 1 | | | | |
| 9407 | 4 | 3 | 1 | | | | |
| 9435 | 4 | | 3 | 1 | | | |
| 9480 | 4 | 4 | | | | | |
| 9482 | 4 | 4 | | | | | |
| 9483 | 4 | 2 | | 1 | 1 | | |
| 0106 | 4 | 4 | | | | | |
| Positive net charge control: 0776 | 4 | | | | | 1 | 3 |
| Weakly positive net charge control: 1235 | 4 | | | 2 | 2 | | |

In conclusion the positive net charge control compound 0776 showed moderate to marked local subcutaneous necrosis 5 days after subcutaneous injections in the pig, whereas the net positively charged CNP peptide 0106 without a fatty acid albumin binder attached shows no observable injection site reactions.

In comparison the compounds 9480 and 9482 showed no local subcutaneous necrosis 5 days after subcutaneous injections in the pig; compounds 9384 and compounds 9407 showed no to minimal local subcutaneous necrosis 5 days after subcutaneous injections in the pig; compounds 9435 and 1235 showed minimal to mild local subcutaneous necrosis 5 days after subcutaneous injections in the pig and compound 9483 showed no to moderate local subcutaneous necrosis 5 days after subcutaneous injections in the pig. The compounds 9384, 9407, 9435, 9480 and 9482 were all assessed as acceptable for human subcutaneous administration.

Example 11—PK/PD of CNP Compounds after i.v. And s.c. Administration to Rats In order to assess the i.v. and s.c. PK/PD profile of CNP compounds of the present invention, formulations of CNP compounds were administered to rats, blood samples taken and exposure and cGMP response measured.

cGMP biomarker assay: The biological activity of CNP compounds in vivo was assessed by measuring cGMP in plasma samples by plasma protein precipitation followed by quantification with LC-MS/MS.

To evaluate the cyclic guanosine monophosphate (cGMP) biomarker response in biological samples, after administration of CNP compounds to study animals, a plasma protein precipitation procedure was applied, followed by liquid chromatography with tandem mass spectrometric (LC-MS/MS) analysis. In principle, the concentration of cGMP in study plasma samples, was determined using a standard curve prepared with a stable isotope labelled (SIL) surrogate analyte ($^{13}C_{10}$ $^{15}N_5$ cGMP) as a reference. The surrogate analyte was spiked in pooled authentic blank matrix to cover an analytical range of 5 nM-2000 nM. 8-Methoxymethyl-3-isobutyl 1-methylxanthine (MMPX) was used as an internal standard. The plasma protein precipitation procedure was conducted using an organic solvent to precipitate the plasma protein, leaving a supernatant that contained the cGMP molecules which would then be analysed on the LC-MS/MS instrument.

To prepare the standard samples, frozen authentic blank plasma matrix was thawed and subsequently centrifuged for 5 min at 4000 RPM, at 4° C. A stock solution of SIL-cGMP was used to prepare a standard of 2000 nM in blank plasma, which is then transferred to a 1 mL Eppendorf 96-well plate (U.S. Pat. No. 8,636,965). This was placed in a liquid handler (TECAN Fluent 78) to prepare standards and QCs (5, 10, 20, 50, 100, 200, 500, 1000, 2000 nM) by serial dilution in blank plasma in a 96-well microplate (Chimney Well 651201). Blank plasma samples were prepared in the same plate. Study samples were thawed by ventilation for 10 min at ambient temperature, shaken on a table shaker for 5 min at ambient temperature, and subsequently centrifuged for 5 min at 4000 RPM at 4° C. The samples were then placed in the liquid handler to perform the plasma protein precipitation procedure. A volume of Standards, QCs, Zero, and study samples were precipitated with 4 volumes of acetonitrile (OPTIMA® LC/MS Grade) containing 30 nM of MMPX (Sigma #M2547). The samples were then shaken on a table shaker for 4 min at ambient temperature, and subsequently, centrifuged for 30 min, at 4000 RPM at 4° C., whereafter the supernatant was transferred to a new 96-well microplate. The plates were subsequently evaporated using an Eppendorf Concentrator Plus™ for 60 min at 30° C. Residues were reconstituted in a volume of 5% acetonitrile and 0.1% formic acid (RATHBURN LC/MS Grade), shaken on a table shaker for 2 min at ambient temperature and centrifuged for 10 min at 4° C. The prepared samples were then analysed on a LC-MS/MS instrument (Sciex ExionLC™ coupled to a Sciex 6500+ Triple quadrupole). Gradient elution was applied on the reverse-phase LC, using 0.1% formic acid as mobile phase A and 95% acetonitrile and 0.1% formic acid as mobile phase B. A Waters Acquity UPLC® CSH™ Fluoro-Phenyl 1.7 µm, 2.1×100 mm column, was used as a stationary phase and thermoregulated at 60° C. SIL-cGMP, endogenous cGMP, and MMPX were detected in the MS/MS in positive ion mode by selective reaction monitoring.

Acceptance criteria for the analytical run: The SIL-cGMP standard curve was established with a 1/x2 weighting and was evaluated in terms of linearity, precision, and accuracy. At least 75% of the calibration standards had to meet the following criteria when back calculated: Calibration standards had to fall within ±15% of the nominal concentration of the respective calibration standards, except for LLOQ that had to fall within ±20% of the nominal concentration of the LLOQ standards. Values falling outside these limits must be discarded provided they did not change the established model. If discarding one calibration standard resulted in another calibration standard being outside the boundaries, then this calibration standard was also discarded.

At least two-thirds of the QC samples had to be within 15% of their respective nominal values. One-third of the QC samples could be outside 15% of their respective nominal value, but never more than 50% of the QC samples at the same nominal concentration.

Quantitative plasma analysis of CNP-compounds: Plasma concentrations of CNP compounds were assayed by plasma protein precipitation and analysed by turboflow liquid chromatography mass spectrometry (TF-LC-MS). Calibrators were prepared by spiking either blank rat or minipig plasma with the relevant CNP compound in the range from 0.5 to 2000 nM. Calibrators, plasma blanks or study samples were prepared for TF-LC-MS by protein precipitation by adding three or four volumes of either ethanol or methanol containing 20 nM of internal standard to one volume of sample. For some compounds, formic acid was added to the precipitation reagent (the final concentration was 1% v/v). After the addition of the precipitation reagent, the mixture was centrifuged at 6200 rpm at 4° C. for 30 minutes. After centrifugation, one volume of supernatant was mixed with two volumes of water (with 1% v/v formic acid). The mixture was analysed by TF-LC-MS using a Cyclone turboflow column (0.5×50 mm, ThermoFisher Scientific) and either a XBridge Protein BEH C4 3.5 μm 300 Å or a XBridge Protein BEH C18 3.5 μm 130 Å analytical column (both were 50×2.1 mm and obtained from Waters). A gradient elution was conducted using mobile phase A (consisting of milli-Q water with 1% formic acid and 5% methanol/acetonitrile (50/50)) and mobile phase B (consisting of methanol/acetonitrile (50/50) with 1% formic acid and 5% milli-Q water). The mass spectrometer was operated in positive ionisation mode. A TSQ Altis mass spectrometer (ThermoFisher Scientific) was used as detector in selected reaction monitoring mode (specific transition were optimised for each CNP compound). Linear calibration curves (weighed 1/x2) were used for calculating the concentration in the plasma samples. Quality control samples were included. The deviation between nominal and calculated concentration in the calibrators and quality control samples were below 15%.

Animals and dosing: Groups of 4-6 rats (male, Sprague Dawley, 350 g at arrival, Janvier, France) per compound and route of administration were dosed with a CNP compound formulated either in A) 8 mM sodium phosphate, 250 mM glycerol, 0.007% polysorbate 20, pH 7.4 or B) 5 mM sodium acetate, 250 mM glycerol, 0.007% polysorbate 20, pH 4.0 depending on the respective compound. S.c. dose was 300 nmol/kg, at a concentration of 1000 nmol/L resulting in a dosing volume of 0.3 mL/kg, whereas i.v. dose was 100 nmol/kg, at a concentration of 100 nmol/L resulting in a dosing volume of 1 mL/kg.

Sampling: Sublingual blood samples of 250 uL were collected from unanaesthetised rats in EDTA-coated vials (Microvette 600K3E ref #15.1673.100 Sarstedt) at baseline (−1 h before dosing) as well as 5 min (only i.v. dosed groups), 2 h, 6 h, 24 h, 48 h and 72 h (only for exposure analysis) post-dosing. The blood samples were quickly stored on ice and centrifuged (4° C., 8000 RPM, 5 min) within 10 min of collection. Plasma samples of 50 μL were transferred to each micronic tube for either exposure or cGMP analysis, kept on dry ice and stored in a freezer (−20° C.). Rats had access to food (Altromin) and tap water ad libitum.

Analysis: PK parameters were calculated by non-compartment analysis (NCA) using software Phoenix WinNonlin (ver. 8.1 or later, Certara) for each animal. Clearance (Cl) was calculated as: Dose/AUCinf (linear up, log down). Half-life (t½) was calculated as ln(2)/λ were λ is estimated by linear regression of time vs. log concentration, typically in a time range between 2 to 48 hours (e.g. from 6 to 48 hours). Bioavailability was calculated as dose normalized AUC's: (AUC(sc)/Dose(sc))/(AUC(iv)/Dose(iv)). Values in the table are means from individual animals (n=4-6 individual animals). The subsequent plots for cGMP plasma concentration versus time are (Y-axis) mean cGMP concentration (n=4-6 individual animals) after IV dosing and (X-axis) nominal plasma sampling time.

Figure 2:
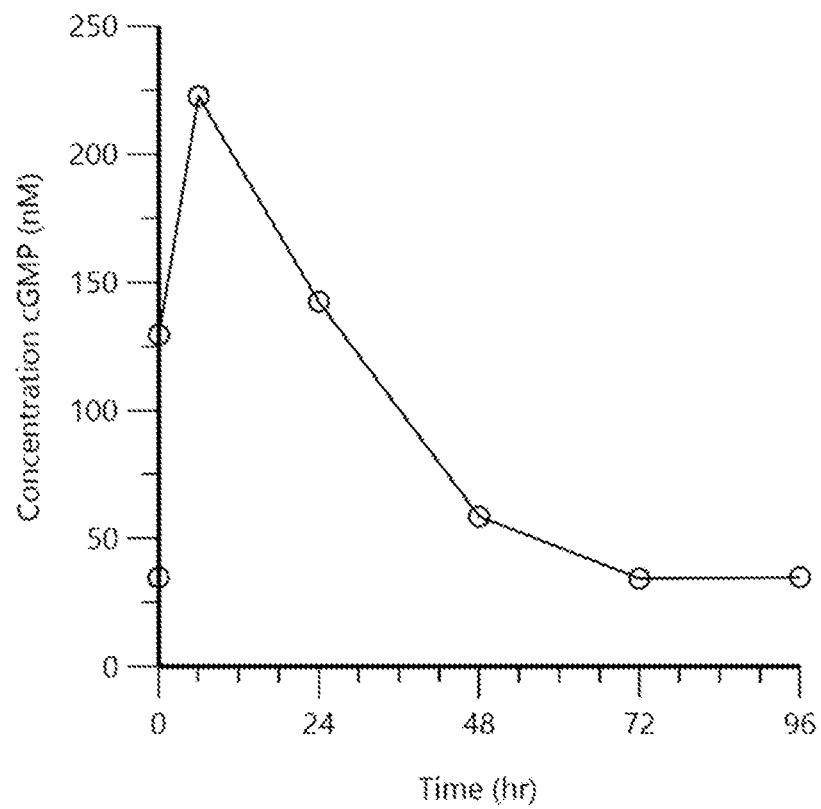
FIG. 2 shows the pharmacodynamic response (cGMP) after i.v. administration of Compound ID 0312 to rats as described in example 11.
Figure 3:
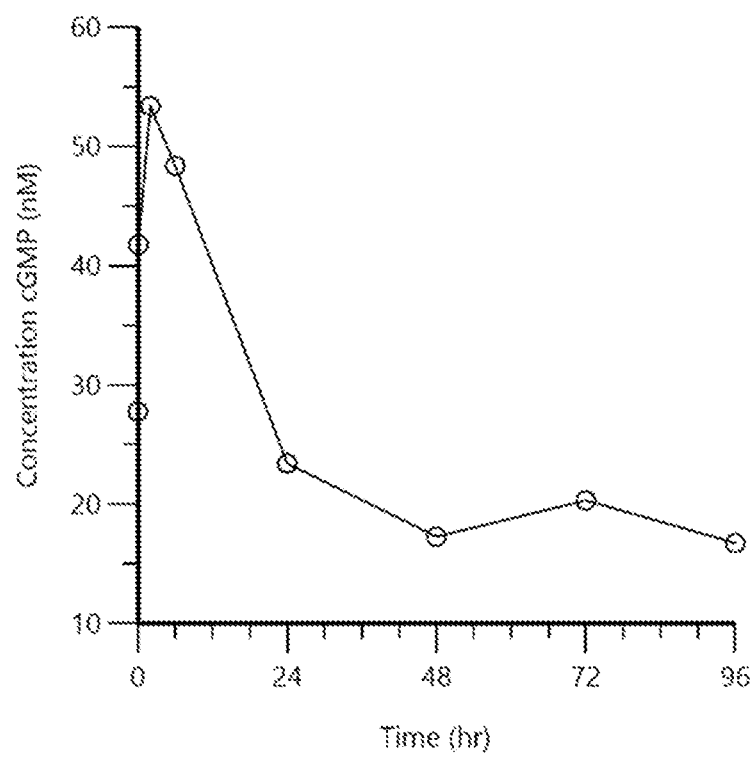
FIG. 3 shows the pharmacodynamic response (cGMP) after i.v. administration of Compound ID 1225 to rats as described in example 11.
Figure 4:
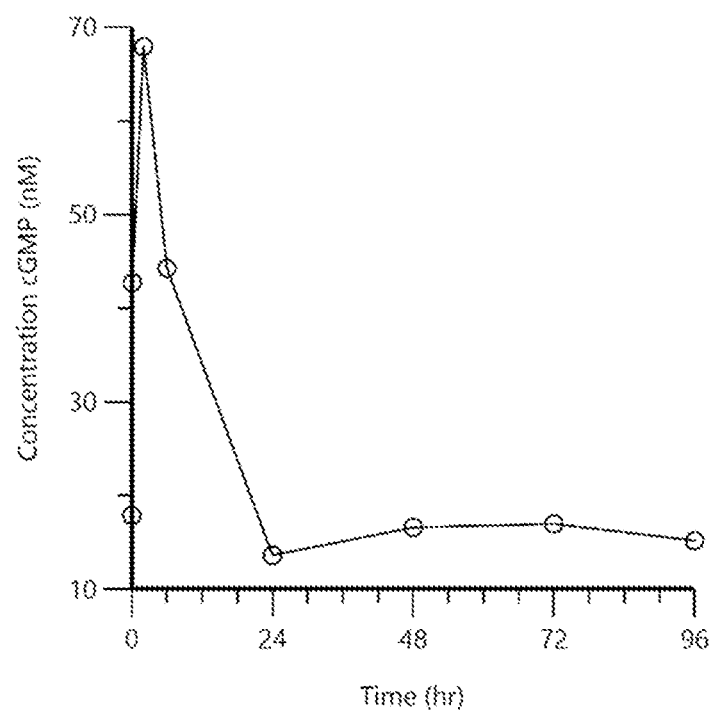
FIG. 4 shows the pharmacodynamic response (cGMP) after i.v. administration of Compound ID 1233 to rats as described in example 11.
Figure 5:
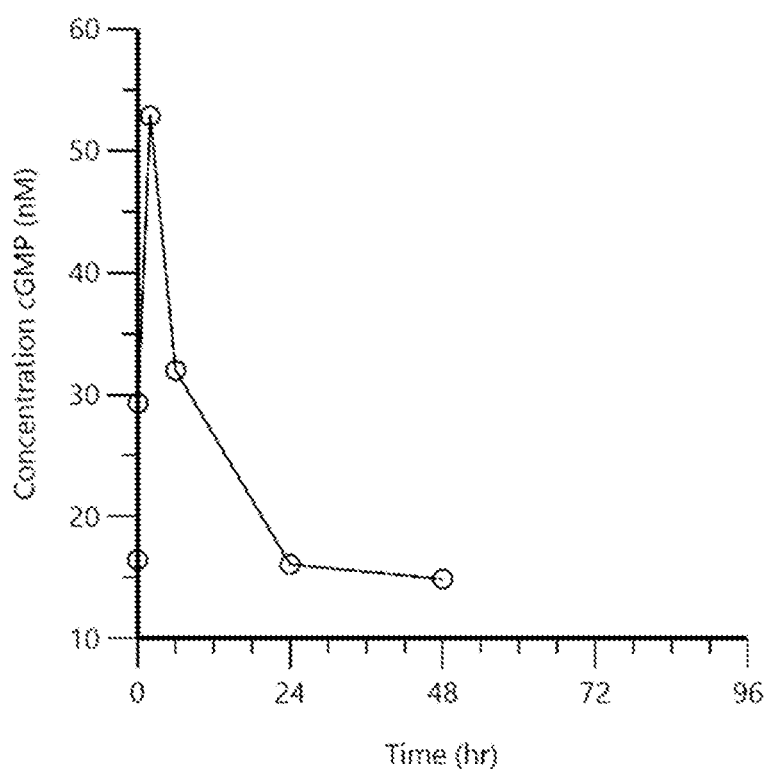
FIG. 5 shows the pharmacodynamic response (cGMP) after i.v. administration of Compound ID 1227 to rats as described in example 11.
Figure 6:
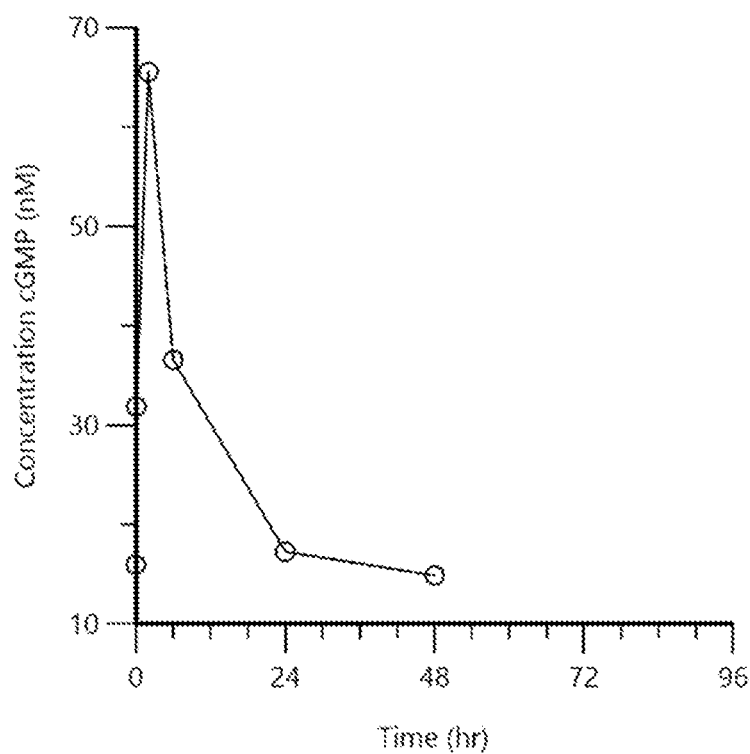
FIG. 6 shows the pharmacodynamic response (cGMP) after i.v. administration of Compound ID 1241 to rats as described in example 11.
Figure 7:
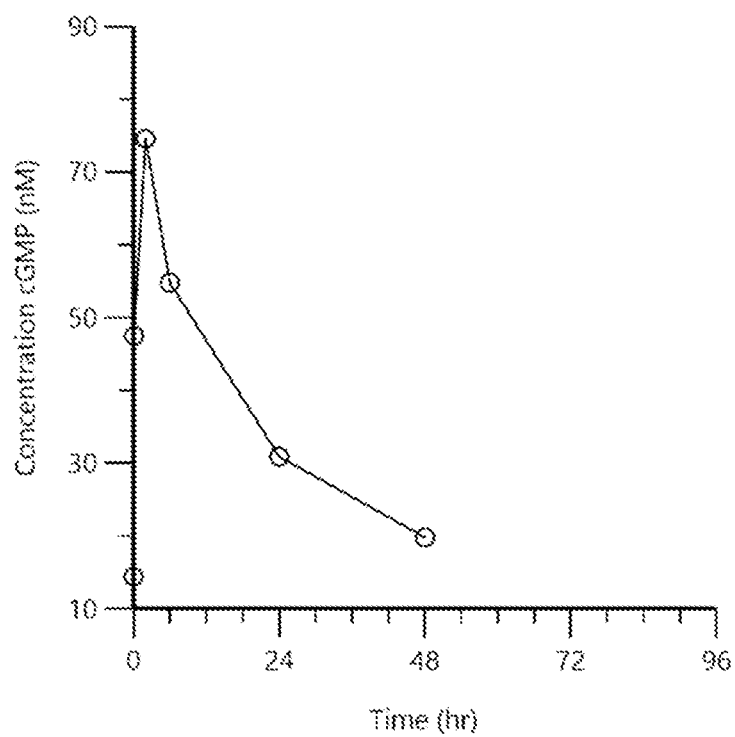
FIG. 7 shows the pharmacodynamic response (cGMP) after i.v. administration of Compound ID 1351 to rats as described in example 11.
Figure 8:
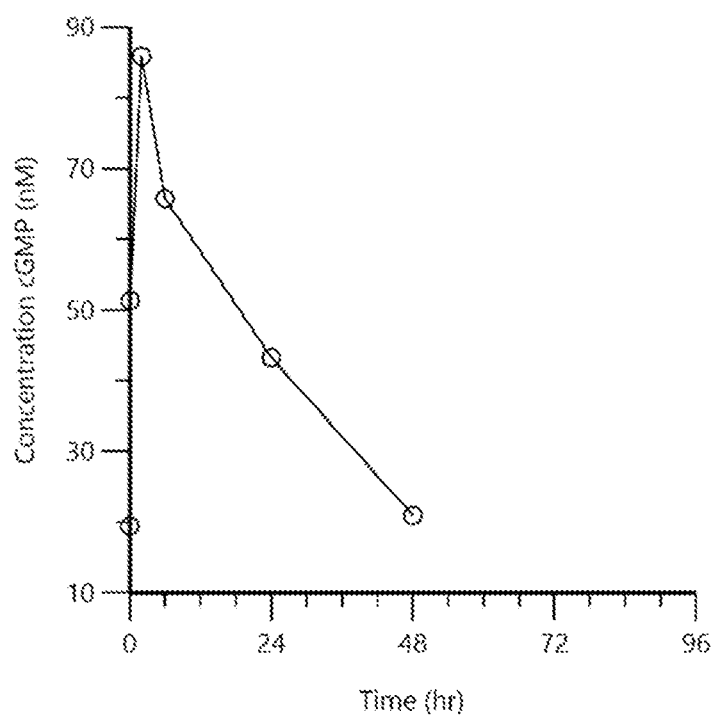
FIG. 8 shows the pharmacodynamic response (cGMP) after i.v. administration of Compound ID 1354 to rats as described in example 11.
Figure 9:
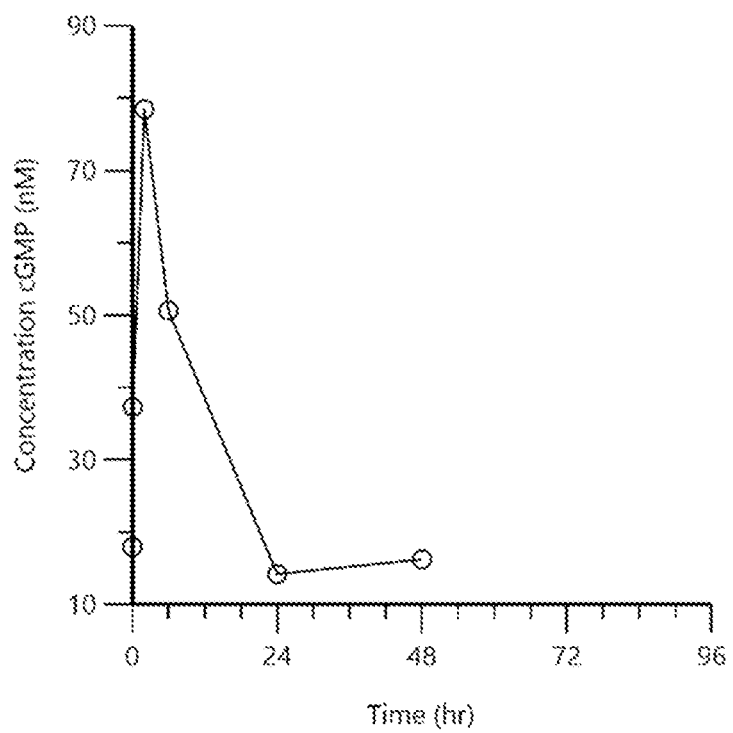
FIG. 9 shows the pharmacodynamic response (cGMP) after i.v. administration of Compound ID 1356 to rats as described in example 11.
Figure 10:
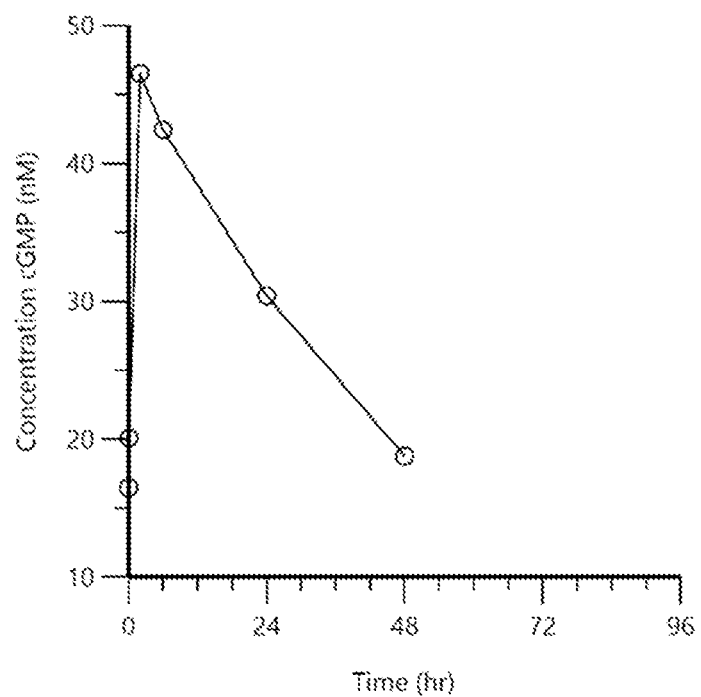
FIG. 10 shows the pharmacodynamic response (cGMP) after i.v. administration of Compound ID 1375 to rats as described in example 11.
Figure 11:
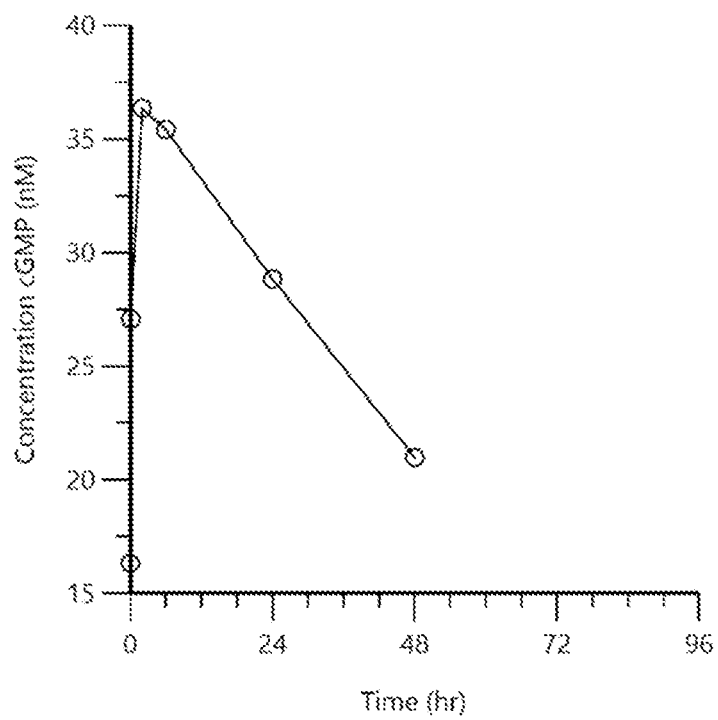
FIG. 11 shows the pharmacodynamic response (cGMP) after i.v. administration of Compound ID 1376 to rats as described in example 11.
Figure 12:
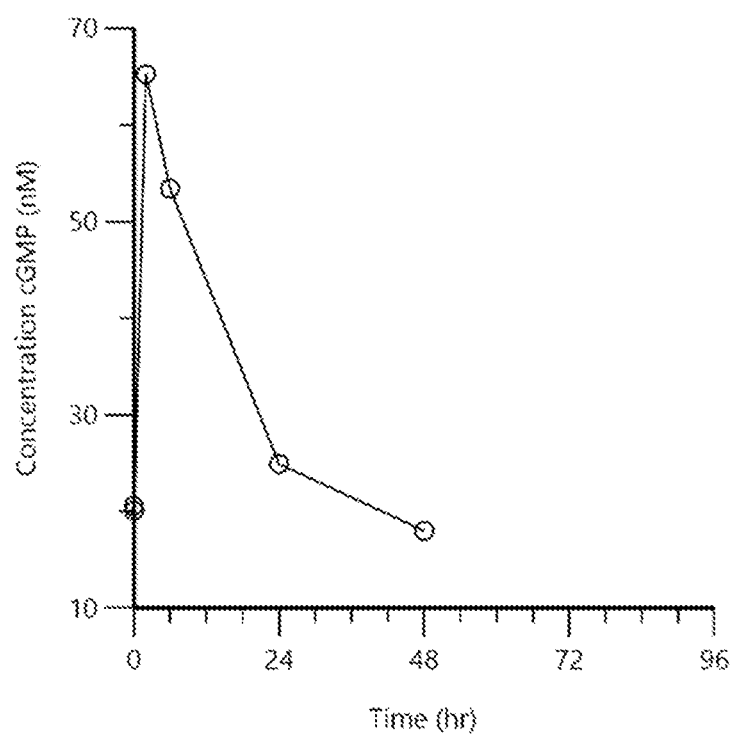
FIG. 12 shows the pharmacodynamic response (cGMP) after i.v. administration of Compound ID 1377 to rats as described in example 11.
Figure 13:
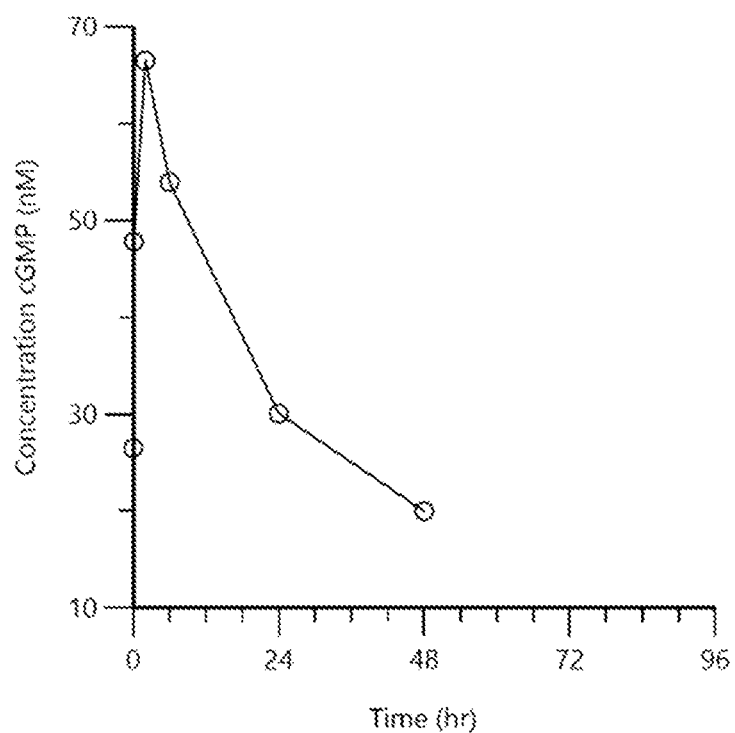
FIG. 13 shows the pharmacodynamic response (cGMP) after i.v. administration of Compound ID 1352 to rats as described in example 11.
Figure 14:
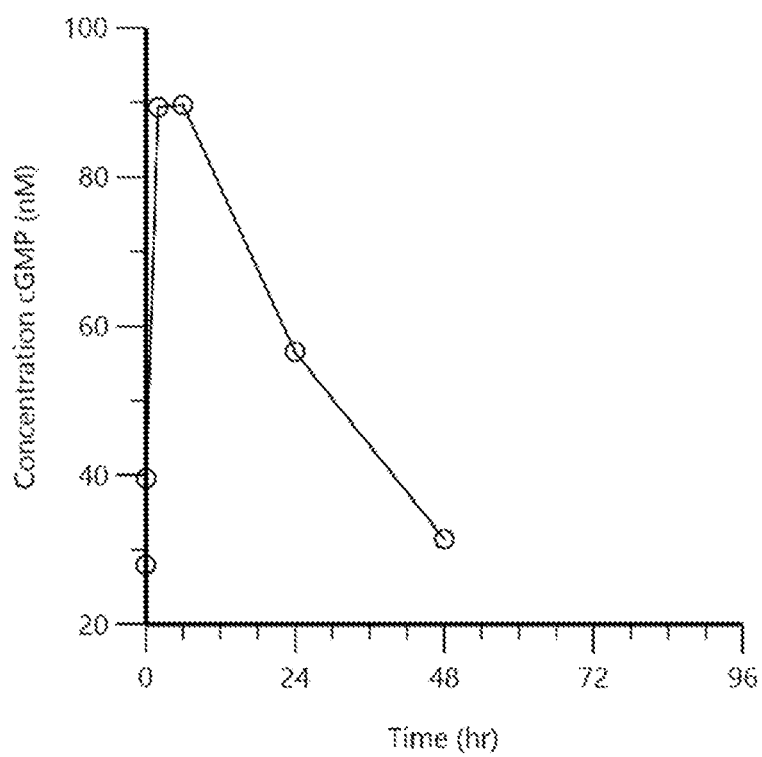
FIG. 14 shows the pharmacodynamic response (cGMP) after i.v. administration of Compound ID 1379 to rats as described in example 11.
Figure 15:
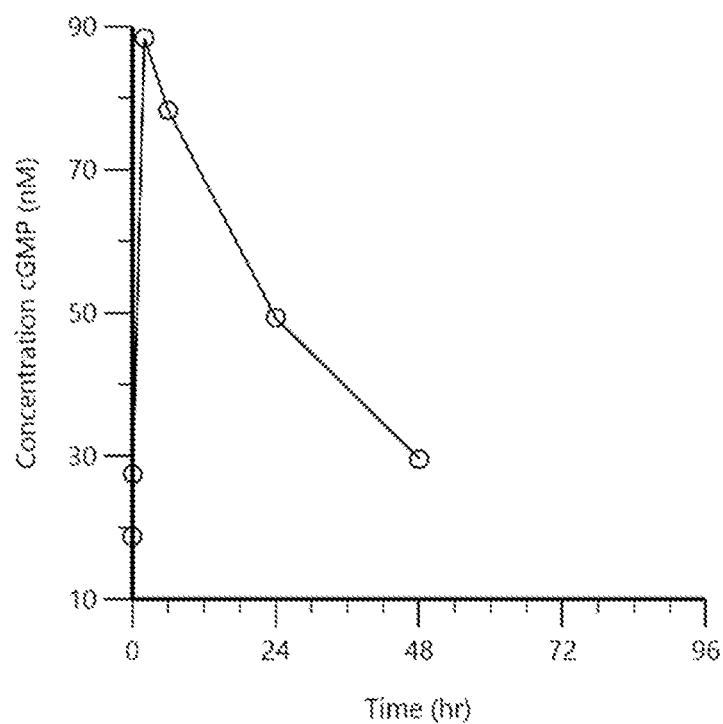
FIG. 15 shows the pharmacodynamic response (cGMP) after i.v. administration of Compound ID 1434 to rats as described in example 11.
Figure 16:
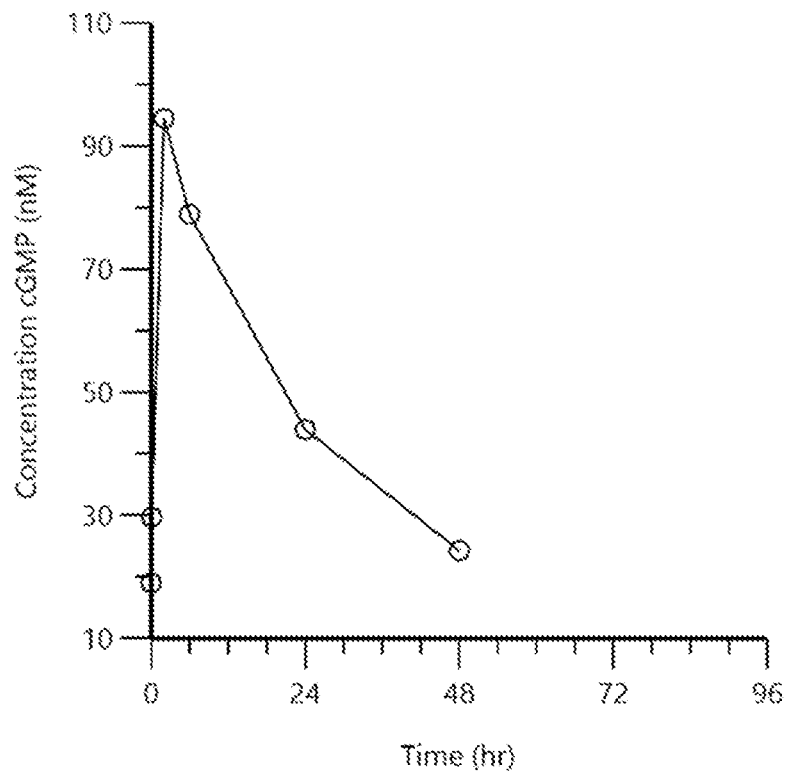
FIG. 16 shows the pharmacodynamic response (cGMP) after i.v. administration of Compound ID 9384 to rats as described in example 11.
Figure 17:
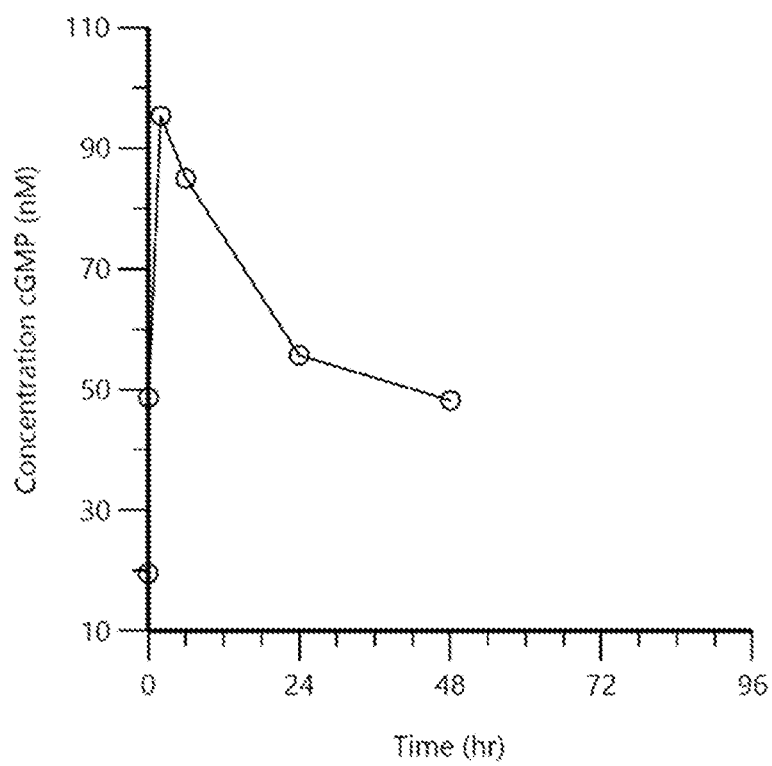
FIG. 17 shows the pharmacodynamic response (cGMP) after i.v. administration of Compound ID 9407 to rats as described in example 11.
Figure 18:
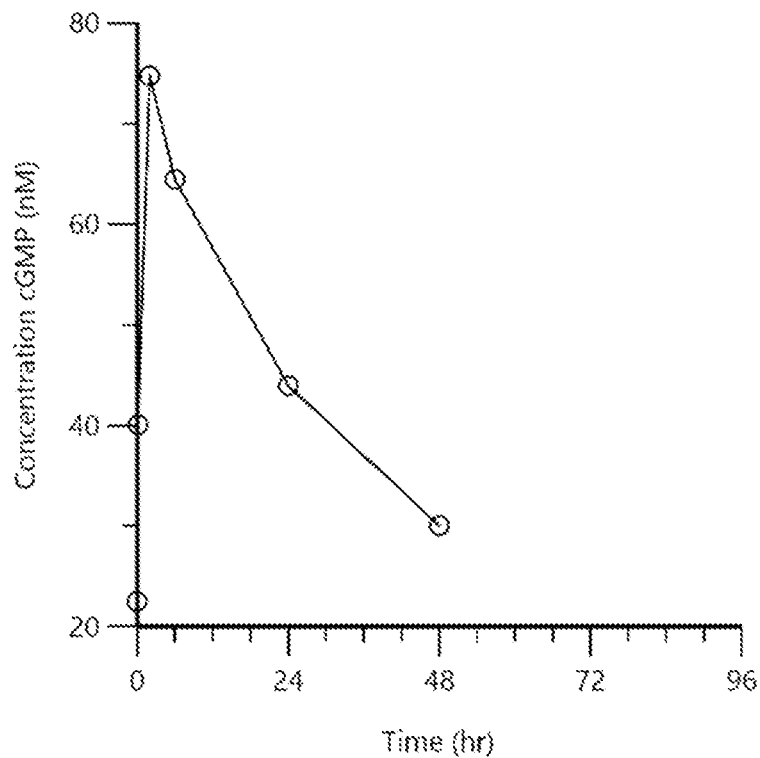
FIG. 18 shows the pharmacodynamic response (cGMP) after i.v. administration of Compound ID 1420 to rats as described in example 11.
Figure 19:
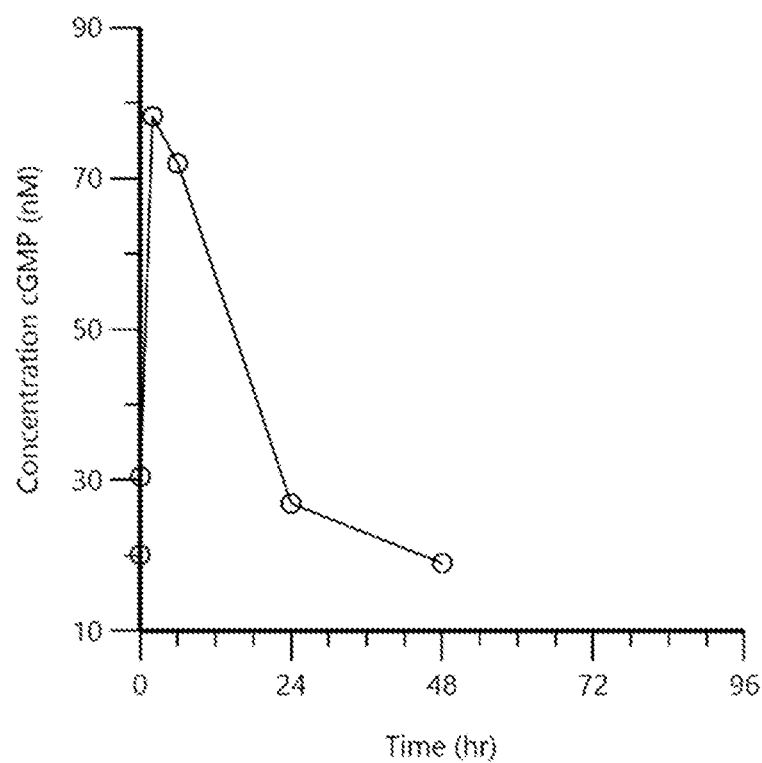
FIG. 19 shows the pharmacodynamic response (cGMP) after i.v. administration of Compound ID 1378 to rats as described in example 11.
Figure 20:
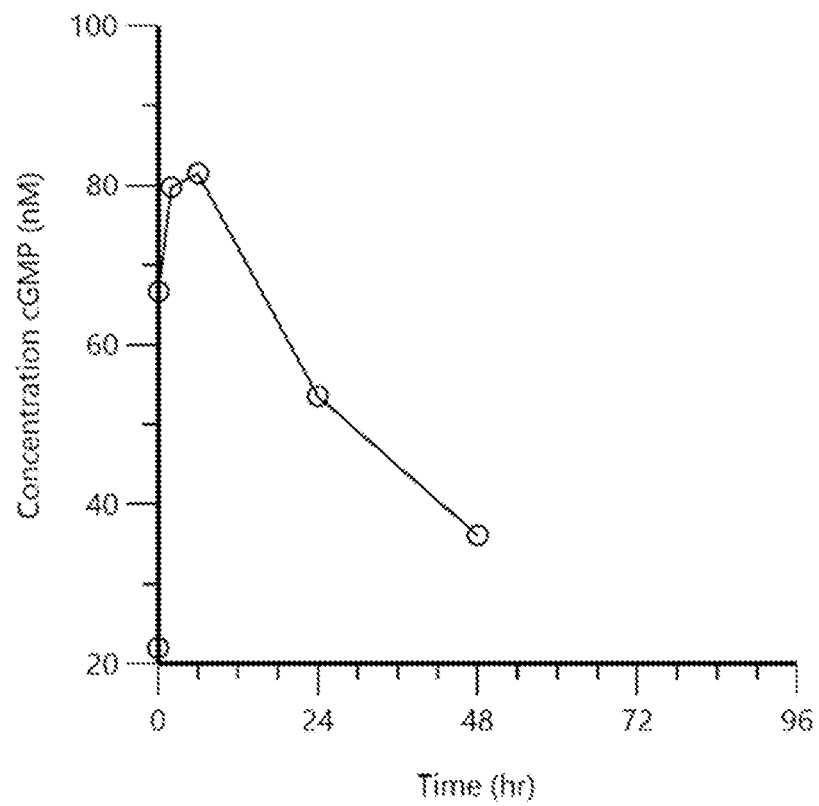
FIG. 20 shows the pharmacodynamic response (cGMP) after i.v. administration of Compound ID 1381 to rats as described in example 11.
Figure 21:
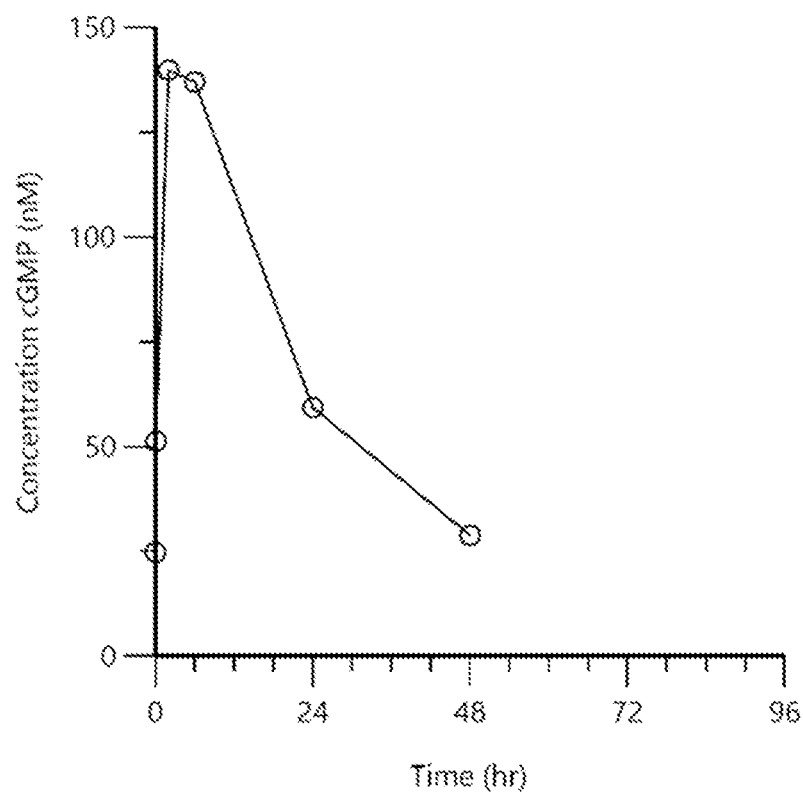
FIG. 21 shows the pharmacodynamic response (cGMP) after i.v. administration of Compound ID 1386 to rats as described in example 11.
Figure 22:
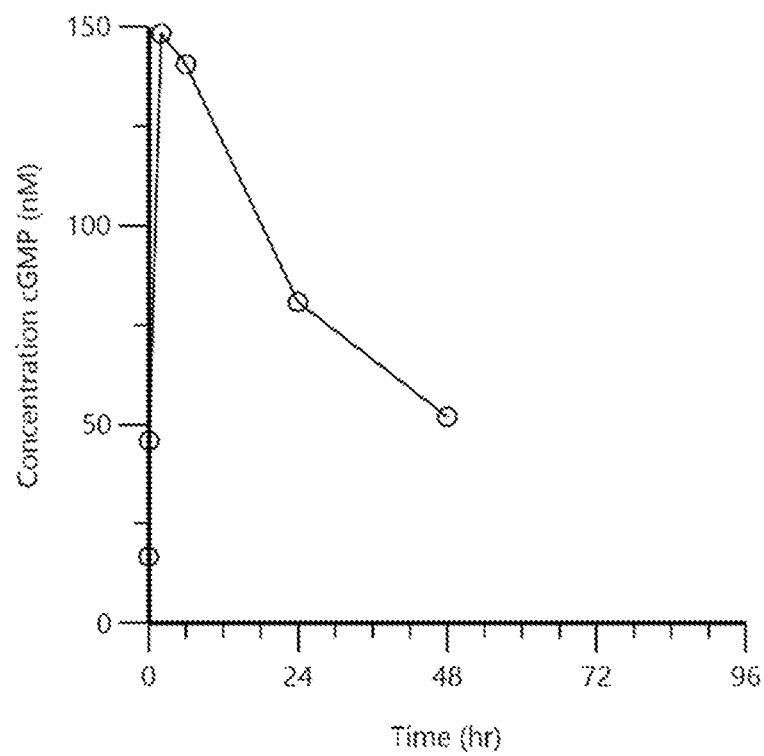
FIG. 22 shows the pharmacodynamic response (cGMP) after i.v. administration of Compound ID 1389 to rats as described in example 11.
Figure 23:
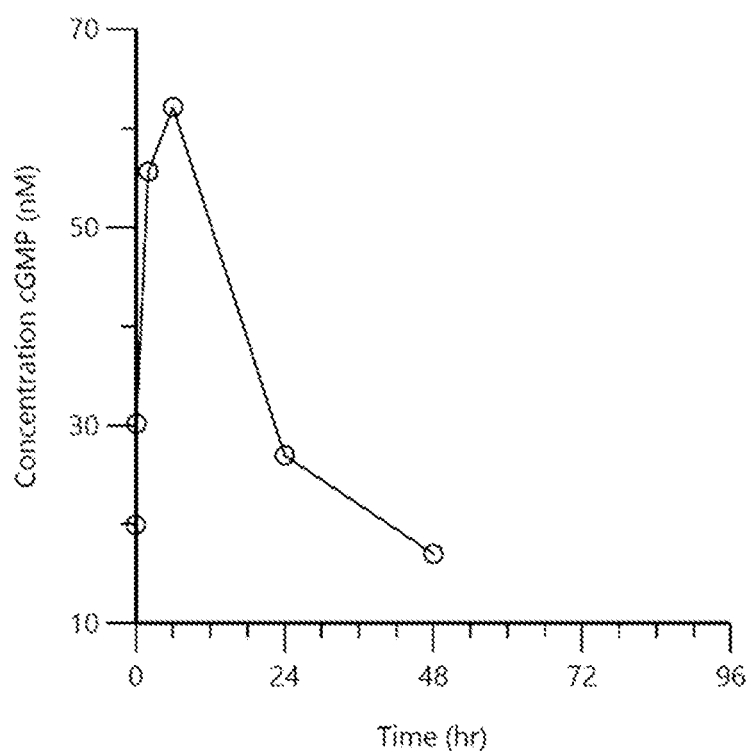
FIG. 23 shows the pharmacodynamic response (cGMP) after i.v. administration of Compound ID 1392 to rats as described in example 11.
Figure 24:
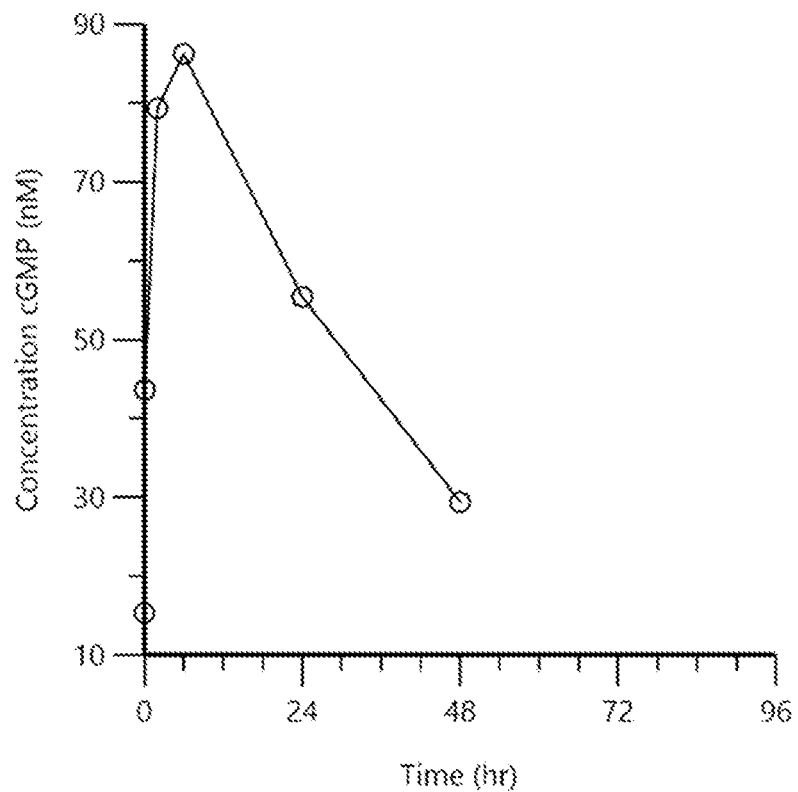
FIG. 24 shows the pharmacodynamic response (cGMP) after i.v. administration of Compound ID 1426 to rats as described in example 11.
Figure 25:
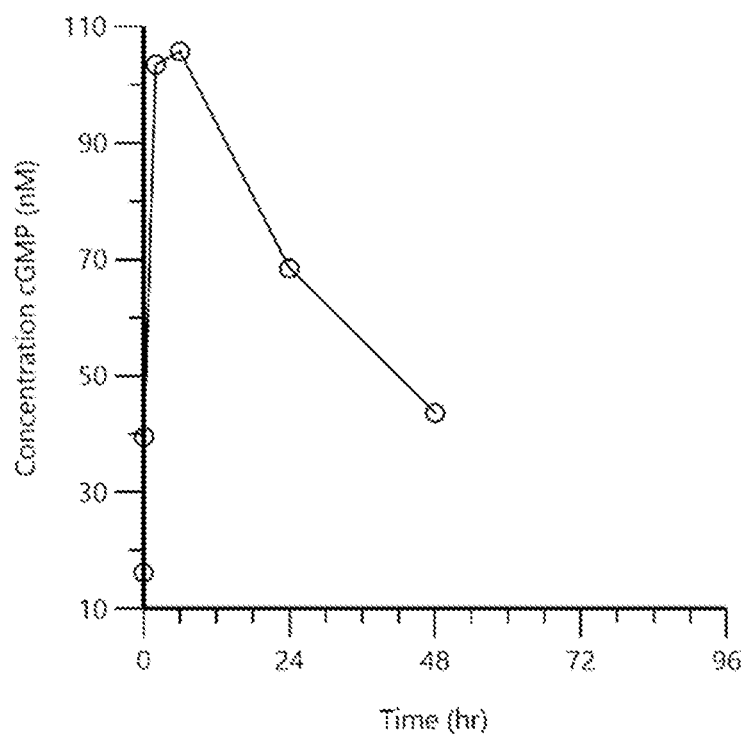
FIG. 25 shows the pharmacodynamic response (cGMP) after i.v. administration of Compound ID 9435 to rats as described in example 11.
Figure 26:
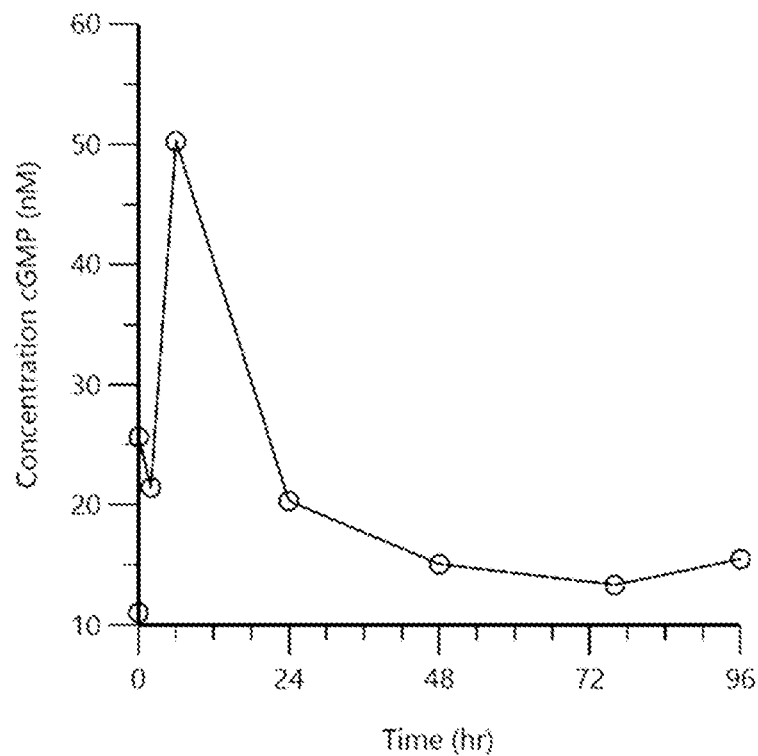
FIG. 26 shows the pharmacodynamic response (cGMP) after i.v. administration of Compound ID 1235 to rats as described in example 11.
Figure 27:
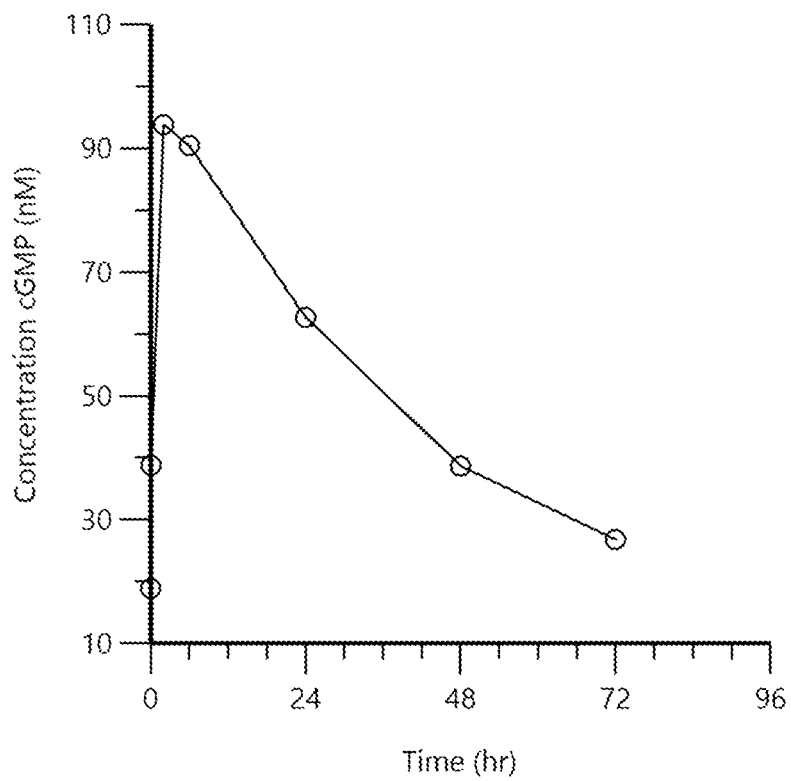
FIG. 27 shows the pharmacodynamic response (cGMP) after i.v. administration of Compound ID 9482 to rats as described in example 11.

Results: The PK data with clearance (CL), half-life T½ and bioavailability (F %) are summarised in Table 20. Plasma cGMP concentrations after i.v. dosing of CNP compounds are shown in FIGS. 1-27, the dose is shown in Table 20. Plasma cGMP are reported as the mean.

TABLE 20

Pharmacokinetic profile of CNP compounds dosed i.v. or s.c. in rats

| | i.v. administration | | | s.c. administration | | |
|---|---|---|---|---|---|---|
| Compound ID | Dose (nmol/kg) | Cl (L/hr/kg) | T½ (hr) | Dose (nmol/kg) | T½ (hr) | F (%) |
| 1225 | 91 | 0.0103 | 5.03 | 286 | 5.1 | 61.2 |
| 1227 | 102 | 0.0168 | 3.56 | n.d. | n.d. | n.d. |
| 1233 | 101 | 0.0246 | 1.42 | 287 | 3.57 | 33.8 |
| 1241 | 92 | 0.0164 | 2.78 | n.d. | n.d. | n.d. |
| 1351 | 102 | 0.0093 | 6.07 | n.d. | n.d. | n.d. |
| 1352 | 102 | 0.0102 | 6.34 | n.d. | n.d. | n.d. |
| 1354 | 100 | 0.00652 | 7.56 | n.d. | n.d. | n.d. |
| 1356 | 102 | 0.0141 | 3.47 | n.d. | n.d. | n.d. |
| 1375 | 100 | 0.0057 | 9.66 | n.d. | n.d. | n.d. |
| 1376 | 103 | 0.00418 | 9.55 | n.d. | n.d. | n.d. |
| 1377 | 94 | 0.00747 | 6.29 | n.d. | n.d. | n.d. |
| 1378 | 100 | 0.00926 | 5.29 | n.d. | n.d. | n.d. |
| 1379 | 90 | 0.0051 | 9.8 | n.d. | n.d. | n.d. |
| 1381 | 94 | 0.00382 | 15.2 | n.d. | n.d. | n.d. |
| 9384 | 99 | 0.00493 | 9.15 | 306 | 9.47 | 49.7 |
| 1386 | 91 | 0.00605 | 8.16 | n.d. | n.d. | n.d. |
| 1389 | 95 | 0.00415 | 14.6 | n.d. | n.d. | n.d. |
| 1392 | 95 | 0.00799 | 5.72 | n.d. | n.d. | n.d. |
| 9407 | 94.2 | 0.00515 | 15.2 | 309 | 14.9 | 37.2 |
| 1420 | 100 | 0.00764 | 8.34 | 306 | 9.47 | 49.7 |
| 1426 | 94 | 0.00348 | 9.96 | n.d. | n.d. | n.d. |
| 1434 | 100 | 0.00764 | 8.34 | n.d. | n.d. | n.d. |
| 9435 | 93 | 0.00458 | 10.4 | n.d. | n.d. | n.d. |
| 9482 | 102 | 0.00549 | 14.5 | 323 | 18.6 | 71.5 |
| 0312 | 99.8 | 0.00738 | 9.4 | 300 | 8.24 | 20.2 |
| 0776 | 100 | 0.00613 | 10.7 | 267 | 5.63 | 7.35 |
| 1235 | 93.9 | 0.0115 | 6.2 | 329 | 6.28 | 65.8 |

In conclusion this experiment shows that the CNP compounds of the present invention show prolonged half-lifes and reduced clearance in a in vivo rat model. Furthermore, the experiment shows that the CNP compounds are biologically active based on their ability to elicit a cGMP response in the dosed animals (FIG. 1-27).

Example 12—PK/PD of CNP Compounds after i.v. and s.c. Administration to Minipiqs and LYD Pigs The purpose of this study was to investigate pharmacokinetic and pharmacodynamic properties after intravenous (i.v.) and subcutaneous (s.c.) administration to Göttingen Minipig and domestic LYD pig, and to estimate bioavailability after s.c. dosing. Quantitative plasma analysis of CNP and cGMP levels were performed as described in Example 11.

Animals and dosing: The pharmacokinetic and pharmacodynamic studies in Göttingen Minipig or domestic LYD pig were conducted at CRO Minerva Imaging or Novo Nordisk A/S, respectively. CNP compounds were dosed to normal female 1) Göttingen minipigs 6-12 months of age with an average weight of 22 kg or 2) domestic LYD pigs 4-5 months of age with and average weight of 80 kg. At least one week prior to dosing, permanent central venous catheters were implanted for blood sampling and intravenous (i.v.) dosing. For subcutaneous (s.c.) dosing, the pigs were ultrasound scanned and the optimal injection area laterally on the neck marked by a permanent tattoo. An insulin pen (NovoPen Echo or NovoPen 4) and insulin needle (NovoFine 32G/4 mm or NovoTwist 32G/5 mm) were used for accurate deposition of the CNP formulations in the subcutaneous fat tissue with the needle perpendicular to the skin.

CNP compounds were formulated according to the principles in General Methods of Preparation—Method G and were either A) 8 mM sodium phosphate, 250 mM glycerol, pH 6.5, B) 5 mM sodium acetate, 250 mM glycerol, pH 4.0, C) 5 mM sodium acetate, 240 mM propylene glycol, pH=4.0, D) 8 mM sodium phosphate, 250 mM glycerol, pH 7.5 or E) 20 mM sodium phosphate, 223 mM propylene glycol, pH 6.0.

Intravenously, the CNP compounds were dosed at 30-60 nmol/kg to Minipig and 15-43 nmol/kg to domestic pig using formulations A-E. Subcutaneously, the CNP compounds were dosed at 55-62 nmol/kg to Minipig and 20-30 nmol/kg to domestic pig using formulations A-D.

Sampling: Blood samples of approximately 1 mL were collected pre dose and up to 14 days post dose into EDTA-coated tubes (8 mM) for cGMP and CNP compound analysis by LC-MS. In few instances, cGMP was only analysed up to 48 hours post dose after intravenous dosing in domestic LYD pig. The blood samples were kept on wet ice for maximum 30 minutes until centrifugation for 10 minutes at 4° C. and minimum 1500G, and the plasma samples were stored at −20° C. until analysis.

Plasma concentration-time profiles were analyzed by non-compartmental PK analysis using Phoenix WinNonlin 8.1, Pharsight Inc., Mountain View, CA, USA. Calculation of the area under the plasma concentration-time curve (AUC) was based on the "linear up log down" method, and uniform weighting was used for estimation of the terminal rate constant ($\lambda z$). S.c. bioavailability (F) was calculated as the dose-normalized AUC (AUC/dose) after s.c. administration divided by the AUC/dose after i.v. administration.

Figure 28:
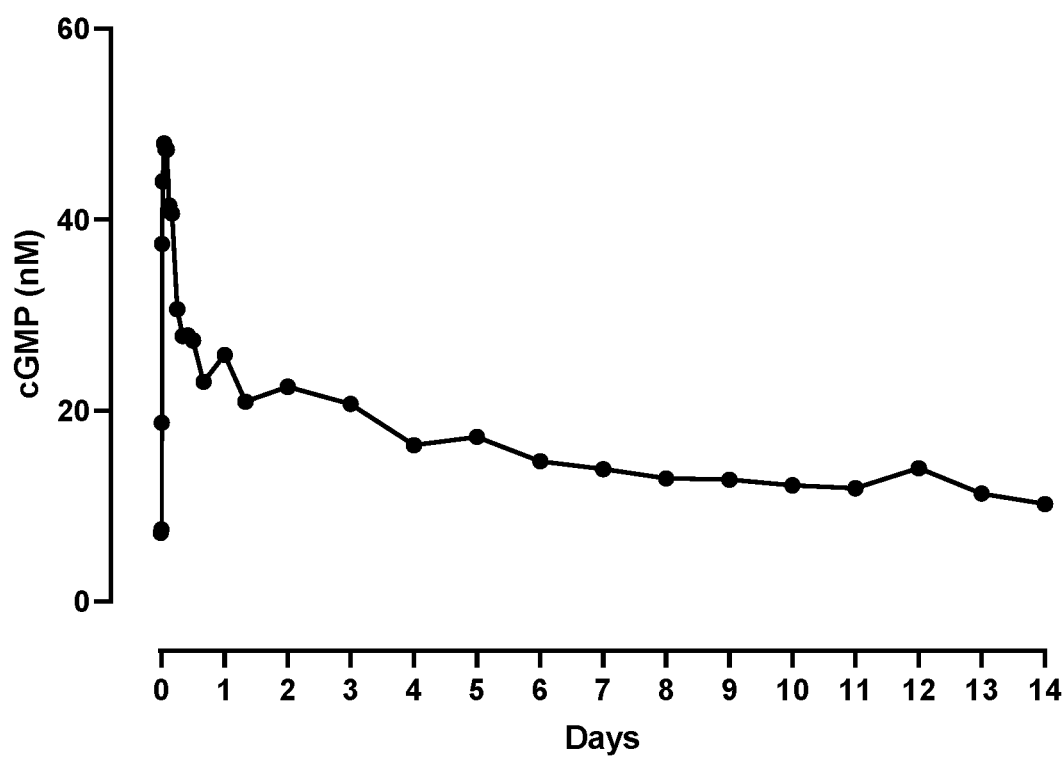
FIG. 28 shows the pharmacodynamic response (cGMP) after i.v. administration of Compound ID 0312 to Göttingen minipigs as described in example 12.
Figure 29:
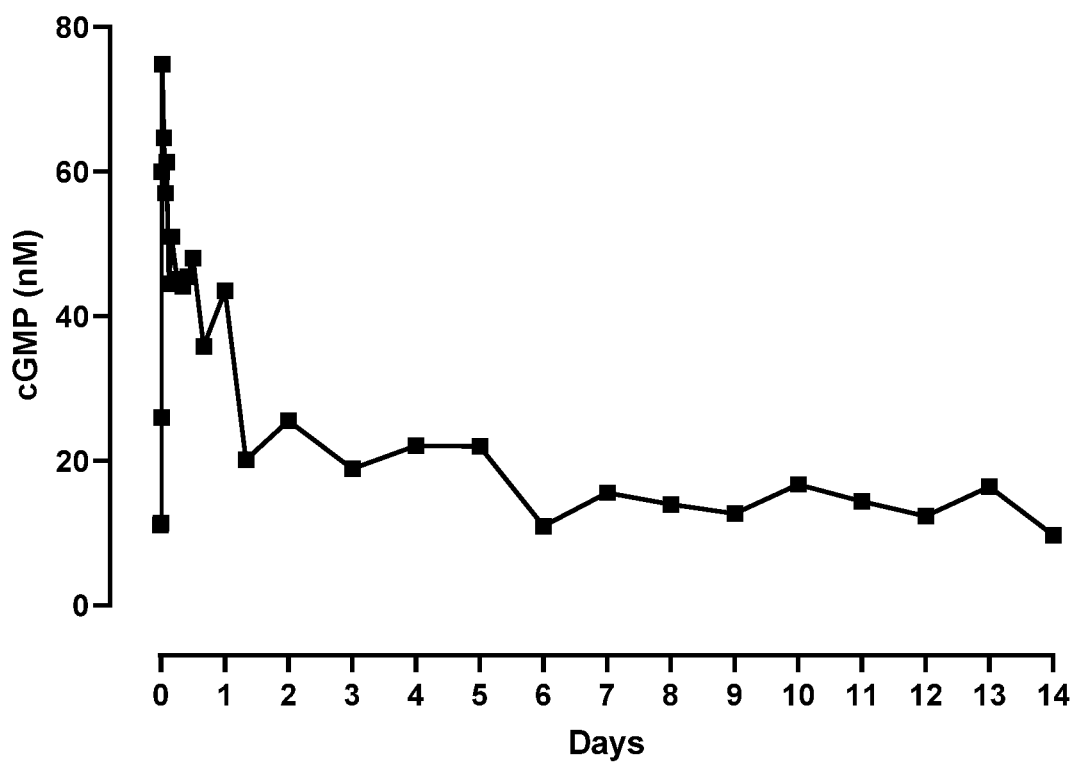
FIG. 29 shows the pharmacodynamic response (cGMP) after i.v. administration of Compound ID 0776 to Göttingen minipigs as described in example 12.
Figure 30:
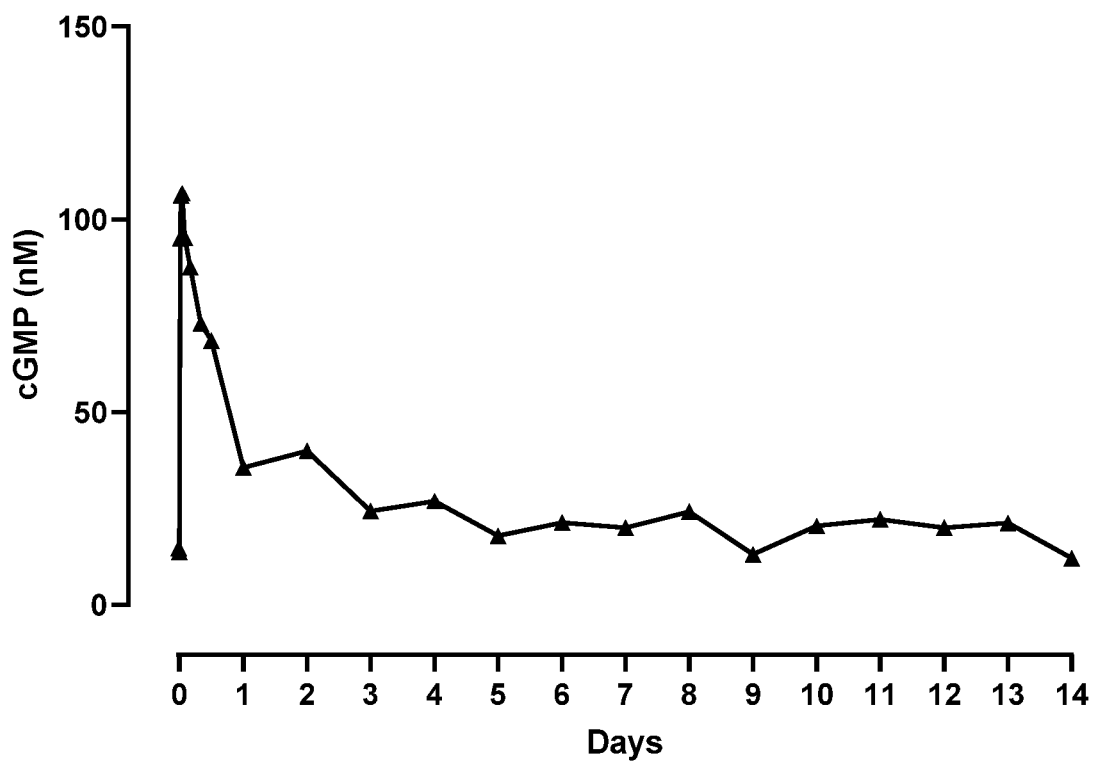
FIG. 30 shows the pharmacodynamic response (cGMP) after i.v. administration of Compound ID 9384 to Göttingen minipigs as described in example 12.
Figure 31:
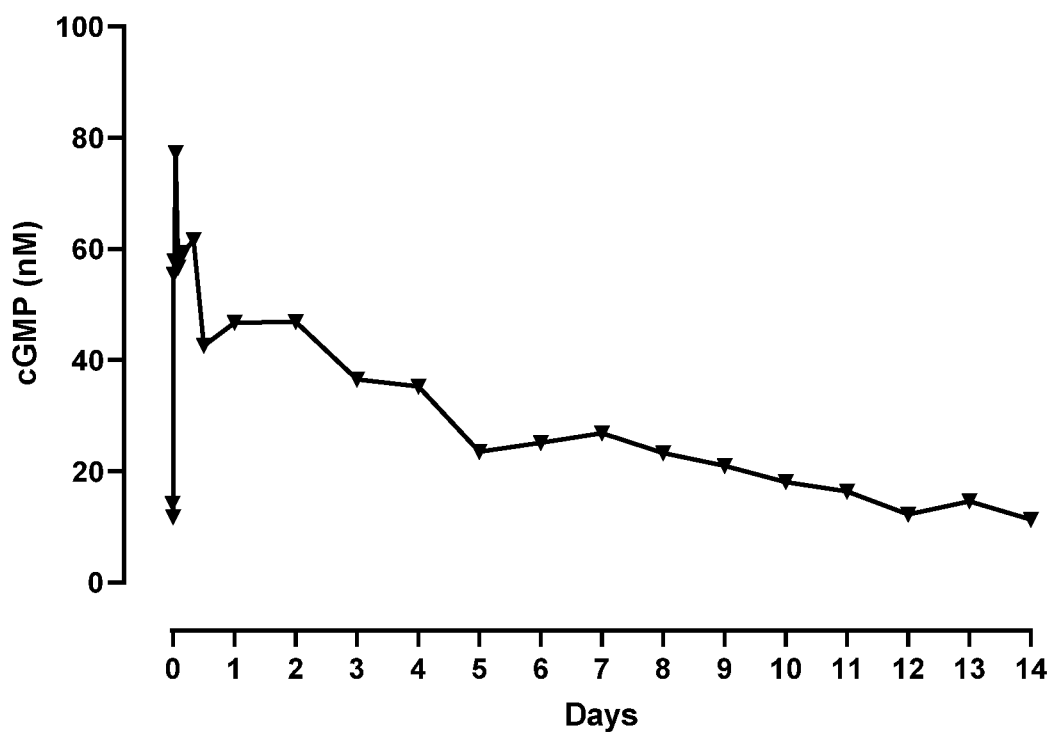
FIG. 31 shows the pharmacodynamic response (cGMP) after i.v. administration of Compound ID 9407 to Göttingen minipigs as described in example 12.
Figure 32:
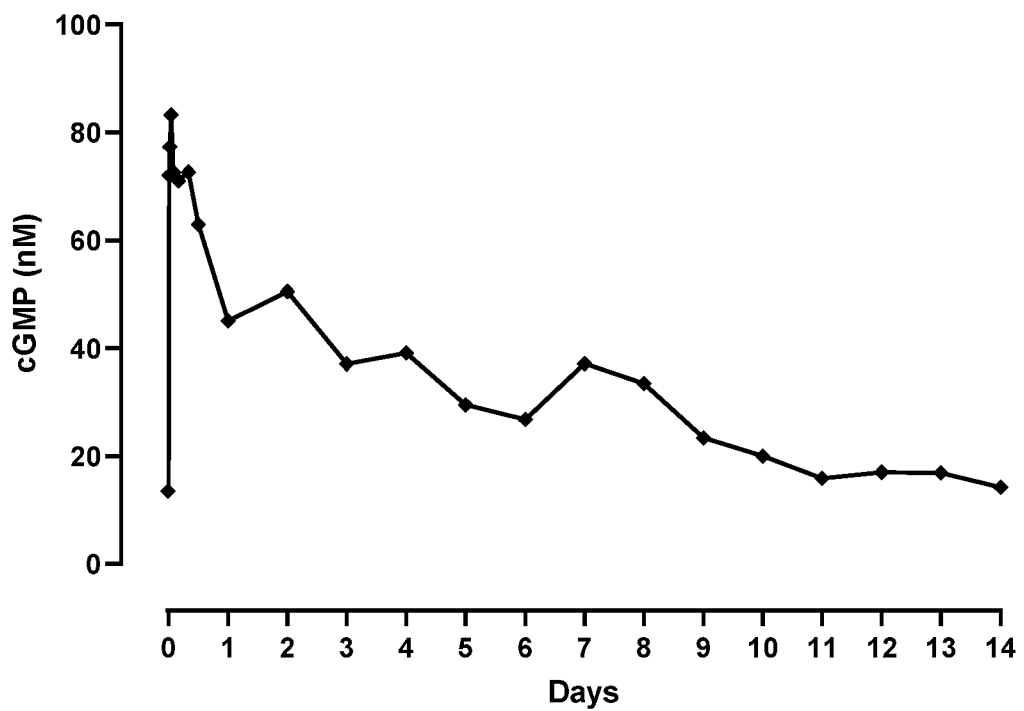
FIG. 32 shows the pharmacodynamic response (cGMP) after i.v. administration of Compound ID 9435 to Göttingen minipigs as described in example 12.
Figure 33:
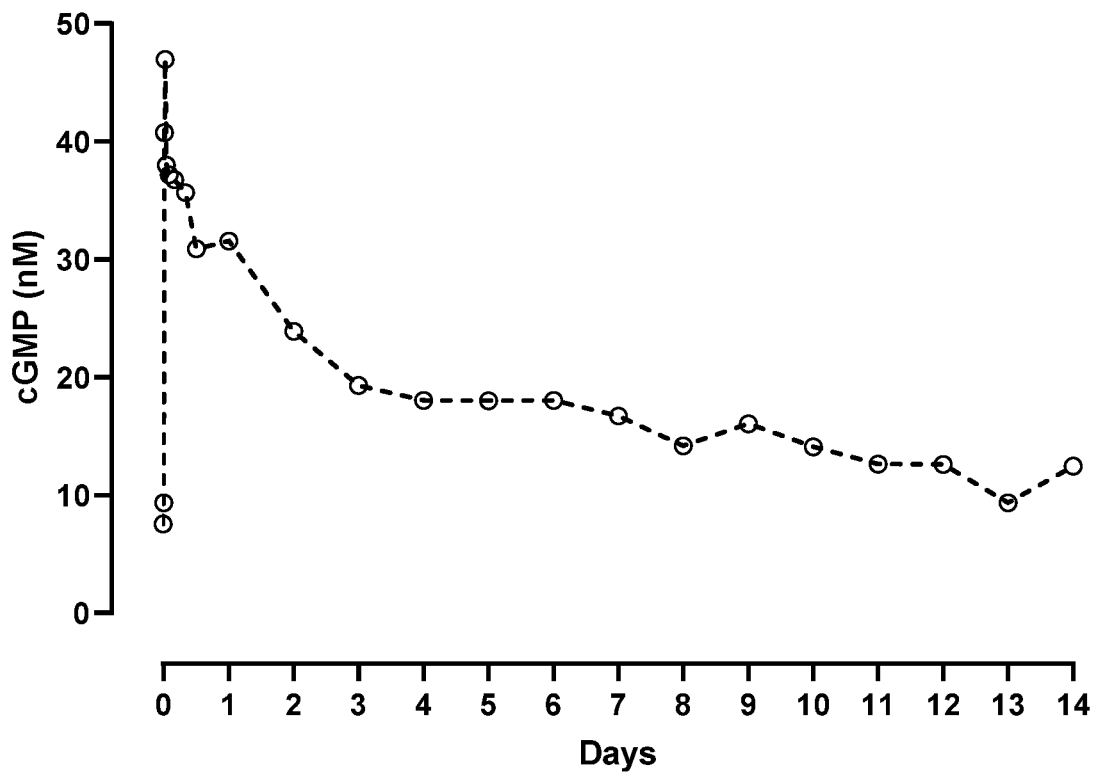
FIG. 33 shows the pharmacodynamic response (cGMP) after i.v. administration of Compound ID 9480 to Göttingen minipigs as described in example 12.
Figure 34:
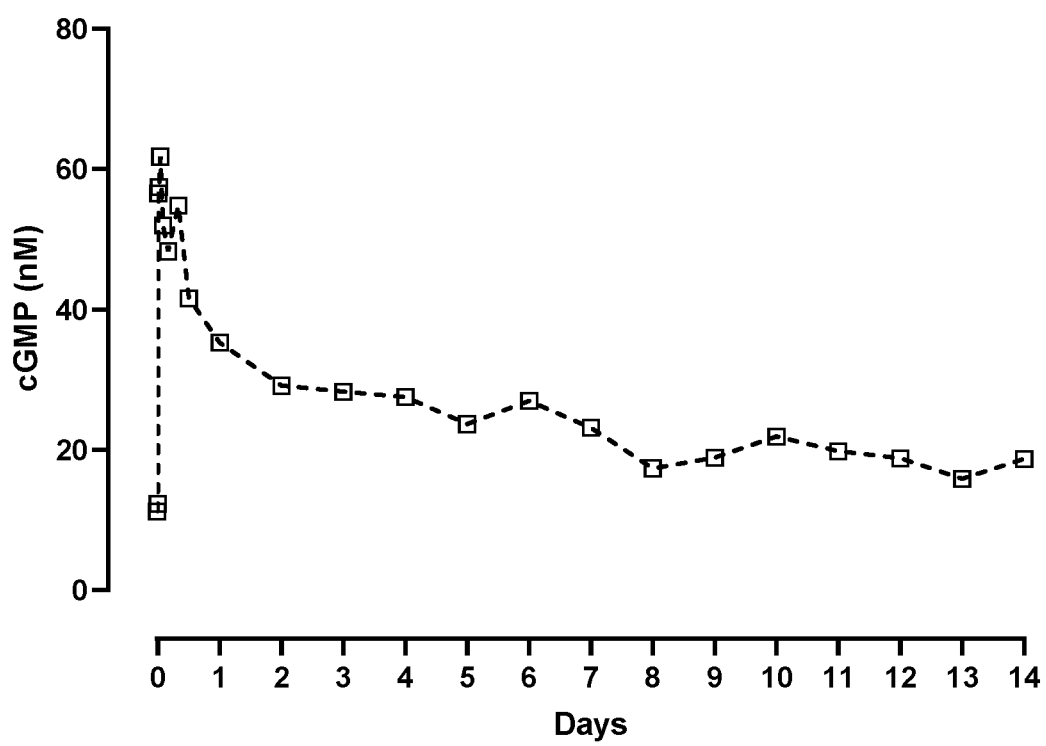
FIG. 34 shows the pharmacodynamic response (cGMP) after i.v. administration of Compound ID 9482 to Göttingen minipigs as described in example 12.
Figure 35:
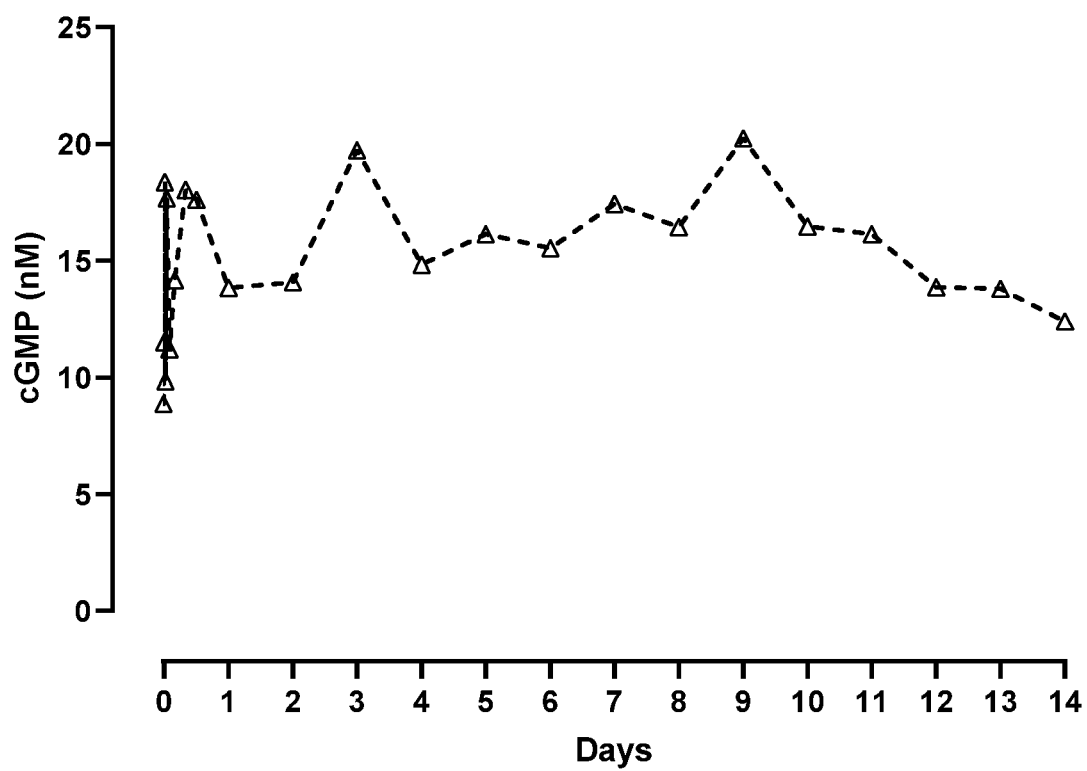
FIG. 35 shows the pharmacodynamic response (cGMP) after i.v. administration of Compound ID 9483 to Göttingen minipigs as described in example 12.
Figure 36:
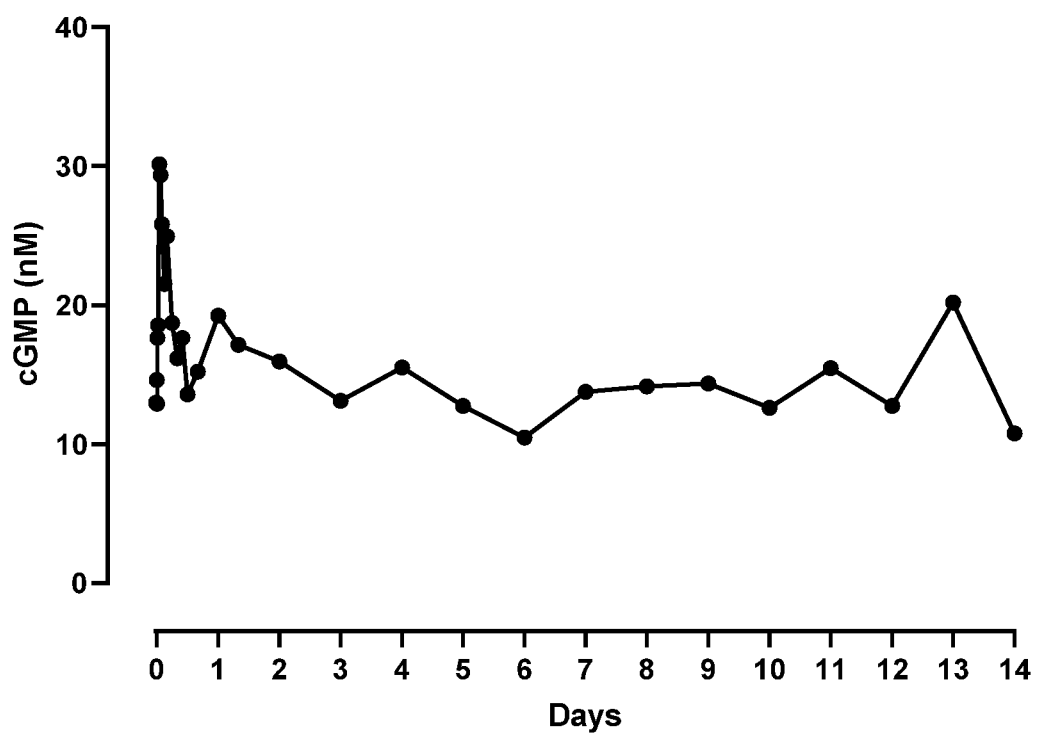
FIG. 36 shows the pharmacodynamic response (cGMP) after s.c. administration of Compound ID 0312 to Göttingen minipigs as described in example 12.
Figure 37:
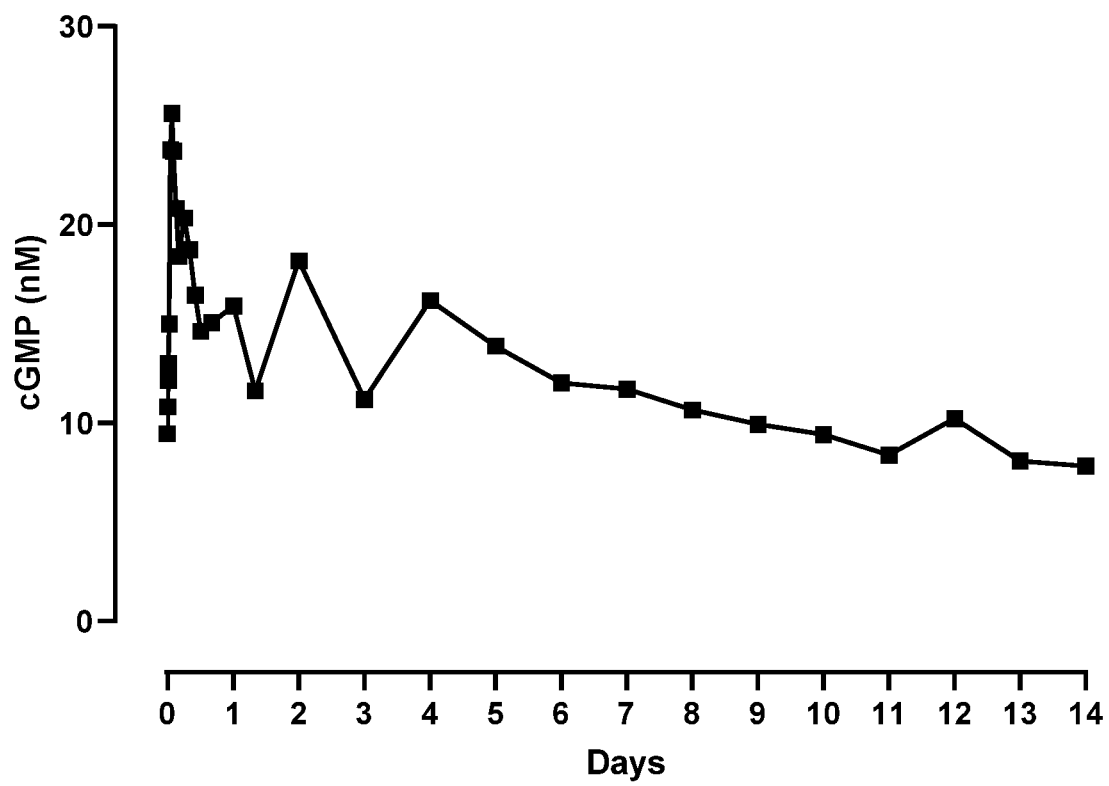
FIG. 37 shows the pharmacodynamic response (cGMP) after s.c. administration of Compound ID 0776 to Göttingen minipigs as described in example 12.
Figure 38:
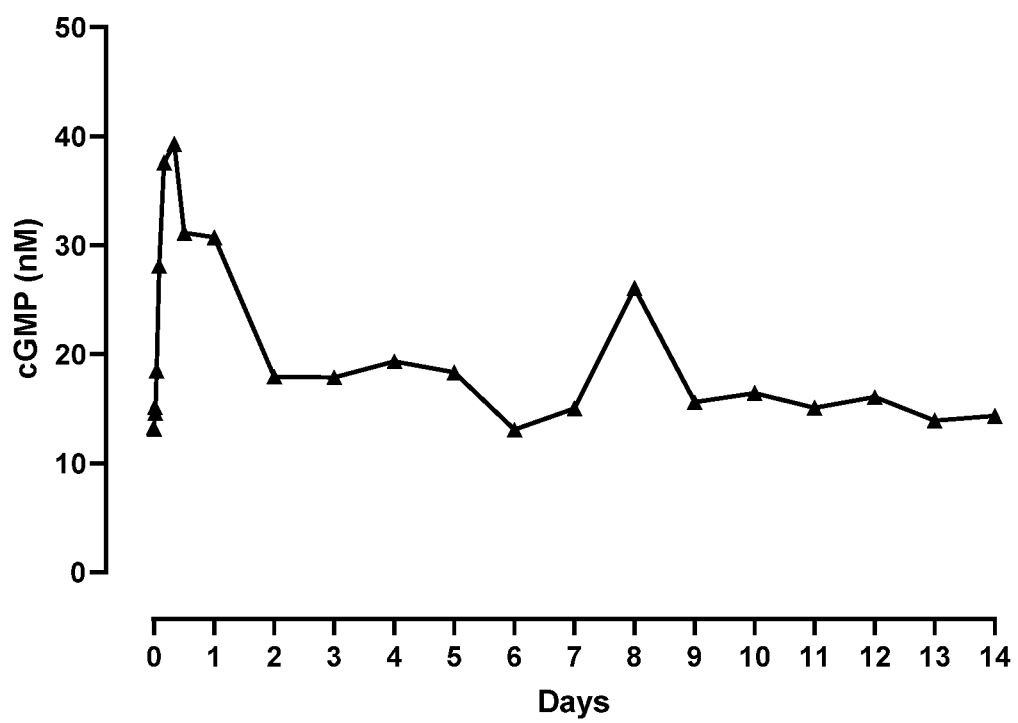
FIG. 38 shows the pharmacodynamic response (cGMP) after s.c. administration of Compound ID 9384 to Göttingen minipigs as described in example 12.
Figure 39:
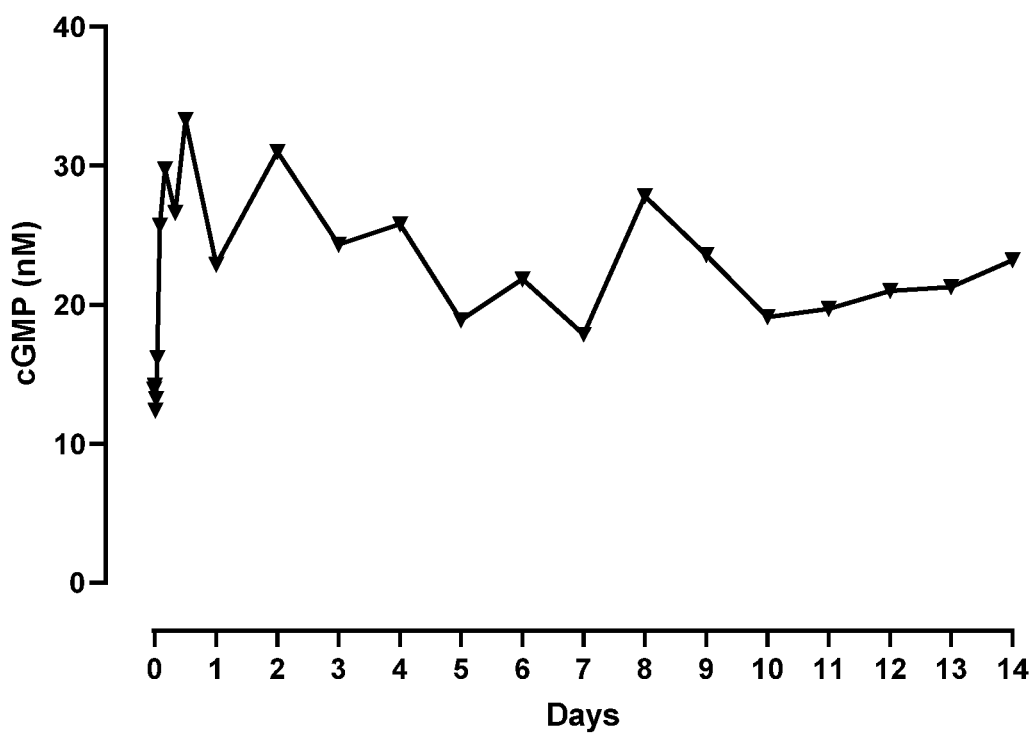
FIG. 39 shows the pharmacodynamic response (cGMP) after s.c. administration of Compound ID 9407 to Göttingen minipigs as described in example 12.
Figure 40:
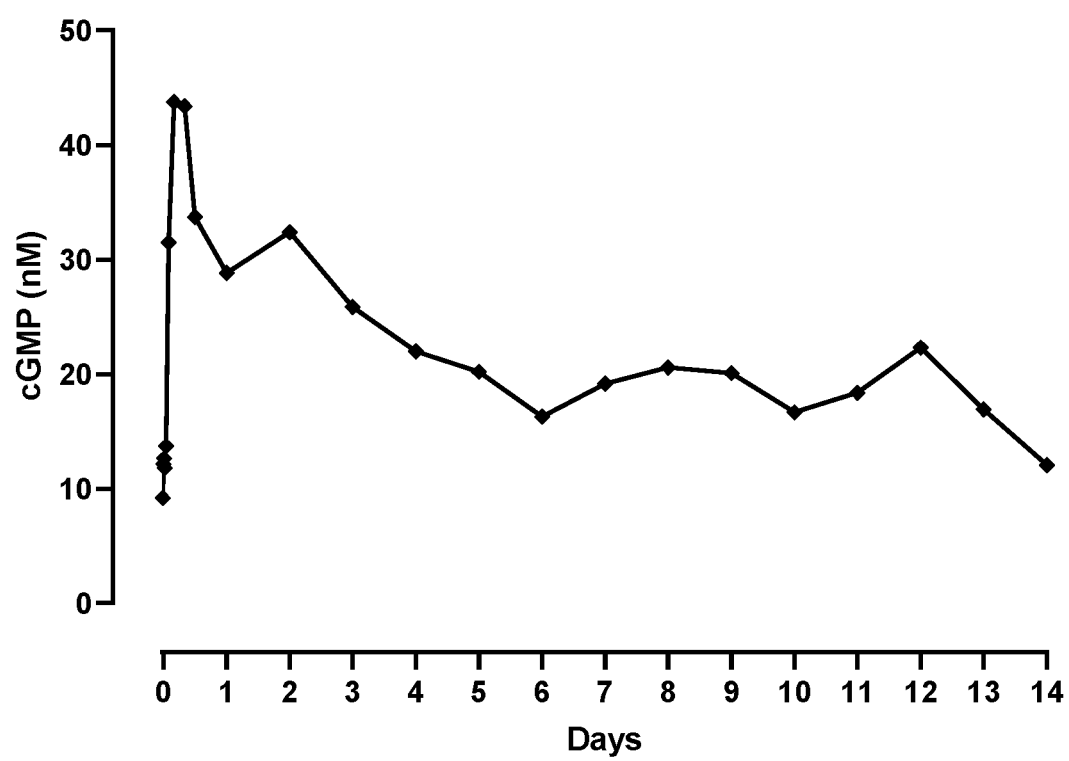
FIG. 40 shows the pharmacodynamic response (cGMP) after s.c. administration of Compound ID 9435 to Göttingen minipigs as described in example 12.
Figure 41:
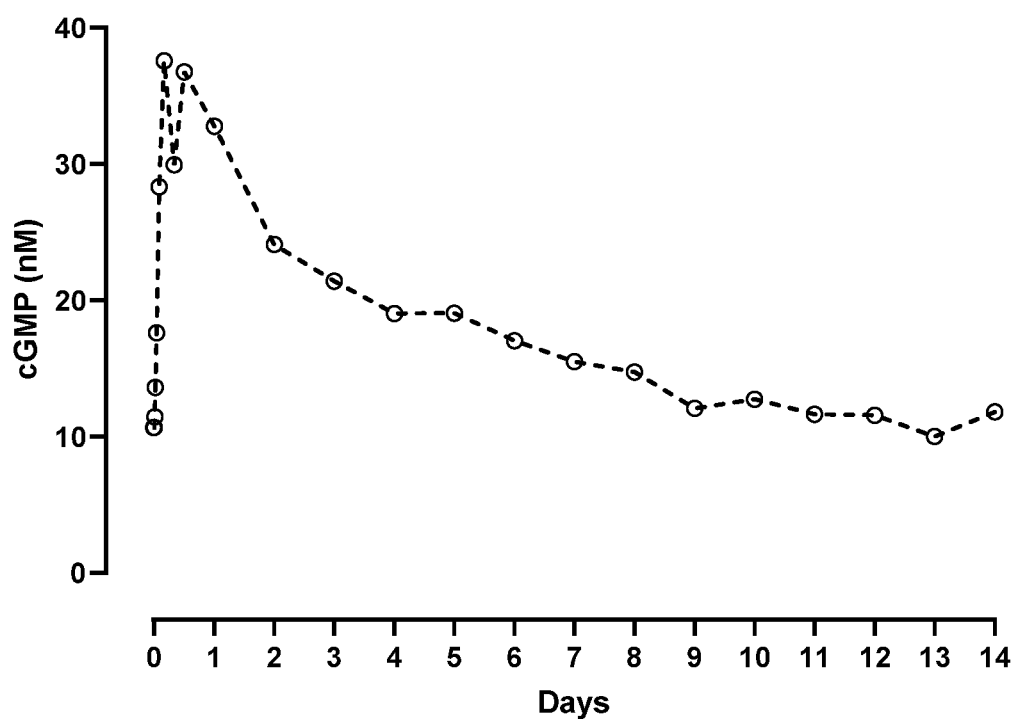
FIG. 41 shows the pharmacodynamic response (cGMP) after s.c. administration of Compound ID 9480 to Göttingen minipigs as described in example 12.
Figure 42:
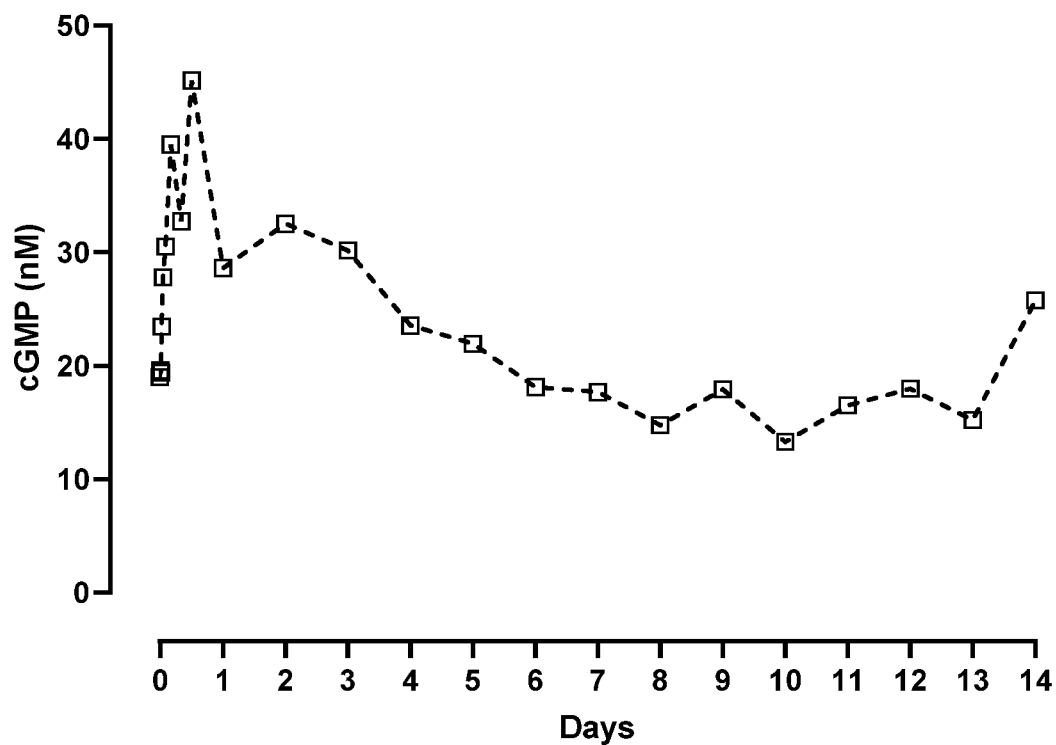
FIG. 42 shows the pharmacodynamic response (cGMP) after s.c. administration of Compound ID 9482 to Göttingen minipigs as described in example 12.
Figure 43:
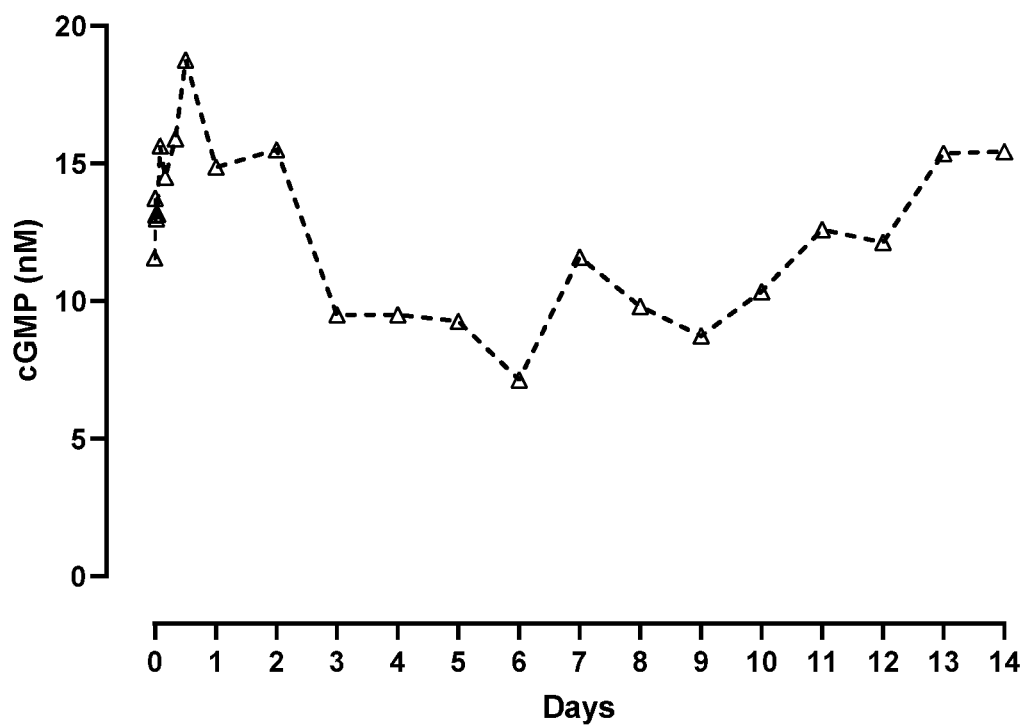
FIG. 43 shows the pharmacodynamic response (cGMP) after s.c. administration of Compound ID 9483 to Göttingen minipigs as described in example 12.
Figure 44:
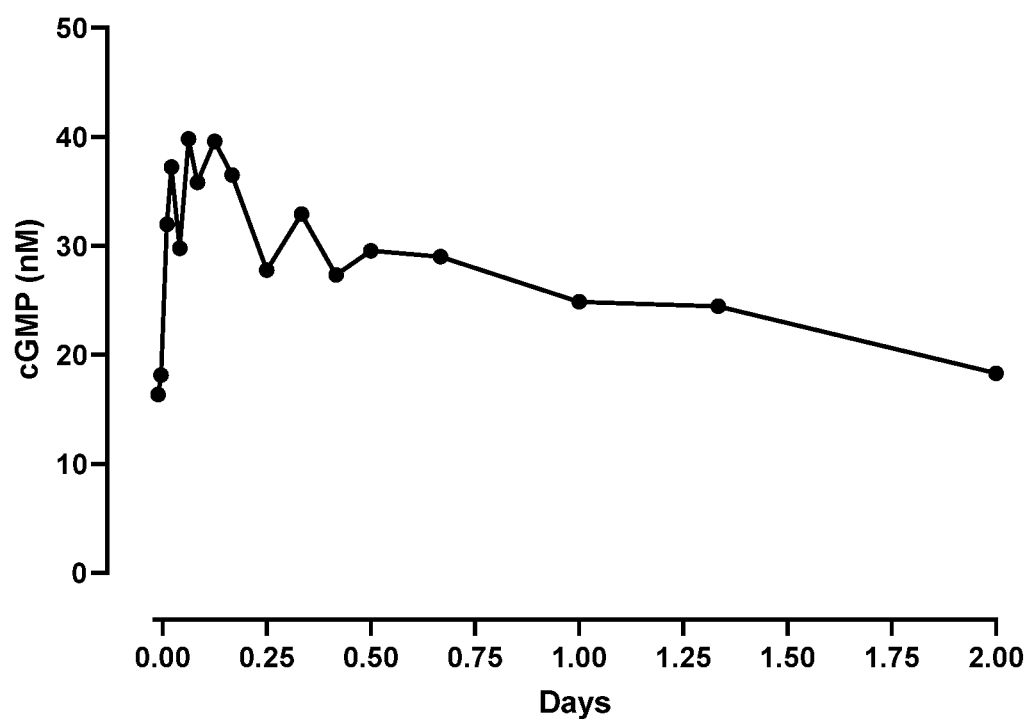
FIG. 44 shows the pharmacodynamic response (cGMP) after i.v. administration of Compound ID 0312 to Domestic LYD pigs as described in example 12.
Figure 45:
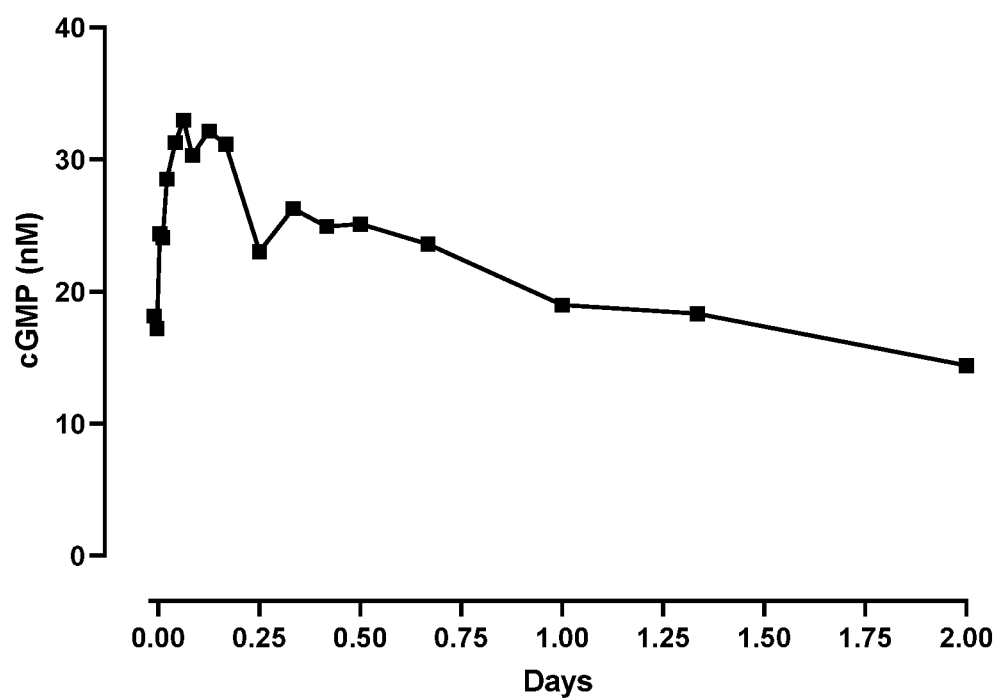
FIG. 45 shows the pharmacodynamic response (cGMP) after i.v. administration of Compound ID 0776 to Domestic LYD pigs as described in example 12.
Figure 46:
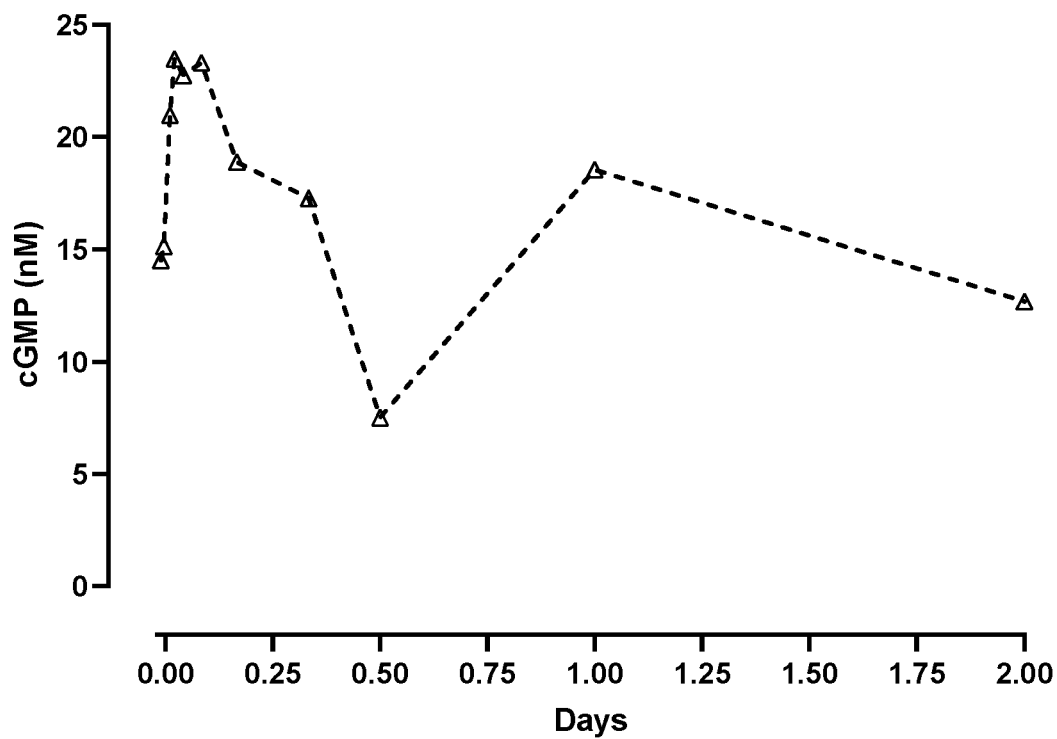
FIG. 46 shows the pharmacodynamic response (cGMP) after i.v. administration of Compound ID 1225 to Domestic LYD pigs as described in example 12.
Figure 47:
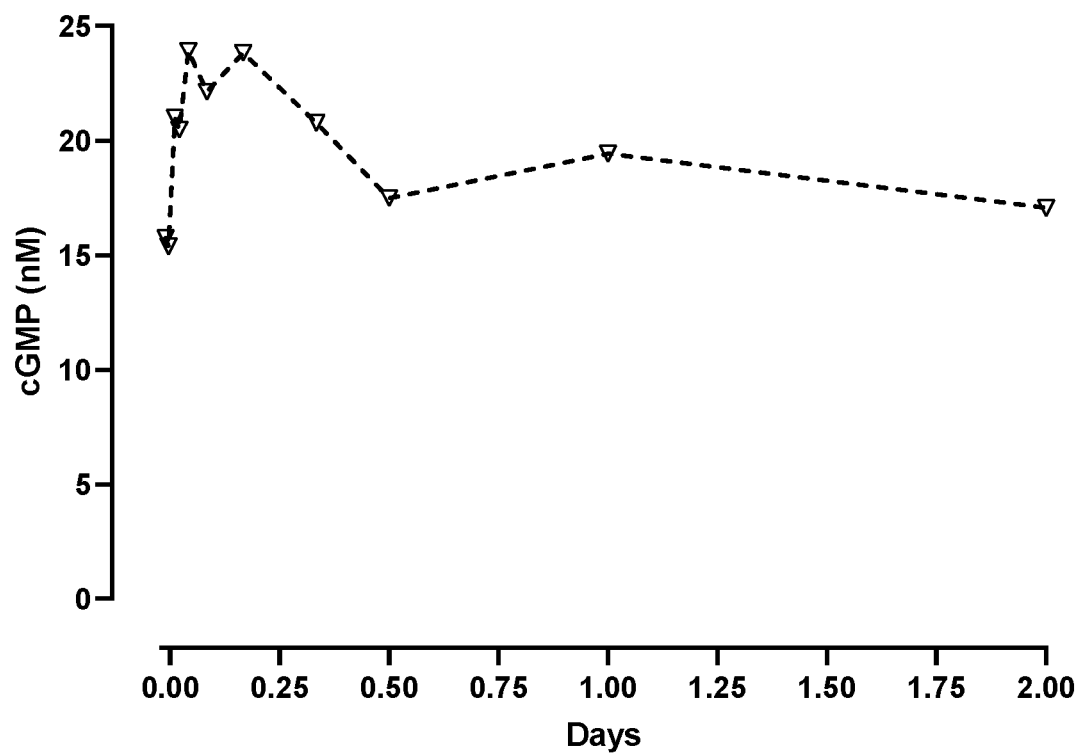
FIG. 47 shows the pharmacodynamic response (cGMP) after i.v. administration of Compound ID 1227 to Domestic LYD pigs as described in example 12.
Figure 48:
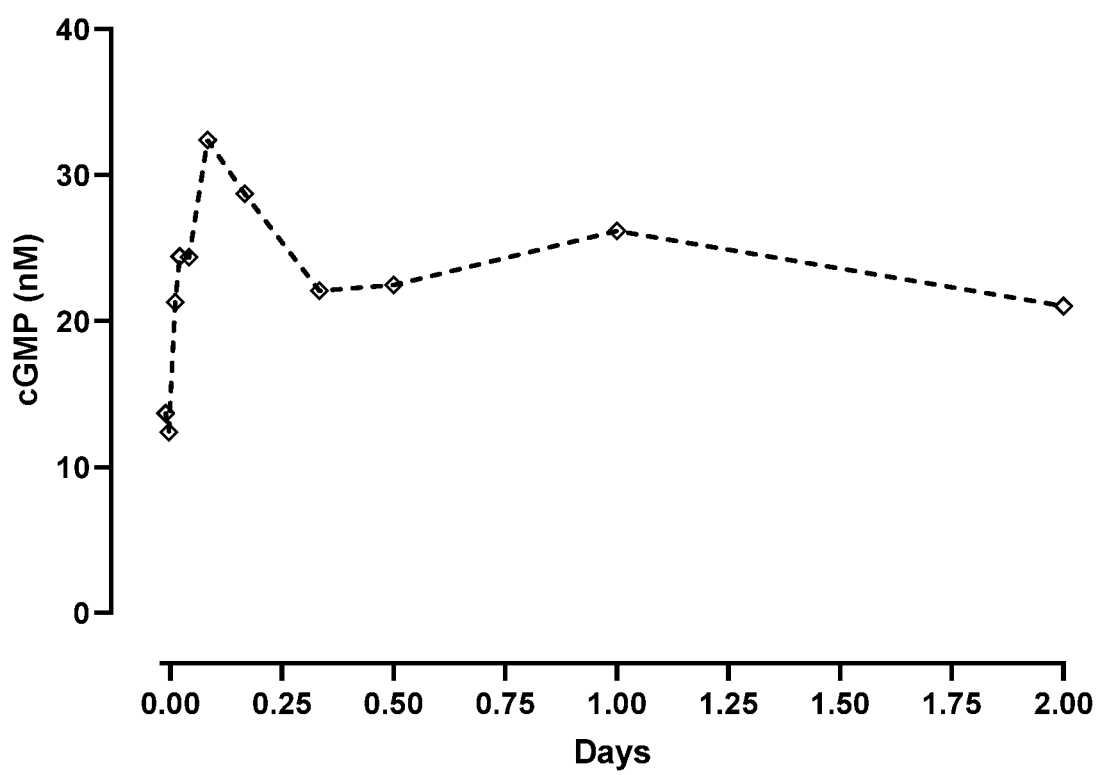
FIG. 48 shows the pharmacodynamic response (cGMP) after i.v. administration of Compound ID 1235 to Domestic LYD pigs as described in example 12.

Results: The PK data with clearance (CL), half-life T½ and bioavailability (F %) in minipig are summarised in Table 21. The PK data with clearance (CL), half-life T½ and bioavailability (F %) in LYD domestic pig are summarised in Table 22. Plasma cGMP concentrations after i.v. or s.c. dosing of CNP compounds in minipigs and domestic pigs are shown in FIGS. 28-48 the dose is shown in Tables 21 and 22. Plasma cGMP are reported as the mean of n=2-4 for 14 days in minipigs and the mean of n=2-4 for 2 days in domestic LYD pigs.

TABLE 21

Pharmacokinetic parameters after i.v. and s.c. administration of CNP compounds to Göttingen Minipig:

| | Göttingen Minipig | | | | | | | |
|---|---|---|---|---|---|---|---|---|
| | Intravenous PK | | | | Subcutaneous PK | | | |
| Compound ID | Dose (nmol/kg) | n | CL (ml/hr/kg) | T½, iv (h) | Dose (nmol/kg) | n | T½, sc (h) | F (%) |
| 9384 | 60 | 3 | 1.53 | 61 | 60 | 3 | 61 | 78 |
| 9407 | 62 | 3 | 1.20 | 82 | 60 | 3 | 92 | 86 |
| 9435 | 55 | 4 | 1.02 | 77 | 60 | 4 | 82 | 77 |
| 9480 | 60 | 3 | 1.13 | 74 | 45 | 3 | 67 | 87 |
| 9482 | 60 | 4 | 1.07 | 89 | 45 | 3 | 84 | 89 |
| 9483 | 60 | 3 | 1.04 | 88 | 60 | 3 | 75 | 44 |
| 0312 | 30 | 3 | 0.927 | 71 | 60 | 3 | 36 | 10 |
| 0776 | 30 | 3 | 0.841 | 60 | 60 | 3 | 56 | 13 |

TABLE 22

Pharmacokinetic parameters after i.v. and s.c. administration of CNP compounds to domestic LYD pig:

| | Domestic LYD pig | | | | | | | |
|---|---|---|---|---|---|---|---|---|
| | Intravenous PK | | | | Subcutaneous PK | | | |
| Compound ID | Dose (nmol/kg) | n | CL (ml/hr/kg) | T½, iv (h) | Dose (nmol/kg) | n | T½, sc (h) | F (%) |
| 1225 | 43 | 2 | 3.23 | 15 | | | | |
| 1227 | 43 | 2 | 5.54 | 11 | 20 | 3 | 9 | 55 |
| 0312 | 15 | 3 | 1.60 | 32 | 30 | 3 | 29 | 11 |
| 0776 | 15 | 4 | 1.34 | 29 | 30 | 3 | 41 | 7 |
| 1235 | 43 | 2 | 3.28 | 20 | 20 | 2 | 29 | 25 |

TABLE 22-continued

Pharmacokinetic parameters after i.v. and s.c. administration of CNP compounds to domestic LYD pig:

| | Domestic LYD pig | | | | | | |
|---|---|---|---|---|---|---|---|
| | Intravenous PK | | | | Subcutaneous PK | | |
| Compound ID | Dose (nmol/kg) | n | CL (ml/hr/kg) | T½, iv (h) | Dose (nmol/kg) | n | T½, sc (h) | F (%) |

Half-life (T½) and s.c. bioavailability (F) given as mean in Table 21 and 22.

Half-life (T½) and s.c. bioavailability (F) given as mean in Table 21 and 22.

Conclusion: this experiment shows that the CNP compounds of the present invention show prolonged half-lifes and reduced clearance in both minipig and domestic LYD pig. Furthermore, the experiment shows that the CNP compounds are biologically active based on their ability to elicit a cGMP response in the dosed animals (FIG. 28-48).

Furthermore, the experiment show subcutaneous bioavailabilities (F) (Table 21 and 22) above 40% for the compounds of the invention. Whereas the non-working positively charged examples (Compound ID 0776 and 0312) show low subcutaneous bioavailabilities (7-13%). The non-working example (Compound ID 1235) with around neutral charge shows medium subcutaneous bioavailability of 25%.

Example 13—Telemetry Measurement of Heart Rate and Blood Pressure

The purpose of the study was to investigate the effect of acute dosing with the CNP compound 9482 (Chem. 137) on mean blood pressure (MAP) and heart rate (HR) in awake rats.

Procedure: The transducers are implanted in Sprague Dawley rats (Charles River) and the rats are allowed a 2-3-week period for recovery. Before surgery, the devices are registered in the software by placing them on a receiver plate and powered on. Sterile saline is added to the transducer catheter before surgery start, and the transmitter is then powered on. The transmitters are placed in the abdomen with the sensor in aorta abdominalis. Isoflurane is used as anaesthetic, and during and after surgery, the rats receive Temgesic (0.05 mg/kg s.c.), Norodyl (5 mg/kg s.c.), and Baytril (10 mg/kg s.c.) as pain relief and to prevent bacterial infection.

Study design: Rats are housed 2/cage (1 with device and 1 as social partner). All animals will have free access to water and food (altromin) throughout the entire study. The rats will be housed in light cycles with light from 6 AM to 6 PM and dark from 6 PM to 6 AM. Eight rats are divided into 2 groups according to a crossover study design.

Telemetry: Each rat is equipped with a transducer (HD-S10 from DSI) capable of measuring blood pressure, heart rate, and activity using Ponemah software with a 100 Hz frequency. During measurements, there should be no disturbances in the room that the rats are housed in to minimize variability in the data. A 4-hour baseline recording will be taken prior to start of the study to capture mean arterial pressure (MAP) and heart rate (HR) patterns in untreated, undisturbed rats. The recording period after drug administration was 24 hours.

Dosing scheme: Rats are dosed in a crossover study design with 4 rats in each group. Each rat is given a washout period of 1 week prior to the next dosing event. Dosing will be intravenous (IV) in the tail vein. Dosing of 9482 was tested in 30, 100, and 300 nmol/kg i.v. in separate experiments. The vehicle consists of 8 mM phosphate, 250 mM glycerol, pH 7.4.

Data analysis and statistics was conducted in Ponemah software and Graphpad prism. For statistics, a paired t test was applied with a confidence level of 95% and P<0.05 denoting statistical significance.

Results: Within the first 30 min after dosing, no difference in MAP and HR was observed with 30, 100, or 300 nmol/kg of CNP compound 9482 compared to vehicle (Table 23 and Table 25). An average of the first 12 h resulted in no differences in MAP between vehicle and the three tested doses of 9482 (Table 24). An increase (P<0.05) of 8.8±10.1% and 6.4±6.6% in HR was detected in the same period with 100 and 300 nmol/kg (Table 26). No change in HR was observed with a dose of 30 nmol/kg (Table 26).

TABLE 23

Mean arterial pressure: 30 min

| Dose | Vehicle | | 9482 | | |
|---|---|---|---|---|---|
| (nmol/kg) | Mean (mmHg) | SD | Mean (mmHg) | SD | P |
| 30 | 117 | 13 | 116 | 15 | ns |
| 100 | 113 | 7 | 114 | 6 | ns |
| 300 | 111 | 8 | 111 | 8 | ns |

TABLE 24

Mean arterial pressure: 12 h

| Dose | Vehicle | | 9482 | | |
|---|---|---|---|---|---|
| (nmol/kg) | Mean (mmHg) | SD | Mean (mmHg) | SD | P |
| 30 | 108 | 14 | 106 | 10 | ns |
| 100 | 104 | 7 | 104 | 7 | ns |
| 300 | 103 | 5 | 102 | 6 | ns |

TABLE 25

Heart rate: 30 min

| Dose | Vehicle | | 9482 | | |
|---|---|---|---|---|---|
| (nmol/kg) | Mean (bpm) | SD | Mean (bpm) | SD | SDP |
| 30 | 366 | 26 | 356 | 24 | ns |
| 100 | 382 | 19 | 388 | 12 | ns |
| 300 | 379 | 18 | 370 | 18 | ns |

TABLE 26

Heart rate: 12 h

| Dose (nmol/kg) | Vehicle | | 9482 | | |
|---|---|---|---|---|---|
| | Mean (bpm) | SD | Mean (bpm) | SD | P |
| 30 | 311 | 13 | 332 | 27 | ns |
| 100 | 335 | 15 | 364 | 28 | 0.04 |
| 300 | 334 | 15 | 355 | 15 | 0.03 |

Conclusion: Acute IV infusion of CNP compound 9482 was not associated with any major hemodynamic changes over a 12 h period as evidenced by unaltered MAP and only minor increases in HR at the two highest doses.

Example 14—Mouse Metatarsal Bone Dissection and Culture

The purpose of this study was to evaluate bone growth after administration of CNP compounds in an ex vivo mouse model.

Procedure: One-day old mouse pups (NMRI, Javier Labs France) were euthanised prior to dissection. All applicable international and internal Novo Nordisk guidelines for care and use of animals were followed. The three middle metatarsal bones were dissected out from each hind paw. The dissected bones were placed in 24-well cell culture plates and cultured in 400 µl α-Minimum Essential Media supplemented with 0.2% BSA, 1% Pen/Strep at 37° C. and 5% $CO_2$. The bones from all animals were randomised into a control group and six CNP compound-treated groups (100 nM; n=8). The medium was changed every 2-3 days. All compounds were formulated according to the principles described in General Methods of Preparation—Method G. Compounds 9435 and 9483 were formulated in A) 5 mM sodium acetate, 250 mM glycerol, pH 4.0 while compounds 9384, 9407, 9480 and 9482 were formulated in B) 8 mM sodium phosphate, 250 mM glycerol, pH 7.4.
Vehicle alone did not affect bone growth compared to media alone.

Digital pictures were captured on day 0, 4, 7, 11, and 14 using a digital camera attached to a Nikon microscope. The length of each metatarsal bone was measured using ImageJ software and increase in bone length was expressed as percentage change from the length measured at the day of dissection (Mean (SD)).

Results: All CNP compounds significantly increased bone length compared to control group after 11 days of treatment (p<0.05; two-way ANOVA). Total increases in bone length were 28-48% higher after treatment with CNP compounds compared to the control group after 14 days in culture. The results from the study are summarised in Table 27.

TABLE 27

Increase in bone length after administration of CNP compounds (100 nM):

| | Compound | | | | | | | | | | |
|---|---|---|---|---|---|---|---|---|---|---|---|
| | control | | 9384 | | | 9407 | | | 9435 | | |
| Day | mean (%) | SD | mean (%) | SD | p< | mean (%) | SD | p< | mean (%) | SD | p< |
| 4 | 25.3 | 4.1 | 33.6 | 8.3 | ns | 35.1 | 4.1 | ns | 36.2 | 3.8 | ns |
| 7 | 32.9 | 4.9 | 42.6 | 7.0 | 0.05 | 45.4 | 4.5 | 0.001 | 47.3 | 2.5 | 0.001 |
| 11 | 36.8 | 3.1 | 50.1 | 7.2 | 0.01 | 53.2 | 6.4 | 0.001 | 53.9 | 4.8 | 0.001 |
| 14 | 40.1 | 3.7 | 54.4 | 7.9 | 0.01 | 55.8 | 8.2 | 0.01 | 59.2 | 3.5 | 0.001 |

| | Compound | | | | | | | | | | |
|---|---|---|---|---|---|---|---|---|---|---|---|
| | control | | 9480 | | | 9482 | | | 9483 | | |
| Day | mean (%) | SD | mean (%) | SD | p< | mean (%) | SD | p< | mean (%) | SD | p< |
| 4 | 25.3 | 4.1 | 33.1 | 5.2 | ns | 37.7 | 10.9 | ns | 30.2 | 4.6 | ns |
| 7 | 32.9 | 4.9 | 43.9 | 4.9 | 0.01 | 47.1 | 10.3 | 0.05 | 39.5 | 8.8 | ns |
| 11 | 36.8 | 3.1 | 49.2 | 5.2 | 0.001 | 54.4 | 13.1 | 0.05 | 49.7 | 6.0 | 0.001 |
| 14 | 40.1 | 3.7 | 52.1 | 5.2 | 0.001 | 57.5 | 12.0 | 0.05 | 51.5 | 5.1 | 0.001 |

In Table 27, metatarsal bones were isolated from mice and cultured for up to 14 days. Length was measured every 3-4 days throughout the study and expressed as percentage change from day 0 (Mean (SD)). Statistically significant differences are indicated compared to control group (two-way ANOVA).

Conclusion: This experiment demonstrates that the CNP compounds of the current invention are able to significantly increase bone length in an ex vivo mouse model.

Example 15—Mouse Growth Study

The purpose of this study was to evaluate growth in mice after treatment with two doses of CNP compound.

Procedure: Mice (C57BL/6J, male, age 4 weeks; n=10) received daily subcutaneous injections of compound 9482 or vehicle for 35 days. Formulations were prepared according to the principles described in General Methods of Preparation—Method G (30 and 70 nmol/kg, 10 mL/kg; Formulation buffer 8 mM sodium phosphate, 250 mM glycerol, 0.007% polysorbate 20, pH 7.4). Body weight and tail and body length were measured weekly throughout the study. The increase in growth was expressed as percentage change from day 0 (mean (SD)).

Results: Both 30 and 70 nmol/kg doses of CNP compound 9482 significantly increased tail and body length after 7 and 18 days, respectively, (p<0.05, two-way ANOVA) compared to control. After 35 days, the change in tail length (from day 0) was increased by 45 and 83%, respectively, after treatment with 30 and 70 nmol/kg CNP compound compared to control animals. Body length was 30 and 67% higher, respectively, compared to control group after treatment with 30 and 70 nmol/kg CNP compound for 35 days. The results from the study are summarised in Tables 28 and Table 29.

TABLE 28

Tail length of mice treated with daily injections of CNP compound for 35 days

| | Vehicle | | 9482 30 nmol/kg | | | 9482 70 nmol/kg | | |
|---|---|---|---|---|---|---|---|---|
| Day | Mean (%) | SD | Mean (%) | SD | p< | Mean (%) | SD | p< |
| 7 | 7.7 | 2.3 | 11.8 | 3.0 | 0.05 | 14.3 | 3.2 | 0.001 |
| 14 | 10.8 | 3.0 | 16.0 | 3.9 | 0.01 | 20.3 | 5.0 | 0.001 |
| 21 | 18.1 | 3.2 | 24.1 | 3.8 | 0.01 | 29.0 | 5.0 | 0.001 |
| 28 | 17.3 | 2.7 | 25.6 | 4.0 | 0.001 | 32.0 | 4.8 | 0.001 |
| 35 | 19.5 | 3.2 | 28.5 | 4.7 | 0.001 | 35.7 | 4.6 | 0.001 |

In Table 28, increase in tail length is expressed as percentage change from day 0 (mean (SD)). Statistically significant differences are indicated compared to control group (two-way ANOVA).

TABLE 29

Body length of mice treated with daily injections of CNP compound for 35 days

| | Vehicle | | 9482 30 nmol/kg | | | 9482 70 nmol/kg | | |
|---|---|---|---|---|---|---|---|---|
| Day | Mean (%) | SD | Mean (%) | SD | p< | Mean (%) | SD | p< |
| 8 | 9.4 | 2.2 | 10.2 | 2.3 | ns | 12.8 | 2.4 | 0.01 |
| 18 | 14.1 | 2.9 | 17.5 | 2.0 | 0.05 | 21.5 | 4.0 | 0.001 |
| 25 | 16.5 | 3.4 | 22.5 | 3.4 | 0.01 | 29.0 | 4.5 | 0.001 |
| 35 | 21.1 | 3.3 | 27.4 | 3.2 | 0.001 | 35.3 | 4.6 | 0.001 |

In Table 29, increase in body length is expressed as percentage change from day 0 (mean (SD)). Statistically significant differences are indicated compared to control group (two-way ANOVA).

Conclusion: This experiment shows that CNP compounds of the present invention increase tail and body length of mice to a significant degree when administered subcutaneously in a pharmaceutically relevant formulation.

The invention claimed is:

1. A C-type natriuretic (CNP) compound comprising a CNP peptide and a modifying group;
wherein the net charge of the compound at physiological pH is 0 or negative;
wherein the amino acid sequence of the CNP peptide is:

$AA_{01}$-$AA_{02}$-$AA_{03}$-$AA_{04}$-$AA_{05}$-$AA_{06}$-$AA_{07}$-$AA_{08}$-$AA_{09}$-$AA_{10}$-$AA_{11}$-$AA_{12}$-$AA_{13}$-$AA_{14}$-$AA_{15}$-$AA_{16}$-$AA_{17}$-$AA_{18}$-$AA_{19}$-$AA_{20}$-$AA_{21}$-$AA_{22}$-$AA_{23}$-$AA_{24}$-$AA_{25}$-$AA_{26}$-$AA_{27}$-$AA_{28}$-$AA_{29}$-$AA_{30}$-$AA_{31}$-$AA_{32}$-$AA_{33}$-$AA_{34}$-$AA_{35}$-$AA_{36}$-$AA_{37}$;

wherein:
  $AA_{01}$ is Gln or absent,
  $AA_{02}$ is Glu or absent,
  $AA_{03}$ is His or absent,
  $AA_{04}$ is Pro or absent,
  $AA_{05}$ is Asn or Gln or Glu or absent,
  $AA_{06}$ is Ala or absent,
  $AA_{07}$ is Arg or His or Ala or absent,
  $AA_{08}$ is Lys or Ser or His or absent,
  $AA_{09}$ is Tyr or Glu or absent,
  $AA_{10}$ is Lys or Glu or Gln or His or absent,
  $AA_{11}$ is Gly,
  $AA_{12}$ is Ala,
  $AA_{13}$ is Gln,
  $AA_{14}$ is Lys or His or Glu,
  $AA_{15}$ is Lys or Ser or Glu or Thr or His,
  $AA_{16}$ is Gly,
  $AA_{17}$ is Leu or Gly or Ser or Val,
  $AA_{18}$ is Ser or His,
  $AA_{19}$ is Gln or Ser,
  $AA_{20}$ is Gly,
  $AA_{21}$ is Cys,
  $AA_{22}$ is Phe,
  $AA_{23}$ is Gly,
  $AA_{24}$ is Leu,
  $AA_{25}$ is Pro,
  $AA_{26}$ is Leu,
  $AA_{27}$ is Asp or Glu,
  $AA_{28}$ is Arg,
  $AA_{29}$ is Ile,
  $AA_{30}$ is Gly,
  $AA_{31}$ is Ser,
  $AA_{32}$ is Leu,
  $AA_{33}$ is Ser,
  $AA_{34}$ is Gly,
  $AA_{35}$ is Leu,
  $AA_{36}$ is Gly, and
  $AA_{37}$ is Cys;
wherein the modifying group comprises Chem A, Chem B, and Chem C;

wherein Chem A is (Chem A1)

(Chem A2)

wherein p is an integer in the range of 14-20, and
wherein * denotes an amide bond connecting Chem A and Chem B;
wherein Chem B is (Chem B1)

(Chem B2)

wherein q is an integer in the range of 1-8,
wherein * denotes an amide bond connecting Chem A- and Chem B-, and
wherein ** denotes an amide bond connecting Chem B- and Chem C-; and
wherein Chem C is selected from the group consisting of:

(Chem C1)

(Chem C2)

-continued

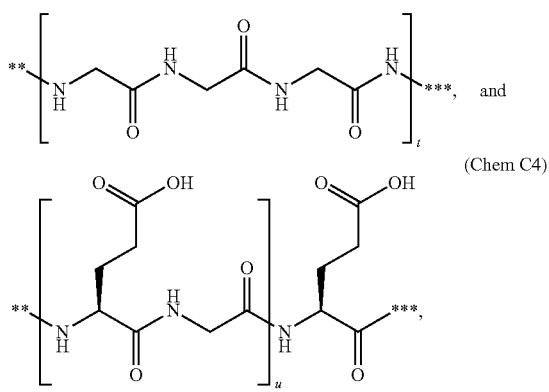

wherein r is an integer in the range of 0-4,
wherein s is an integer in the range of 0-3,
wherein t is an integer in the range of 0-1,
wherein u is an integer in the range of 0-3,
wherein ** denotes an amide bond connecting Chem B- and Chem C-, and
wherein *** denotes an amide bond connecting Chem C- and the N-terminal alpha-amine on the CNP peptide.

2. The CNP compound according to claim 1, wherein $AA_5$ of the CNP peptide is Gln.

3. The CNP compound according to claim 1, wherein the amino acid sequence of the CNP peptide is selected from the group consisting of:
GAQKKGSSQGCFGLPLDRIGSLSGLGC (SEQ ID NO: 136),
ARKYKGAQKKGLSQGCFGLPLDRIGSLSGLGC (SEQ ID NO: 77),
YKGAQKKGGSQGCFGLPLDRIGSLSGLGC (SEQ ID NO: 88),
YKGAQKKGLSQGCFGLPLDRIGSLSGLGC (SEQ ID NO: 103),
QEHPQARKYKGAQKKGLSSGCFGLPLDRI-GSLSGLGC (SEQ ID NO: 67), and
QEHPQARKYK-GAQKKGLSSGCFGLPLERIGSLSGLGC (SEQ ID NO: 104).

4. The CNP compound according to claim 3, wherein the amino acid sequence of the CNP peptide is QEHPQARKYKGAQKKGLSSGCFGLPLDRI-GSLSGLGC (SEQ ID NO: 67).

5. The CNP compound according to claim 1, wherein q is in the range of 1-5.

6. The CNP compound according to claim 1, wherein the modifying group is selected from the group consisting of:

(Chem E)

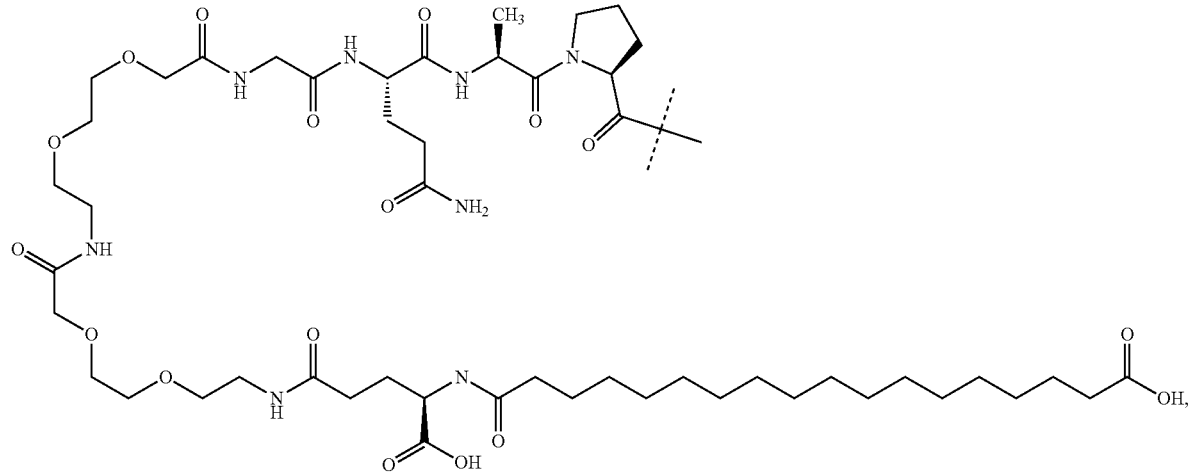

(Chem F)

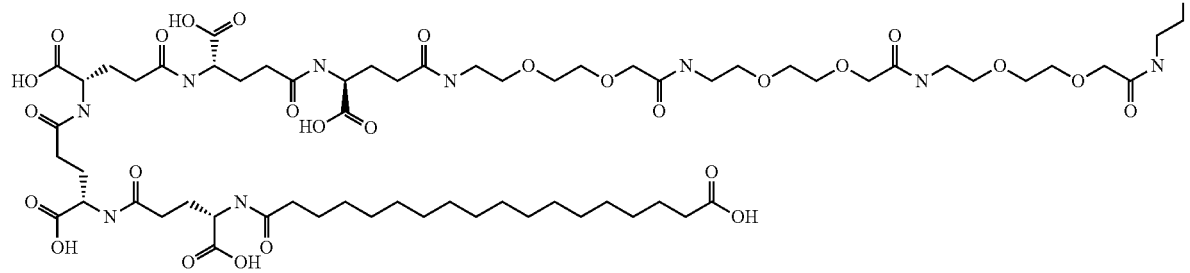

-continued
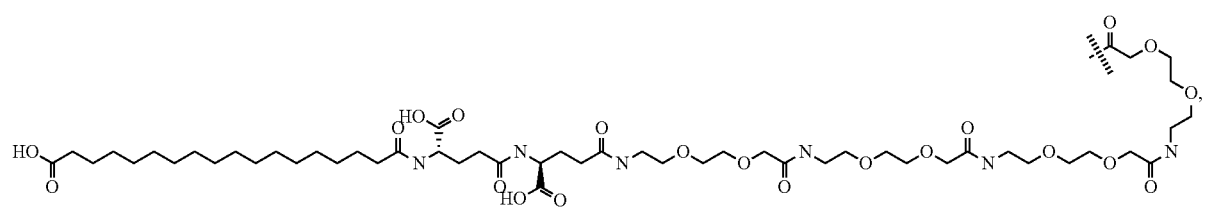
(Chem G)
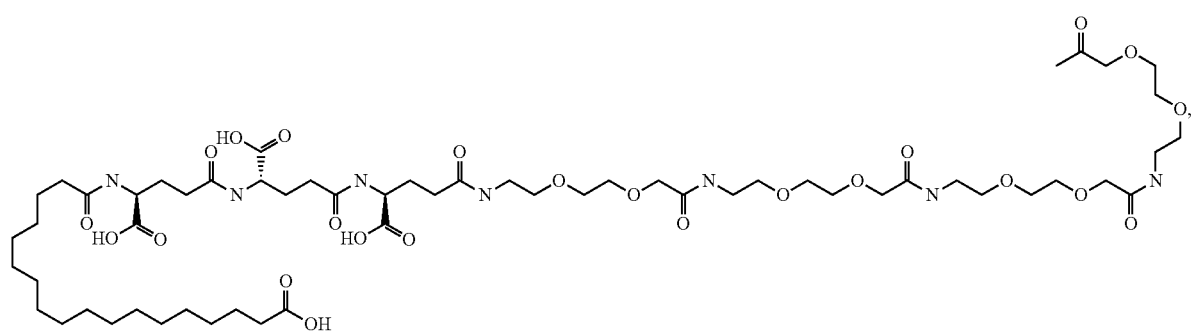
(Chem H)
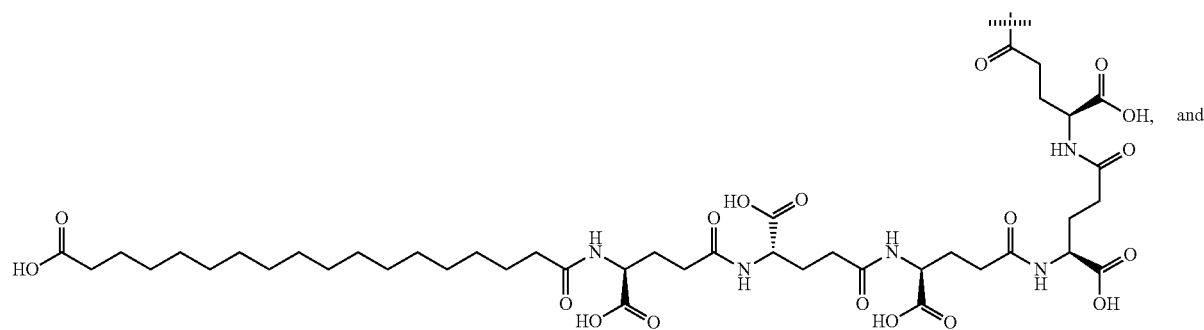
(Chem I)
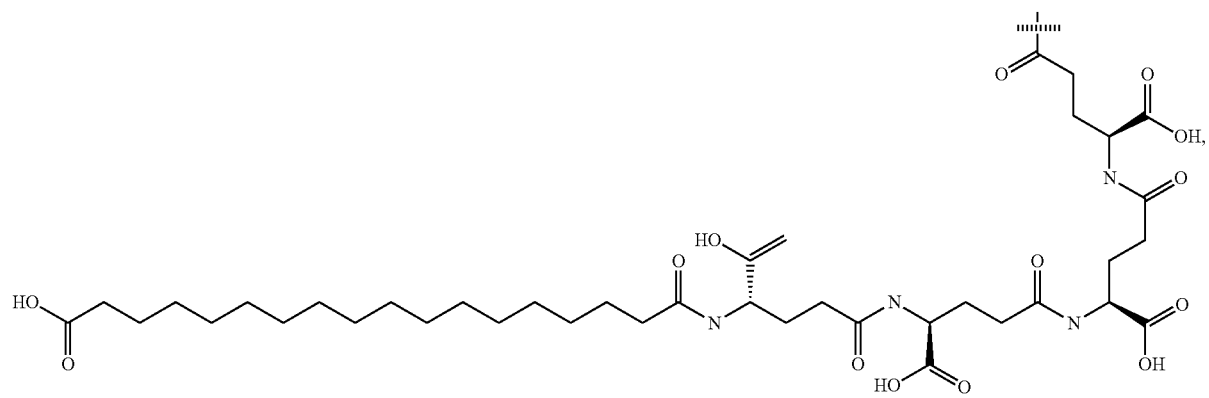
(Chem J)

wherein the dotted line denotes the attachment of the modifying group to the N-terminal alpha-amine of the CNP peptide via an amide bond.
7. The CNP compound according to claim 1, wherein the CNP compound is selected from the group consisting of:
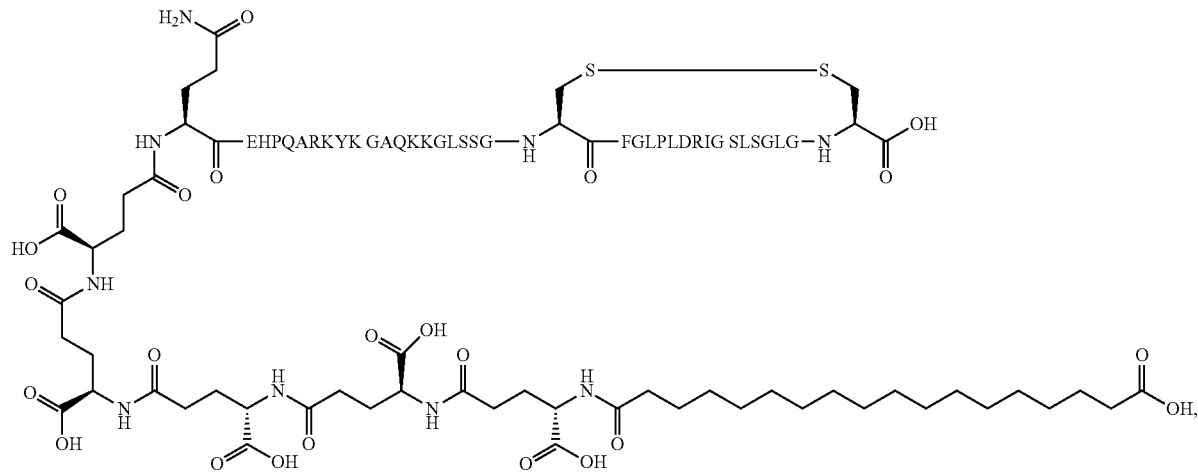
(Formula II)
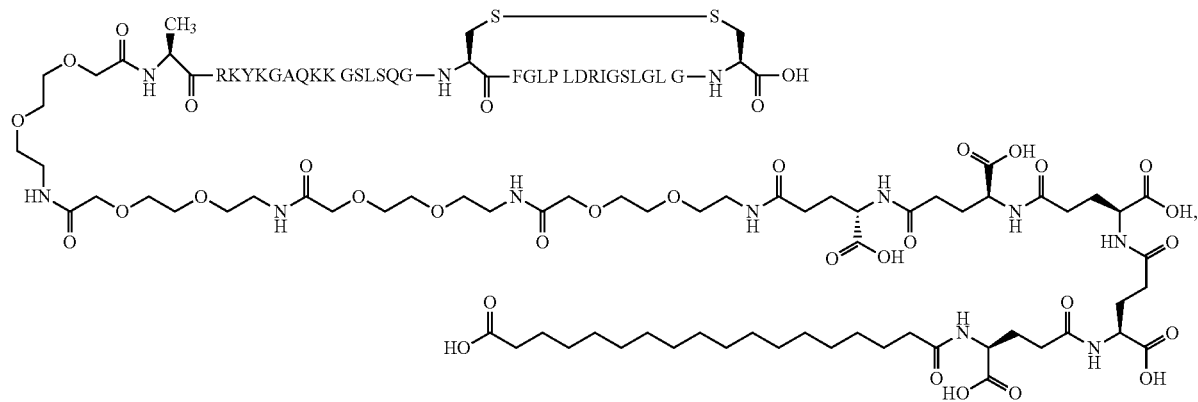
(Formula IV)
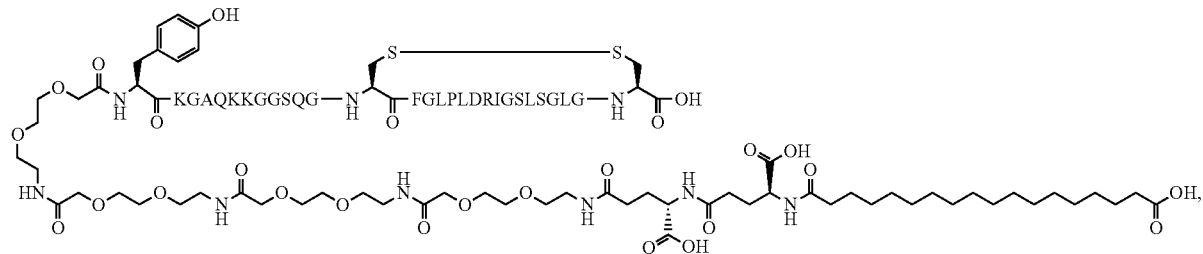
(Formula V)

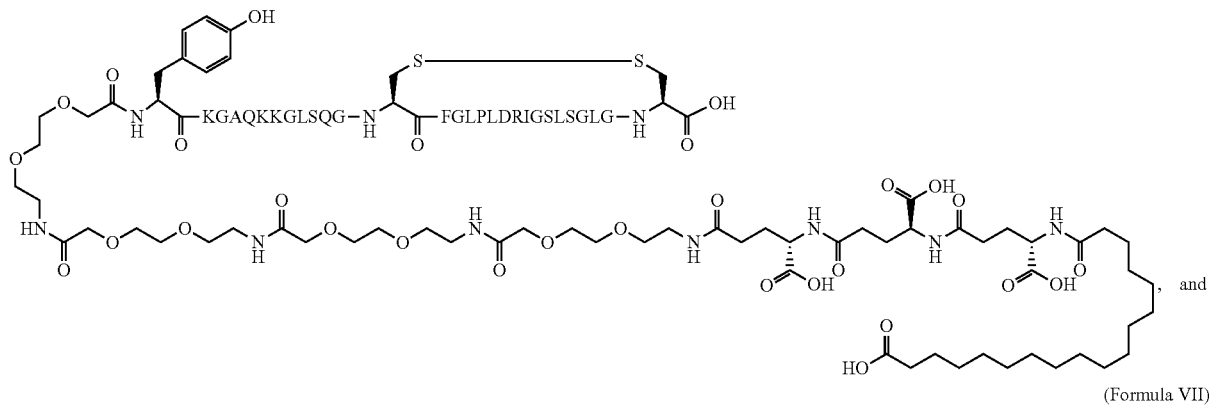
(Formula VI)
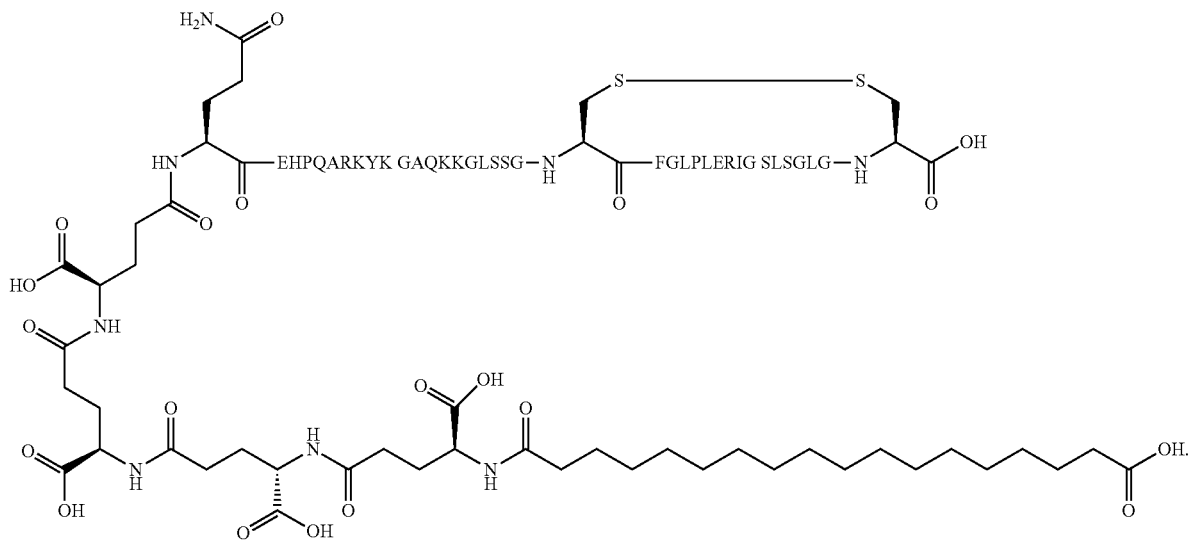
(Formula VII)
8. The CNP compound according to claim 7, wherein the CNP compound is
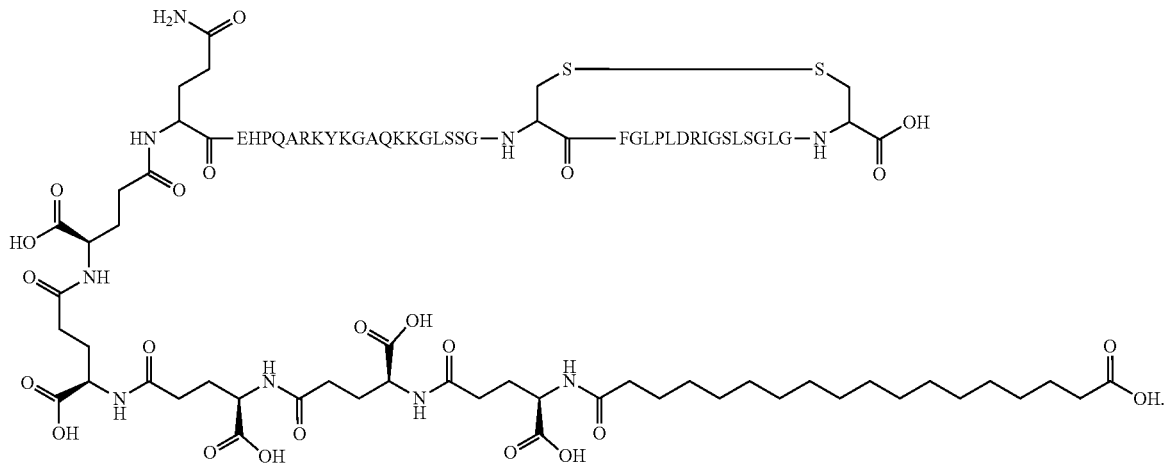
(Formula II)

9. The CNP compound according to claim 7, wherein the CNP compound is
(Formula IV)
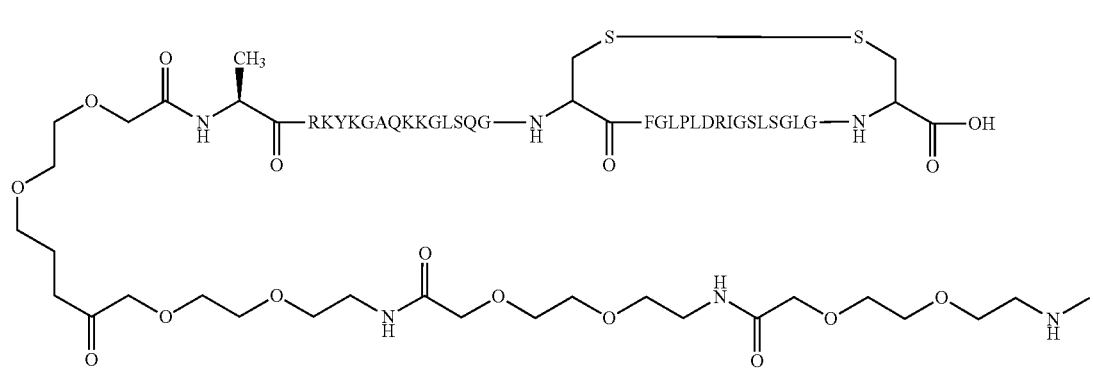
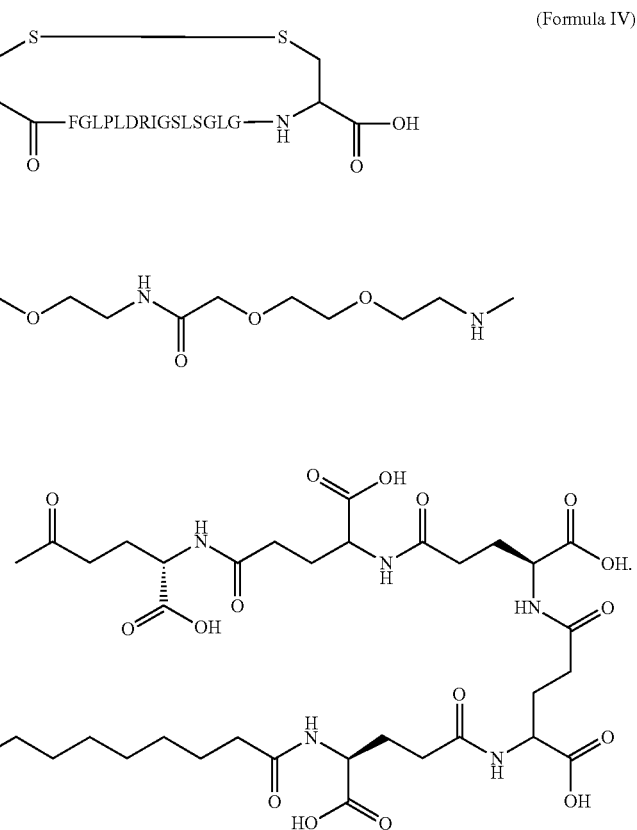
10. The CNP compound according to claim 7, wherein the CNP compound is
(Formula V)
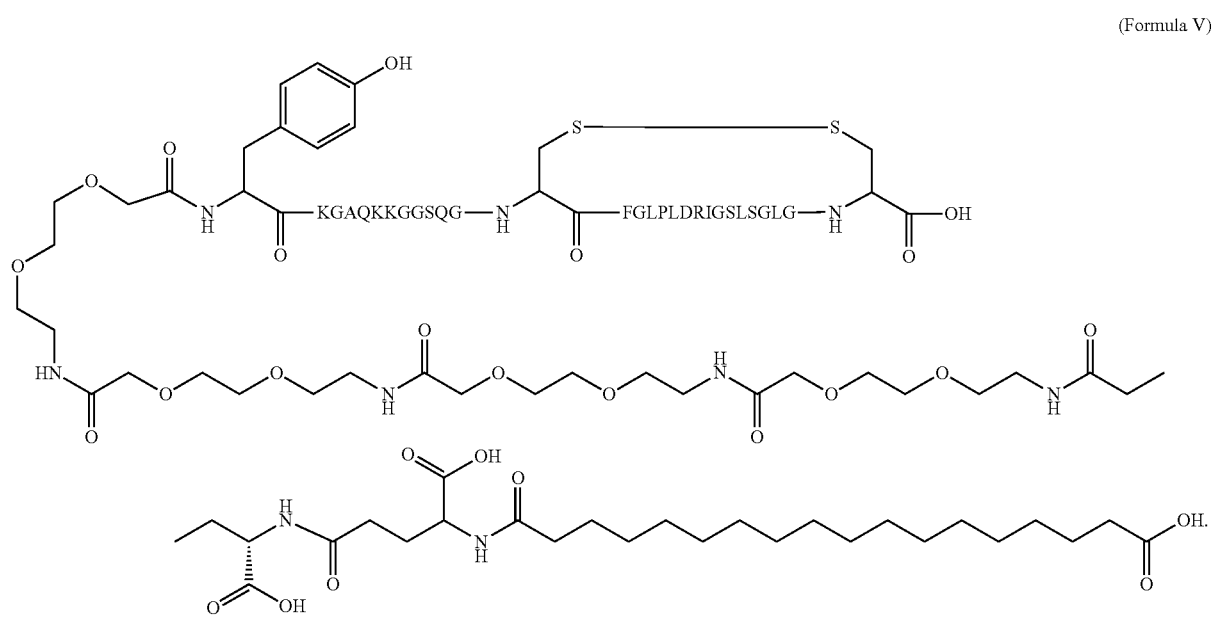

11. The CNP compound according to claim 7, wherein the CNP compound is
(Formula VI)
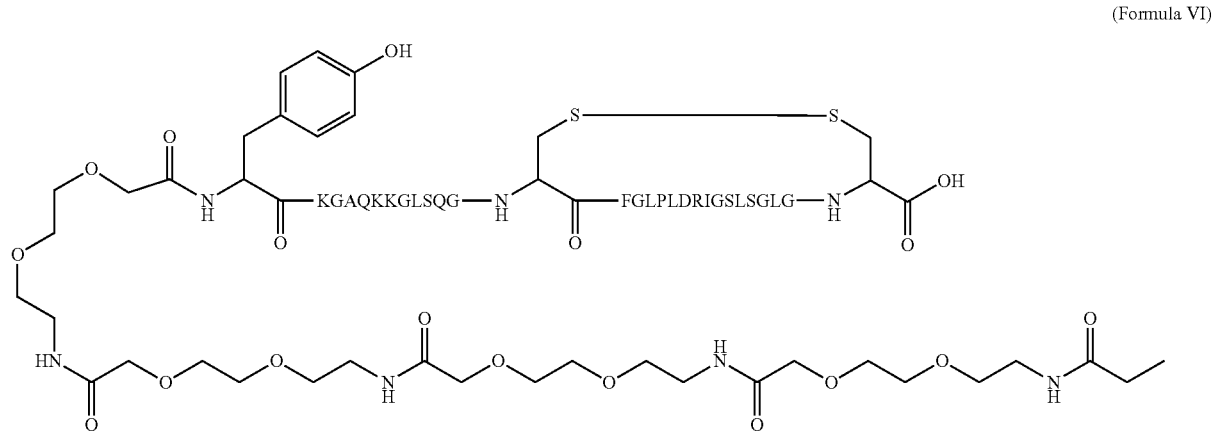
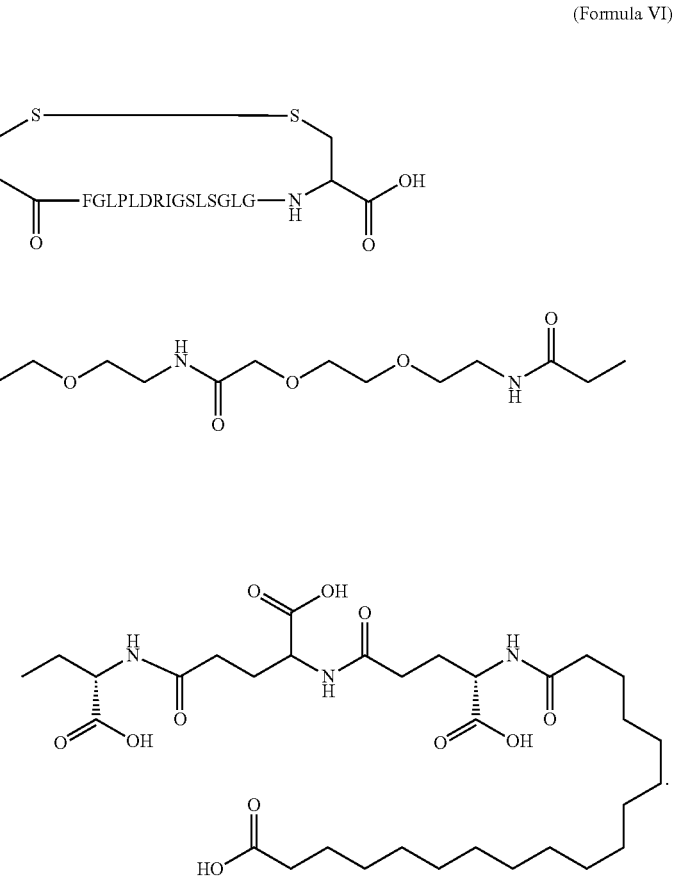
12. The CNP compound according to claim 7, wherein the CNP compound is
(Formula VII)
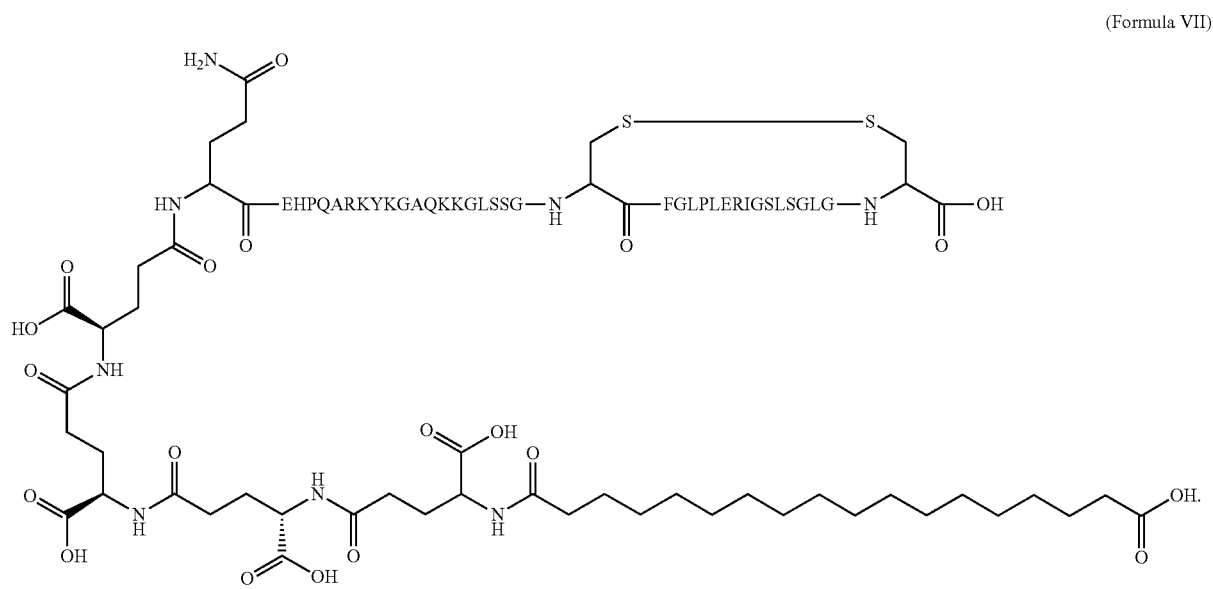

13. A CNP compound that is
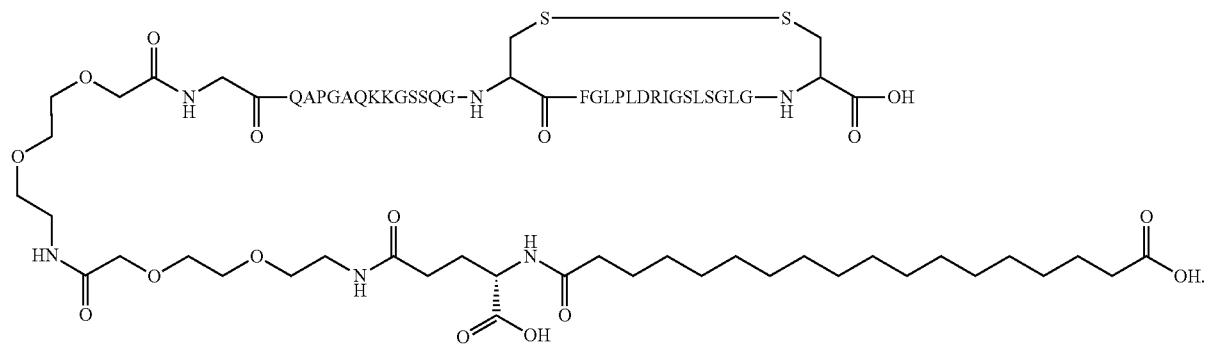
(Formula III)
* * * * *

SEQUENCE LISTING

```
Sequence total quantity: 236
SEQ ID NO: 1           moltype = AA   length = 22
FEATURE                Location/Qualifiers
source                 1..22
                       mol_type = protein
                       organism = Homo sapiens
SEQUENCE: 1
GLSKGCFGLK LDRIGSMSGL GC                                                22

SEQ ID NO: 2           moltype = AA   length = 37
FEATURE                Location/Qualifiers
source                 1..37
                       mol_type = protein
                       organism = Homo sapiens
SEQUENCE: 2
QEHPNARKYK GANKKGLSKG CFGLKLDRIG SMSGLGC                                37

SEQ ID NO: 3           moltype = AA   length = 33
FEATURE                Location/Qualifiers
source                 1..33
                       mol_type = protein
                       organism = Synthetic construct
SITE                   28
                       note = Nle
SEQUENCE: 3
QARKYKGAQK KGLSKGCFGL KLDRIGSXSG LGC                                    33

SEQ ID NO: 4           moltype = AA   length = 32
FEATURE                Location/Qualifiers
source                 1..32
                       mol_type = protein
                       organism = Synthetic construct
SEQUENCE: 4
ARKYKGAQKK GLSKGCFGLK LERIGSLSGL GC                                     32

SEQ ID NO: 5           moltype = AA   length = 29
FEATURE                Location/Qualifiers
source                 1..29
                       mol_type = protein
                       organism = Synthetic construct
SEQUENCE: 5
EHGAQKKGLS KGCFGLKLDR IGSLSGLGC                                         29

SEQ ID NO: 6           moltype = AA   length = 29
FEATURE                Location/Qualifiers
source                 1..29
                       mol_type = protein
                       organism = Synthetic construct
SITE                   24
```

```
                        note = Nle
SEQUENCE: 6
YKGANKKGLS KGCFGLKLDR IGSXSGLGC                                  29

SEQ ID NO: 7            moltype = AA   length = 33
FEATURE                 Location/Qualifiers
source                  1..33
                        mol_type = protein
                        organism = Synthetic construct
SITE                    28
                        note = Nle
SEQUENCE: 7
NARKYKGANK SGLSSGCFGL KLDRIGSXSG LGC                             33

SEQ ID NO: 8            moltype = AA   length = 27
FEATURE                 Location/Qualifiers
source                  1..27
                        mol_type = protein
                        organism = Synthetic construct
SITE                    22
                        note = Nle
SEQUENCE: 8
GANKKGLSKG CFGLKLDRIG SXSGLGC                                    27

SEQ ID NO: 9            moltype = AA   length = 27
FEATURE                 Location/Qualifiers
source                  1..27
                        mol_type = protein
                        organism = Synthetic construct
SITE                    22
                        note = Nle
SEQUENCE: 9
GAQKKGLSKG CFGLKLDRIG SXSGLGC                                    27

SEQ ID NO: 10           moltype = AA   length = 29
FEATURE                 Location/Qualifiers
source                  1..29
                        mol_type = protein
                        organism = Synthetic construct
SEQUENCE: 10
YEGAQKKGLS KGCFGLKLDR IGSLSGLGC                                  29

SEQ ID NO: 11           moltype = AA   length = 29
FEATURE                 Location/Qualifiers
source                  1..29
                        mol_type = protein
                        organism = Synthetic construct
SEQUENCE: 11
EEGAQKKGLS KGCFGLKLDR IGSLSGLGC                                  29

SEQ ID NO: 12           moltype = AA   length = 29
FEATURE                 Location/Qualifiers
source                  1..29
                        mol_type = protein
                        organism = Synthetic construct
SEQUENCE: 12
YEGAQEKGLS KGCFGLKLDR IGSLSGLGC                                  29

SEQ ID NO: 13           moltype = AA   length = 29
FEATURE                 Location/Qualifiers
source                  1..29
                        mol_type = protein
                        organism = Synthetic construct
SEQUENCE: 13
YEGAQKKGLS SGCFGLKLDR IGSLSGLGC                                  29

SEQ ID NO: 14           moltype = AA   length = 29
FEATURE                 Location/Qualifiers
source                  1..29
                        mol_type = protein
                        organism = Synthetic construct
SEQUENCE: 14
YEGAQKKGLS KGCFGLPLDR IGSLSGLGC                                  29

SEQ ID NO: 15           moltype = AA   length = 29
FEATURE                 Location/Qualifiers
source                  1..29
                        mol_type = protein
                        organism = Synthetic construct
```

```
SEQUENCE: 15
YEGAQEKGLS KGCFGLPLDR IGSLSGLGC                                          29

SEQ ID NO: 16           moltype = AA   length = 29
FEATURE                 Location/Qualifiers
source                  1..29
                        mol_type = protein
                        organism = Synthetic construct
SEQUENCE: 16
YEGAQKKGLS SGCFGLPLDR IGSLSGLGC                                          29

SEQ ID NO: 17           moltype = AA   length = 29
FEATURE                 Location/Qualifiers
source                  1..29
                        mol_type = protein
                        organism = Synthetic construct
SEQUENCE: 17
YEGAQEKGLS SGCFGLPLDR IGSLSGLGC                                          29

SEQ ID NO: 18           moltype = AA   length = 29
FEATURE                 Location/Qualifiers
source                  1..29
                        mol_type = protein
                        organism = Synthetic construct
SEQUENCE: 18
EKGAQEKGLS KGCFGLKLDR IGSLSGLGC                                          29

SEQ ID NO: 19           moltype = AA   length = 29
FEATURE                 Location/Qualifiers
source                  1..29
                        mol_type = protein
                        organism = Synthetic construct
SEQUENCE: 19
EKGAQEKGLS SGCFGLKLDR IGSLSGLGC                                          29

SEQ ID NO: 20           moltype = AA   length = 29
FEATURE                 Location/Qualifiers
source                  1..29
                        mol_type = protein
                        organism = Synthetic construct
SEQUENCE: 20
EQGAQEKGLS KGCFGLKLDR IGSLSGLGC                                          29

SEQ ID NO: 21           moltype = AA   length = 29
FEATURE                 Location/Qualifiers
source                  1..29
                        mol_type = protein
                        organism = Synthetic construct
SEQUENCE: 21
YKGAQEKGLS KGCFGLKLDR IGSLSGLGC                                          29

SEQ ID NO: 22           moltype = AA   length = 29
FEATURE                 Location/Qualifiers
source                  1..29
                        mol_type = protein
                        organism = Synthetic construct
SEQUENCE: 22
YKGAQKKGLS SGCFGLPLDR IGSLSGLGC                                          29

SEQ ID NO: 23           moltype = AA   length = 29
FEATURE                 Location/Qualifiers
source                  1..29
                        mol_type = protein
                        organism = Synthetic construct
SEQUENCE: 23
EHGAQEKGLS KGCFGLKLDR IGSLSGLGC                                          29

SEQ ID NO: 24           moltype = AA   length = 29
FEATURE                 Location/Qualifiers
source                  1..29
                        mol_type = protein
                        organism = Synthetic construct
SEQUENCE: 24
YHGAQEKGLS KGCFGLKLDR IGSLSGLGC                                          29

SEQ ID NO: 25           moltype = AA   length = 29
FEATURE                 Location/Qualifiers
source                  1..29
                        mol_type = protein
```

```
                         organism = Synthetic construct
SEQUENCE: 25
YHGAQEKGLS KGCFGLPLDR IGSLSGLGC                                           29

SEQ ID NO: 26            moltype = AA  length = 29
FEATURE                  Location/Qualifiers
source                   1..29
                         mol_type = protein
                         organism = Synthetic construct
SEQUENCE: 26
YHGAQKKGLS SGCFGLPLDR IGSLSGLGC                                           29

SEQ ID NO: 27            moltype = AA  length = 29
FEATURE                  Location/Qualifiers
source                   1..29
                         mol_type = protein
                         organism = Synthetic construct
SEQUENCE: 27
YHGAQEKGLS SGCFGLPLDR IGSLSGLGC                                           29

SEQ ID NO: 28            moltype = AA  length = 29
FEATURE                  Location/Qualifiers
source                   1..29
                         mol_type = protein
                         organism = Synthetic construct
SEQUENCE: 28
YEGAEKKGLS QGCFGLPLDR IGSLSGLGC                                           29

SEQ ID NO: 29            moltype = AA  length = 28
FEATURE                  Location/Qualifiers
source                   1..28
                         mol_type = protein
                         organism = Synthetic construct
SEQUENCE: 29
EGAQEKGLSS GCFGLPLDRI GSLSGLGC                                            28

SEQ ID NO: 30            moltype = AA  length = 28
FEATURE                  Location/Qualifiers
source                   1..28
                         mol_type = protein
                         organism = Synthetic construct
SEQUENCE: 30
EGAQKEGLSS GCFGLPLDRI GSLSGLGC                                            28

SEQ ID NO: 31            moltype = AA  length = 29
FEATURE                  Location/Qualifiers
source                   1..29
                         mol_type = protein
                         organism = Synthetic construct
SEQUENCE: 31
YEGAQKEGLS SGCFGLPLDR IGSLSGLGC                                           29

SEQ ID NO: 32            moltype = AA  length = 29
FEATURE                  Location/Qualifiers
source                   1..29
                         mol_type = protein
                         organism = Synthetic construct
SEQUENCE: 32
YHGAQKTGLS SGCFGLPLDR IGSLSGLGC                                           29

SEQ ID NO: 33            moltype = AA  length = 29
FEATURE                  Location/Qualifiers
source                   1..29
                         mol_type = protein
                         organism = Synthetic construct
SEQUENCE: 33
YHGAQKTGVS SGCFGLPLDR IGSLSGLGC                                           29

SEQ ID NO: 34            moltype = AA  length = 29
FEATURE                  Location/Qualifiers
source                   1..29
                         mol_type = protein
                         organism = Synthetic construct
SEQUENCE: 34
YHGAQHTGLS SGCFGLPLDR IGSLSGLGC                                           29

SEQ ID NO: 35            moltype = AA  length = 29
FEATURE                  Location/Qualifiers
source                   1..29
```

```
                        mol_type = protein
                        organism = Synthetic construct
SEQUENCE: 35
YKGAQHTGLS SGCFGLPLDR IGSLSGLGC                                          29

SEQ ID NO: 36           moltype = AA  length = 29
FEATURE                 Location/Qualifiers
source                  1..29
                        mol_type = protein
                        organism = Synthetic construct
SEQUENCE: 36
EHGAQKKGLS KGCFGLPLDR IGSLSGLGC                                          29

SEQ ID NO: 37           moltype = AA  length = 29
FEATURE                 Location/Qualifiers
source                  1..29
                        mol_type = protein
                        organism = Synthetic construct
SEQUENCE: 37
EHGAQKKGLS SGCFGLPLDR IGSLSGLGC                                          29

SEQ ID NO: 38           moltype = AA  length = 29
FEATURE                 Location/Qualifiers
source                  1..29
                        mol_type = protein
                        organism = Synthetic construct
SEQUENCE: 38
EHGAQKKGVS SGCFGLPLDR IGSLSGLGC                                          29

SEQ ID NO: 39           moltype = AA  length = 29
FEATURE                 Location/Qualifiers
source                  1..29
                        mol_type = protein
                        organism = Synthetic construct
SEQUENCE: 39
EHGAQKTGVS SGCFGLPLDR IGSLSGLGC                                          29

SEQ ID NO: 40           moltype = AA  length = 29
FEATURE                 Location/Qualifiers
source                  1..29
                        mol_type = protein
                        organism = Synthetic construct
SEQUENCE: 40
YHGAQHHGLS KGCFGLKLER IGSLSGLGC                                          29

SEQ ID NO: 41           moltype = AA  length = 29
FEATURE                 Location/Qualifiers
source                  1..29
                        mol_type = protein
                        organism = Synthetic construct
SEQUENCE: 41
YKGAQHHGLS QGCFGLKLER IGSLSGLGC                                          29

SEQ ID NO: 42           moltype = AA  length = 29
FEATURE                 Location/Qualifiers
source                  1..29
                        mol_type = protein
                        organism = Synthetic construct
SEQUENCE: 42
YEGAQKKGLS SGCFGLPLER IGSLSGLGC                                          29

SEQ ID NO: 43           moltype = AA  length = 28
FEATURE                 Location/Qualifiers
source                  1..28
                        mol_type = protein
                        organism = Synthetic construct
SEQUENCE: 43
EGAQKKGLSS GCFGLPLDRI GSLSGLGC                                           28

SEQ ID NO: 44           moltype = AA  length = 29
FEATURE                 Location/Qualifiers
source                  1..29
                        mol_type = protein
                        organism = Synthetic construct
SEQUENCE: 44
YKGAQHHGLS QGCFGLKLDR IGSLSGLGC                                          29

SEQ ID NO: 45           moltype = AA  length = 29
FEATURE                 Location/Qualifiers
```

-continued

```
source                   1..29
                         mol_type = protein
                         organism = Synthetic construct
SEQUENCE: 45
YKGAQHHGLS QGCFGLPLDR IGSLSGLGC                                    29

SEQ ID NO: 46            moltype = AA   length = 29
FEATURE                  Location/Qualifiers
source                   1..29
                         mol_type = protein
                         organism = Synthetic construct
SEQUENCE: 46
YHGAQHHGLS KGCFGLKLDR IGSLSGLGC                                    29

SEQ ID NO: 47            moltype = AA   length = 29
FEATURE                  Location/Qualifiers
source                   1..29
                         mol_type = protein
                         organism = Synthetic construct
SEQUENCE: 47
YHGAQHHGLS KGCFGLPLDR IGSLSGLGC                                    29

SEQ ID NO: 48            moltype = AA   length = 27
FEATURE                  Location/Qualifiers
source                   1..27
                         mol_type = protein
                         organism = Synthetic construct
SEQUENCE: 48
GAQKKGLSHG CFGLPLDRIG SLSGLGC                                      27

SEQ ID NO: 49            moltype = AA   length = 27
FEATURE                  Location/Qualifiers
source                   1..27
                         mol_type = protein
                         organism = Synthetic construct
SEQUENCE: 49
GAQKKGLHSG CFGLPLDRIG SLSGLGC                                      27

SEQ ID NO: 50            moltype = AA   length = 32
FEATURE                  Location/Qualifiers
source                   1..32
                         mol_type = protein
                         organism = Synthetic construct
SEQUENCE: 50
ARKYHGAQHT GLSSGCFGLP LDRIGSLSGL GC                                32

SEQ ID NO: 51            moltype = AA   length = 32
FEATURE                  Location/Qualifiers
source                   1..32
                         mol_type = protein
                         organism = Synthetic construct
SEQUENCE: 51
ARKYHGAQHT GVSSGCFGLP LDRIGSLSGL GC                                32

SEQ ID NO: 52            moltype = AA   length = 32
FEATURE                  Location/Qualifiers
source                   1..32
                         mol_type = protein
                         organism = Synthetic construct
SEQUENCE: 52
ARKYHGAQKT GVSSGCFGLP LDRIGSLSGL GC                                32

SEQ ID NO: 53            moltype = AA   length = 32
FEATURE                  Location/Qualifiers
source                   1..32
                         mol_type = protein
                         organism = Synthetic construct
SEQUENCE: 53
ARKEHGAQKT GVSSGCFGLP LDRIGSLSGL GC                                32

SEQ ID NO: 54            moltype = AA   length = 32
FEATURE                  Location/Qualifiers
source                   1..32
                         mol_type = protein
                         organism = Synthetic construct
SEQUENCE: 54
ARKEHGAQHT GVSSGCFGLP LDRIGSLSGL GC                                32

SEQ ID NO: 55            moltype = AA   length = 29
```

```
FEATURE                 Location/Qualifiers
source                  1..29
                        mol_type = protein
                        organism = Synthetic construct
SEQUENCE: 55
YEGAQKKGGS KGCFGLPLDR IGSLSGLGC                                          29

SEQ ID NO: 56           moltype = AA  length = 32
FEATURE                 Location/Qualifiers
source                  1..32
                        mol_type = protein
                        organism = Synthetic construct
SEQUENCE: 56
GGGYEGAQKK GLSSGCFGLP LDRIGSLSGL GC                                      32

SEQ ID NO: 57           moltype = AA  length = 37
FEATURE                 Location/Qualifiers
source                  1..37
                        mol_type = protein
                        organism = Synthetic construct
SEQUENCE: 57
QEHPQARSYE GAQKKGLSSG CFGLPLDRIG SLSGLGC                                 37

SEQ ID NO: 58           moltype = AA  length = 37
FEATURE                 Location/Qualifiers
source                  1..37
                        mol_type = protein
                        organism = Synthetic construct
SEQUENCE: 58
QEHPEARSYE GAQKKGLSSG CFGLPLDRIG SLSGLGC                                 37

SEQ ID NO: 59           moltype = AA  length = 37
FEATURE                 Location/Qualifiers
source                  1..37
                        mol_type = protein
                        organism = Synthetic construct
SEQUENCE: 59
QEHPQAHKYH GAQHHGSSQG CFGLPLDRIG SLSGLGC                                 37

SEQ ID NO: 60           moltype = AA  length = 37
FEATURE                 Location/Qualifiers
source                  1..37
                        mol_type = protein
                        organism = Synthetic construct
SEQUENCE: 60
QEHPQAHKYK GAQKKGLSQG CFGLPLDRIG SLSGLGC                                 37

SEQ ID NO: 61           moltype = AA  length = 37
FEATURE                 Location/Qualifiers
source                  1..37
                        mol_type = protein
                        organism = Synthetic construct
SEQUENCE: 61
QEHPQAHKYH GAQKHGSSQG CFGLPLDRIG SLSGLGC                                 37

SEQ ID NO: 62           moltype = AA  length = 31
FEATURE                 Location/Qualifiers
source                  1..31
                        mol_type = protein
                        organism = Synthetic construct
SEQUENCE: 62
GQAPGAQKKG SSQGCFGLPL DRIGSLSGLG C                                       31

SEQ ID NO: 63           moltype = AA  length = 32
FEATURE                 Location/Qualifiers
source                  1..32
                        mol_type = protein
                        organism = Synthetic construct
SEQUENCE: 63
ARKYEGAQKK GLSKGCFGLP LDRIGSLSGL GC                                      32

SEQ ID NO: 64           moltype = AA  length = 32
FEATURE                 Location/Qualifiers
source                  1..32
                        mol_type = protein
                        organism = Synthetic construct
SEQUENCE: 64
ARKYKGAQKK GLSSGCFGLP LDRIGSLSGL GC                                      32
```

```
SEQ ID NO: 65          moltype = AA   length = 32
FEATURE                Location/Qualifiers
source                 1..32
                       mol_type = protein
                       organism = Synthetic construct
SEQUENCE: 65
GGGYKGAQKK GLSSGCFGLP LDRIGSLSGL GC                                  32

SEQ ID NO: 66          moltype = AA   length = 32
FEATURE                Location/Qualifiers
source                 1..32
                       mol_type = protein
                       organism = Synthetic construct
SEQUENCE: 66
GGGYKGAQKK GLSKGCFGLP LDRIGSLSGL GC                                  32

SEQ ID NO: 67          moltype = AA   length = 37
FEATURE                Location/Qualifiers
source                 1..37
                       mol_type = protein
                       organism = Synthetic construct
SEQUENCE: 67
QEHPQARKYK GAQKKGLSSG CFGLPLDRIG SLSGLGC                             37

SEQ ID NO: 68          moltype = AA   length = 37
FEATURE                Location/Qualifiers
source                 1..37
                       mol_type = protein
                       organism = Synthetic construct
SEQUENCE: 68
QEHPQARKYE GAQKKGLSSG CFGLPLDRIG SLSGLGC                             37

SEQ ID NO: 69          moltype = AA   length = 29
FEATURE                Location/Qualifiers
source                 1..29
                       mol_type = protein
                       organism = Synthetic construct
SEQUENCE: 69
YEGAQKKGLS QGCFGLPLDR IGSLSGLGC                                      29

SEQ ID NO: 70          moltype = AA   length = 37
FEATURE                Location/Qualifiers
source                 1..37
                       mol_type = protein
                       organism = Synthetic construct
SEQUENCE: 70
QEHPQARKYE GAQKKGLSQG CFGLPLDRIG SLSGLGC                             37

SEQ ID NO: 71          moltype = AA   length = 37
FEATURE                Location/Qualifiers
source                 1..37
                       mol_type = protein
                       organism = Synthetic construct
SEQUENCE: 71
QEHPQAAKYE GAQKKGLSQG CFGLPLDRIG SLSGLGC                             37

SEQ ID NO: 72          moltype = AA   length = 37
FEATURE                Location/Qualifiers
source                 1..37
                       mol_type = protein
                       organism = Synthetic construct
SEQUENCE: 72
QEHPQARHYK GAQKKGSSQG CFGLPLDRIG SLSGLGC                             37

SEQ ID NO: 73          moltype = AA   length = 37
FEATURE                Location/Qualifiers
source                 1..37
                       mol_type = protein
                       organism = Synthetic construct
SEQUENCE: 73
QEHPQAHKYK GAQKKGGSQG CFGLPLDRIG SLSGLGC                             37

SEQ ID NO: 74          moltype = AA   length = 37
FEATURE                Location/Qualifiers
source                 1..37
                       mol_type = protein
                       organism = Synthetic construct
SEQUENCE: 74
QEHPQARKYK GAQKKGLSKG CFGLKLDRIG SLSGLGC                             37
```

```
SEQ ID NO: 75            moltype = AA  length = 37
FEATURE                  Location/Qualifiers
source                   1..37
                         mol_type = protein
                         organism = Synthetic construct
SEQUENCE: 75
QEHPQARKYK GAQKKGLSQG CFGLPLDRIG SLSGLGC                                  37

SEQ ID NO: 76            moltype = AA  length = 37
FEATURE                  Location/Qualifiers
source                   1..37
                         mol_type = protein
                         organism = Synthetic construct
SEQUENCE: 76
QEHPQARKYK GAQKKGGSQG CFGLPLDRIG SLSGLGC                                  37

SEQ ID NO: 77            moltype = AA  length = 32
FEATURE                  Location/Qualifiers
source                   1..32
                         mol_type = protein
                         organism = Synthetic construct
SEQUENCE: 77
ARKYKGAQKK GLSQGCFGLP LDRIGSLSGL GC                                       32

SEQ ID NO: 78            moltype = AA  length = 32
FEATURE                  Location/Qualifiers
source                   1..32
                         mol_type = protein
                         organism = Synthetic construct
SEQUENCE: 78
ARKYHGAQHT GVSKGCFGLP LDRIGSLSGL GC                                       32

SEQ ID NO: 79            moltype = AA  length = 32
FEATURE                  Location/Qualifiers
source                   1..32
                         mol_type = protein
                         organism = Synthetic construct
SEQUENCE: 79
ARKYKGAQKT GVSSGCFGLP LDRIGSLSGL GC                                       32

SEQ ID NO: 80            moltype = AA  length = 32
FEATURE                  Location/Qualifiers
source                   1..32
                         mol_type = protein
                         organism = Synthetic construct
SEQUENCE: 80
ARKYHGAQKK GVSSGCFGLP LDRIGSLSGL GC                                       32

SEQ ID NO: 81            moltype = AA  length = 32
FEATURE                  Location/Qualifiers
source                   1..32
                         mol_type = protein
                         organism = Synthetic construct
SEQUENCE: 81
ARKYHGAQKT GVSKGCFGLP LDRIGSLSGL GC                                       32

SEQ ID NO: 82            moltype = AA  length = 32
FEATURE                  Location/Qualifiers
source                   1..32
                         mol_type = protein
                         organism = Synthetic construct
SEQUENCE: 82
ARKYKGAQKT GVSKGCFGLP LDRIGSLSGL GC                                       32

SEQ ID NO: 83            moltype = AA  length = 29
FEATURE                  Location/Qualifiers
source                   1..29
                         mol_type = protein
                         organism = Synthetic construct
SEQUENCE: 83
YHGAQKTGVS KGCFGLPLDR IGSLSGLGC                                           29

SEQ ID NO: 84            moltype = AA  length = 32
FEATURE                  Location/Qualifiers
source                   1..32
                         mol_type = protein
                         organism = Synthetic construct
SEQUENCE: 84
```

```
ARKYHGAQKS GLSQGCFGLP LDRIGSLSGL GC                              32

SEQ ID NO: 85           moltype = AA   length = 29
FEATURE                 Location/Qualifiers
source                  1..29
                        mol_type = protein
                        organism = Synthetic construct
SEQUENCE: 85
YEGAQKKGGS HGCFGLPLDR IGSLSGLGC                                  29

SEQ ID NO: 86           moltype = AA   length = 32
FEATURE                 Location/Qualifiers
source                  1..32
                        mol_type = protein
                        organism = Synthetic construct
SEQUENCE: 86
ARKYEGAQHK GGSQGCFGLP LDRIGSLSGL GC                              32

SEQ ID NO: 87           moltype = AA   length = 29
FEATURE                 Location/Qualifiers
source                  1..29
                        mol_type = protein
                        organism = Synthetic construct
SEQUENCE: 87
YHGAQKKGGS QGCFGLPLDR IGSLSGLGC                                  29

SEQ ID NO: 88           moltype = AA   length = 29
FEATURE                 Location/Qualifiers
source                  1..29
                        mol_type = protein
                        organism = Synthetic construct
SEQUENCE: 88
YKGAQKKGGS QGCFGLPLDR IGSLSGLGC                                  29

SEQ ID NO: 89           moltype = AA   length = 29
FEATURE                 Location/Qualifiers
source                  1..29
                        mol_type = protein
                        organism = Synthetic construct
SEQUENCE: 89
YKGAQKKGVS QGCFGLPLDR IGSLSGLGC                                  29

SEQ ID NO: 90           moltype = AA   length = 29
FEATURE                 Location/Qualifiers
source                  1..29
                        mol_type = protein
                        organism = Synthetic construct
SEQUENCE: 90
YHGAQKKGVS QGCFGLPLDR IGSLSGLGC                                  29

SEQ ID NO: 91           moltype = AA   length = 37
FEATURE                 Location/Qualifiers
source                  1..37
                        mol_type = protein
                        organism = Synthetic construct
SEQUENCE: 91
QEHPQARKYE GAQKKGLSKG CFGLPLDRIG SLSGLGC                         37

SEQ ID NO: 92           moltype = AA   length = 32
FEATURE                 Location/Qualifiers
source                  1..32
                        mol_type = protein
                        organism = Synthetic construct
SEQUENCE: 92
ARKYHGAQKK GVSSGCFGLP LERIGSLSGL GC                              32

SEQ ID NO: 93           moltype = AA   length = 39
FEATURE                 Location/Qualifiers
source                  1..39
                        mol_type = protein
                        organism = Synthetic construct
SEQUENCE: 93
GQAPGQAPGQ APGAQKKGSS QGCFGLPLDR IGSLSGLGC                       39

SEQ ID NO: 94           moltype = AA   length = 35
FEATURE                 Location/Qualifiers
source                  1..35
                        mol_type = protein
                        organism = Synthetic construct
```

```
SEQUENCE: 94
GQAPGQAPGA QKKGSSQGCF GLPLDRIGSL SGLGC                                35

SEQ ID NO: 95           moltype = AA  length = 36
FEATURE                 Location/Qualifiers
source                  1..36
                        mol_type = protein
                        organism = Synthetic construct
SEQUENCE: 95
GQAPARKYKG AQKKGSSQGC FGLPLDRIGS LSGLGC                               36

SEQ ID NO: 96           moltype = AA  length = 32
FEATURE                 Location/Qualifiers
source                  1..32
                        mol_type = protein
                        organism = Synthetic construct
SEQUENCE: 96
ARKYKGAQKK GLSKGCFGLP LDRIGSLSGL GC                                   32

SEQ ID NO: 97           moltype = AA  length = 29
FEATURE                 Location/Qualifiers
source                  1..29
                        mol_type = protein
                        organism = Synthetic construct
SEQUENCE: 97
YHGAQKKGLS QGCFGLPLDR IGSLSGLGC                                       29

SEQ ID NO: 98           moltype = AA  length = 32
FEATURE                 Location/Qualifiers
source                  1..32
                        mol_type = protein
                        organism = Synthetic construct
SEQUENCE: 98
ARKYKGAQKK GLSQGCFGLK LDRIGSLSGL GC                                   32

SEQ ID NO: 99           moltype = AA  length = 32
FEATURE                 Location/Qualifiers
source                  1..32
                        mol_type = protein
                        organism = Synthetic construct
SEQUENCE: 99
ARKYKGANKK GLSQGCFGLP LDRIGSLSGL GC                                   32

SEQ ID NO: 100          moltype = AA  length = 32
FEATURE                 Location/Qualifiers
source                  1..32
                        mol_type = protein
                        organism = Synthetic construct
SEQUENCE: 100
ARKYKGAQKK GLSQGCFGLP LDRIGSMSGL GC                                   32

SEQ ID NO: 101          moltype = AA  length = 37
FEATURE                 Location/Qualifiers
source                  1..37
                        mol_type = protein
                        organism = Synthetic construct
SEQUENCE: 101
QEHPQARKYK GAQKKGLSKG CFGLPLDRIG SLSGLGC                              37

SEQ ID NO: 102          moltype = AA  length = 32
FEATURE                 Location/Qualifiers
source                  1..32
                        mol_type = protein
                        organism = Synthetic construct
SEQUENCE: 102
ARKYKGAQKK GLSQGCFGLP LERIGSLSGL GC                                   32

SEQ ID NO: 103          moltype = AA  length = 29
FEATURE                 Location/Qualifiers
source                  1..29
                        mol_type = protein
                        organism = Synthetic construct
SEQUENCE: 103
YKGAQKKGLS QGCFGLPLDR IGSLSGLGC                                       29

SEQ ID NO: 104          moltype = AA  length = 37
FEATURE                 Location/Qualifiers
source                  1..37
                        mol_type = protein
```

```
                              organism = Synthetic construct
SEQUENCE: 104
QEHPQARKYK GAQKKGLSSG CFGLPLERIG SLSGLGC                              37

SEQ ID NO: 105           moltype = AA   length = 31
FEATURE                  Location/Qualifiers
source                   1..31
                         mol_type = protein
                         organism = Synthetic construct
SEQUENCE: 105
GQAPGAQKKG LSQGCFGLPL DRIGSLSGLG C                                    31

SEQ ID NO: 106           moltype = AA   length = 31
FEATURE                  Location/Qualifiers
source                   1..31
                         mol_type = protein
                         organism = Synthetic construct
SEQUENCE: 106
GQAPGAQKKG SSQGCFGLPL ERIGSLSGLG C                                    31

SEQ ID NO: 107           moltype = AA   length = 39
FEATURE                  Location/Qualifiers
source                   1..39
                         mol_type = protein
                         organism = Synthetic construct
SEQUENCE: 107
GQAPGQAPGQ APGAQKKGLS QGCFGLPLDR IGSLSGLGC                            39

SEQ ID NO: 108           moltype = AA   length = 29
FEATURE                  Location/Qualifiers
source                   1..29
                         mol_type = protein
                         organism = Synthetic construct
SEQUENCE: 108
YKGAQKKGGS QGCFGLPLER IGSLSGLGC                                       29

SEQ ID NO: 109           moltype = AA   length = 29
FEATURE                  Location/Qualifiers
source                   1..29
                         mol_type = protein
                         organism = Synthetic construct
SEQUENCE: 109
YKGAQKKGLS QGCFGLPLER IGSLSGLGC                                       29

SEQ ID NO: 110           moltype = AA   length = 42
FEATURE                  Location/Qualifiers
source                   1..42
                         mol_type = protein
                         organism = Synthetic construct
SEQUENCE: 110
EEEEEQEHPQ ARKYKGAQKK GLSSGCFGLP LDRIGSLSGL GC                        42

SEQ ID NO: 111           moltype = AA   length = 41
FEATURE                  Location/Qualifiers
source                   1..41
                         mol_type = protein
                         organism = Synthetic construct
SEQUENCE: 111
EEEEQEHPQA RKYKGAQKKG LSSGCFGLPL ERIGSLSGLG C                         41

SEQ ID NO: 112           moltype = AA   length = 27
FEATURE                  Location/Qualifiers
source                   1..27
                         mol_type = protein
                         organism = Synthetic construct
SEQUENCE: 112
GAQKKGLSQG CFGLPLDRIG SLSGLGC                                         27

SEQ ID NO: 113           moltype = AA   length = 27
FEATURE                  Location/Qualifiers
source                   1..27
                         mol_type = protein
                         organism = Synthetic construct
SEQUENCE: 113
GAQKKGLSSG CFGLPLDRIG SLSGLGC                                         27

SEQ ID NO: 114           moltype = AA   length = 27
FEATURE                  Location/Qualifiers
source                   1..27
```

```
                    mol_type = protein
                    organism = Synthetic construct
SEQUENCE: 114
GAQKKGGSQG CFGLPLDRIG SLSGLGC                                           27

SEQ ID NO: 115      moltype = AA   length = 27
FEATURE             Location/Qualifiers
source              1..27
                    mol_type = protein
                    organism = Synthetic construct
SEQUENCE: 115
GAQKKGGSSG CFGLPLDRIG SLSGLGC                                           27

SEQ ID NO: 116      moltype = AA   length = 27
FEATURE             Location/Qualifiers
source              1..27
                    mol_type = protein
                    organism = Synthetic construct
SEQUENCE: 116
GAQKKGLSQG CFGLKLDRIG SLSGLGC                                           27

SEQ ID NO: 117      moltype = AA   length = 27
FEATURE             Location/Qualifiers
source              1..27
                    mol_type = protein
                    organism = Synthetic construct
SEQUENCE: 117
GAQKKGLSSG CFGLKLDRIG SLSGLGC                                           27

SEQ ID NO: 118      moltype = AA   length = 27
FEATURE             Location/Qualifiers
source              1..27
                    mol_type = protein
                    organism = Synthetic construct
SEQUENCE: 118
GAQKKGGSQG CFGLKLDRIG SLSGLGC                                           27

SEQ ID NO: 119      moltype = AA   length = 27
FEATURE             Location/Qualifiers
source              1..27
                    mol_type = protein
                    organism = Synthetic construct
SEQUENCE: 119
GAQKKGGSSG CFGLKLDRIG SLSGLGC                                           27

SEQ ID NO: 120      moltype = AA   length = 27
FEATURE             Location/Qualifiers
source              1..27
                    mol_type = protein
                    organism = Synthetic construct
SEQUENCE: 120
GANKKGLSQG CFGLPLDRIG SLSGLGC                                           27

SEQ ID NO: 121      moltype = AA   length = 27
FEATURE             Location/Qualifiers
source              1..27
                    mol_type = protein
                    organism = Synthetic construct
SEQUENCE: 121
GANKKGLSSG CFGLPLDRIG SLSGLGC                                           27

SEQ ID NO: 122      moltype = AA   length = 27
FEATURE             Location/Qualifiers
source              1..27
                    mol_type = protein
                    organism = Synthetic construct
SEQUENCE: 122
GANKKGGSQG CFGLPLDRIG SLSGLGC                                           27

SEQ ID NO: 123      moltype = AA   length = 27
FEATURE             Location/Qualifiers
source              1..27
                    mol_type = protein
                    organism = Synthetic construct
SEQUENCE: 123
GANKKGGSSG CFGLPLDRIG SLSGLGC                                           27

SEQ ID NO: 124      moltype = AA   length = 27
FEATURE             Location/Qualifiers
```

```
source                  1..27
                        mol_type = protein
                        organism = Synthetic construct
SEQUENCE: 124
GAQKKGLSQG CFGLPLDRIG SMSGLGC                                        27

SEQ ID NO: 125          moltype = AA   length = 27
FEATURE                 Location/Qualifiers
source                  1..27
                        mol_type = protein
                        organism = Synthetic construct
SEQUENCE: 125
GAQKKGLSSG CFGLPLDRIG SMSGLGC                                        27

SEQ ID NO: 126          moltype = AA   length = 27
FEATURE                 Location/Qualifiers
source                  1..27
                        mol_type = protein
                        organism = Synthetic construct
SEQUENCE: 126
GAQKKGGSQG CFGLPLDRIG SMSGLGC                                        27

SEQ ID NO: 127          moltype = AA   length = 27
FEATURE                 Location/Qualifiers
source                  1..27
                        mol_type = protein
                        organism = Synthetic construct
SEQUENCE: 127
GAQKKGGSSG CFGLPLDRIG SMSGLGC                                        27

SEQ ID NO: 128          moltype = AA   length = 27
FEATURE                 Location/Qualifiers
source                  1..27
                        mol_type = protein
                        organism = Synthetic construct
SEQUENCE: 128
GAQKKGLSKG CFGLPLDRIG SLSGLGC                                        27

SEQ ID NO: 129          moltype = AA   length = 27
FEATURE                 Location/Qualifiers
source                  1..27
                        mol_type = protein
                        organism = Synthetic construct
SEQUENCE: 129
GAQKKGGSKG CFGLPLDRIG SLSGLGC                                        27

SEQ ID NO: 130          moltype = AA   length = 27
FEATURE                 Location/Qualifiers
source                  1..27
                        mol_type = protein
                        organism = Synthetic construct
SEQUENCE: 130
GAQKKGLSQG CFGLPLERIG SLSGLGC                                        27

SEQ ID NO: 131          moltype = AA   length = 27
FEATURE                 Location/Qualifiers
source                  1..27
                        mol_type = protein
                        organism = Synthetic construct
SEQUENCE: 131
GAQKKGLSSG CFGLPLERIG SLSGLGC                                        27

SEQ ID NO: 132          moltype = AA   length = 27
FEATURE                 Location/Qualifiers
source                  1..27
                        mol_type = protein
                        organism = Synthetic construct
SEQUENCE: 132
GANKKGLSQG CFGLPLDRIG SMSGLGC                                        27

SEQ ID NO: 133          moltype = AA   length = 27
FEATURE                 Location/Qualifiers
source                  1..27
                        mol_type = protein
                        organism = Synthetic construct
SEQUENCE: 133
GANKKGLSSG CFGLPLDRIG SMSGLGC                                        27

SEQ ID NO: 134          moltype = AA   length = 27
```

```
FEATURE                 Location/Qualifiers
source                  1..27
                        mol_type = protein
                        organism = Synthetic construct
SEQUENCE: 134
GANKKGLSQG CFGLPLERIG SMSGLGC                                          27

SEQ ID NO: 135          moltype = AA  length = 27
FEATURE                 Location/Qualifiers
source                  1..27
                        mol_type = protein
                        organism = Synthetic construct
SEQUENCE: 135
GANKKGLSSG CFGLPLERIG SMSGLGC                                          27

SEQ ID NO: 136          moltype = AA  length = 27
FEATURE                 Location/Qualifiers
source                  1..27
                        mol_type = protein
                        organism = Synthetic construct
SEQUENCE: 136
GAQKKGSSQG CFGLPLDRIG SLSGLGC                                          27

SEQ ID NO: 137          moltype = AA  length = 27
FEATURE                 Location/Qualifiers
source                  1..27
                        mol_type = protein
                        organism = Synthetic construct
SEQUENCE: 137
GAQKKGSSSG CFGLPLDRIG SLSGLGC                                          27

SEQ ID NO: 138          moltype = AA  length = 27
FEATURE                 Location/Qualifiers
source                  1..27
                        mol_type = protein
                        organism = Synthetic construct
SEQUENCE: 138
GAQKKGSSQG CFGLKLDRIG SLSGLGC                                          27

SEQ ID NO: 139          moltype = AA  length = 27
FEATURE                 Location/Qualifiers
source                  1..27
                        mol_type = protein
                        organism = Synthetic construct
SEQUENCE: 139
GAQKKGSSSG CFGLKLDRIG SLSGLGC                                          27

SEQ ID NO: 140          moltype = AA  length = 27
FEATURE                 Location/Qualifiers
source                  1..27
                        mol_type = protein
                        organism = Synthetic construct
SEQUENCE: 140
GANKKGSSQG CFGLPLDRIG SLSGLGC                                          27

SEQ ID NO: 141          moltype = AA  length = 27
FEATURE                 Location/Qualifiers
source                  1..27
                        mol_type = protein
                        organism = Synthetic construct
SEQUENCE: 141
GANKKGSSSG CFGLPLDRIG SLSGLGC                                          27

SEQ ID NO: 142          moltype = AA  length = 27
FEATURE                 Location/Qualifiers
source                  1..27
                        mol_type = protein
                        organism = Synthetic construct
SEQUENCE: 142
GAQKKGSSQG CFGLPLDRIG SMSGLGC                                          27

SEQ ID NO: 143          moltype = AA  length = 27
FEATURE                 Location/Qualifiers
source                  1..27
                        mol_type = protein
                        organism = Synthetic construct
SEQUENCE: 143
GAQKKGSSSG CFGLPLDRIG SMSGLGC                                          27
```

```
SEQ ID NO: 144         moltype = AA   length = 27
FEATURE                Location/Qualifiers
source                 1..27
                       mol_type = protein
                       organism = Synthetic construct
SEQUENCE: 144
GAQKKGSSKG CFGLPLDRIG SLSGLGC                                         27

SEQ ID NO: 145         moltype = AA   length = 29
FEATURE                Location/Qualifiers
source                 1..29
                       mol_type = protein
                       organism = Synthetic construct
SEQUENCE: 145
YKGAQKKGGS SGCFGLPLDR IGSLSGLGC                                       29

SEQ ID NO: 146         moltype = AA   length = 29
FEATURE                Location/Qualifiers
source                 1..29
                       mol_type = protein
                       organism = Synthetic construct
SEQUENCE: 146
YKGAQKKGLS QGCFGLKLDR IGSLSGLGC                                       29

SEQ ID NO: 147         moltype = AA   length = 29
FEATURE                Location/Qualifiers
source                 1..29
                       mol_type = protein
                       organism = Synthetic construct
SEQUENCE: 147
YKGAQKKGLS SGCFGLKLDR IGSLSGLGC                                       29

SEQ ID NO: 148         moltype = AA   length = 29
FEATURE                Location/Qualifiers
source                 1..29
                       mol_type = protein
                       organism = Synthetic construct
SEQUENCE: 148
YKGAQKKGGS QGCFGLKLDR IGSLSGLGC                                       29

SEQ ID NO: 149         moltype = AA   length = 29
FEATURE                Location/Qualifiers
source                 1..29
                       mol_type = protein
                       organism = Synthetic construct
SEQUENCE: 149
YKGAQKKGGS SGCFGLKLDR IGSLSGLGC                                       29

SEQ ID NO: 150         moltype = AA   length = 29
FEATURE                Location/Qualifiers
source                 1..29
                       mol_type = protein
                       organism = Synthetic construct
SEQUENCE: 150
YKGANKKGLS QGCFGLPLDR IGSLSGLGC                                       29

SEQ ID NO: 151         moltype = AA   length = 29
FEATURE                Location/Qualifiers
source                 1..29
                       mol_type = protein
                       organism = Synthetic construct
SEQUENCE: 151
YKGANKKGLS SGCFGLPLDR IGSLSGLGC                                       29

SEQ ID NO: 152         moltype = AA   length = 29
FEATURE                Location/Qualifiers
source                 1..29
                       mol_type = protein
                       organism = Synthetic construct
SEQUENCE: 152
YKGANKKGGS QGCFGLPLDR IGSLSGLGC                                       29

SEQ ID NO: 153         moltype = AA   length = 29
FEATURE                Location/Qualifiers
source                 1..29
                       mol_type = protein
                       organism = Synthetic construct
SEQUENCE: 153
YKGANKKGGS SGCFGLPLDR IGSLSGLGC                                       29
```

```
SEQ ID NO: 154          moltype = AA   length = 29
FEATURE                 Location/Qualifiers
source                  1..29
                        mol_type = protein
                        organism = Synthetic construct
SEQUENCE: 154
YKGAQKKGLS QGCFGLPLDR IGSMSGLGC                                      29

SEQ ID NO: 155          moltype = AA   length = 29
FEATURE                 Location/Qualifiers
source                  1..29
                        mol_type = protein
                        organism = Synthetic construct
SEQUENCE: 155
YKGAQKKGLS SGCFGLPLDR IGSMSGLGC                                      29

SEQ ID NO: 156          moltype = AA   length = 29
FEATURE                 Location/Qualifiers
source                  1..29
                        mol_type = protein
                        organism = Synthetic construct
SEQUENCE: 156
YKGAQKKGGS QGCFGLPLDR IGSMSGLGC                                      29

SEQ ID NO: 157          moltype = AA   length = 29
FEATURE                 Location/Qualifiers
source                  1..29
                        mol_type = protein
                        organism = Synthetic construct
SEQUENCE: 157
YKGAQKKGGS SGCFGLPLDR IGSMSGLGC                                      29

SEQ ID NO: 158          moltype = AA   length = 29
FEATURE                 Location/Qualifiers
source                  1..29
                        mol_type = protein
                        organism = Synthetic construct
SEQUENCE: 158
YKGAQKKGLS KGCFGLPLDR IGSLSGLGC                                      29

SEQ ID NO: 159          moltype = AA   length = 29
FEATURE                 Location/Qualifiers
source                  1..29
                        mol_type = protein
                        organism = Synthetic construct
SEQUENCE: 159
YKGAQKKGGS KGCFGLPLDR IGSLSGLGC                                      29

SEQ ID NO: 160          moltype = AA   length = 29
FEATURE                 Location/Qualifiers
source                  1..29
                        mol_type = protein
                        organism = Synthetic construct
SEQUENCE: 160
YKGAQKKGLS QGCFGLPLER IGSLSGLGC                                      29

SEQ ID NO: 161          moltype = AA   length = 29
FEATURE                 Location/Qualifiers
source                  1..29
                        mol_type = protein
                        organism = Synthetic construct
SEQUENCE: 161
YKGAQKKGLS SGCFGLPLER IGSLSGLGC                                      29

SEQ ID NO: 162          moltype = AA   length = 29
FEATURE                 Location/Qualifiers
source                  1..29
                        mol_type = protein
                        organism = Synthetic construct
SEQUENCE: 162
YKGANKKGLS QGCFGLPLDR IGSMSGLGC                                      29

SEQ ID NO: 163          moltype = AA   length = 29
FEATURE                 Location/Qualifiers
source                  1..29
                        mol_type = protein
                        organism = Synthetic construct
SEQUENCE: 163
```

```
YKGANKKGLS SGCFGLPLDR IGSMSGLGC                                           29

SEQ ID NO: 164          moltype = AA   length = 29
FEATURE                 Location/Qualifiers
source                  1..29
                        mol_type = protein
                        organism = Synthetic construct
SEQUENCE: 164
YKGANKKGLS QGCFGLPLER IGSMSGLGC                                           29

SEQ ID NO: 165          moltype = AA   length = 29
FEATURE                 Location/Qualifiers
source                  1..29
                        mol_type = protein
                        organism = Synthetic construct
SEQUENCE: 165
YKGANKKGLS SGCFGLPLER IGSMSGLGC                                           29

SEQ ID NO: 166          moltype = AA   length = 29
FEATURE                 Location/Qualifiers
source                  1..29
                        mol_type = protein
                        organism = Synthetic construct
SEQUENCE: 166
YKGAQKKGSS QGCFGLPLDR IGSLSGLGC                                           29

SEQ ID NO: 167          moltype = AA   length = 29
FEATURE                 Location/Qualifiers
source                  1..29
                        mol_type = protein
                        organism = Synthetic construct
SEQUENCE: 167
YKGAQKKGSS SGCFGLPLDR IGSLSGLGC                                           29

SEQ ID NO: 168          moltype = AA   length = 29
FEATURE                 Location/Qualifiers
source                  1..29
                        mol_type = protein
                        organism = Synthetic construct
SEQUENCE: 168
YKGAQKKGSS QGCFGLKLDR IGSLSGLGC                                           29

SEQ ID NO: 169          moltype = AA   length = 29
FEATURE                 Location/Qualifiers
source                  1..29
                        mol_type = protein
                        organism = Synthetic construct
SEQUENCE: 169
YKGAQKKGSS SGCFGLKLDR IGSLSGLGC                                           29

SEQ ID NO: 170          moltype = AA   length = 29
FEATURE                 Location/Qualifiers
source                  1..29
                        mol_type = protein
                        organism = Synthetic construct
SEQUENCE: 170
YKGANKKGSS QGCFGLPLDR IGSLSGLGC                                           29

SEQ ID NO: 171          moltype = AA   length = 29
FEATURE                 Location/Qualifiers
source                  1..29
                        mol_type = protein
                        organism = Synthetic construct
SEQUENCE: 171
YKGANKKGSS SGCFGLPLDR IGSLSGLGC                                           29

SEQ ID NO: 172          moltype = AA   length = 29
FEATURE                 Location/Qualifiers
source                  1..29
                        mol_type = protein
                        organism = Synthetic construct
SEQUENCE: 172
YKGAQKKGSS QGCFGLPLDR IGSMSGLGC                                           29

SEQ ID NO: 173          moltype = AA   length = 29
FEATURE                 Location/Qualifiers
source                  1..29
                        mol_type = protein
                        organism = Synthetic construct
```

```
SEQUENCE: 173
YKGAQKKGSS SGCFGLPLDR IGSMSGLGC                                         29

SEQ ID NO: 174          moltype = AA  length = 29
FEATURE                 Location/Qualifiers
source                  1..29
                        mol_type = protein
                        organism = Synthetic construct
SEQUENCE: 174
YKGAQKKGSS KGCFGLPLDR IGSLSGLGC                                         29

SEQ ID NO: 175          moltype = AA  length = 32
FEATURE                 Location/Qualifiers
source                  1..32
                        mol_type = protein
                        organism = Synthetic construct
SEQUENCE: 175
ARKYKGAQKK GGSQGCFGLP LDRIGSLSGL GC                                     32

SEQ ID NO: 176          moltype = AA  length = 32
FEATURE                 Location/Qualifiers
source                  1..32
                        mol_type = protein
                        organism = Synthetic construct
SEQUENCE: 176
ARKYKGAQKK GGSSGCFGLP LDRIGSLSGL GC                                     32

SEQ ID NO: 177          moltype = AA  length = 32
FEATURE                 Location/Qualifiers
source                  1..32
                        mol_type = protein
                        organism = Synthetic construct
SEQUENCE: 177
ARKYKGAQKK GLSSGCFGLK LDRIGSLSGL GC                                     32

SEQ ID NO: 178          moltype = AA  length = 32
FEATURE                 Location/Qualifiers
source                  1..32
                        mol_type = protein
                        organism = Synthetic construct
SEQUENCE: 178
ARKYKGAQKK GGSQGCFGLK LDRIGSLSGL GC                                     32

SEQ ID NO: 179          moltype = AA  length = 32
FEATURE                 Location/Qualifiers
source                  1..32
                        mol_type = protein
                        organism = Synthetic construct
SEQUENCE: 179
ARKYKGAQKK GGSSGCFGLK LDRIGSLSGL GC                                     32

SEQ ID NO: 180          moltype = AA  length = 32
FEATURE                 Location/Qualifiers
source                  1..32
                        mol_type = protein
                        organism = Synthetic construct
SEQUENCE: 180
ARKYKGANKK GLSQGCFGLP LDRIGSLSGL GC                                     32

SEQ ID NO: 181          moltype = AA  length = 32
FEATURE                 Location/Qualifiers
source                  1..32
                        mol_type = protein
                        organism = Synthetic construct
SEQUENCE: 181
ARKYKGANKK GLSSGCFGLP LDRIGSLSGL GC                                     32

SEQ ID NO: 182          moltype = AA  length = 32
FEATURE                 Location/Qualifiers
source                  1..32
                        mol_type = protein
                        organism = Synthetic construct
SEQUENCE: 182
ARKYKGANKK GGSQGCFGLP LDRIGSLSGL GC                                     32

SEQ ID NO: 183          moltype = AA  length = 32
FEATURE                 Location/Qualifiers
source                  1..32
                        mol_type = protein
```

```
                        organism = Synthetic construct
SEQUENCE: 183
ARKYKGANKK GGSSGCFGLP LDRIGSLSGL GC                                32

SEQ ID NO: 184          moltype = AA   length = 32
FEATURE                 Location/Qualifiers
source                  1..32
                        mol_type = protein
                        organism = Synthetic construct
SEQUENCE: 184
ARKYKGAQKK GLSQGCFGLP LDRIGSMSGL GC                                32

SEQ ID NO: 185          moltype = AA   length = 32
FEATURE                 Location/Qualifiers
source                  1..32
                        mol_type = protein
                        organism = Synthetic construct
SEQUENCE: 185
ARKYKGAQKK GLSSGCFGLP LDRIGSMSGL GC                                32

SEQ ID NO: 186          moltype = AA   length = 32
FEATURE                 Location/Qualifiers
source                  1..32
                        mol_type = protein
                        organism = Synthetic construct
SEQUENCE: 186
ARKYKGAQKK GGSQGCFGLP LDRIGSMSGL GC                                32

SEQ ID NO: 187          moltype = AA   length = 32
FEATURE                 Location/Qualifiers
source                  1..32
                        mol_type = protein
                        organism = Synthetic construct
SEQUENCE: 187
ARKYKGAQKK GGSSGCFGLP LDRIGSMSGL GC                                32

SEQ ID NO: 188          moltype = AA   length = 32
FEATURE                 Location/Qualifiers
source                  1..32
                        mol_type = protein
                        organism = Synthetic construct
SEQUENCE: 188
ARKYKGAQKK GGSKGCFGLP LDRIGSLSGL GC                                32

SEQ ID NO: 189          moltype = AA   length = 32
FEATURE                 Location/Qualifiers
source                  1..32
                        mol_type = protein
                        organism = Synthetic construct
SEQUENCE: 189
ARKYKGAQKK GLSQGCFGLP LERIGSLSGL GC                                32

SEQ ID NO: 190          moltype = AA   length = 32
FEATURE                 Location/Qualifiers
source                  1..32
                        mol_type = protein
                        organism = Synthetic construct
SEQUENCE: 190
ARKYKGAQKK GLSSGCFGLP LERIGSLSGL GC                                32

SEQ ID NO: 191          moltype = AA   length = 32
FEATURE                 Location/Qualifiers
source                  1..32
                        mol_type = protein
                        organism = Synthetic construct
SEQUENCE: 191
ARKYKGANKK GLSQGCFGLP LDRIGSMSGL GC                                32

SEQ ID NO: 192          moltype = AA   length = 32
FEATURE                 Location/Qualifiers
source                  1..32
                        mol_type = protein
                        organism = Synthetic construct
SEQUENCE: 192
ARKYKGANKK GLSSGCFGLP LDRIGSMSGL GC                                32

SEQ ID NO: 193          moltype = AA   length = 32
FEATURE                 Location/Qualifiers
source                  1..32
```

```
                            mol_type = protein
                            organism = Synthetic construct
SEQUENCE: 193
ARKYKGANKK GLSQGCFGLP LERIGSMSGL GC                                      32

SEQ ID NO: 194              moltype = AA  length = 32
FEATURE                     Location/Qualifiers
source                      1..32
                            mol_type = protein
                            organism = Synthetic construct
SEQUENCE: 194
ARKYKGANKK GLSSGCFGLP LERIGSMSGL GC                                      32

SEQ ID NO: 195              moltype = AA  length = 32
FEATURE                     Location/Qualifiers
source                      1..32
                            mol_type = protein
                            organism = Synthetic construct
SEQUENCE: 195
ARKYKGAQKK GSSQGCFGLP LDRIGSLSGL GC                                      32

SEQ ID NO: 196              moltype = AA  length = 32
FEATURE                     Location/Qualifiers
source                      1..32
                            mol_type = protein
                            organism = Synthetic construct
SEQUENCE: 196
ARKYKGAQKK GSSSGCFGLP LDRIGSLSGL GC                                      32

SEQ ID NO: 197              moltype = AA  length = 32
FEATURE                     Location/Qualifiers
source                      1..32
                            mol_type = protein
                            organism = Synthetic construct
SEQUENCE: 197
ARKYKGAQKK GSSQGCFGLK LDRIGSLSGL GC                                      32

SEQ ID NO: 198              moltype = AA  length = 32
FEATURE                     Location/Qualifiers
source                      1..32
                            mol_type = protein
                            organism = Synthetic construct
SEQUENCE: 198
ARKYKGAQKK GSSSGCFGLK LDRIGSLSGL GC                                      32

SEQ ID NO: 199              moltype = AA  length = 32
FEATURE                     Location/Qualifiers
source                      1..32
                            mol_type = protein
                            organism = Synthetic construct
SEQUENCE: 199
ARKYKGANKK GSSQGCFGLP LDRIGSLSGL GC                                      32

SEQ ID NO: 200              moltype = AA  length = 32
FEATURE                     Location/Qualifiers
source                      1..32
                            mol_type = protein
                            organism = Synthetic construct
SEQUENCE: 200
ARKYKGANKK GSSSGCFGLP LDRIGSLSGL GC                                      32

SEQ ID NO: 201              moltype = AA  length = 32
FEATURE                     Location/Qualifiers
source                      1..32
                            mol_type = protein
                            organism = Synthetic construct
SEQUENCE: 201
ARKYKGAQKK GSSQGCFGLP LDRIGSMSGL GC                                      32

SEQ ID NO: 202              moltype = AA  length = 32
FEATURE                     Location/Qualifiers
source                      1..32
                            mol_type = protein
                            organism = Synthetic construct
SEQUENCE: 202
ARKYKGAQKK GSSSGCFGLP LDRIGSMSGL GC                                      32

SEQ ID NO: 203              moltype = AA  length = 32
FEATURE                     Location/Qualifiers
```

```
source                  1..32
                        mol_type = protein
                        organism = Synthetic construct
SEQUENCE: 203
ARKYKGAQKK GSSKGCFGLP LDRIGSLSGL GC                                32

SEQ ID NO: 204          moltype = AA  length = 37
FEATURE                 Location/Qualifiers
source                  1..37
                        mol_type = protein
                        organism = Synthetic construct
SEQUENCE: 204
QEHPQARKYK GAQKKGGSSG CFGLPLDRIG SLSGLGC                           37

SEQ ID NO: 205          moltype = AA  length = 37
FEATURE                 Location/Qualifiers
source                  1..37
                        mol_type = protein
                        organism = Synthetic construct
SEQUENCE: 205
QEHPQARKYK GAQKKGLSQG CFGLKLDRIG SLSGLGC                           37

SEQ ID NO: 206          moltype = AA  length = 37
FEATURE                 Location/Qualifiers
source                  1..37
                        mol_type = protein
                        organism = Synthetic construct
SEQUENCE: 206
QEHPQARKYK GAQKKGLSSG CFGLKLDRIG SLSGLGC                           37

SEQ ID NO: 207          moltype = AA  length = 37
FEATURE                 Location/Qualifiers
source                  1..37
                        mol_type = protein
                        organism = Synthetic construct
SEQUENCE: 207
QEHPQARKYK GAQKKGGSQG CFGLKLDRIG SLSGLGC                           37

SEQ ID NO: 208          moltype = AA  length = 37
FEATURE                 Location/Qualifiers
source                  1..37
                        mol_type = protein
                        organism = Synthetic construct
SEQUENCE: 208
QEHPQARKYK GAQKKGGSSG CFGLKLDRIG SLSGLGC                           37

SEQ ID NO: 209          moltype = AA  length = 37
FEATURE                 Location/Qualifiers
source                  1..37
                        mol_type = protein
                        organism = Synthetic construct
SEQUENCE: 209
QEHPNARKYK GANKKGLSQG CFGLPLDRIG SLSGLGC                           37

SEQ ID NO: 210          moltype = AA  length = 37
FEATURE                 Location/Qualifiers
source                  1..37
                        mol_type = protein
                        organism = Synthetic construct
SEQUENCE: 210
QEHPNARKYK GANKKGLSSG CFGLPLDRIG SLSGLGC                           37

SEQ ID NO: 211          moltype = AA  length = 37
FEATURE                 Location/Qualifiers
source                  1..37
                        mol_type = protein
                        organism = Synthetic construct
SEQUENCE: 211
QEHPNARKYK GANKKGGSQG CFGLPLDRIG SLSGLGC                           37

SEQ ID NO: 212          moltype = AA  length = 37
FEATURE                 Location/Qualifiers
source                  1..37
                        mol_type = protein
                        organism = Synthetic construct
SEQUENCE: 212
QEHPNARKYK GANKKGGSSG CFGLPLDRIG SLSGLGC                           37

SEQ ID NO: 213          moltype = AA  length = 37
```

```
FEATURE                 Location/Qualifiers
source                  1..37
                        mol_type = protein
                        organism = Synthetic construct
SEQUENCE: 213
QEHPQARKYK GAQKKGLSQG CFGLPLDRIG SMSGLGC                                    37

SEQ ID NO: 214          moltype = AA  length = 37
FEATURE                 Location/Qualifiers
source                  1..37
                        mol_type = protein
                        organism = Synthetic construct
SEQUENCE: 214
QEHPQARKYK GAQKKGLSSG CFGLPLDRIG SMSGLGC                                    37

SEQ ID NO: 215          moltype = AA  length = 37
FEATURE                 Location/Qualifiers
source                  1..37
                        mol_type = protein
                        organism = Synthetic construct
SEQUENCE: 215
QEHPQARKYK GAQKKGGSQG CFGLPLDRIG SMSGLGC                                    37

SEQ ID NO: 216          moltype = AA  length = 37
FEATURE                 Location/Qualifiers
source                  1..37
                        mol_type = protein
                        organism = Synthetic construct
SEQUENCE: 216
QEHPQARKYK GAQKKGGSSG CFGLPLDRIG SMSGLGC                                    37

SEQ ID NO: 217          moltype = AA  length = 37
FEATURE                 Location/Qualifiers
source                  1..37
                        mol_type = protein
                        organism = Synthetic construct
SEQUENCE: 217
QEHPQARKYK GAQKKGGSKG CFGLPLDRIG SLSGLGC                                    37

SEQ ID NO: 218          moltype = AA  length = 37
FEATURE                 Location/Qualifiers
source                  1..37
                        mol_type = protein
                        organism = Synthetic construct
SEQUENCE: 218
QEHPQARKYK GAQKKGLSQG CFGLPLERIG SLSGLGC                                    37

SEQ ID NO: 219          moltype = AA  length = 37
FEATURE                 Location/Qualifiers
source                  1..37
                        mol_type = protein
                        organism = Synthetic construct
SEQUENCE: 219
QEHPNARKYK GANKKGLSQG CFGLPLDRIG SMSGLGC                                    37

SEQ ID NO: 220          moltype = AA  length = 37
FEATURE                 Location/Qualifiers
source                  1..37
                        mol_type = protein
                        organism = Synthetic construct
SEQUENCE: 220
QEHPNARKYK GANKKGLSSG CFGLPLDRIG SMSGLGC                                    37

SEQ ID NO: 221          moltype = AA  length = 37
FEATURE                 Location/Qualifiers
source                  1..37
                        mol_type = protein
                        organism = Synthetic construct
SEQUENCE: 221
QEHPNARKYK GANKKGLSQG CFGLPLERIG SMSGLGC                                    37

SEQ ID NO: 222          moltype = AA  length = 37
FEATURE                 Location/Qualifiers
source                  1..37
                        mol_type = protein
                        organism = Synthetic construct
SEQUENCE: 222
QEHPNARKYK GANKKGLSSG CFGLPLERIG SMSGLGC                                    37
```

```
SEQ ID NO: 223            moltype = AA   length = 37
FEATURE                   Location/Qualifiers
source                    1..37
                          mol_type = protein
                          organism = Synthetic construct
SEQUENCE: 223
QEHPQARKYK GAQKKGSSQG CFGLPLDRIG SLSGLGC                                   37

SEQ ID NO: 224            moltype = AA   length = 37
FEATURE                   Location/Qualifiers
source                    1..37
                          mol_type = protein
                          organism = Synthetic construct
SEQUENCE: 224
QEHPQARKYK GAQKKGSSSG CFGLPLDRIG SLSGLGC                                   37

SEQ ID NO: 225            moltype = AA   length = 37
FEATURE                   Location/Qualifiers
source                    1..37
                          mol_type = protein
                          organism = Synthetic construct
SEQUENCE: 225
QEHPQARKYK GAQKKGSSQG CFGLKLDRIG SLSGLGC                                   37

SEQ ID NO: 226            moltype = AA   length = 37
FEATURE                   Location/Qualifiers
source                    1..37
                          mol_type = protein
                          organism = Synthetic construct
SEQUENCE: 226
QEHPQARKYK GAQKKGSSSG CFGLKLDRIG SLSGLGC                                   37

SEQ ID NO: 227            moltype = AA   length = 37
FEATURE                   Location/Qualifiers
source                    1..37
                          mol_type = protein
                          organism = Synthetic construct
SEQUENCE: 227
QEHPNARKYK GANKKGSSQG CFGLPLDRIG SLSGLGC                                   37

SEQ ID NO: 228            moltype = AA   length = 37
FEATURE                   Location/Qualifiers
source                    1..37
                          mol_type = protein
                          organism = Synthetic construct
SEQUENCE: 228
QEHPNARKYK GANKKGSSSG CFGLPLDRIG SLSGLGC                                   37

SEQ ID NO: 229            moltype = AA   length = 37
FEATURE                   Location/Qualifiers
source                    1..37
                          mol_type = protein
                          organism = Synthetic construct
SEQUENCE: 229
QEHPQARKYK GAQKKGSSQG CFGLPLDRIG SMSGLGC                                   37

SEQ ID NO: 230            moltype = AA   length = 37
FEATURE                   Location/Qualifiers
source                    1..37
                          mol_type = protein
                          organism = Synthetic construct
SEQUENCE: 230
QEHPQARKYK GAQKKGSSSG CFGLPLDRIG SMSGLGC                                   37

SEQ ID NO: 231            moltype = AA   length = 37
FEATURE                   Location/Qualifiers
source                    1..37
                          mol_type = protein
                          organism = Synthetic construct
SEQUENCE: 231
QEHPQARKYK GAQKKGSSKG CFGLPLDRIG SLSGLGC                                   37

SEQ ID NO: 232            moltype = AA   length = 27
FEATURE                   Location/Qualifiers
source                    1..27
                          mol_type = protein
                          organism = synthetic construct
SEQUENCE: 232
GAQKKGSSQG CFGLPLERIG SLSGLGC                                              27
```

```
SEQ ID NO: 233          moltype = AA  length = 32
FEATURE                 Location/Qualifiers
source                  1..32
                        mol_type = protein
                        organism = synthetic construct
SITE                    1
                        note = d-alanine
SITE                    2
                        note = d-arginine
SITE                    3
                        note = d-lysine
SITE                    4
                        note = d-tyrosine
SITE                    5
                        note = d-lysine
SITE                    7
                        note = d-alanine
SITE                    8
                        note = d-glutamine
SITE                    9
                        note = d-lysine
SITE                    10
                        note = d-lysine
SITE                    12
                        note = d-leucine
SITE                    13
                        note = d-serine
SITE                    14
                        note = d-lysine
SITE                    16
                        note = d-cystenine
SITE                    17
                        note = d-phenylalanine
SITE                    19
                        note = d-leucine
SITE                    20
                        note = d-lysine
SITE                    21
                        note = d-leucine
SITE                    22
                        note = d-glutamic acid
SITE                    23
                        note = d-arginine
SITE                    24
                        note = d-isoleucine
SITE                    26
                        note = d-serine
SITE                    27
                        note = d-leucine
SITE                    28
                        note = d-serine
SITE                    30
                        note = d-leucine
SITE                    32
                        note = d-cysteine
SEQUENCE: 233
ARKYKGAQKK GLSKGCFGLK LERIGSLSGL GC                                      32

SEQ ID NO: 234          moltype = AA  length = 39
FEATURE                 Location/Qualifiers
source                  1..39
                        mol_type = protein
                        organism = synthetic construct
SEQUENCE: 234
PGQEHPNARK YKGANKKGLS KGCFGLKLDR IGSMSGLGC                               39

SEQ ID NO: 235          moltype = AA  length = 42
FEATURE                 Location/Qualifiers
source                  1..42
                        mol_type = protein
                        organism = synthetic construct
SEQUENCE: 235
GQAPGQAPGQ APGQAPGQAP GLSKGCFGLK LDRIGSMSGL GC                           42
```

```
SEQ ID NO: 236        moltype = AA  length = 30
FEATURE               Location/Qualifiers
source                1..30
                      mol_type = protein
                      organism = synthetic construct
SEQUENCE: 236
QAPGAQKKGS SQGCFGLPLD RIGSLSGLGC                                              30
```